(12) United States Patent
Vaillancourt et al.

(10) Patent No.: US 6,310,211 B1
(45) Date of Patent: *Oct. 30, 2001

(54) 8-HYDROXY-7-SUBSTITUTED QUINOLINES AS ANTI-VIRAL AGENTS

(75) Inventors: Valerie Ann Vaillancourt, Kalamazoo; Karen Rene Romines, Paw Paw; Arthur Glenn Romero; John Alan Tucker, both of Kalamazoo; Joseph Walter Strohbach, Mendon; Olivier Bezencon; Suvit Thaisrivongs, both of Kalamazoo, all of MI (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/924,683

(22) Filed: Sep. 5, 1997

Related U.S. Application Data

(60) Provisional application No. 60/050,720, filed on Jun. 25, 1997, and provisional application No. 60/025,870, filed on Sep. 10, 1996.

(51) Int. Cl.[7] ............. C07D 401/12; C07D 215/26; C07D 405/06; C07D 417/12
(52) U.S. Cl. .......... 546/143; 546/153; 546/159; 546/161; 546/169; 546/14; 546/177; 544/128; 514/307; 514/311; 514/314
(58) Field of Search ................... 546/153, 159, 546/160, 169, 161, 143; 514/311, 312, 313, 314, 128, 235.2

(56) References Cited

U.S. PATENT DOCUMENTS

| | | | |
|---|---|---|---|
| 4,881,969 | 11/1989 | Saupe et al. | 71/94 |
| 4,959,363 | 9/1990 | Wentland | 514/235.2 |
| 5,240,940 | 8/1993 | Arnold et al. | 514/312 |
| 5,378,694 | 1/1995 | Afonso et al. | 514/82 |
| 5,412,104 | 5/1995 | Afonso et al. | 548/525 |
| 5,459,146 | 10/1995 | Afonso et al. | 514/292 |
| 5,463,072 | 10/1995 | Bergthaller | 548/255 |
| 5,506,236 | 4/1996 | Afonso et al. | 514/293 |

FOREIGN PATENT DOCUMENTS

| | | |
|---|---|---|
| 1 908 548 | 6/1971 | (DE) . |
| 44 25 647 | 1/1996 | (DE) . |
| 44 25 648 | 1/1996 | (DE) . |
| 44 25 659 | 1/1996 | (DE) . |
| 44 25 650 | 11/1996 | (DE) . |
| 0 206 751 | 12/1986 | (EP) . |
| 0 326 328 | 2/1989 | (EP) . |
| 0 326 330 | 2/1989 | (EP) . |
| 0 399 818 | 11/1990 | (EP) . |
| 63-307451 | 12/1988 | (JP) . |
| H1-136152 | 5/1989 | (JP) . |
| HEI 2-152966 | 6/1990 | (JP) . |
| HEI 3-73949 | 3/1991 | (JP) . |
| 7-033729 | 2/1995 | (JP) . |
| 7-165748 | 7/1995 | (JP) . |
| 8-099957 | 8/1996 | (JP) . |
| WO 95/11592 | 5/1995 | (WO) . |
| WO 96/06084 | 2/1996 | (WO) . |
| WO 96/25399 | 8/1996 | (WO) . |
| WO 96/32015 | 10/1996 | (WO) . |
| WO 97/03069 | 1/1997 | (WO) . |

OTHER PUBLICATIONS

Derwent Abstract No. 22,706.
Derwent Abstract No. 85–063337/11.
Derwent Abstract No. 90–264471/35.
Derwent Abstract No. 90–290145/38.
Derwent Abstract No. 90–343755/46.
Derwent Abstract No. 91–232424/32.
Kemp et al., "Peptide Synthesis with Benzisoxazolium Salts," Tetrahedron, vol. 30, pp. 3677–3688, 1974.*
Urbanski et al., "Research on New Antituberculous Drugs," Chemical Abstract, vol. 53, No. 5, 4567, Mar. 10, 1959.*

* cited by examiner

Primary Examiner—Emily Bernhardt
(74) Attorney, Agent, or Firm—Lucy X. Yang

(57) ABSTRACT

The present invention provides for 8-hydroxy-7-substituted quinoline compounds such as formula IA

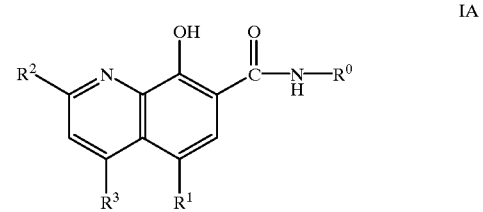

IA

These compounds are useful as anti-viral agents. Specifically, these compounds have anti-viral activity against the herpes virus, cytomegalovirus (CMV). Many of these compounds are also active against other herpes viruses, such as the varicella zoster virus, the Epstein-Barr virus, the herpes simplex virus and the human herpes virus type 8 (HHV-8).

9 Claims, No Drawings

8-HYDROXY-7-SUBSTITUTED QUINOLINES AS ANTI-VIRAL AGENTS

CROSS-REFERENCE TO RELATED APPLICATIONS

This application claims the benefit of U.S. Ser. No. 60/025,870, filed Sep. 10, 1996, and U.S. Ser. No. 60/050,720, filed Jun. 25, 1997.

FIELD OF THE INVENTION

The present invention provides for 8-hydroxy-7-substituted quinoline compounds and pharmaceutically acceptable salts thereof which are useful as antiviral agents. The invention also relates to a pharmaceutical composition containing such compound in combination with a suitable excipient, the composition being useful in combating viral infections. The invention also relates to a method for selectively combating viral infections in animals, including man. Specifically, these compounds have anti-viral activity against the herpes virus, cytomegalovirus (CMV). Many of these compounds are also active against other herpes viruses, such as the varicella zoster virus, the Epstein-Barr virus, the herpes simplex virus, and the human herpes virus type 8 (HHV-8).

BACKGROUND OF THE INVENTION

The herpesviruses comprise a large family of double stranded DNA viruses. The herpesvirus family can be divided into three subfamilies ($\alpha$, $\beta$, $\gamma$) based upon a number of biological properties such as host range and tropism, viral life cycle, and viral persistence and latency. Eight of the herpesviruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 are the prototypic $\alpha$-herpesviruses. These two serotypes share approximately 50% nucleotide homology. Both are neurotropic viruses, but their primary sites of replication are different. HSV-1 typically infects the oral mucosa resulting in ulcerations commonly referred to as cold sores. HSV-2 infects and causes ulcerations of the genital mucosa. HSV infection can also result in disseminated disease and encephalitis, especially in immunocompromised patients. D. O. White and F. J. Fenner, In Medical Virology, D. O. White and F. J. Fenner, eds., Academic Press, p. 318–347 (1994).

VZV is also an $\alpha$-herpesvirus and is the causitive agent of chicken pox. VZV establishes a latent infection in the dorsal root ganglia of the peripheral nervous system. From its latent site, VZV can cause recurrent disease commonly referred to as shingles or zoster. The probability of shingles increases with age and frequently occurs in immunocompromised patients. A. M. Arvin, In Virology, B. N. Field, D. M. Knipe, and P. M. Howley, ed., Lippincott-Raven Press, New York, p. 2547–2586 (1996).

Human cytomegalovirus (HCMV), a $\beta$-herpesvirus, is an ubiquitous agent producing infection in individuals of all age groups. Infection rates of 60–100%, depending on geographic area and socioeconomic status have been reported. R. J. Whitley, S. Goldsmith and J. Gnann, In Society for General Microbiology. 45th Symposium: Control of Virus Diseases, Mimmock, N.J.; P. D. Griffiths and C. R. Madely, eds., Cambridge University Press, Cambridge, p. 315 (1990). The majority of infections are asymptomatic. However infections occuring in the immunocompromised patient, including organ transplant recipients and individuals with AIDS may be severe and include HCMV induced pneumonia, colitis, and retinitis. L. W. Drew, Clin. Infect. Dis. 14:608–615 (1992). HCMV is the leading cause of blindness in AIDS patients. T. C. Merigan and S. Resta, Rev. Infect. Dis.12: S693 (1990). HCMV also establishes lifelong latency in the host.

HCMV DNA polymerase (HCMV pol) is an enzyme essential for viral replication. D. H. Spector, K. M. Klucher, D. K. Rabert and D. A. Wright, In Herpesvirus Transcription and Its Regulation, E. K. Wagner, ed., CRC Press, Boca Raton, Fla., p. 261 (1991). The current therapies for HCMV; Ganciclovir, Foscarnet and Vistide act by inhibition of HCMV pol. A. K. Field and K. K. Biron, Clin. Micro. Reviews 7:(1) 1–13 (1994). See also U.S. Pat. Nos. 4,199,574; 4,215,113; 4,355,032; and E. DeClercq et al., Antiviral Research, Vol 8, pages 261–272 (1987). Ganciclovir and Foscarnet display significant toxicity and induction therapy is restricted to an intravenous route of administration. D. Faulds and R. C. Heel, Drugs, 39:597 (1990). Maintenance therapy with Ganciclovir and Foscarnet will likely contribute to drug resistant virus. A. K. Field and K. K. Biron, Clin. Micro. Reviews 7:(1) 1–13 (1994). Clearly less toxic, orally bioavailable alternatives are needed.

EBV is a $\gamma$-herpesvirus which replicates in the epithelial cells of the nasopharynx and salivary glands and resides latently in B-cells. Childhood infections of EBV are normally asymptomatic. However, EBV infection is associated with several diseases in adults such as infectious mononucleosis, Burkitt's lymphoma, nasopharyngeal carcinoma, and Hodgkins disease. A. B. Rickinson and E. Kieff, In Virology, B. N. Fields, D. M. Knipe, and P. M. Howley, eds., Lippincott-Raven Press, New York, p. 2397–2446 (1996).

HHV-6 is a $\beta$-herpesvirus which causes roseola (exanthem subitum) in children. P. Lusso, Antivir. Res. 31:1–21 (1996). HHV-7 shares 50–60% nucleotide sequence homology with HHV-6. It's disease association is unclear, but it may be involved in some cases of roseola. N. Frenkel and E. Roffman, In Virology, B. N. Fields, D. M. Knipe, P. M. Howley, eds., Lippincott-Raven Press, New York, p. 2609–2622 (1996). HHV-8, also known as Kaposi's sarcoma associated herpesvirus (KSHV), is a $\gamma$-herpesvirus which has recently been associated with Kaposi's sarcoma in AIDS patients and multiple myeloma. M. B. Rettig et al., Science, 276:1851–1854 (1997).

INFORMATION DISCLOSURE

Published Japanese patent application H1-136152 published May 29, 1989 discloses a silver halide photographic light-sensitive material comprising a support, and thereon, at least 1 silver halide emulsion layer containing a cyan dye-forming coupler represented by a broad generic formula. This broad generic formula includes 8-hydroxyquinoline derivatives substituted by a wide variety of substituents, e.g., substituted carboxamide groups at the 7-position. None of the specific compounds disclosed in this reference are structurally similar to the compounds of the present invention. Also, the compounds of the present invention are useful as pharmaceutical agents, specifically HCMV inhibitors, whereas the reference compounds are useful in color photography.

Published Japanese patent application HEI 3-73949 published Mar. 28, 1991 discloses a thermally developable color light-sensitive material comprising at least a light-sensitive silver halide, a reducing agent, a binder, and a coupler represented by a first generic formula and/or a second generic formula on a support. These broad generic formulas include 8-hydroxy-quinoline derivatives substituted by a wide variety of substituents, e.g., substituted carboxamide groups at the 7-position. As noted for the previous Japanese reference, none of the specific compounds disclosed in this reference are structurally similar to the compounds of the present invention. Also, the compounds of the present invention are useful as pharmaceutical agents, specifically HCMV inhibitors, whereas the reference compounds are useful in color photography.

Published Japanese patent application 02152966 A2 discloses 4-hydroxy-carbostyryl derivatives as anti-allergy and antiinflammatory agents. The compounds of the present invention are 1-(N-unsubstituted)-8-hydroxy-7-quinolinecarboxamides.

U.S. Pat. No. 4,959,363 discloses 1-(N-substituted)-1,4-dihydro-4-oxo-6- and/or -7-substituted-3-quinolinecarboxamides as antiviral agents. The compounds of the present invention are 1-(N-unsubstituted)-8-hydroxy-7-quinolinecarboxamides.

U.S. Pat. Nos. 5,459,146 and 5,506,236 disclose 4-substituted- 3-alkyl-pyrazolo[3,4-b]quinoline compounds as antiviral agents. Basically, these compounds are the tricyclic version of compounds such as those disclosed in the '363 patent above, and are structurally very different from the compounds of the present invention.

U.S. Pat. No. 5,378,694 discloses compounds such as 1-(N-substituted)-3-substituted-4-hydroxy-2-quinolinones, and generically, 3-substituted-4-hydroxycoumarin compounds as antiviral agents. U.S. Pat. No. 5,412,104 discloses compounds similar to those disclosed in the '694 patent for anti-viral or anti-hypertensive use; however, these 1-(N-substituted) reference compounds are disclosed as having substituents other than hydroxy at the 4-position of the quinolinone ring. The compounds of the present invention are 1-(N-unsubstituted)-8-hydroxy-7-quinolinecarboxamides.

German patent DE 1 908 548 discloses a variety of compounds including 4-hydroxy-quinoline compounds which may be substituted at the 3-position by carboxamide groups, and which are useful against cold viruses.

Published German patent application DE 44 25 647 A1 discloses heterocyclic-1-phenyl substituted quinolone and naphthyridone carboxylic acids for treating retroviral infections; Published German patent application DE 44 25 648 A1 discloses 6 and 6,8-substituted 1-[4-(1H-1,2,4-triazol-1-yl-methyl)phenyl] quinolone carboxylic acids for treating retroviral infections; Published German patent application DE 44 25 650 A1 discloses substituted triazolylmethylphenylnaphthyridone carboxylic acids for treating retroviral infections; Published German patent application DE 44 25 659 A1 discloses N1-diverse 6-fluoro-8-difluoromethoxy substituted quinolone carboxylic acids for treating retroviral infections. The compounds of these references are structurally very different from the compounds of the present invention.

Derwent Abstract 96-246942/25 of JP 8099957-A discloses optionally heterocyclyl substituted 4-oxo-quinoline and naphthyridine derivatives which are useful for treating herpes, particularly herpes simplex virus, herpex zoster virus and cytomegalovirus.

Derwent Abstract 95-271358/36 of JP 7165748-A discloses compounds having heterocyclic ketones which are used in antiviral agents for treating cytomegalovirus infectious disease.

Nowhere do these references teach or suggest the specific 8-hydroxyquinoline-7-carboxamide compounds of the present invention which are useful as anti-HCMV agents.

U.S. Pat. No. 5,463,072 discloses a process for the preparation of naphtholic 2-equivalent cyan couplers which are useful in color photography. It discloses an 8-hydroxyquinoline compound having a substituted thiazole moiety at the 6-position and a carbamoyl moiety at the 7-position.

International Publication WO 95/11592, published May 4, 1995, discloses a marine structure carrying a coating comprising a layer which contains a quinoline compound, or an N-oxide or a salt thereof, having antifouling activity. It generically discloses such compounds with a variety of substituents, such as hydroxy, (optionally substituted $C_{1-12}$-alkyl)sulphonyl, (optionally substituted aryl)sulphonyl, mono or di (optionally substituted $C_{1-12}$alkyl) aminosulphonyl.

Derwent Abstract 91-232424/32 (Sandoz A G) discloses the use of 5HT-3 antagonists for the prevention or reduction of dependence on alcohol, psycho-stimulants, nicotine or opiates. A variety of compounds is disclosed including quinoline compounds having unsubstituted phenyl rings.

Derwent Abstract 90-343755/46 (Sandoz Ltd.) discloses serotonin 5HT3 antagonists used for treating stress related psychiatric disorders, rhinitis, nasal disorders and lung embolism. It discloses a variety of compounds, including quinoline compounds substituted by bridged piperidine groups.

Derwent Abstract 90-290145/38 (DuPont DeNemours Co.) discloses n-substituted naphthalene or quinoline sulphonamides which are radio and chemo-sensitising agents in tumour treatment. Other than the sulfonamide bonds, the quinoline compounds are not further substituted on their phenyl rings.

Derwent Abstract 90-264471/35 (Yoshitomi Pharm. Ind. KK.) discloses (iso)quinoline-sulphonamide compounds and their acid addition salts as vasodilators and cerebral circulation improving agents.

Derwent Abstract 85-063337/11 (Sandoz-Patent-Gmbh) discloses a variety of new fused heterocyclic sulphonic amide and ester derivatives with analgesic, antiarrythmic and antipsychotic activities.

Derwent Abstract 22,706 (Pfizer & Co.) discloses quinoline derivatives and their acid addition salts as bronchodilators, but no sulfonamide substituents are disclosed for these compounds.

U.S. Pat. No. 5,240,940 discloses fungicidal compositions comprising a combination of two fungicides, one of which is a quinoline or cinnoline compound. U.S. Pat. No. 4,881,969 discloses sulfonamides as herbicidal agents.

European Published applications 0326330 and 0326328 discloses quinoline, quinazoline and cinnoline fungicides.

JP 63307451 discloses a silver halide color photographic photosensitive material with improved granularity containing a water-soluble coupler capable of a coupling reaction with an oxidant main ingredient in color developing, which coupler may include specific 8-hydroxy-quinoline compounds.

JPO7033729-A discloses the production of N-cyano-N-substituted-arylcarboxyimidamide compounds in which aryl may be 8-quinolyl groups.

International Publication Number WO 96/25399, published Aug. 22, 1996, discloses aroylaniline derivatives which exhibit anti-retroviral activity.

International Publication Number WO 97/03069, published Jan. 30, 1997, discloses substituted heteroaromatic compounds which are protein tyrosine kinase inhibitors, in particular to substituted quinolines and quinazolines.

International Publication Number WO 96/06084, published Feb. 29, 1996, discloses quinolylamine derivatives which are usefull for the treatment of arrhythmia European Patent Application No. 0206751, published Dec. 30, 1996, discloses 2-substituted-phenylalkenyl-quinoline derivatives which are useful as selective antagonists of leukotrienes of $D_4$.

International Application No. WO 9632015 discloses synergistic fungicidal compositions made of quinoline derivatives and cytochrome complex III inhibitors.

European Patent Application No. 0399818 discloses diarylstyrylquinoline diacids which are leukotriene antagonists and inhibitors of leukotriene biosynthesis. These compounds are useful as anti-asthmatic, anti-allergic, anti-inflammatory and cytoprotective agents.

SUMMARY OF THE INVENTION

The present invention particularly provides:
A compound of formula IA
wherein $R^0$ is
- a) —$(CH_2)_n$—$X^1$,
- b) —$(CH_2)_n$—$C_3$–$C_8$ cycloalkyl substituted by zero (0) or one (1) $R^8$,
- c) —$(CH_2)_p$ $W^1X^2$,
- d) —$(CH_2)_p$ $W^1CH_2X^1$, or
- e) —$(CH_2)_n$—$CHR^9$—$(CH_2)_n$—$X^1$;

wherein $R^1$ is
- a) —H,
- b) —F,
- c) —Cl,
- d) —Br,
- e) —$CF_3$, or
- f) —$NO_2$;

wherein $R^2$ is
- a) —H,
- b) —$C_1$–$C_3$alkyl,
- c) —OH,
- d) —$CF_3$,
- e) —CH=CH-furanyl,
- f) —CH=CH-phenyl substituted by zero (0) or one (1) $R^4$,
- g) —CH=CH-pyridinyl,
- h) —$(CH_2)_p$-phenyl substituted by zero (0) or one (1) $R^4$,
- i) —$NHV^1$,
- j) —$CH_2NHV^1$, or
- k) —$CH_2Z^1$;

wherein $R^3$ is
- a) —H,
- b) —OH,
- c) —$CF_3$, or
- d) —$C_1$–$C_3$alkyl;

wherein $R^4$ is
- a) —H
- b) —F,
- c) —Cl,
- d) —Br,
- e) —$NO_2$,
- f) —$CF_3$,
- g) —$W^1$—$R^{10}$,
- h) —$C_1$–$C_6$ alkyl,
- i) —$C_3$–$C_8$ cycloalkyl,
- j) —$[CH_2]_n$-aryl,
- k) —$[CH_2]_n$-het,
- l) —$C_2C_3$–$C_8$ cycoalkyl,
- m) —$SO_2NH$-het
- n) —CN,
- o) —I, or
- p) —$CH_2$—OH;

wherein $R^5$ is
- a) —H,
- b) —F,
- c) —Cl,
- d) —Br,
- e) —$W^1$—$R^{10}$,
- f) —$CF_3$,
- g) —$C_1$–$C_6$ alkyl,
- h) —$C_3$–$C_8$ cycloalkyl,
- i) —$(CH_2)_n$-aryl substituted by $R^6$,
- j) —$(CH_2)_n$-het substituted by $R^7$, or
- k) —$CH_2$—$C_3$–$C_8$ cycloalkyl;

wherein $R^6$ is
- a) —H,
- b) —F,
- c) —Cl, or
- d) —Br;

wherein $R^7$ is
- a) —H,
- b) —F,
- c) —Cl, or
- d) —Br;

wherein $R^8$ is
- a) —$C_1$–$C_4$ alkyl,
- b) —$W^1$—H, or
- c) —$CH_2W^1H$;

wherein $R^9$ is
- a) —$C_1$–$C_7$ alkyl,
- b) —$C_3$–$C_8$ cycloalkyl,
- c) —$C(O)R^{11}$,
- d) —$C(O)NHR^{11}$,
- e) —$CH(OH)R^{11}$,
- f) —$CH_2OH$,
- g) —$CO_2R^{11}$, or
- h) -aryl;

wherein $R^{10}$ is
- a) —H,
- b) —$C_1$–$C_6$ alkyl,
- c) —$C_3$–$C_8$ cycloalkyl,
- d) —$(CH_2)_n$-aryl optionally substituted with F, Cl, $CH_2OH$ or —$NO_2$,
- e) —$(CH_2)_n$-het, or
- f) —$CH_2$—$C_3$–$C_8$ cycloalkyl;

wherein $R^{11}$ is
- a) —$C_1$–$C_7$ alkyl,
- b) —$C_3$–$C_8$ cycloalkyl,
- c) —$(CH_2)_n$ $X^1$, or
- d) —$CH_2$—$C_3$–$C_8$ cycloalkyl;

wherein $X^1$ is
  a) -aryl substituted by zero (0), one (1), two (2), or three (3) $R^4$,
  b) -het substituted by zero (0), one (1) or two (2) $R^6$,
  c) —$C_1$–$C_8$ alkyl,
  d) —CH(OH)-phenyl,
  e) —S-phenyl,
  f) —$NHSO_2$-phenyl substituted by one (1), two (2) or three (3) $R^4$,
  g) —CN,
  h) —OH,
  i) —$C_8$–$C_8$ cycloalkyl substituted by zero (0), one (1) or two (2) $R^8$, or
  j) 4-eyano2,3,5,6tetrafluoro-phenyl;
wherein $X^2$ is
  a) -aryl substituted by zero (0), one (1), two (2) or three (3) $R^4$,
  b) -het substituted by zero (0), one (1) or two (2) $R^5$,
  c) —$C_1$–$C_8$ alkyl,
  d) —CH(OH)-phenyl, or
  e) —$C_3$–$C_8$ cycloalkyl substituted by zero (0), one (1) or two (2) $R^8$;
wherein $W^1$ is
  a) —NH,
  b) -oxygen, or
wherein $V^1$ is
  a) —$R^{11}$,
  b) —C(O)$R^{11}$,
  c) —$SO_2R^{11}$, or
  d) —C(O)NH$R^{11}$;
wherein $Z^1$ is
  a) —$C_1$–$C_7$ alkyl,
  b) —$C_3$–$C_8$ cycloalkyl,
  c) —C(O)$R^{11}$,
  d) —C(O)NH$R^{11}$, or
  e) —$CO_2R^{11}$;
wherein -aryl is
  a) -phenyl,
  b) -naphthyl,
  c) -biphenyl,
  d) -tetrahydro-naphthyl, or
  e) fluorenyl;
wherein -het is a 5-, 6 or 7-membered saturated or unsaturated ring containing from one (1) to three (3) heteroatoms selected from the group consisting of nitrogen, oxygen and sulfur, and including any bicyclic group in which any of the above heterocyclic rings is fused to a benzene ring or another heterocyclic; wherein -cycloalkyl is a saturated or unsaturated hydrocarbon ring including any bicyclic group in which the above ring is connected to a benzene, heterocyclic or other hydrocarbon ring;
wherein n is zero (0) to six (6), inclusive;
wherein p is one (1), two (2) or three (3);
or a pharmaceutically acceptable salt or N-oxide thereof.

The present invention furer provides:
The compound of formula IA provided that:
  a) when $R^0$ is —$(CH_2)_nX^1$ and $X^1$ is —OH, then n is one or greater; and
  b) when $R^0$ is $CH_2)_p$ $W^1X^2$, $W^1$ is -oxygen or -sulfur and $X^2$ is phenyl then $R^4$ is other than t-pentyl.
The present invention also provides:

A compound of formula I
wherein $R^1$ is
  a) —H,
  b) —F,
  c) —Cl,
  d) —Br,
  e) —$CF_3$, or
  f) —$NO_2$;
wherein $R^2$ is
  a) —H,
  b) —$C_1$–$C_3$alkyl,
  c) —OH,
  d) —$CF_3$,
  e) —CH=CH-furanyl,
  f) —CH=CH-phenyl substituted by zero (0) or one (1) $R^4$,
  g) —CH=CH-pyridinyl, or
  h) —$(CH_2)_p$-phenyl substituted by zero (0) or one (1) $R^4$;
wherein $R^3$ is
  a) —H,
  b) —OH,
  c) —$CF_3$, or
  d) —$C_1$–$C_3$alkyl;
wherein $X^1$ is
  a) -phenyl substituted by zero (0) or one (1) $R^4$,
  b) -het substituted by zero (0) or one (1) $R^5$,
  c) —$C_1$–$C_{12}$ alkyl,
  d) —CH(OH)-phenyl,
  e) —S-phenyl,
  f) -naphthyl,
  g) —$NHSO_2$-phenyl substituted by one (1) $R^4$, or
  h) —CN;
wherein het is
  a) -1,3,4-thiadiazol-2-yl,
  b) -4,5-dihydro-4-oxo-2-thiazolyl,
  c) -thiazolyl,
  d) -benzothiazolyl,
  e) -pyridinyl,
  f) -morpholinyl, or
  g) -imidazolyl;
wherein $R^4$ is
  a) —H
  b) —F,
  c) —Cl,
  d) —Br,
  e) —$NO_2$,
  f) —$OCH_2$,
  g) —$CF_3$, or
  h) —$C_1$–$C_4$ alkyl;
wherein $R^5$ is
  a) —H,
  b) —F,
  c) —Cl,
  d) —Br,
  e) —$(CH)_n$-phenyl substituted by $R^6$),
  f) -thienyl substituted by $R^7$, or
  g) —OH;
wherein $R^6$ is a) —H,
b) —F,
c) —Cl, or
d) —Br;
wherein $R^7$ is
a) —H,
b) —F,
c) —Cl, or
d) —Br;
wherein n is zero (0) to six (6) inclusive; or a pharmaceutically acceptable salt or a Nexide thereof.

The present invention further provides compounds of formula II
wherein $R^1$ is
a) —H,
b) —Cl,
c) —Br, or
d) —NO$_2$;
wherein $R^2$ is
a) —H,
b) —CH$_3$,
c) —CF$_3$,
d) —(CH$_2$)$_p$-phenyl substituted by zero (0) or one (1) $R^4$,
e) —CH=CH-furanyl, or
f) —CH=CH-phenyl substituted by zero (0) or one (1) $R^4$;
wherein $X^1$ is
a) -phenyl substituted by one (1) $R^4$,
b) -het substituted by one (1) $R^5$,
c) —CH(OH)-phenyl,
d) —S-phenyl,
e) -naphthyl,
f) —NHSO$_2$-phenyl substituted by one (1), two (2) or three (3) $R^4$, or
g) —CN;
wherein het is
a) -1,3,4-thiadiazol-2-yl,
b) 4,5-dihydro-4-oxo-2-thiazolyl,
c) -2-thiazolyl, or
d) -2-benzothiazolyl;
wherein $R^4$ is
a) —H,
b) —Cl,
c) —Br,
d) —NO$_2$, or
e) —OCHS;
wherein $R^5$ is
a) —H,
b) —Cl,
c) —(CH$_2$)$_n$-(phenyl substituted by $R^6$),
d) -2-thienyl substituted by $R^7$, or
e) OH;
wherein $R^6$ is
a) —H,
b) —Cl, or
c) —Br,
wherein $R^7$ is
a) —H,
b) —Cl, or
c) —Br.

In another aspect, the present invention provides
A use of a compound of formula IA to prepare a medicament for treating a susceptible cytomegaloviral infection in a mammal
wherein $R^0$ is
a) —(CH$_2$)$_n$—X$^1$,
b) —(CH$_2$)$_n$C$_3$–C$_8$ cycloalkyl substituted by zero (0) or one (1) $R^8$,
c) —(CH$_2$)$_p$W$^1$X$^2$,
d) —(CH$_2$)$_p$W$^1$CH$_2$X$^1$, or
e) —(CH$_2$)$_n$—CHR$^9$—(CH$_2$)$_n$—X$^1$;
wherein $R^1$ is
a) —H,
b) —F,
c) —Cl,
d) —Br,
e) —CF$_3$, or
f) —NO$_2$;
wherein $R^2$ is
a) —H,
b) —C$_1$–C$_3$alkyl,
c) —OH,
d) —CF$_3$,
e) —CH=CH-furanyl,
f) —CH=CH-phenyl substituted by zero (0) or one (1) $R^4$,
g) —CH=CH-pyridinyl,
h) —(CH$_2$)$_p$-phenyl substituted by zero (0) or one (1) $R^4$,
i) —NHV$^1$,
j) —CH$_2$NHV$^1$, or
k) —CH$_2$Z$^1$;
wherein $R^3$ is
a) —H,
b) —OH,
c) —CF$_3$, or
d) —C$_1$–C$_3$alkyl;
wherein $R^4$ is
a) —H
b) —F,
c) —Cl,
d) —Br,
e) —NO$_2$,
f) —CF$_3$,
g) —W$^1$—R$^{10}$,
h) —C$_1$–C$_6$ alkyl,
i) —C$_3$–C$_8$ cycloalkyl,
j) —[CH$_2$]$_n$-aryl,
k) —[CH$_2$]$_n$-het,
l) —CH$_2$—C$_3$–C$_8$ cycloalkyl,
m) —SO$_2$NH-het
n) —CN,
o) —I, or
p) —CH$_2$—OH;
wherein $R^5$ is
a) —H,
b) —F,
c) —Cl, d) —Br,
e) —W$^1$—R$^{10}$,
f) —CF$_3$,
g) —C$_1$–C$_6$ alkyl,
h) —C$_3$–C$_8$ cycloalkyl,
i) —(CH$_2$)$_n$-aryl substituted by R$^6$,
j) —(CH$_2$)$_n$-het substituted by R$^7$, or
k) —CH$_2$—C$_3$–C$_8$ cycloalkyl;
wherein R$^6$ is
a) —H,
b) —F,
c) —Cl, or
d) —Br,
wherein R$^7$ is
a) —H,
b) —F,
c) —Cl, or
d) —Br;
wherein R$^8$ is
a) —C$_1$–C$_4$ alkyl,
b) —W$^1$—H, or
c) —CH$_2$W$^1$H;
wherein R$^9$ is
a) —C$_1$–C$_7$ alkyl,
b) —C$_3$–C$_8$ cycloalkyl,
c) —C(O)R$^{11}$,
d) —C(O)NHR$^{11}$,
e) —CH(OH)R$^{11}$,
f) —CH$_2$OH,
g) —CO$_2$R$^{11}$, or
h) -aryl;
wherein R$^{10}$ is
a) —H,
b) —C$_1$–C$_6$ alkyl,
c) —C$_3$–C$_8$ cycloalkyl,
d) —(CH$_2$)$_n$-aryl optionally substituted with F, Cl, CH$_2$OH or —NO$_2$,
e) —(CH$_2$)$_n$-het, or
f) —CH$_2$—C$_3$–C$_8$ cycloalkyl;
wherein R$^{11}$ is
a) —C$_1$–C$_7$ alkyl,
b) —C$_3$–C$_8$ cycloalkyl,
c) —(CH$_2$)$_n$X$^1$, or
d) —CH$_2$—C$_3$–C$_8$ cycloalkyl;
wherein X$^1$ is
a) -aryl substituted by zero (0), one (1), two (2), or three (3) R$^4$,
b) -het substituted by zero (0), one (1) or two (2) R$^5$,
c) —C$_1$–C$_8$ alkyl,
d) —CH(OH)-phenyl,
e) —S-phenyl,
f) —NHSO$_2$-phenyl substituted by one (1), two (2) or three (3) R$^4$,
g) —CN,
h) —OH,
i) —C$_3$–C$_8$ cycloalkyl substituted by zero (0), one (1) or two (2) R$^8$, or
j) -4-cyano-2,3,5,6-tetrafluoro-phenyl;

wherein X$^2$ is
a) -aryl substituted by zero (0), one (1), two (2) or three (3) R$^4$,
b) -het substituted by zero (0), one (1) or two (2) R$^5$,
c) —C$_1$–C$_8$ alkyl,
d) —CH(OH)-phenyl, or
e) —C$_3$–C$_8$ cycloalkyl substituted by zero (0), one (1) or two (2) R$^8$;
wherein W$^1$ is
a) —NH,
b) -oxygen, or
c) -sulfur;
wherein V$^1$ is
a) —R$^{11}$,
b) —C(O)R$^{11}$,
c) SO$_2$R$^{11}$, or
d) —C(O)NHR$^{11}$;
wherein Z$^1$ is
a) —C$_1$–C$_7$ alkyl,
b) —C$_3$–C$_8$ cycloalkyl,
c) —C(O)R$^{11}$,
d) —C(O)NHR$^{11}$, or
e) —CO$_2$R$^{11}$;
wherein -aryl is
a) -phenyl,
b) -naphthyl,
c) -biphenyl,
d) -tetrahydronaphthyl, or
e) fluorenyl;
wherein -het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocyclic;
wherein -cycloalkyl is a saturated or unsaturated hydrocarbon ring including any bicyclic group in which the above ring is connected to a benzene, heterocyclic or other hydrocarbon ring;
wherein n is zero (0) to six (6), inclusive;
wherein p is one (1), two (2) or three (3);
or a pharmaceutically acceptable salt or N-oxide thereof; as well as a method of treating a cytomegalovirus comprising the administration of an effective amount of a compound of the formula IA.

The present invention also provides:

An antiviral pharmaceutical composition which comprises a pharmaceutically acceptable excipient and an effective amount of a compound of formula I.

Further, the present invention provides:

A compound of the formula III
wherein R$^1$ is
a) —H,
b) —C$_1$–C$_5$ alkyl, or
c) —CH═CH-aryl;
wherein R$^2$ is
a) —C$_1$–C$_{10}$ allyl,
b) —(CH$_2$)$_n$R$^3$,
c) —CH(R$^4$)R$^3$, or
d) —(CH$_2$)$_n$—X$^2$R$^3$;
wherein R$^3$ is a) -aryl,
b) -het substituted by zero (0) to two (2) $R^5$, or
c) —$C_3$–$C_6$ cycloalkyl;
wherein $R^4$ is
a) —$C_1$–$C_5$ alkyl, or
b) -aryl;
wherein $X^1$ is
a) —H,
b) —F,
c) —Cl,
d) —Br, or
e) —I;
wherein $X^2$ is
a) —O—,
b) —S—, or
c) —NH—;
wherein n is zero (0) to four (4) inclusive;
wherein aryl is
  a) phenyl substituted by zero (0) to two (2) $R^5$, or
  b) naphthyl substituted by zero (0) to two (2) $R^5$;
wherein het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; and the ring may be connected through a carbon or secondary nitrogen in the ring or an exocyclic nitrogen; and if chemically feasible, the nitrogen and sulfur atoms may be in the oxidized forms; and if chemically feasible, the nitrogen atom may be in the protected form;
wherein $R^5$ is
a) —H,
b) —$C_1$–$C_5$ alkyl,
c) —F,
d) —Cl,
e) —$OCH_3$,
f) —$CF_3$,
g) —$NHSO_2$-het substituted by zero (0) to two (2) —$C_1$–$C_5$ alkyl, or
h) —$NHSO_2$-phenyl;
or a pharmaceutically acceptable salt thereof;
A compound of formula III
wherein $R^1$ is
a) —H,
b) —$CH_3$, or
c) —CH=CH-phenyl;
wherein $R^2$ is
a) —$(CH_2)_n R^3$,
b) —$(CH_2)_n$—$X^2$—$R^3$, or
c) —$CH(R^4)R^3$;
wherein $R^3$ is
a) -phenyl substituted by zero (0) to two (2) $R^5$,
b) -het,
c) -naphthyl, or
d) —$C_{3-6}$ cycloalkyl;
wherein $R^4$ is
a) —$CH_3$, or
b) -phenyl;
wherein $R^5$ is
a) —F,
b) —Cl,
c) —$NHSO_2$-phenyl;
wherein $X^1$ is
a) —Cl, or
b) —Br;
wherein $X^2$ is
a) —O—, or
b) —S—;
wherein het is
a) -imidazolyl, or
b) -indolyl.
The present invention also provides:
A compound of the formula IV
where $X^1$ is
a) —H,
b) —F,
d) —Br, or
e) —I;
wherein $R_2$, $R_3$ and $R_4$ may be the same or different and are
a) —$C_1$–$C_5$ alkyl, or
b) -phenyl.
Also provided is:
A compound of formula V
wherein $X^1$ is
a) phenyl substituted by zero (0) to three (3) $R^4$,
b) naphthyl substituted by zero (0) to three (3) $R^4$,
c) fluorenyl substituted by zero (0) to three (3) $R^4$,
d) het substituted by zero (0) to one (1) $R^5$, or
e) 4-cyano-2,3,5,6-tetrafluorophenyl;
wherein $R^4$ is
a) —F,
b) —Cl,
c) —Br,
d) —I,
e) —$NO_2$,
f) —CN,
g) —$CF_3$,
h) —$C_1$–$C_6$ alkyl,
i) phenyl,
j) cyclohexyl,
k) hydroxymethyl,
l) —$OR^{10}$,
m) —$SR^{10}$, or
n) —$SO_2NH$-het;
wherein het is
a) 1,3-benzodioxol-4-yl,
b) 1,3-benzodioxo-5-yl,
c) coumarinyl,
d) indazoyl,
e) indolyl,
f) benzothiazolyl,
g) benzothiadiazolyl,
h) quinolinyl,
i) pyridinyl,
j) 1,3,4-thiadiazol-2-yl, or
k) isoxazolyl substituted with one or two $C_1$–$C_4$ alkyl;
wherein $R^5$ is
a) —F, b) —Cl,
c) —Br,
d) —I,
e) —CF$_3$,
f) —C$_1$–C$_4$-alkyl, or
g) —C$_1$–C$_2$-alkylsubstituted with an aryl;
wherein R$^{10}$ is
a) hydrogen,
b) —C$_1$–C$_4$ alkyl,
c) phenyl,
d) benzyl, or
e) 4-nitrophenyl; as well as A compound of formula V
wherein het is
a) indazoyl,
b) indoyl, or
c) isoxazolyl substituted with one (1) or two (2) C$_1$–C$_4$ alkyl Finally, the present invention provides:
A compound of formula VI or VII
wherein X is
a) —C, or
b) —SO;
wherein Y is
a) —NH,
b) —O, or
c) —S;
wherein EWG is an electron withdrawing group;
wherein R$^1$, R$^2$ and R$^3$ are as defined in claim 1;
wherein R$^4$ is
a) —H,
b) —(CH$_2$)$_n$—CO$_2$—C$_1$–C$_6$ alkyl,
c) —(CH$_2$)$_m$-phenyl optionally substituted with one (1) or two (2) R$^7$,
d) —(CH)$_m$-het,
e) —C$_1$–C$_6$ alkyl optionally substituted by one R$^6$,
f) —C$_1$–C$_4$ alkyl-NH—COOCH$_2$-benzyl, or
g) —C$_1$–C$_4$ alyl-S—CH$_3$;
wherein R$^5$ is pyrrolidin-1-yl optionally substituted with EWG or R$^6$;
wherein n is zero (0) to three (3);
wherein m is zero (0) to one (1);
wherein -het is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocyclic;
wherein R$^6$ is
a) hydroxy,
b) —C$_1$–C$_6$ alkyloxy,
c) mercapto, or
d) —C$_1$–C$_6$ alkylmercapto;
wherein R$^7$ is
a) hydroxy, or
b) —C$_1$–C$_6$ alkyloxy; as well as A compound of formula VI or VII
wherein R$^7$ is t-butyl;
wherein EWG is
a) —NH—CO$_2$C(CH$_3$)$_3$,
b) —CN,
c) —COX$^2$—C$_1$–C$_6$ alkyl, or
d) —COOH;
wherein X$^2$ is
a) —O—, or
b) —NH; and
wherein het is
a) 1,3-benzodioxol-4-yl,
b) 1,3-benzodioxol-5-yl, or
c) indolyl.

"Pharmaceutically acceptable salts" refers to those salts which possess the biological effectiveness and properties of the parent compound and which are not biologically or otherwise undesirable.

"Noide" refers to the oxidized form of the nitrogen in the ring of the 8-hydroxy-quinoline compounds of the present invention. The preparation of such compounds is well known to one of ordinary skill in organic chemistry, including methods such as oxidation with metachloro-peroxybenzoic acid.

"Electron-withdrawing group" means any substituent on the ring which tends to draw electron density from the ring. Examples of such groups include halogen, nitro, cyano, carboxylic acids, carboxylic esters, sulfoxides, sulfones, sulfonamides, ketones and aldehydes.

"Halogen" means fluroine, chlorine, or bromine.

"Het" is a 5-, 6- or 7-membered saturated or unsaturated ring containing from one (1) to three (3) heteroatoms selected from the group consisting of nitrogen, oxygen and sulfur; and including any bicyclic group in which any of the above heterocyclic rings is fused to a benzene ring or another heterocycle; and the ring may be connected through a carbon or secondary nitrogen in the ring or an exocyclic nitrogen; and if chemically feasible, the nitrogen and sulfur atoms may be in the oxidized forms; and if chemically feasible, the nitrogen atom may be in the protected form; and substituted or unsubstituted. Examples of "het" include the following: thiadiazolyl, thiazolyl, benzothiazolyl, pyridinyl (or pyridyl), morpholinyl, imidazolyl, indolyl, and piperazinyl.

The compounds of the present invention are named according to the IUPAC or CAS nomenclature system.

The carbon atom content of various hydrocarbon-containing moieties is indicated by a prefix designating the minimum and maximum number of carbon atoms in the moiety, i.e., the prefix C$_i$–C$_j$ indicates a moiety of the integer "i" to the integer "j" carbon atoms, inclusive. Thus, for example, (C$_1$–C$_3$)alkyl refers to alkyl of one to three carbon atoms, inclusive, or methyl, ethyl, propyl and isopropyl, straight and branched forms thereof.

Throughout this application, abbreviations which are well known to one of ordinary skill in the art may be used, such as "Ph" for phenyl, "Me" for methyl, and "Et" for ethyl.

The following Charts A–I describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts or by procedures analogous thereto, which would be well known to one of ordinary skill in organic chemistry. All of the variables used in the charts are as defined below or as in the claims.

CHART A

The preparation of the starting materials, 8-hydroxyquinoline-7-carboxylic acids, is accomplished in low to moderate yields by the carboxylation of 8-hydroxyquinolines, which are either commercially available or which are prepared by literature methods: G. S. Bawa, K. E. Hartman, and M. N. Jouillie, Journal of Medicinal Chemistry, Vol.16, No. 2, pages 134–138 (1973); L. C. March, W. A. Romanchick, G. S. Bawa, and M. M. Jouillie, Journal of Medicinal Chemistry, Vol. 16, No. 4, pages 337–342 (1973). The compound of formula A-1 is reacted with $K_2CO_3$ (3 eq.), $CO_2$(800 p.s.i) at 170° for 7 days, to yield the compound of formula A-2. J. Hannah et al., Journal of Medicinal Chemistry, Vol. 21, No. 11, pages 1093–1100 (1978). ($R^1$ and $R^2$ in formula A-1 are the same as $R^1$ and $R^2$ in formula A-2.)

The compound of formula A-2 wherein $R^1$ is —H and $R^2$ is —H is the intermediate compound of Preparation 1 below. The compound of formula A-2 wherein $R^1$ is —F and $R^2$ is —H is the intermediate compound of Preparation 4 below. The compound of formula A-2 wherein $R^1$ is —Cl and $R^2$ is —H is the intermediate compound of Preparation 3 below. The compound of formula A-2 wherein $R^1$ is —H and $R^2$ is —CH$_3$ is the intermediate compound of Preparation 5 below.

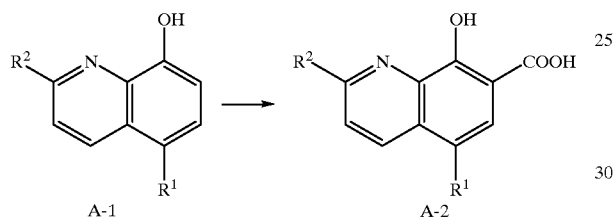

A-1   A-2

CHART B

Bromination of 8-hydroxyquinoline-7-carboxylic acid of formula B-1 with one equivalent of bromine (HOAc, reflux, 1 hr) yields 5-bromo-8-hydroxy-7-quinolinecarboxylic acid of formula B-2 in quantitative yield, which is prepared in Preparation 2 below. R. Schmitt and F. Engelmann, Chem. Ber., 20; 1887; 2694.

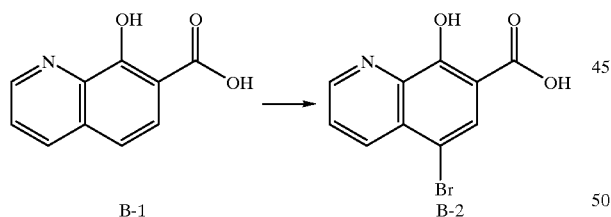

B-1   B-2

CHART C

The acid of formula C-1, prepared as described in Charts A and B above, is condensed with the amine of formula C-2, which is commercially available (e.g, p-chloro or p-nitrobenzylamine), under appropriate conditions (EDC is used as the coupling agent, HOBt, DMF, rt, 18 hr) to yield the compound of formula C-3. ($R^1$ and $R^2$ in formula C-1 are the same as $R^1$ and $R^2$ in formula C-3. X in formula C-2 is the same as X in formula C-3.) The compound of formula C-3 wherein $R^1$ is —Br, $R^2$ is —H and X is —Cl is the final compound of Example 9 below. The compound of formula C-3 wherein $R^3$ is —H, $R^2$ is —CH$_3$ and X is —Cl is the final compound of Example 10 below. The compound of formula C-3 wherein $R^1$ is —Cl, $R^2$ is —H and X is —Cl is the final compound of Example 11 below. The compound of formula C-3 wherein $R^1$ is —H, $R^2$ is —H and X is —NO$_2$ is the final compound of Example 12 below. The compound of formula C-3 wherein $R^1$ is —F, $R^2$ is —H and X is —Cl is the final compound of Example 16 below. Chart C is the preferred coupling method for benzylamines.

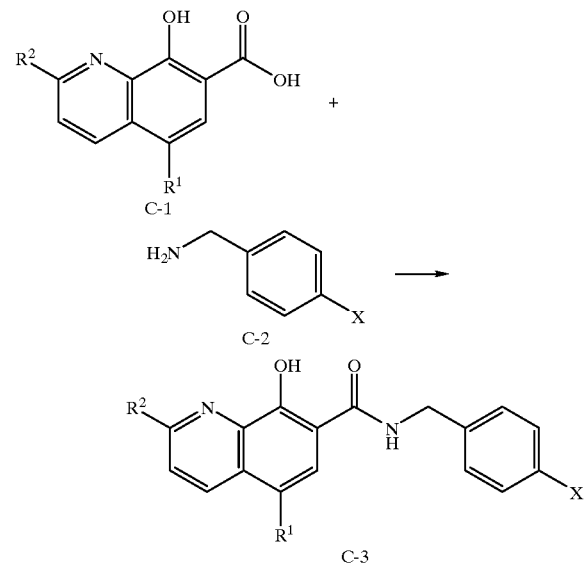

CHART D

Under the same conditions as in Chart C above (i.e., EDC, HOBt, DMF, rt, 7 days), the acid of formula D-1 is condensed with the heterocyclic amine of formula D-2 to give the final compound of formula D-3, which is prepared in Example 8 below.

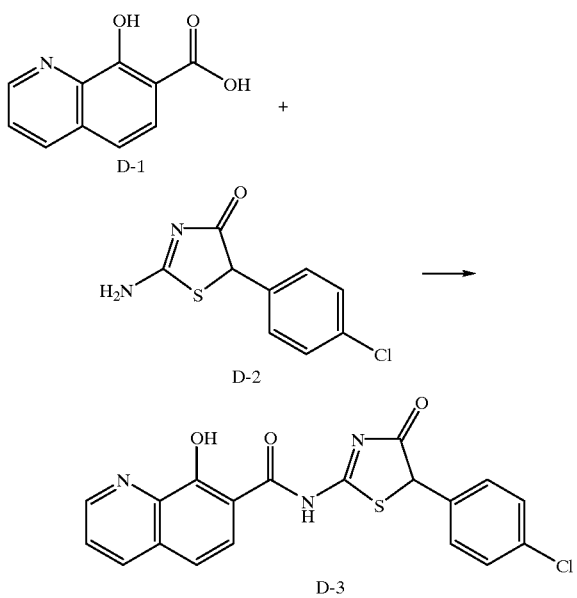

CHART E

Chart E discloses a more efficient method of coupling the 8-hydroxyquinoline-7-carboxylic acids with anilines and heterocyclic amines utilizing PCl$_3$ as the condensing agent.

H. Singh, A. K. Singh, S. Sharma, R. N. Iyer, J. Med. Chem., 20:826 (1977); H. Singh, S. Sharma, R. N. Iyer, Ind. J. Chem., 15B:73 (1977); S. K. Dubey, A. K. Singh, H. Singh, S. Sharma, R. N. Iyer, J. Med. Chem., 37:999 (1994). The compound of formula E-1 is coupled with the compound of formula E-2 (using $PCl_3$, xylenes, at reflux, for 18 hr) to yield the compound of formula E-3 wherein X is —H (which is the final compound of Example 5 below) or X is —Br (which is the final compound of Example 6 below). (X in formula E-1 is the same as X in formula E-3.) Chart E is the preferred coupling method for heterocyclic amines.

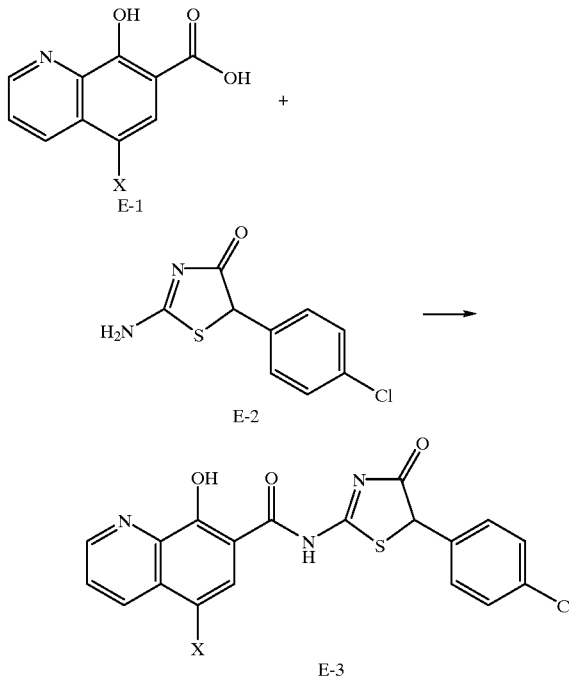

CHART F

The required thiazolones of formula F-3 are prepared in three steps from commercially available acids of formula F-1 as follows: the compound of formula F-1 is first treated with $P_{(red)}$ in Br and is then treated with AcCl in methanol to yield the compound of formula F-2. This compound is then reacted with thiourea at ethanol at reflux to yield the compound of formula F-3. T. Sohda et al., Chem. Pharm. Bull., Vol. 30, No. 10, pages 3601–3616 (1982).

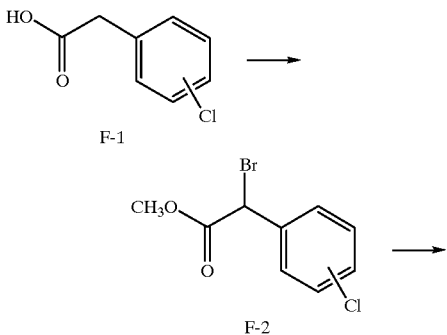

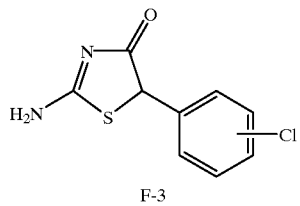

CHART G

Anilines are also coupled in low to moderate yields under the conditions of Chart E. Thus, the compound of formula G-1 is coupled with the compound of formula G-2 (using $PCl_3$, xylenes, at reflux, for 18 hours) to yield the compound of formula G-3. ($R^1$ in formula G-1 is the same as $R^1$ in formula G-3.) The compound of formula C-3 wherein $R^1$ is —H is the final compound of Example 3 below; the compound of formula G-3 wherein $R^1$ is —Br is the final compound of Example 4 below; and the compound of formula G-3 wherein $R^1$ is —Cl is the final compound of Example 15 below. The coupling conditions of this reaction are preferred when anilines are used.

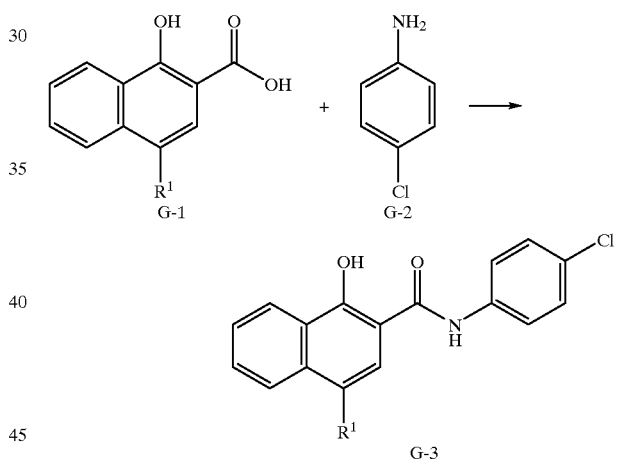

CHART H

Chart H discloses another method of coupling which is used in the condensation of benzylamines, although the yields are lower than found for the EDC couplings. The compound of formula H-1 is coupled with the compound of formula H-2 (using $PCl_3$, xylenes, at reflux for 18 hr) to yield the compound of formula H-3, which is the final compound of Example 1 below.

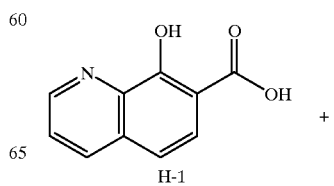

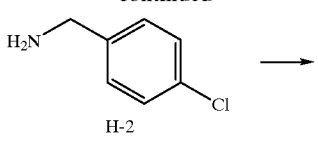
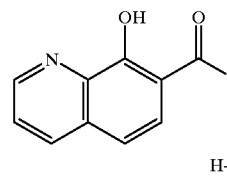

CHART I

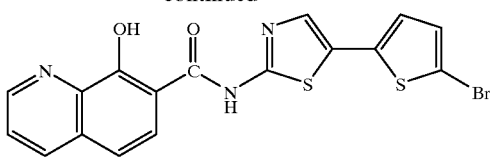
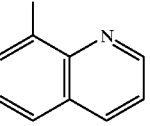
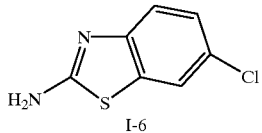
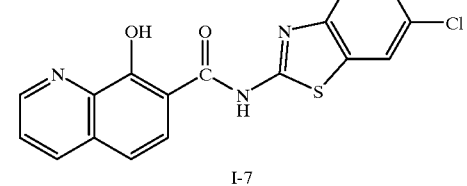
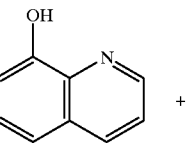
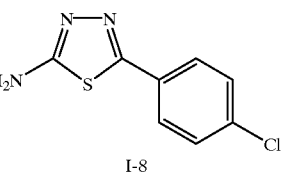
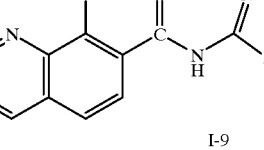

Other heterocyclic amines are also condensed with quinoline carboxylic acids under these conditions. The quinoline carboxylic acid of formula I-1 (which was prepared in Chart A above) is coupled with the appropriate heterocyclic amine of formula I-2, I-4, I-6 or I-8 (using $PCl_3$, xylenes, at reflux, for 18 hours) to yield the compound of formula I-3, I-5, I-7 or I-9, respectively. The compound of formula I-3 is the final compound of Example 2 below; the compound of formula I-5 is the final compound of Example 7 below; the compound of formula I-7 is the compound of Example 13 below which is useful as an intermediate; and the compound of formula I-9 is the final compound of Example 14 below.

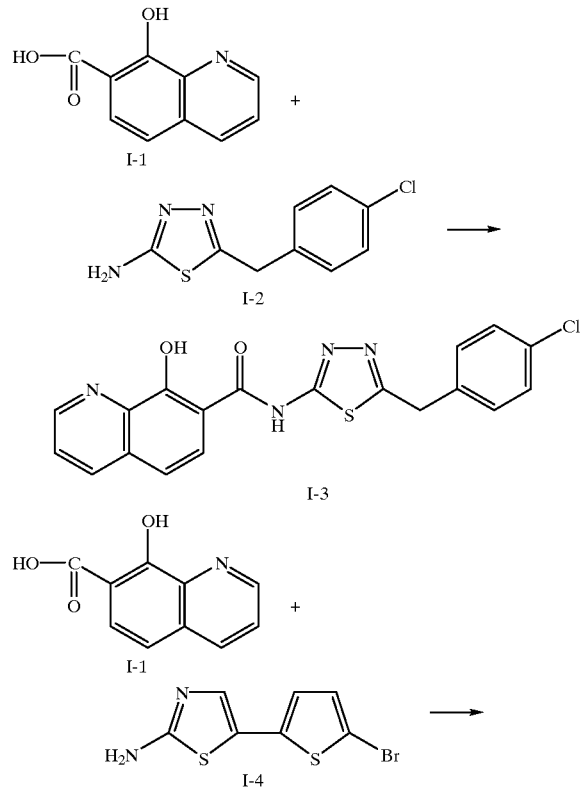

CHART J

The preparation of the starting materials is accomplished by O-methylation of commercially-available 5,7-dihalo-8-hydroxyquinolines according to the procedure of R. A. W. Johnstone and M. E. Rose in Tetrahedron, vol. 35, page 21169 (1979). The compound of formula J-1 is treated with t-butyllithium or n-butyllithium at low temperature in ether/toluene, then exposed to sulfur dioxide gas to prepare the compound of formula J-2. Conversion of the compound of formula J-2 to the sulfonyl chloride of formula J-3 is accomplished by treatment with N-chlorosuccinimide ($CH_4Cl_2$, 3 hr). The sulfonamide of formula J-4 is then prepared by reaction of the sulfonyl chloride of formula J-3 with 1 equivalent of a primary amine of the formula $R^2NH_2$ and 2 equivalents of pyridine in $CH_2Cl_2$ (15 hr). Finally, the compound of formula J-5 is prepared using either excess pyridinium hydrochloride (220° C., 10 min) or excess boron tribromide ($CH_2Cl_2$, 1.5 hr).

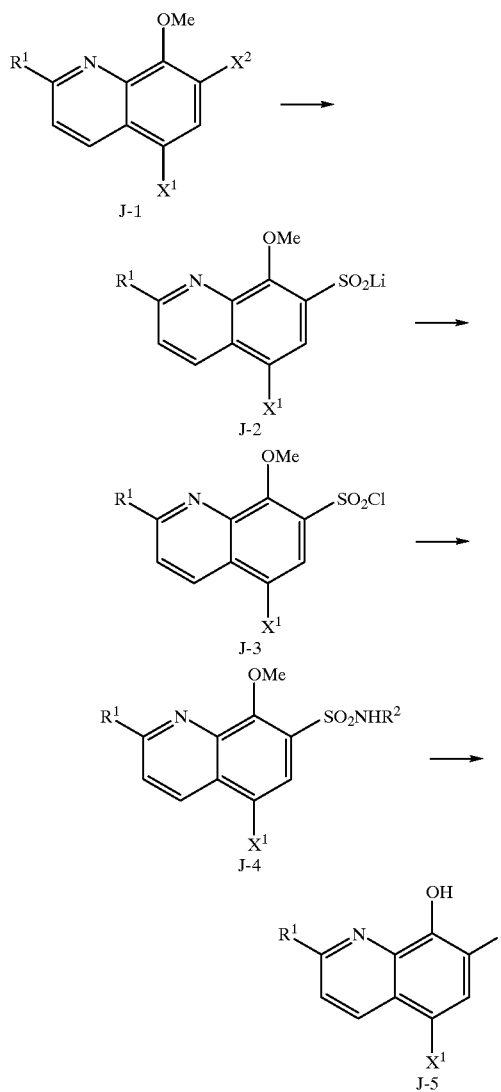

CHART K

Compounds of the structure K-3 are prepared from commercially-available 5,7-dihalo-8-hydroxyquolines (K-1) in two steps. Formation of the silylether intermediates K-2 is accomplished by reaction of the 8-hydroxyquinolines K-1 with chlorotrialkylsilanes in the presence of imidazole and DMF at room temperature for 18–20 hours. The intermediates are then treated with t-butyllithium or n-butyllithium at low temperature in THF to give the compound of formula K-3.

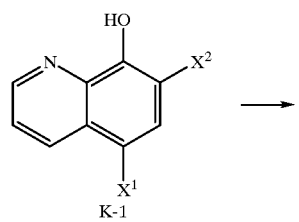

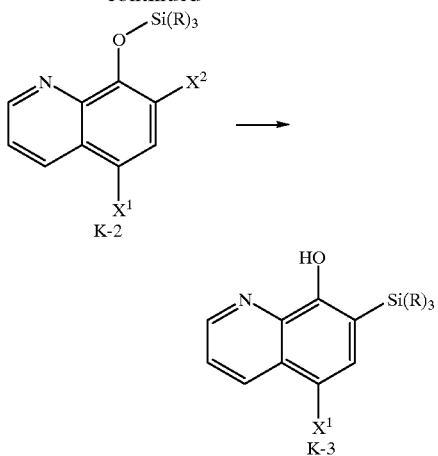

CHART L

To a mixture of o-anidisine of L-1 and ethyl-4,4,4-trifluoroacetoacetate of L-2 is added 6N HCl. The resulting enamine is heated in diphenylether at 250° C. to produce 4-hydroxy-8-methoxy-2-trifluoromethylquioline of L-3.

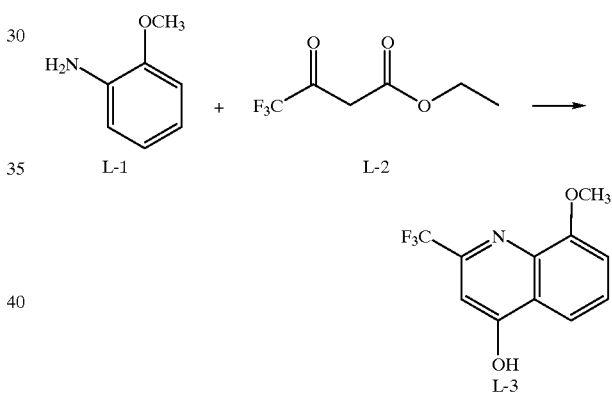

CHART M

The compound of M-1 is chlorinated with phosphorus oxychloride in $CH_2Cl_2$/DMF at room temperature. The resulting chloride of M-2 is reductively cleaved by hydrogenation in EtOH, $Et_3N$ to give M-3. Methyl ether deprotection with pyridine hydrochloride at 220° C. gives 2-trifluoromethyl-8-hydroxyquinoline of M-4. This material is carboxylated to M-5 under Kolbe-Schmidt conditions. Standard amide couplings gives the desired products of M-6.

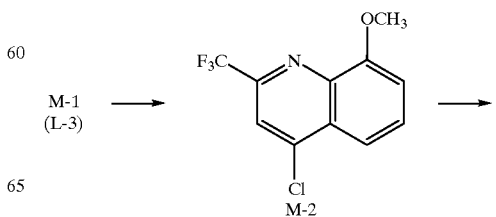

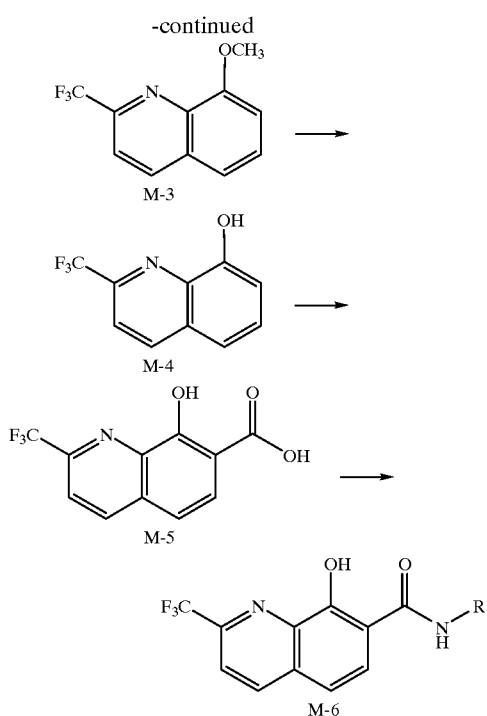

CHART N

Alternatively, pyridine hydrochloride deprotection of N-1 gives the 4,8-dihydroxyquinoline of N-2, which again is carboxylated under Kolbe-Schmidt conditions to give N-3. Standard amide couplings give the desired products of N-4.

CHART O

Aryl aldehydes of O-2 are condensed with 8-hydroxyquinaldine of O-1 at 180° C. to form the 2-styryl-8-hydroxyquinolines of O-3. These are carboxylated under Kolbe-Schmidt conditions to give O-4. Standard couplings of the resulting acid with amines gives the desired amides O-5.

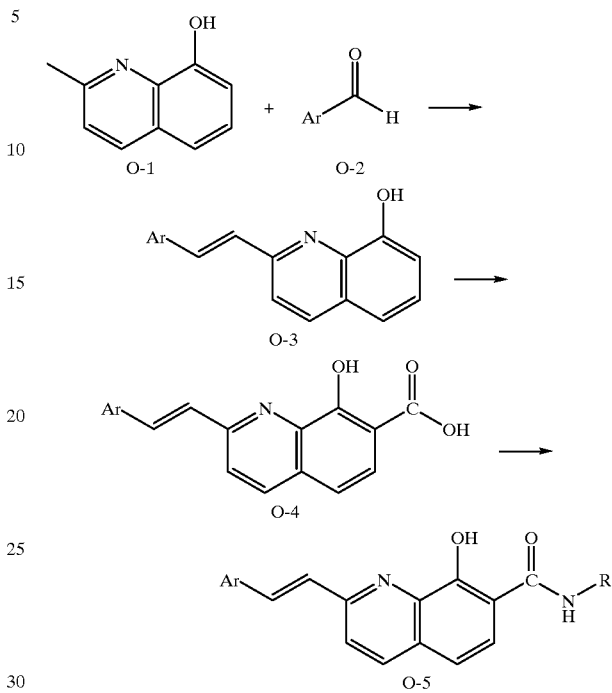

CHART P

The preparation of the starting material of formula P-1 is accomplished by chlorination of commercially-available 8-hydroxyquinaldine according to the procedure described in DE 1770065. The compound of formula P-1 is then treated with neat flourosulfonic acid at 120° C. to form the compound of formula P-2. Finally, the sulfonamides of formula P-3 are prepared by heating to 140° C. a mixture of 1 eq of the sulfonyl flouride of formula P-2, 2 eq of the primary amine of formula $RNH_2$ and 3 eq of N,N-diisopropylethylamine in chlorobenzene.

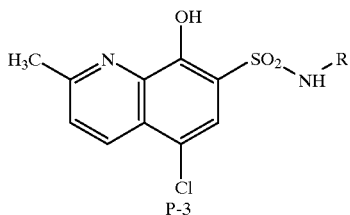

CHART Q

The preparation of the starting material of formula Q-1 is accomplished by O-methylation of commercially-available 5,7-dibromo-2-methyl-8-quinolinol according to the procedure of R. A. W. Johnstone and M. E. Rose in Tetrahedron, vol. 35, page 21169 (1979). The styrene derivative of formula Q-2 is obtained by heating the 2-methylquinoline of formula Q-1 with benzaldehyde for 18 h. The intermediate of formula Q-2 (which corresponds to J-1, $R^1$=CH=CHPh, $X^1$=$X^2$=Br) is then advanced in four steps to the sulfonamides of formula Q-3 (which corresponds to J-5, $R^1$=CH=CHPh, $X^1$=Cl; $R^2$=R) following the route previously described in Chart J.

N-chlorosuccinimide in methylene chloride at room temperature for 2 h. The sulfonamide of formula R-5 is then prepared by reaction of the sulfonyl chloride of formula R4 with 2-(4-aminophenyl)ethylamine and pyridine in methylene chloride. Finally, the compound of formula R-6 is prepared by reaction of the compound of formula R-5 with excess sulfonyl chloride of the formula $RSO_2Cl$ in pyridine.

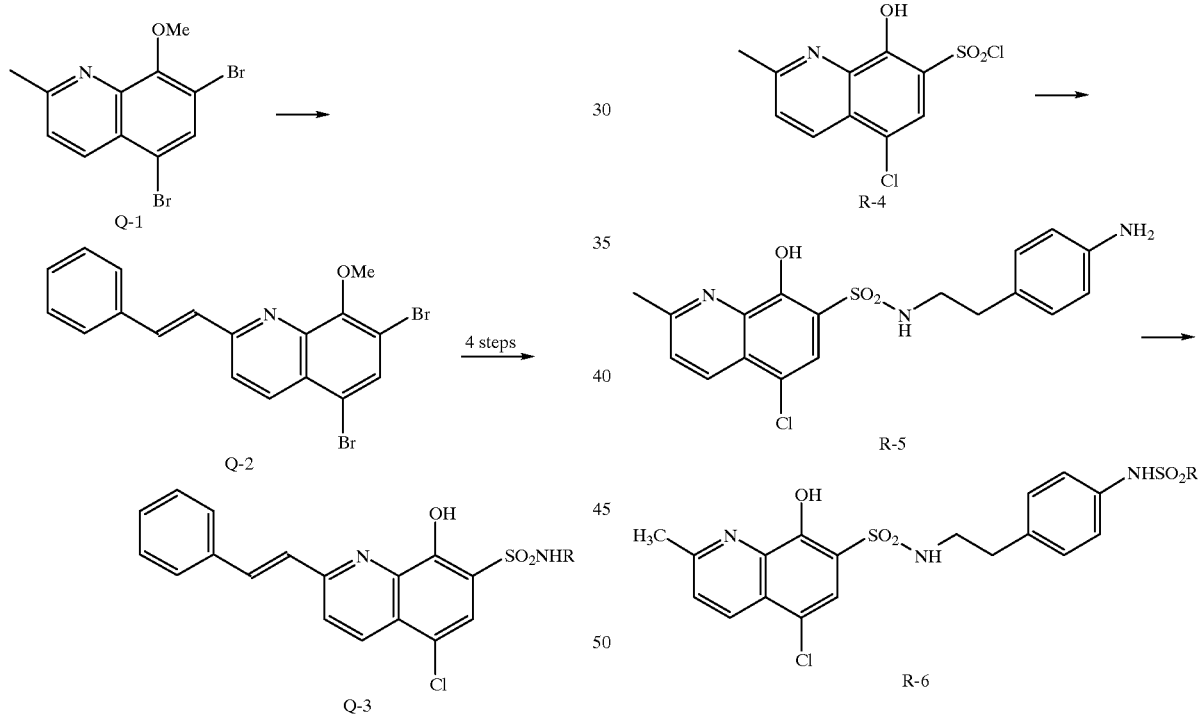

CHART R

The preparation of the starting material of formula R-1 is accomplished by chlorination of commercially-available 8-hydroxyquinaldine according to the procedure described in DE 1770065. The 7-iodo derivative of formula R-2 is their prepared by reaction of the quinoline of formula R-1 with iodine monochloride in methanol. The compound of formula R-2 is treated successively with methyl magnesium bromide and n-butyllithium at −78° C. in THF, then exposed to sulfur dioxide gas to prepare the compound of formula R-3. Conversion of the compound of formula R-3 to the sulfonyl chloride of formula R-4 is accomplished by treatment with

CHART S

The commercially-available 5-flouro-8-hydroxyquinoline of formula S-1 is treated with neat chlorosulfonic acid at 90–105° C. to form the sulfonyl chloride of formula S-2. The sulfonamide of formula S-3 is then prepared by reaction of 1 eq of the sulfonyl chloride of formula S-2 with 3 eq of benzylamine in THF.

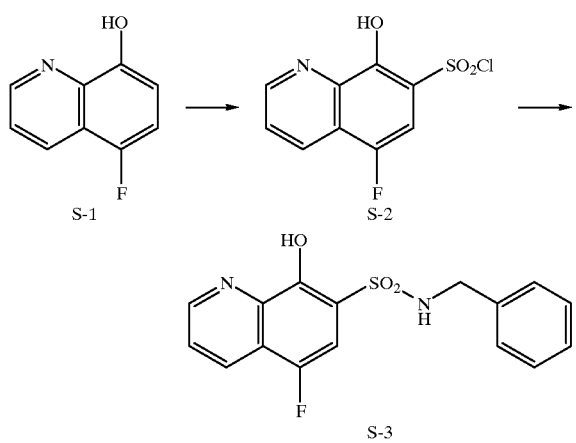

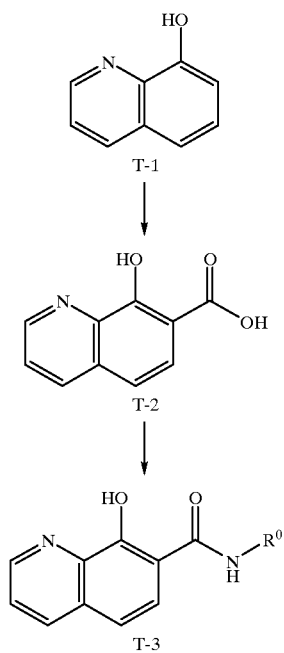

CHART T

Commercially available 8-hydroxyquinoline (T-1) is converted to the 7-carboxylic acid (T-2) by heating at 175° C. in the presence of potassium carbonate under 800 psi carbon dioxide gas for 7 days. The acid is then condensed with various aliphatic amines after activation with either 1,1'-carbonyldiimidazole, or alternatively 1-(3-dimethylaminopropyl)-3-ethylcarbodiimide and 1-hydroxybenzotriazole to afford the desired amides of the formula T-3. The above amides are prepared either as discrete analogues or as part of a parallel synthesis block.

CHART U

Anhydride U-1 is prepared from 8-hydroxy-7-quinoline carboxylic acid using 2,2,2-trichloroethyl chloroformate and diisopropylethylamine. The purity of the starting materials is crucial for this reaction to succeed; particularly, any trace of any metalic cations but alkali cations, or Lewis acids, has to be avoided, as they lead to an inhibition of the reaction as well as to decarboxylation of anhydride U-1, probably through a chelation of both starting material and product; during the whole course of the reaction, strictly basic conditions have to be maintained, acidic conditions favoring a decarboxylation of the product as well. Ester U-3 is prepared from 8-hydroxy-7-quinoline carboxylic acid as well, the 8-hydroxy substituent being first protected to ester U-2 according to a literature procedure (German Patent No. 540842, Dec. 10, 1931) and subsequent activation of the 7-carboxylic acid as its fluoride, using cyanuric fluoride and diisopropylethylamine.

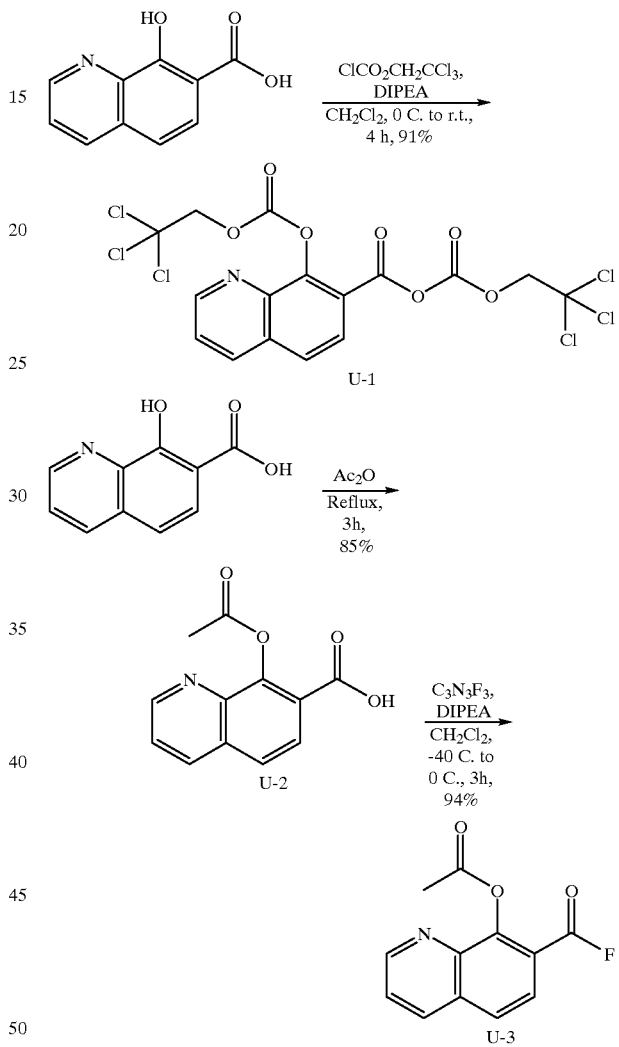

CHART V

N-Aryl-8-hydroxy-7-quinolinecarboxamides V-4-14 are prepared as single compounds from anhydride U-1 (Chart U) following GP II described below. Both amide coupling and deprotection of the 8-hydroxy substituent can be realized in a single step with primary amines, provided some traces of water are present in the reaction mixture. (No water needs to be added; water coming from glassware and used solvents is enough to ensure a complete deprotectino, at least on small scale.) Probably, the amide function of the still protected intermediate is nucleophic enough to attack the carbonate at the 7-position via a six-membered ring, subsequent hydrolysis, catalyzed by pyridinium chloride, leads to the desired amides. Similarly, N-Aryl-8-hydroxy-7- quinolinecarboxamides V-21-36 are prepared by parallel synthesis from anhydride U-1, following GP III described below. N-Aryl-8-hydroxy-7-quinolinecarboxamides V-15-20 are prepared as single compounds following GP IV described below from ester U-3 (Chart U). After the coupling step is achieved (6 h to 5 days depending on the amine), methanol is added, which leads to the deprotection of the 8-hydroxy substituent within 6 to 24 h. N-aryl-8-hydroxyquinoline-7-carboxamidies V-17-20 as well as V-37-94 are also prepared by parallel synthesis from ester U-3, following GP V described below.

When parallel synthesis is used, some impurities appear occasionally besides the desired product, mainly the carbamate resulting from an attack of the amine at the carbonate positions when anhydride U-1 is involved, or methyl 8-hydroxy-7-quinoline carboxylate after methanolic treatment of the reaction mite from ester

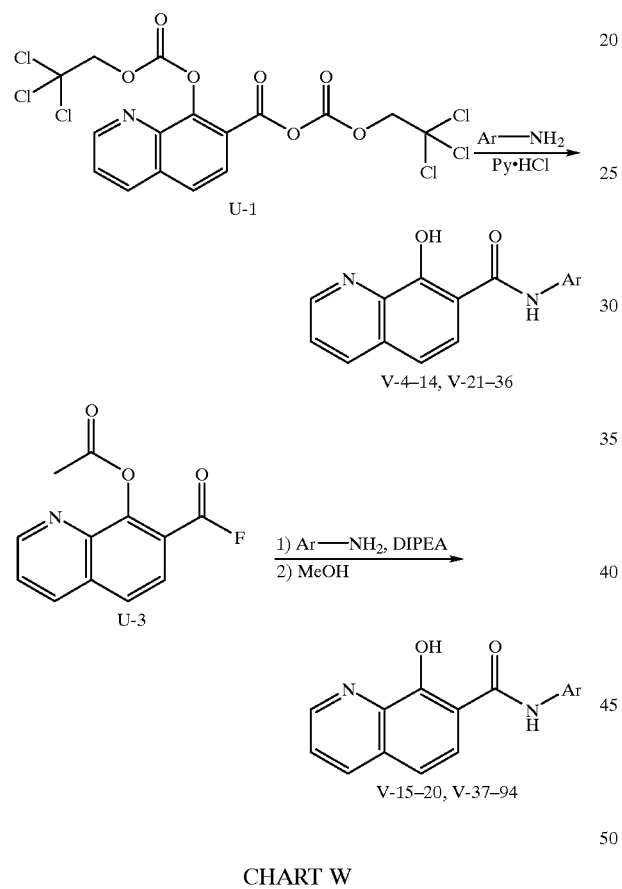

CHART W

The synthesis of 2-amino5-alkyl-1,3,4-thiadiazoles W-95-98, W-100-102, W-105, W-108 and X-109-117, which are to be coupled with the activated 8-hydroxy-7-quinoline carboxylic acid derivatives U-1 or U-3 (refer to Chart U) to afford the corresponding 8-hydroxy-N-(1,3,4-thiadiazol-2-yl)-7-quinolinecarboxamides X-118-136, required one to four steps. 2-Amino5-bromo-1,3,4-thiadiazole W-95 is prepared through bromination of commercially available 2-amino-1,3,4-thiadiazole. Thiadiazole derivatives W-96-98 are prepared through direct bromide displacement of thiadiazole W-95 with the corresponding amines. Using the same strategy, nitrile W-100 is prepared from aminonitrile W-99, itself prepared from piperonal through a Strecker synthesis. Displacement of the bromide of thiadiazole W-95 with L- and D-phenylalanine methyl esters leads to esters W-101 and W-102, though in low yields. Known literature procedures are used to prepare amino acids W-103 and W-106, of which acid groups are converted into the corresponding tert-butyl esters (compounds W-104 and W-107) by standard procedures; subsequent bromide displacement as last step affords esters W-105 and W-108.

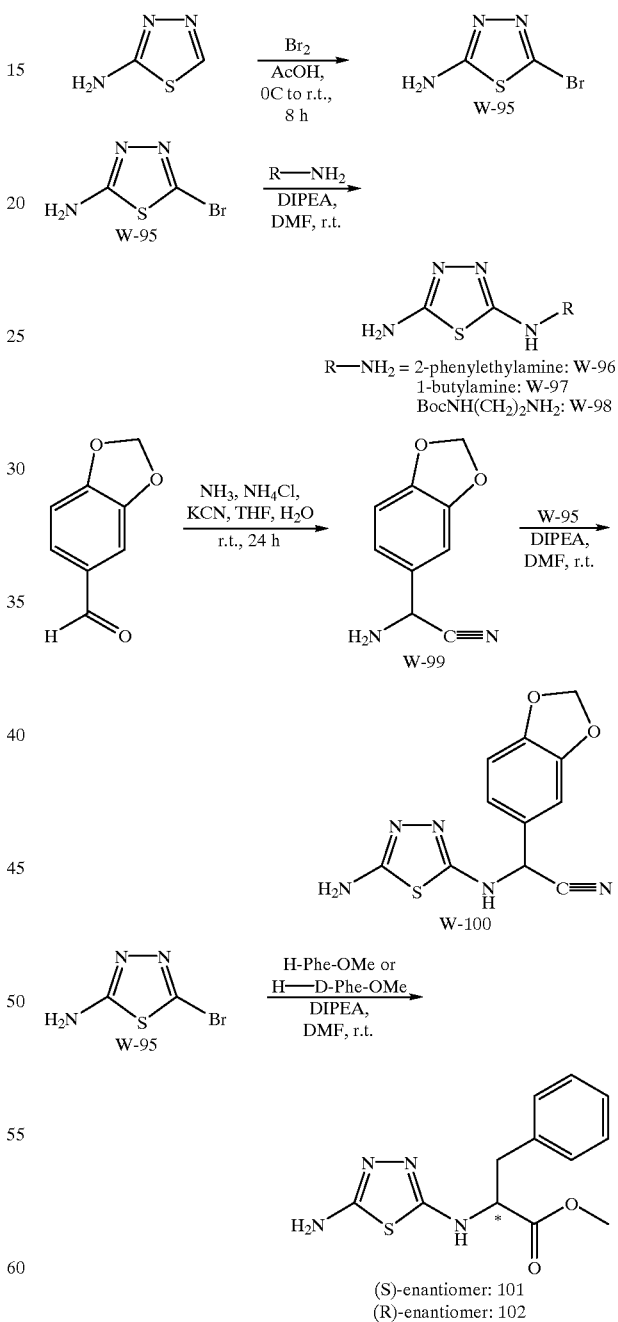

-continued

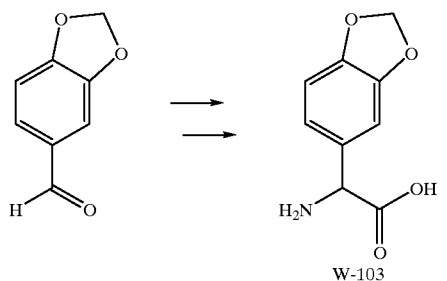

W-103

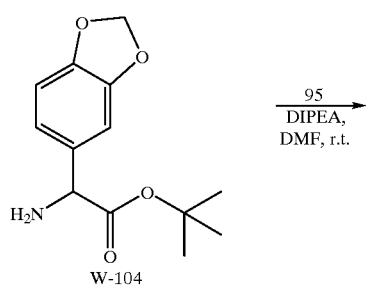

W-104

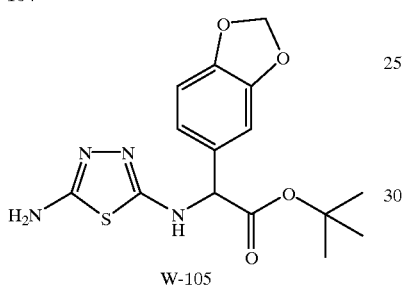

W-105

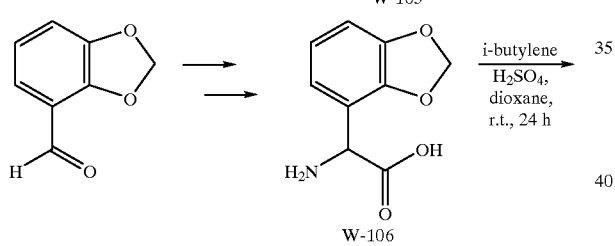

W-106

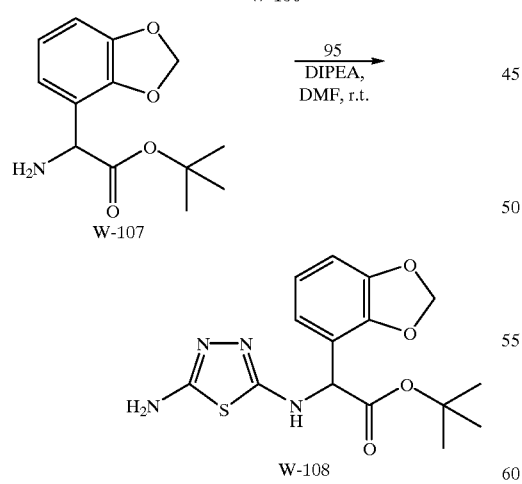

W-107

W-108

CHART X

Bromide displacement with commercially available piperonyl amine leads to thiadiazole W-109; similarly, using some amino acid tert-butyl esters leads to esters X-110 to X-117.

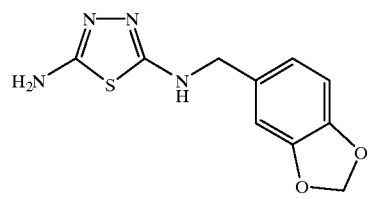

X-109

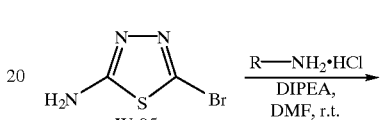

W-95

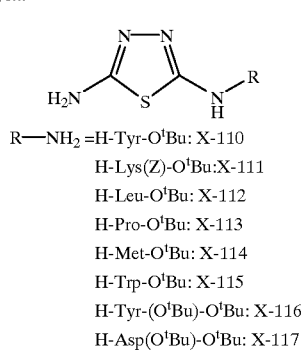

R—NH$_2$ = H-Tyr-O$^t$Bu: X-110
H-Lys(Z)-O$^t$Bu: X-111
H-Leu-O$^t$Bu: X-112
H-Pro-O$^t$Bu: X-113
H-Met-O$^t$Bu: X-114
H-Trp-O$^t$Bu: X-115
H-Tyr-(O$^t$Bu)-O$^t$Bu: X-116
H-Asp(O$^t$Bu)-O$^t$Bu: X-117

CHART Y

These thiadiazoles, as well as commercially available 2-amino-5-(trifluoromethyl)-1,3,4-thiadiazole, are then coupled using the same methodology as described for the amides V-4-20 from anhydride U-1 or ester U-3 to give amides Y-118-125 or y-126-136, respectively. Depending on the applied work-up procedure, these compounds are isolated as the free compounds, as the hydrochloride salt or as a hydrate.

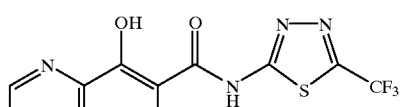

Y-118

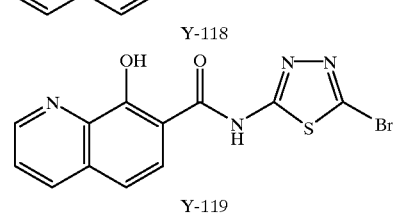

Y-119

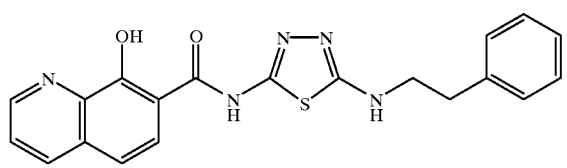
Y-120
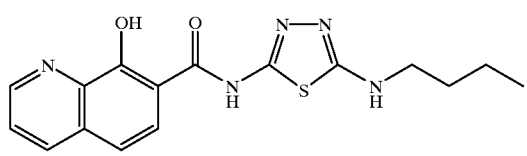
Y-121
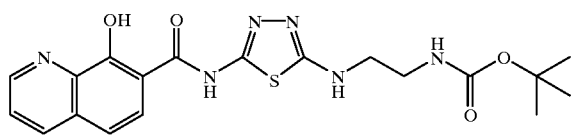
Y-122
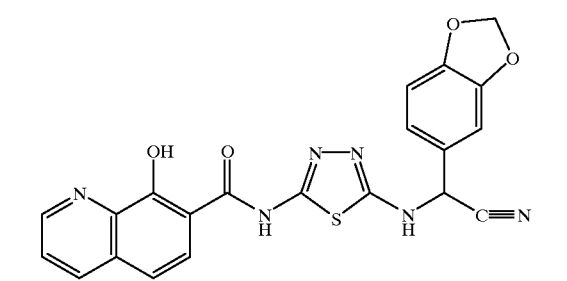
Y-123
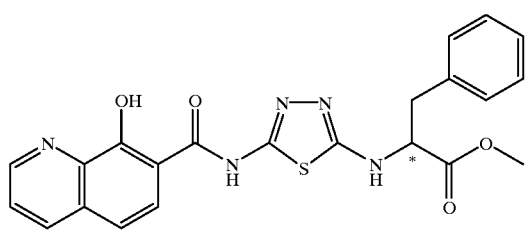
(S)-enantiomer: Y-124
(R)-enantiomer: Y-125
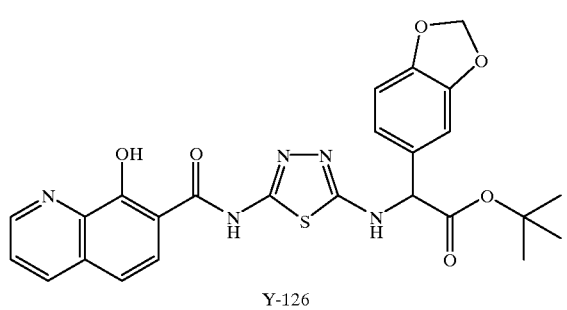
Y-126
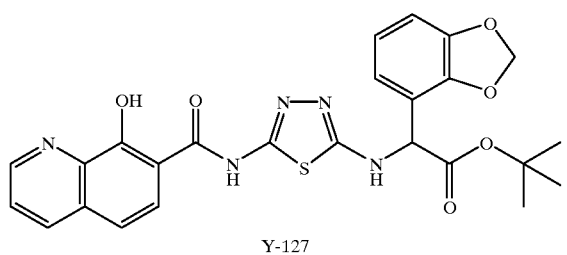
Y-127
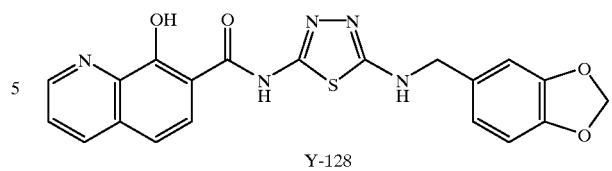
Y-128
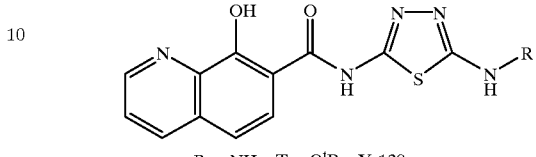
R—NH = Tyr-O$^t$Bu: Y-129
Lys(Z)-O$^t$Bu: Y-130
Leu-O$^t$Bu: Y-131
Pro-O$^t$Bu: Y-132
Met-O$^t$Bu: Y-133
Trp-O$^t$Bu: Y-134
Tyr(O$^t$Bu)-O$^t$Bu: Y-135
Asp(O$^t$Bu)-O$^t$Bu: Y-136
CHART Z
The tert-butyl esters are hydrolyzed in selected examples to yield acids Z137–139. These acids are isolated as their corresponding hydrotrifluoroacetates.
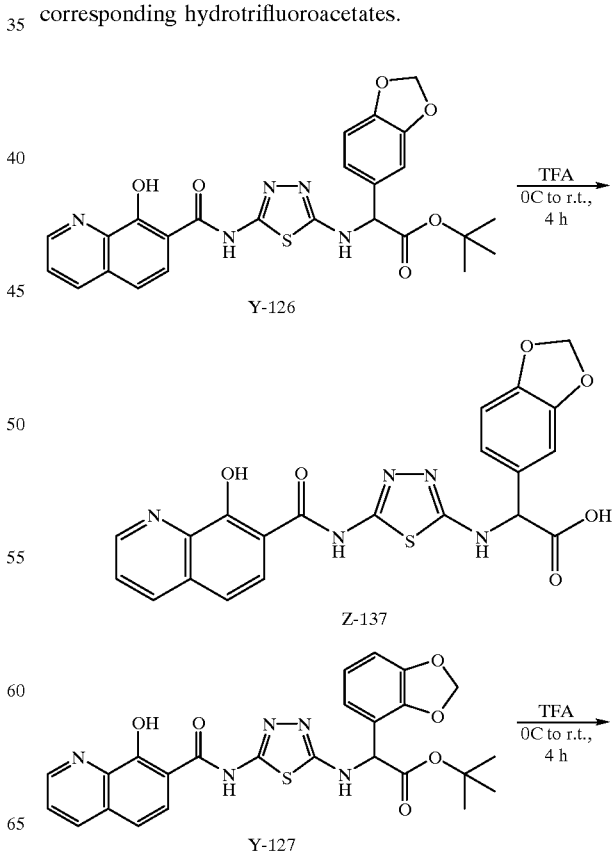
Y-126
Z-137
Y-127

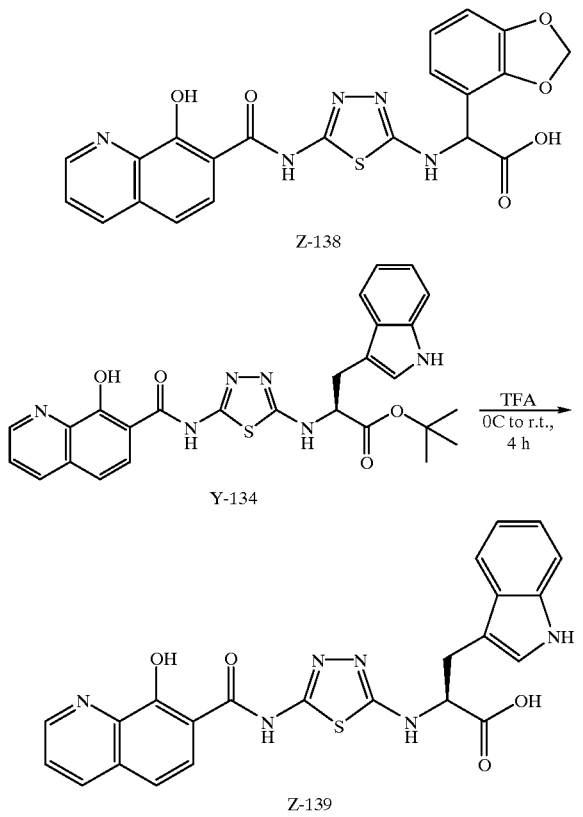

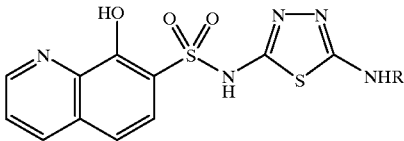

It will be apparent to those skilled in the art that the described synthetic procedures are merely representative in nature and that alternative synthetic processes are known to one of ordinary skill in organic chemistry.

The compounds of the present invention and pharmaceutically acceptable salts thereof are usefull as antiviral agents. Thus, these compounds are useful to combat viral infections in animals, including man. Specifically, these compounds have anti-viral activity against the herpes virus, cytomegalovirus (CMV). Many of these compounds are also active against other herpes viruses, such as the varicella zoster virus, the Epstein-Barr virus, the herpes simplex virus, and the human herpes virus type 8 (HHV-8).

Also, while many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The compounds of the present invention have shown activity in one or more of the assays described below. All of these assays are indicative of a compound's activity and thus of its use as an anti-viral agent.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM $MgCl_2$, 0.36 mg/ml BSA, and 90 nM $^3$H-dTTP. Assays are run with and without CHAPS, (3-[(3-Cholamidopropyl)-dimethylammonio]-1-propane-sulfonate), at a final concentration of 2 mM. HCMV is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. $H_2O$ bath and terminated via the addition of 40 µl/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten µl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and

CHART AA

N-(5-alkylamino-1,3,4-thiadiazol-2-yl)-8-hydroxy-7-quinolinesulfonamides are prepared from the corresponding thiadiazoles and 8-hydroxy-7-quinolinesulfonyl chloride AA-C, prepared in two steps from a 8-hydroxy-7-halogenoquinoline AA-A.

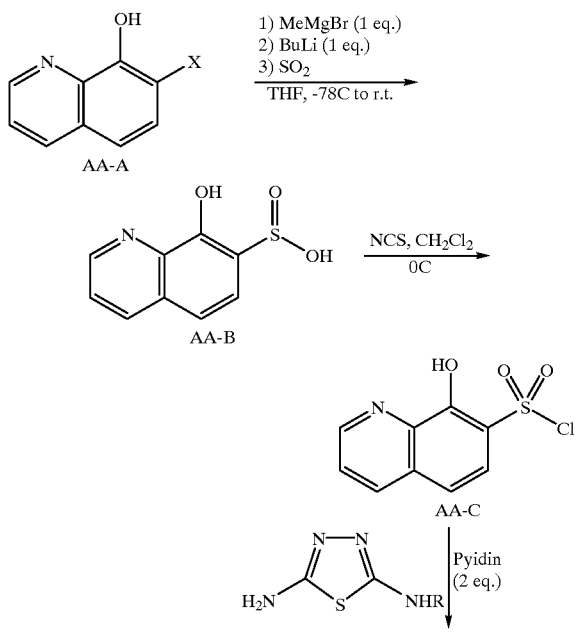

$IC_{50}$'s are calculated using computer software. Results of the testing of compounds of the present invention in this assay are shown in Tables 1, 2, 5, 9, 10, 11, 13 (except for the last compound which was tested under modified conditions) and 14 below.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of compounds of the present invention in this assay are shown in Tables 3, 6 and 7 below.

Compounds are tested for direct antiviral activity against HCMV using a cell culture based assay. An ELISA (enzyme linked immunosorbant assay) format is used as described in W. A. Tatarowicz, N. S. Lurain and K. D. Thompson, J. Virol. Meth., 35:207–215 (1991). Human foreskin fibroblast cells are infected with HCMV at a multiplicity of 0.025 plaque forming units per microtiter plate well for a period of 90 minutes. The virus inocula is removed and a suspension of test compound prepared in tissue culture media is added for a period of 4 days. The growth media is aspirated and replaced with 95% ethanol to allow fixation of virus infected cultures. The ethanol is removed and the wells are washed twice with saline. A solution of 2% dry fat milk, 1% bovine sera albumin prepared in saline is added to wells to allow for non-specific binding of protein material to plastic surfaces for 1 hr. Murine monoclonal antibody prepared in saline directed against the late (65 KD) matrix protein of HCMV is added to test wells for 1 hr. The wells are washed twice and antibody, conjugated with the enzyme horse radish peroxidase, with specificity against murine IgG is added to test wells for 1 hr. Test wells are washed three times with saline. A solution of o-phenylene diamine, a substrate for horse radish peroxidase is added for 15 minutes at which time enzymatic conversion occurs indicating reactivity of the enzyme with its substrate. This conversion is evident as a color reaction which was spectrophoretically monitored at 490 nm. The intensity of the color indirectly reflects the presence of antibody directed against the viral 65 KD matrix antigen. The presence of the viral matrix antigen reflects the amount of HCMV replication. Thus, test wells, in which little viral replication has occurred, would have little or no antibody binding and are present with low levels of color. Non-infected wells serve as the assay background control. Results of the testing of compounds of the present invention in this assay are shown in Tables 4, 7 and 12 below.

These compounds of the present invention are administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975), which is hereby incorporated by reference herein.

The compounds of the present invention are administered parenterally (for example, by intravenous, intraperitoneal or intramuscular injection), topically, orally, or rectally, depending on whether the preparation is used to treat internal or external viral infections.

For internal infections, the compositions are administered orally or parenterally at dose levels, calculated as the free base, of about 0.1 to 300 mg/kg, preferably 1.0 to 30 mg/kg of mammal body weight, and are used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to 10%, more preferably about 0.1 to 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The following compounds of the present invention are preferred:

N-[5-[(4-Chlorophenyl)methyl]-1,3,4-thiadiazol-2-yl-8-hydroxy-7-quinolinecarboxamide;

5-Bromo-N-(4-chlorophenyl)-8-hydroxy-7-quinolinecarboxamide;

5-Chloro-N-(4-chlorophenyl)-8-hydroxy-7-quinolinecarboxamide;

N-[(4-Chlorophenyl)methyl]-8-hydroxy-2-[2-(4-methoxyphenyl)ethenyl]-7-quinolinecarboxamide;

8-Hydroxy-N-(2-hydroxy-2-phenylethyl)-2-(2-phenylethenyl)-7-quinolinecarboxamide;

N-[(4-Chlorophenyl)methyl]-8-hydroxy-2-(2-phenylethenyl)-7-quinolinecarboxamide;

8-Hydroxy-2-(2-phenylethenyl)-N-[2-(phenylthio)ethyl]-7-quinolinecarboxamide;

8-Hydroxy-N-(2-hydroxy-2-phenylethyl)-2-[2-(4-methoxyphenyl)ethenyl]-7-quinolinecarboxamide;

N-[(4-Chlorophenyl)methyl]-2-[2-(2-furyl)ethenyl]-8-hydroxy-7-quinolinecarboxamide;

5-chloro-8-hydroxy-2-methyl-N-(3-phenylpropyl)-7-quinolinecarboxamide;

5-chloro-8-hydroxy-2-methyl-N-[(2-phenylthio)ethyl]-7-quinolinecarboxamide;

8-hydroxy-N-[5-[4-[(1-methylethyl)phenylsulfonyl]amino]pentyl]-7-quinolinecarboxamide;

8-hydroxy-N-(cyanomethyl)-7-quinolinecarboxamide;

8-hydroxy-N-(2-hydroxy-2-phenylethyl)-2-[2-(4-methoxyphenyl)ethyl]-7-quinolinecarboxamide;

N-(2,2-Diphenylethyl)-8-hydroxy-7-quinolinecarboxamide;

N-(3,3-Diphenylpropyl)-8-hydroxy-7-quinolinecarboxamide;

8-Hydroxy-N-(cis-myrtanyl)-7-quinolinecarboxamide;

8-Hydroxy-N-(diphenylmethyl)-7-quinolinecarboxamide;

8-Hydroxy-N-(2-octyl)-7-quinolinecarboxamide;

N-[2-((1R,2S)-1,2-Diphenyl-1-hydroxy)ethyl]-8-hydroxy-7-quinolinecarboxamide;

8-Hydroxy-N-nonyl-7-quinolinecarboxamide;

N-(4-tert-Butylcyclohexyl)-8-hydroxy-7-quinolinecarboxamide;

R-8-Hydroxy-N-[1-(1-naphthyl)ethyl]-7-quinolinecarboxamide;

S-N-[1-(4-Bromophenyl)ethyl]-8-hydroxy-7-quinolinecarboxamide;

N-[2-((1S,2R)-1,2-Diphenyl-1-hydroxy)ethyl]-8-hydroxy-7-quinolinecarboxamide;

S-8-Hydroxy-N-[1-(1-naphthyl)ethyl]-7-quinolinecarboxamide;
N-[(2-Chloro-6-phenoxy-phenyl)methyl]-8-hydroxy-7-quinolinecarboxamide;
S-8-Hydroxy-N-[2-(1-hydroxy-3-[4-hydroxyphenyl])propyl]-7-quinolinecarboxamide;
8-Hydroxy-N-undecyl-7-quinolinecarboxamide;
8-Hydroxy-N-(2-methylcyclohexyl)-7-quinolinecarboxamide;
N-[1-(2-Ethyl)hexyl]-8-hydroxy-7-quiolinecarboxamide;
8-Hydroxy-N-(1-naphthalenylmethyl)-7-quinolinecarboxamide;
8-Hydroxy-N-[2-(2-[4-phenoxy]phenyl)ethyl]-7-quiolinecarboxamide;
R-N-[1-(4-Bromophenyl)ethyl]-8-hydroxy-7-quinolinecarboxamide;
S-O-Benzyl-N-[7-(7-Carboxy-8-hydroxy)quinolyl]-tyrosine, methyl ester;
N-[2-(4-Bromophenyl)ethyl]-8-hydroxy-7-quinolinecarboxamide;
N-(4-Cyanophenyl)-8-hydroxy-7-quinolinecarboxamide monohydrochloride;
N-(3-Chlorophenyl)-8-hydroxy-7-quinolinecarboxamide monohydrochloride;
N-Fluoren-2-yl-8-hydroxy-7-quinolinecarboxamide monohydrochloride;
8-Hydroxy-N-{4-[(indazo-6-ylamino)sulfonyl]phenyl}-7-quinolinecarboxamide monohydrochloride;
N-(3-Benzoxyphenyl)-8-hydroxy-7-quinolinecarboxamide monohydrochloride;
N-(4-Benzoxyphenyl)-8-hydroxy-7-quinolinecarboxamide monohydrochloride;
8-Hydroxy-N-[4-(4-nitrophenoxy)phenyl]-7-quinolinecarboxamide monohydrochloride;
8-Hydroxy-N-naphth-1-yl-7-quinolinecarboxamide;
N-(2-Chloro-4-nitrophenyl)-8-hydroxy-7-quinolinecarboxamide;
N-Biphen-2-yl-8-hydroxy-7-quinolinecarboxamide;
N-(4-Chloro-2-methylphenyl)-8-hydroxy-7-quinolinecarboxamide;
8-Hydroxy-N-(4-propylphenyl)-7-quinolinecarboxamide;
8-Hydroxy-N-[4-(hydroxymethyl)phenyl]-7-quinolinecarboxamide;
8-Hydroxy-N-indazol-5-yl-7-quinolinecarboxamide;
8-Hydroxy-N-(5-iodo-2-methylphenyl)-7-quinolinecarboxamide;
8-Hydroxy-N-[5-(2-phenylethyl)amino-1,3,4-thiadiazol-2-yl]-7-quinolinecarboxamide monohydrochloride;
N-[5-(Butylamino)-1,3,4-thiadiazol-2-yl]-8-hydroxy-7-quinolinecarboxamide monohydrochloride;
5-Bromo-N-[(4-chlorophenyl)methyl]-8-hydroxy-7-quinolinecarboxamide;
5-Chloro-N-[(4-chlorophenyl)methyl]-8-hydroxy-7-quinolinecarboxamide;
N-Heptyl-8-hydroxy-2-[2-(4-methoxyphenyl)ethenyl]-7-quinolinecarboxamide;
N-Heptyl-8-hydroxy-2-(2-phenylethenyl)-7-quinolinecarboxamide;
8-Hydroxy-2-[2-(4-methoxyphenyl)ethenyl]-N-[2-(phenylthio)ethyl]-7-quinolinecarboxamide;
5-Chloro-N-[(4-chlorophenyl)methyl]-8-hydroxy-2-methyl-7-quinolinecarboxamide;
N-[(4-Chlorophenyl)methyl]-8-hydroxy-5-nitro-7-quinolinecarboxamide;
N-[5-[3-(4-Chlorophenyl)methyl]-4,5-dihydro-4-oxo-2-thiazolyl]-8-hydroxy-7-quinolinecarboxamide;
(E)-8-Hydroxy-2-(2-phenylethenyl)-N-(3-phenylpropyl)-7-quinolinecarboxamide;
N-{5-[(1,3-Benzodioxol-5-ylcyanomethyl)amino]-1,3,4-thiadiazol-2-yl}-8-hydroxy-7-quinolinecarboxamide monohydrochloride;
N-[5-({1,3-Benzodioxol-5-yl-[(tert-butoxy)carbonyl]methyl}amino)-1,3,4-thiadiazol-2-yl]-8-hydroxy-7-quinolinecarboxamide semihydrate;
N-[5-({1,3-Benzodioxol-4-yl-[(tert-butoxy)carbonyl]methyl}amino)-1,3,4-thiadiazol-2-yl]-8-hydroxy-7-quinolinecarboxamide semihydrate;
(S)-N-[5-({[(tert-Butoxy)carbonyl]-[4-hydroxybenzyl]methyl}amino)-1,3,4-thiadiazol-2-yl]-8-hydroxy-7-quinolinecarboxamide;
(S)-N-[5-({5-[Benzoxy]amido-1-[(tert-butoxy)carbonyl]pentyl}amino)-1,3,4-thiadiazol-2-yl]-8-hydroxy-7-quinolinecarboxamide;
(S)-N-[5-({1-[(tert-Butoxy)carbonyl]-2-indol-3-ylethyl}amino)-1,3,4-thiadiazol-2-yl]-8-hydroxy-7-quinolinecarboxamide monohydrate; and
(S)-N-[5-({1-[(tert-Butoxy)carbonyl]-2-[4-(tert-butoxy)phenyl]ethyl}amino)-1,3,4-thiadiazol-2-yl]-8-hydroxy-7-quinolinecarboxamide monohydrate.

The following sulfonamide compounds of the present invention are preferred:

5-Chloro-8-hydroxy-2-methyl-N-[2-(phenylthio)ethyl]-7-quinolinesulfonamide;
5-Chloro-N-(4-chlorophenyl)-8-hydroxy-2-methyl-7-quinolinesulfonamide;
5-Chloro-N-[4-fluorophenyl)methyl]-8-hydroxy-2-methyl-7-quinolinesulfonamide;
5-Chloro-8-hydroxy-2-methyl-N-(1-naphthalenylmethyl)-7-quinolinesulfonamide;
5-Chloro-N-(cyclohexylmethyl)-8-hydroxy-2-methyl-7-quinolinesulfonamide;
5-Chloro-8-hydroxy-2-methyl-N-(3-phenylpropyl)-7-quinolinesulfonamide;
5-Chloro-8-hydroxy-2-methyl-N-(2-phenoxyethyl)-7-quinolinesulfonamide;
5-Chloro-N-(diphenylmethyl)-8-hydroxy-2-methyl-7-quinolinesulfonamide;
(R)-5-Chloro-8-hydroxy-2-methyl-N-(1-phenylethyl)-7-quinolinesulfonamide;
(S)-5-Chloro-8-hydroxy-2-methyl-N-(1-phenylethyl)-7-quinolinesulfonamide;
5-Chloro-N-[2-(4-chlorophenyl)ethyl]-8-hydroxy-7-quinolinesulfonamide;
5-Bromo-8-hydroxy-N-(phenylmethyl)-7-quinolinesulfonamide;
5-Chloro-N-[2-(2,4-dichlorophenyl)ethyl]-8-hydroxy-2-methyl-7-quinolinesulfonamide;
(E)-5-Chloro-8-hydroxy-2-(2-phenylethenyl)-N-[2-(phenylthio)ethyl]-7-quinolinesulfonamide; and
5-Chloro-8-hydroxy-2-methyl-N-[2-[4[(phenylsulfonyl)amino]phenyl]ethyl]-7-quinolinesulfonamide.

DESCRIPTION OF PREFERRED EMBODIMENTS

PREPARATION 1

8-Hydroxyquinoline-7-carboxylic Acid (Formula A-2 wherein $R^1$ is —H and $R^2$ is —H) Refer to Chart A

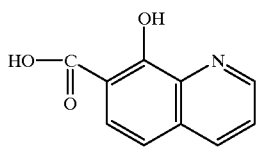

8-Hydroxyquinoline (50.0 g) and potassium carbonate (142.8 g) are mixed together in a stainless steel bomb and heated at 170° C. under 1200 p.s.i. $CO_2$ for 7 days. The reaction is then cooled and the resulting solid is partitioned between water (6 L) and EtOAc (1 L). The organic layer is extracted with water (2×300 mL). The combined aqueous layers are extracted with EtOAc (3×500 mL). The aqueous layer is then acidified to pH 4.5 with conc. HCl. The resulting solid is collected, dried and triturated with i-PrOH to yield 51.97 g of the title compound as a tan solid.

Physical characteristics are as follows:

$^1$H NMR (300 MHz, DMSO) δ 8.89, 8.58, 7.89, 7.78, 7.28.

EXAMPLE 1

N-[(4-Chlorophenyl)methyl]-8-hydroxy-7-quinolinecarboxamide (Formula H-3) Refer to Chart H

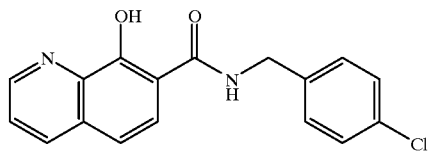

A solution of 8-hydroxyquinoline-7-carboxylic acid (0.250 g) of Preparation 1 and 4-chlorobenzylamine (0.187 g) in 25 mL xylenes is heated to reflux. To this is added dropwise $PCl_3$ (0.073 g). Refluxing is continued overnight. The reaction is then cooled and water is added to destroy excess $PCl_3$. The resulting solid is collected and recrystallized from EtOAc/hexanes to yield 0.088 g of the title product as a yellow solid.

Physical characteristics are as follows:

MP 162–165° C.; $^1$H NMR (300 MHz, DMSO) δ 9.46, 8.93, 8.43, 8.03, 7.70, 7.46, 7.39, 4.56. $^{13}$C NMR (75 MHz, DMSO) δ 168.5, 156.8, 149.2, 138.6, 137.5, 132.0, 129.7, 128.8, 125.8, 124.1, 117.5, 113.2, 42.5. IR (mull) 3081, 1964, 1932, 1635, 1610, 1601, 1577, 1558, 1500, 1492, 1325, 1295, 846, 836, 800 cm$^{-1}$. MS (FAB) m/z 313 (M+H), 315, 314, 313, 312, 173, 172, 69, 57, 55, 43. HRMS (EI) found 312.0669.

EXAMPLE 2

N-[5-[(4-Chlorophenyl)methyl]-1,3,4-thiadiazol-2-yl]-8-hydroxy-7-quinolinecarboxamide (Formula I-3) Refer to Chart I

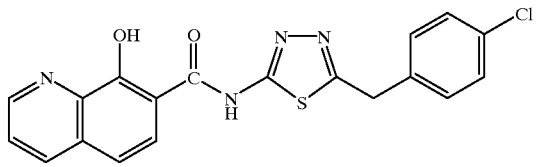

A solution of 8-hydroxyquinoline-7-carboxylic acid (0.236 g) of Preparation 1 and 2-amino5-(4chlorobenzyl)thiadiazole (0.282 g) in 25 mL xylenes is heated to reflux. To this is added dropwise $PCl_3$ (0.069 g). Refluxing is continued overnight. The reaction is then cooled and water is added to destroy excess $PCl_3$. The resulting solid is collected, dried and recrystallized HOAc to yield 0.079 g of the title product as a gold solid.

Physical characteristics are as follows:

MP 276–278° C.; $^1$H NMR (300 MHz, DMSO) δ 8.87, 8.75, 8.04, 7.88, 7.39, 7.17, 4.37. IR (mull) 1661, 1608, 1567, 1537, 1489, 1422, 1292, 1218, 1212, 819, 810, 789, 740, 652, 613 cm$^{-1}$. MS (EI) m/z 396 (M+), 398, 397, 396, 173, 172, 171, 125, 116, 89, 63 (4). HRMS (EI) found 396.0471.

EXAMPLE 3

N-(4-Chlorophenyl)-8-hydroxy-7-quinolinecarboxamide (Formula G-3 wherein $R^1$ is —H) Refer to Chart G

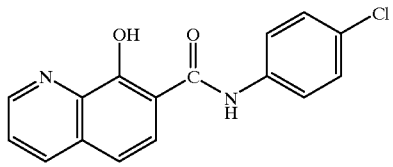

A solution of 8-hydroxyquinoline-7-carboxylic acid (3.78 g) of Preparation 1 and 4-chloroaniline (2.55 g) in 250 mL xylenes is heated to reflux. To this is added dropwise $PCl_3$ (1.37 g). Refluxing is continued overnight. The reaction is then cooled and water is added to destroy excess $PCl_3$. The resulting solid is collected, washed with water and dried. The crude product is recrystallized from EtOAc/hexanes to yield 1.96 g of the title product as an orange solid.

Physical characteristics are as follows:

MP 207–209° C.; $^1$H NMR (300 MHz, DMSO) δ 11.15, 8.91, 8.47, 8.00, 7.77, 7.71, 7.40, 7.39. $^{13}$C NMR (75 MHz, DMSO) δ 165.8, 156.0, 147.9, 138.5, 138.4, 138.2, 131.3, 129.2, 127.7, 127.6, 123.9, 122.1, 116.1, 115.9. IR (mull) 3048, 1996, 1939, 1659, 1588, 1539, 1531, 1485, 1397, 1288, 1253, 1235, 1215, 809, 745 cm$^{-1}$. MS (EI) m/z 298 (M+), 300, 299, 298, 173, 172, 127, 117, 116, 89, 63. HRMS (EI) found 298.0518. Anal. found: C, 64.39; H, 3.68; N, 9.32; Cl, 11.82.

EXAMPLE 4

5-Bromo-N-(4-chlorophenyl)-8-hydroxy-7-quinolinecarboxamide (Formula G3 wherein $R^1$ is —Br) Refer to Chart G

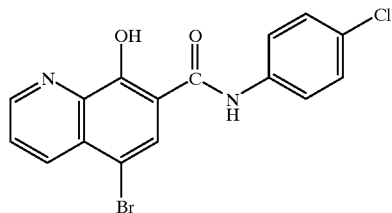

A solution of 5-bromo-8-hydroxyquinoline-7-carboxylic acid (2.68 g) of Preparation 2 and 4-chloroaniline (1.28 g) in 250 mL xylenes is heated to reflux. To this is added dropwise $PCl_3$ (0.69 g). Refluxing is continued overnight. The reaction is then cooled and water is added to destroy excess $PCl_3$. The resulting solid is collected, washed with water and dried. The crude product is recrystallized from EtOAc/hexanes to yield 1.97 g of the title product as an orange solid.

Physical characteristics are as follows:

MP 213–215° C.; $^1H$ NMR (300 MHz, DMSO) δ 10.99, 9.00, 8.55, 8.25, 7.87, 7.75, 7.42. $^{13}C$ NMR (75 MHz, DMSO) δ 164.5, 155.6, 149.1, 139.7, 137.9, 136.9, 130.5, 129.6, 129.3, 128.0, 125.4, 122.2, 117.2, 107.4. IR (mull) 2043, 1957, 1926, 1658, 1594, 1558, 1552, 1521, 1493, 1480, 1400, 1395, 1291, 807, 634 $cm^{-1}$. MS (EI) m/z 376 (M+), 378, 376, 252, 251, 250, 196, 194, 129, 127, 115; HRMS (EI) found 375.9618. Anal. found: C, 50.15; H, 2.60; N, 7.27; Br, 20.85; Cl, 9.23.

PREPARATION 2

5-Bromo-8-hydroxyquinoline-7-carboxylic Acid (Formula B-2) Refer to Chart B

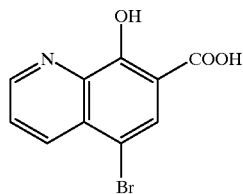

8-Hydroxyquinoline-7-carboxylic acid (1.00 g) is suspended in 25 mL acetic acid. To this is added bromine (0.845 g) dropwise. The mixture is heated to reflux for 1 h, then poured into cold water. The resulting solid is collected, washed with water and dried to yield 1.43 g of the title product as a yellow solid.

Physical characteristics are as follows:

MP 244–246° C.; IR (mull) 3093, 2138, 1995, 1590, 1553, 1396, 1312, 1233, 1108, 911, 820, 779, 67, 730, 671 $cm^{-1}$. MS (EI) m/z 267 (M+), 269, 267, 251, 249, 225, 223, 195, 193, 115, 114. HRMS (EI) found 266.9507. Anal. found: C, 41.84; H, 2.83; N, 4.98; Br, 28.00.

EXAMPLE 5

N-[5-(4-Chlorophenyl)-4,5-dihydro-4-oxo-2-thiazolyl]-8-hydroxy-7-quinolinecarboxamide (Formula E-3 wherein X is —Cl) Refer to Chart E

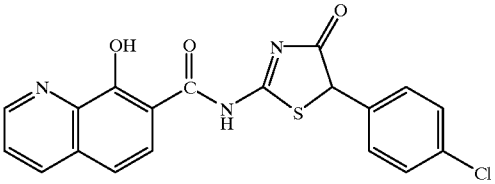

A solution of 8-hydroxyquinoline-7-carboxylic acid (0.280 g) of Preparation 1 and 2-amino-5-(4-chlorophenyl)-4-hydroxy-1,3-thiazole (0.340 g) in 50 mL xylenes is heated to reflux. To this is added dropwise $PCl_3$ (0.103 g). Refluxing is continued overnight. The reaction is then cooled and water is added to destroy excess $PCl_3$. The resulting solid is collected, washed with water and dried. The crude product is triturated with HOAc to yield 0.236 g of the title product as a gold solid.

Physical characteristics are as follows:

MP 272–276° C. (dec). $^1H$ NMR (300 MHz, DMSO) δ 13.75, 8.87, 8.72, 8.09, 7.86, 7.63, 7.37, 7.23. IR (mull) 2042, 1954, 1702, 1685, 1535, 1482, 1424, 1338, 1300, 1262, 1223, 1186, 1181, 1093, 833 $cm^{-1}$. MS (EI) m/z 397 (M+), 397, 241, 226, 173, 172, 171, 155, 145, 116, 89. HRMS (EI) found 397.0278.

EXAMPLE 6

5-Bromo-N-[5-(4-chlorophenyl)-4,5-dihydro-4-oxo-2-thiazolyl]-8-hydroxy-7-quinolinecarboxamide (Formula E-3 wherein X is —Br) Refer to Chart E

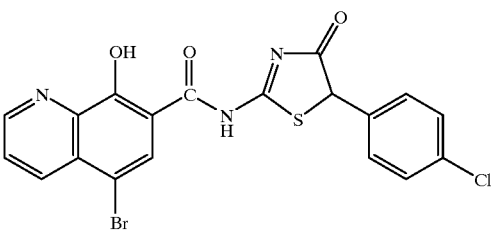

A solution of 5-bromo-8-hydroxyquinoline-7-carboxylic acid (0.268 g) of Preparation 2 and 2-amino-5-(4-chlorophenyl)-4-hydroxy-1,3-thiazole (0.227 g) in 50 mL xylenes is heated to reflux. To this is added dropwise $PCl_3$ (0.069 g). Refluxing is continued overnight. The reaction is then cooled and water is added to destroy excess $PCl_3$. The resulting solid is collected, washed with water and dried. The crude product is recrystallized from HOAc to yield 0.055 g of the title product as an orange solid.

Physical characteristics are as follows:

MP 254–556° C. (dec). $^1H$ NMR (300 MHz, DMSO) δ 13.25, 8.98 8.72, 8.28, 7.99, 7.63, 7.45, 7.37. IR (mull) 3077, 1996, 1705, 1698, 1676, 1652, 1594, 1531, 1492, 1319, 1306, 1262, 1218, 1170, 1093 $cm^{-1}$. MS (EI) m/z 475 (M+), 252, 251, 250, 226, 157, 156, 155, 115, 114, 89. HRMS (EI) found 474.9391.

EXAMPLE 7

N-[5-(5-Bromo-2-thienyl)-2-thiazolyl]-8-hydroxy-7-quinolinecaraoxidede (Formula I-5) Refer to Chart I

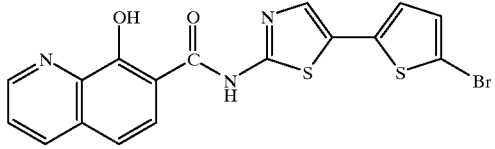

A solution of 8-hydroxyquinoline-7-carboxylic acid (0.43 g) of Preparation 1 in 80 mL xylenes is heated to reflux. $PCl_3$ (0.12 mL) is added dropwise and the mixture stirred for 20 minutes. 2-Amino-5-(5-bromothien-2-yl)thiazole (0.62 g) is added in one portion and the reaction refluxed overnight. The reaction is cooled to room temperature and $H_2O$ is added to quench excess $PCl_3$. The solvents are removed and the residue is dissolved in acetic acid. A dark orange solid precipitates upon addition of hexanes (0.28 g) to yield the title product.

Physical characteristics are as follows:

MP 279–281° C. dec. $^1$H NMR (300 MHz, DMSO-$d_6$) δ 8.89, 8.71, 8.09, 7.86, 7.55, 7.38, 7.25, 7.21. $^{13}$C NMR (75 MHz, TFA-d) δ 167.26, 161.84, 153.55, 148.16, 144.66, 135.44, 132.94, 131.36, 128.99, 128.85, 128.71, 127.06, 125.24, 119.44, 117.29, 113.07, 109.38. IR (mull) 3082, 1996, 1925, 1664, 1608, 1539, 1490, 1428, 1343, 1299, 1273, 1230, 1212, 1034, 7376. MS (EI) m/z 431 (M+), 433, 431, 262, 260, 180, 173, 172, 117, 116, 89. HRMS (EI) found 430.9401.

EXAMPLE 8

N-[5-(3-Chlorophenyl)-4,5-dihydro-4-oxo-2-thiazolyl]-8-hydroxy-7-quinolinecarboxamide (Formula D-3) Refer to Chart D

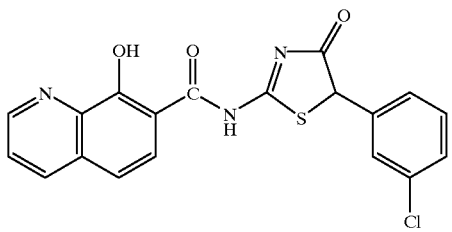

To a solution of 8-hydroxyquinoline-7-carboxylic acid (0.284 g,) of Preparation 1 and 2-amino-5-(3-chlorophenyl)-4-hydroxy-1,3-thiazole (0.340 g) in 20 mL DMF is added 1-(3-dimethylaminopropyl)-3-ethylcarbodiimide hydrochloride (0.305 g) and 1-hydroxybenzotriazole monohydrate (0.217 g). The mixture is stirred at room temperature for 7 days. The solution is then poured into 30 mL ice-water. The resulting solid is collected and dried. The crude product is triturated with hot EtOAc, then with hot i-PrOH to yield 0.182 g of the title product as a yellow solid.

Physical characteristics are as follows:

MP 268–272° C. (dec). $^1$H NMR (300 MHz, DMSO) δ 13.88, 8.87, 8.72, 8.08, 7.86, 7.73, 7.47, 7.34, 7.22. 7.14. $^{13}$C NMR (75 MHz, DMSO) δ 164.6, 160.2, 155.6, 153.8, 144.4. 142.4, 136.7, 135.6,133.9, 132.8, 131.0, 129.3, 124.7, 124.6, 124.3, 123.7, 113.6, 111.8, 97.9. IR (mull) 2047, 1996, 1945, 1703, 1684, 1571, 1536, 1423, 1300, 1261, 1222, 1185, 1113, 1085, 833 cm$^{-1}$. MS (EI) m/z 397 (M+), 397, 241, 213, 173, 172, 171, 145, 116, 115, 89. HRMS (EI) found 397.0290. Anal. found: C, 56.78; H, 3.08; N, 10.31; Cl, 8.43; S, 7.66.

EXAMPLE 9

5-Bromo-N-[(4-chlorophenyl)methyl]-8-hydroxy-7-quinolinecarboxamide (Formula C-3 wherein $R^1$ is —Br, $R^2$ is —H, and X is —Cl) Refer to Chart C

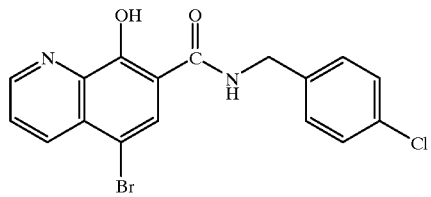

To a solution of 5-bromo-8-hydroxyquinoline-7-carboxylic acid (0.402 g) of Preparation 2 and 4-chlorobenzylamine (0.219 g) in 20 mL DMF is added 1-(3-dimethylaminopropyl)-3-ethylcarbodiimide hydrochloride (0.305 g) and 1-hydroxybenzotriazole monohydrate (0.217 g). The mixture is stirred overnight. The solution is then poured into 30 mL ice-water. The resulting solid is collected and dried to yield 0.157 g of the title product as an off-white solid.

Physical characteristics are as follows:

MP 148–151° C.; $^1$H NMR (300 MHz, DMSO) δ 9.38, 8.97, 8.44, 8.32, 7.80, 7.38, 4.55. $^{13}$C NMR (75 MHz, DMSO) δ 167.1, 156.9, 150.3, 140.5, 138.4, 135.6, 132.0, 129.8, 129.6, 129.0, 128.8, 125.5, 114.2, 108.9, 42.6. IR (mull) 3372, 3291, 2427, 1996, 1960, 1926, 1637, 1535, 1492, 1433, 1414, 1337, 931, 798, 681 cm$^{-1}$. MS (EI) m/z 390 (M+), 392, 252, 251, 250, 225, 223, 142, 140, 125, 115. HRMS (EI) found 389.9777. Anal. found: C, 52.48; H, 3.05; N, 7.27; Br, 19.70; Cl, 9.09.

EXAMPLE 10

N-[(4-Chlorophenyl)methyl]-8-hydroxy-2-methyl-7-quinolinecarboxamide (Formula C-3 wherein $R^1$ is —H, $R^2$ is —$CH_3$, and X is —Cl) Refer to Chart C

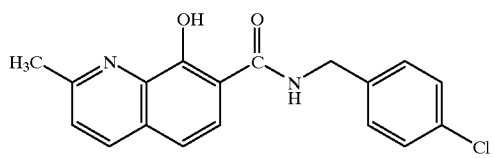

To a solution of 8-hydroxy-2-methylquinoline-7-carboxylic acid (0.305 g) of Preparation 5 and 4-chlorobenzylamine (0.219 g) in 20 mL DMF is added 1-(3-dimethylaminopropyl)-3-ethylcarbodiimide hydrochloride (0.305 g) and 1-hydroxybenzotriazole monohydrate (0.217 g). The mixture is stirred overnight. The solution is then poured into 30 mL ice-water. The resulting solid is collected and dried to yield 0.337 g of the title product as an off-white solid.

Physical characteristics are as follows:

MP 95–98° C.; $^1$H NMR (300 MHz, DMSO) δ 9.40, 8.21, 7.90, 7.51, 7.39, 7.35, 4.54, 2.67. $^{13}$C NMR (75 MHz, DMSO) δ 169.0, 158.1, 157.2, 139.0, 138.6, 136.6, 132.0, 129.7, 129.5, 128.8, 124.8, 124.3, 117.1, 112.6, 21.4, 25.1. IR (mull) 1950, 1905, 1645, 1635, 1607, 1561, 1539, 1507, 1491, 1423, 1410, 1338, 1286, 1245, 846 cm$^{-1}$. MS (EI) m/z 326 (M+), 326, 187, 186, 160, 159, 131, 130, 125, 103, 77. HRMS (EI) found 326.0829. Anal. found: C, 65.52; H, 4.74; N, 8.57; Cl, 10.79.

EXAMPLE 11

5-Chloro-N-[(4-chlorophenyl)methyl]-8-hydroxy-7-quinolinecarboxamide (Formula C-3 wherein R$^1$ is —Cl, R$^2$ is —H, and X is —Cl) Refer to Chart C

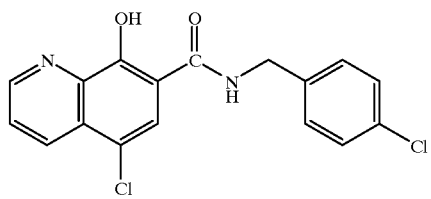

To a solution of 5-chloro-8-hydroxyquinoline-7-carboxylic acid (0.335 g) of Preparation 3 and 4-chlorobenzylamine (0.219 g) in 20 mL DMF is added 1-(3-dimethylaminopropyl)-3-ethylcarbodiimide hydrochloride (0.305 g) and 1-hydroxybenzotriazole monohydrate (0.217 g). The mixture is stirred overnight. The solution is then poured into 30 mL ice-water. The resulting solid is collected and dried to yield 0.167 g of the title product as an off-white solid.

Physical characteristics are as follows:

MP 163–166° C.; $^1$H NMR (300 MHz, DMSO) δ 9.37, 9.00, 8.50, 8.15, 7.80, 7.38, 4.55. $^{13}$C NMR (75 MHz, DMSO) δ 167.2, 156.3, 150.3, 140.3, 138.4, 133.1, 132.0, 129.8, 128.8, 128.4, 125.5, 125.1, 119.1, 113.5, 42.6. IR (mull) 3362, 3292, 2429, 2280, 1962, 1929, 1636, 1619, 1537, 1493, 1433, 1338, 953, 799, 680 cm$^{-1}$. Ms (EI) m/z 346 (M+), 346, 207, 206, 181, 179, 150, 142, 140, 127, 125. Anal. found: C, 58.59; H, 3.71; N, 8.19; Cl, 19.72.

EXAMPLE 12

8-Hydroxy-N-[(4-nitrophenyl)methyl]-7-quinolinecarboxamide (Formula C-3 wherein R$^1$ is —H, R$^2$ is —H, and X is —NO$_2$) Refer to Chart C

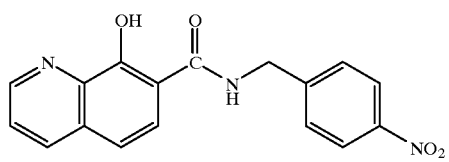

8-Hydroxyquinoline-7-carboxylic acid (0.51 g) of Preparation 1 is added to 20 mL DMF. 4-Nitrobenzylamine hydrochloride (0.53 g) followed by diisopropylethylamine (0.49 mL) is then added. After 10 minutes, all solids go into solution. 1-(3-Dimethylaminopropyl)-3-ethylcarbodiimide hydrochloride (0.54 g) and 1-hydroxybenzotriazole monohydrate (0.38 g) are added and the reaction stirred at room temperature overnight. The reaction is poured into 75 mL H$_2$O. The resulting solid is filtered and dried to give the title product (0.53 g).

Physical characteristics are as follows:

MP 210–212° C.; $^1$H NMR (300 MHz, DMSO-d$_6$) δ 9.45, 8.91, 8.35, 8.20, 7.99, 7.64, 7.61, 7.43, 4.70. $^{13}$C NMR (75 MHz, DMSO-d$_6$) δ 168.42, 156.84, 149.50, 147.82, 146.95, 139.50, 136.63, 131.16, 128.75, 125.85, 124.04, 117.49, 113.29, 42.73. IR (mull) 2450, 2292, 1927, 1612, 1602, 1575, 1556, 1518, 1344, 1325, 1296, 1107, 855, 837, 697. MS (electrospray) m/z 322 (M+). Anal. found: C, 62.80; H, 4.29; N, 12.99.

EXAMPLE 13

N(6-Chloro-2-benzothiazolyl)-8-hydroxy-7-quinolinecarboxamide (Formula I-7) Refer to Chart I

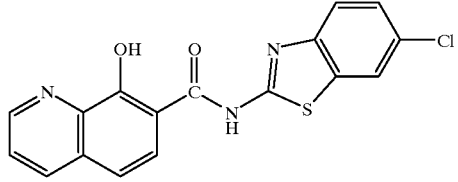

A solution of 8-hydroxyquinoline-7-carboxylic acid (0.30 g) of Preparation 1 in 75 mL xylenes is heated to reflux. PCl$_3$ (0.07 mL) is added dropwise and the mixture stirred for 15 minutes. 2-Amino-6-chlorobenzothiazole (0.31 g) is added in one portion and the reaction refluxed overnight. The reaction is cooled to room temperature and H$_2$O is added to quench excess PCl$_3$. After stirring the solution for 30 minutes, a yellow solid is filtered, dried, and recrystallized from DMSO to give the title product (0.31 g).

Physical characteristics are as follows:

MP>320° C.; $^1$H NMR (300 MHz, TFA-d) δ 9.29, 9.23, 8.56, 8.35, 8.08, 8.01, 7.96, 7.81. $^{13}$C NMR (75 MHz, TFA-d) δ 167.92, 163.82, 154.19, 148.65, 145.25, 135.42, 133.94, 133.52, 131.34, 129.40, 128.01, 127.33, 125.86, 122.74, 120.06, 117.47, 113.33. IR (mull) 2188, 2026, 1954, 1918, 1661, 1657, 1612, 1598, 1546, 1531, 1494, 1441, 1258, 1210, 809. MS (EI) m/z 355 (M+), 357, 355, 186, 184, 173, 172, 117, 116, 89, 63. HRMS (EI) found 355.0179.

EXAMPLE 14

N-[5-(4-Chlorophenyl)-1,3,4-thiadiazol-2-yl]-8-hydroxy-7-quinolinecarboxamide (Formula I-9) Refer to Chart I

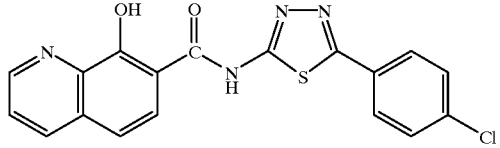

A suspension of 8-hydroxyquinoline-7-carboxylic acid (0.236 g) of Preparation 1 in 50 mL xylenes is heated to reflux. To this is added dropwise PCd$_3$ (0.069 g). After 15 min, 2-amino-5-(4-chlorophenyl)-thiadiazole (0.264 g) is added. Refluxing is continued overnight. The reaction is then cooled and water is added to destroys excess PCl$_3$. The resulting solid is collected, washed with water and dried. The crude product is recrystallized from DMSO to yield 0.204 g of the title product as a yellow-orange solid.

Physical characteristics are as follows:

$^1$H NMR (300 MHz, TFA) δ 9.54, 9.48, 8.83, 8.59, 8.24, 7.95. $^{13}$C NMR (75 MHz, TFA) δ 167.9, 167.3, 159.9, 153.5, 147.9, 144.5, 142.7, 132.8, 130.4, 128.8, 126.6, 125.1, 121.5, 119.3. IR (mull) 2031, 1966, 1924, 1673, 1611, 1572, 1536, 1489, 1211, 1090, 1086, 829, 807, 740, 639 cm$^{-1}$. MS (EI) m/z 382 (M+), 384, 383, 382, 173, 172, 155, 117, 116, 89, 63. HRMS (EI) found 382.0018.

EXAMPLE 15

5-Chloro-N-(4-chlorophenyl)-8-hydroxy-7-quinolinecarboxamide (Formula G-3 wherein R$^1$ is —Cl) Refer to Chart G

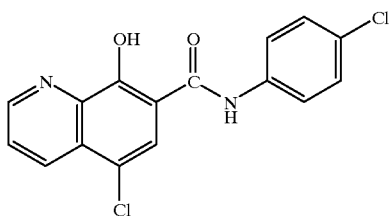

A suspension of 5-chloro-8-hydroxyquinoline-7-carboxylic acid (0.224 g) of Preparation 3 in 50 mL xylene is heated to reflux. To this is added dropwise PCl$_3$ (0.069 g). After 15 min, 4-chloroaniline (0.128 g) is added. Refluxing is continued overnight. The reaction is then cooled and water is added to destroy excess PCl$_3$. The resulting solid is collected, washed with water and dried. The solid is then partitioned between EtOAc and water. The aqueous layer is extracted with EtOAc (3×). The combined organic layers are washed with water, dried and condensed. The crude product is recrystallized from EtOAc to yield 0.073 g of the title product as an orange solid.

Physical characteristics are as follows:

MP 214–216° C.; $^1$H NMR (300 MHz, DMSO) δ 10.92, 9.02, 8.59, 8.09, 7.86, 7.75, 7.41. $^{13}$C NMR (75 MHz, DMSO-d$_6$) δ 164.6, 154.9, 149.2, 139.6, 137.9, 134.3, 129.2, 128.3, 128.0, 126.9, 125.1, 122.2, 118.0, 116.4. IR (mull) 2055, 1962, 1931, 1658, 1597, 1553, 1532, 1525, 1495, 1482, 1402, 1393, 1293, 807, 640 cm$^{-1}$. MS (EI) m/z 332 (M+), 333, 332, 208, 207, 206, 152, 150, 129, 115. Anal. found: C, 57.60; H, 3.03; N, 8.35; Cl, 20.96.

PREPARATION 3

5-Chloro-8-hydroxyquinoline-7-carboxylic Acid (Formula A-2 wherein R$^1$ is —Cl and R$^2$ is —H) Refer to Chart A

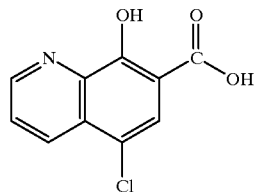

5Chloro-8-hydroxyquinoline (5.00 g) and potassium carbonate (11.54 g) are mixed together in a stainless steel bomb and heated to 170° C. under 800 p.s.i. CO$_2$ for 7 days. The reaction is cooled and the resulting solid is dissolved in 800 mL water. The insoluble material is filtered and partitioned between 800 mL water and 400 mL EtOAc in a separatory funnel. The aqueous layer is washed with EtOAc (3×400 mL). The aqueous layer is then acidified to pH 4.5 with conc. HCl. The resulting solid is collected, washed with water and dried. The crude product is triturated with i-PrOH and dried to yield 1.481 g of the title product as a brown solid.

Physical characteristics are as follows:

MP 285–287° C.; $^1$H NMR (300 MHz, DMSO) δ 8.99, 8.58, 7.89, 7.78. IR (mull) 2471, 2420, 1994, 1964, 1902, 1393, 1296, 1232, 1222, 1115, 1109, 955, 923, 819, 788 cm$^{-1}$. MS (EI) m/z 222 (M+), 223, 207, 205, 181, 179, 151, 150, 149, 115, 114. Anal. found: C, 53.63; H, 2.90; N, 6.17; Cl, 15.34.

PREPARATION 4

5-Fluoro-8-hydroxyquinoline-7-carboxylic Acid (Formula A-2 wherein R$^1$ is —F and R$^2$ is —H) Refer to Chart A

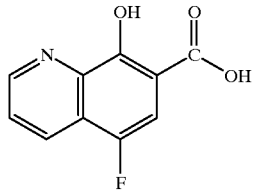

5-Fluoro-8-hydroxyquinoline (3.00 g) and potassium carbonate (7.62 g) are mixed together in a stainless steel bomb and heated to 170° C. under 800 p.s.i. CO$_2$ for 7 days. The reaction is cooled and the resulting solid is partitioned between 800 mL water and 400 mL EtOAc in a separatory funnel. The aqueous layer is washed with EtOAc (3×400 mL). The aqueous layer is then acidified to pH 4.5 with conc. HCl and cooled. The resulting solid is collected, washed with water and dried. The crude product is triturated with i-PrOH and dried to yield 1.67 g of the title product as a brown solid.

Physical characteristics are as follows:

MP 277–279° C.; $^1$H NMR (300 MHz, DMSO) δ 9.01, 8.49, 7.79, 7.57. IR (mull) 2446, 2417, 1995, 1965, 1637, 1445, 1405, 1270, 1257, 1215, 1068, 1032, 819, 785, 742 cm$^{-1}$. MS (EI) m/z 207 (M+), 207, 189, 163, 161, 135, 134, 133, 132, 107, 81. Anal. found: C, 57.95; H, 2.88; N, 6.66.

EXAMPLE 16

5-Fluoro-N-[[4-chlorophenyl]methyl]-8-hydroxy-7-quinolinecarboxamide (Formula C-3 wherein R$^1$ is —F, R$^2$ is —H, and X is —Cl) Refer to Chart C

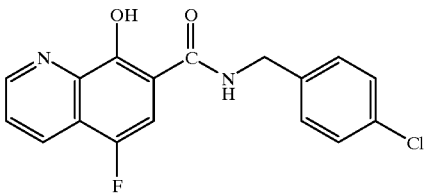

To a solution of 5-fluoro-8-hydroxyquinoline-7-carboxylic acid (0.311 g) of reparation 4 and 4-chlorobenzylamine (0.219 g) in 20 mL DMF is added 1-(3-dimethylaminopropyl)-3-ethylcarbodiimide hydrochloride (0.305 g) and 1-hydroxybenzotriazole monohydrate (0.217 g). The mixture is stirred overnight. The solution is then poured into 30 mL ice-water. The resulting solid is collected and dried. The crude product is recrystallized from EtOAc/hexanes to yield 0.207 g of the title product as an off-white solid.

Physical characteristics are as follows:

MP 184–185° C.; $^1$H NMR (300 MHz, DMSO) δ 9.31, 9.00, 8.45, 7.82, 7.75, 7.38, 4.55. $^{13}$C NMR (75 MHz, DMSO-$d_6$) δ 167.4, 153.7, 150.7, 149.4, 147.7, 139.7, 138.5, 132.0, 129.8, 129.5, 128.8, 124.5, 121.5, 111.8, 108.6, 42.6. IR (mull) 3303, 2302, 2185, 1971, 1940, 1910, 1648, 1634, 1545, 1531, 1494, 1435, 1402, 1066, 798 cm$^{-1}$. MS (EI) m/z 330 (M+), 330, 191, 190, 163, 142, 140, 135, 134, 125, 107. Anal. found: C, 61.05; H, 3.74; N, 8.35; Cl, 10.56.

PREPARATION 5

2-Methyl-8-hydroxyquinoline-7-carboxylic Acid
(Formula A-2 wherein $R^1$ is —H and $R^2$ is —CH$_3$)
Refer to Chart A

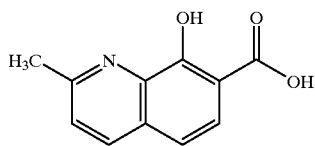

8-Hydroxyquinaldine (5.0 g) and potassium carbonate (13.02 g) are mixed together in a stainless steel bomb and heated to 170° C. under 800 p.s.i. CO$_2$ for 6 days. The reaction is then cooled and the resulting solid is partitioned between EtOAc and water. The organic layer is extracted with water (3x). The combined aqueous layers are washed with EtOAc (3x). The aqueous layer is then acidified to pH 4.5 with conc. HCl. The resulting solid is collected, dried and recrystallized from i-PrOH to yield 1.86 g of the title compound as a gold solid.

Physical characteristics are as follows:

MP 217–219° C.; $^1$H NMR (300 MHz, DMSO) δ 8.54, 7.85, 7.71, 7.19, 2.79. IR (mull) 3414, 2181, 2044, 1995, 1959, 1921, 1668, 1639, 1611, 1589, 1486, 1432, 1324, 858, 757 cm$^{-1}$. MS (EI) m/z 203 (M+), 203, 185, 159, 131, 130, 129, 103, 102, 77, 51. HRMS 203.0600. Anal. found: C, 59.53; H, 4.98; N, 6.37.

PREPARATION 6

5-Bromo-8-methoxy-2-methyl-7-quinolinesulfinic
Acid, Lithium Salt (Formula J-2 wherein $R^1$=Me
and $X^1$=Br) Refer to Chart J

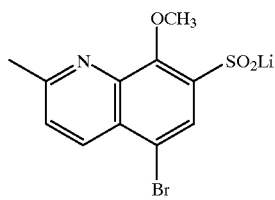

Under N$_2$, a flame dried, 250-mL, three-necked flask with attached addition funnel and bubbler is charged with 5,7-dibromo-8-methoxy-2-methyl-quinoline (3 g), ether (18 mL) and toluene (18 mL). The flask is cooled in a dry ice/acetone bath, degassed and flushed with N$_2$. To facilitate stirring, additional ether (5 mL) and toluene (5 mL) are added. The addition funnel is charged with 1.6 M nBuLi (5.6 mL) which is then added dropwise over 7 min to the thick slurry. The reaction mixture is stirred at −78° C. for 3 hrs. Sulfur dioxide is then introduced via a needle positioned directly above the reaction surface. Within 5 min, the reaction mixture becomes a pale yellow opaque solution, and SO$_2$ introduction is terminated. The reaction mixture is flushed with N$_2$, the cooling bath is removed, and the reaction mixture is allowed to warm to room temperature over 1 hr. 100 mL hexane is added to aid precipitation of the solid, which is then collected by filtration. Drying under vacuum yields 2.844 g of the title compound as a yellow solid.

PREPARATION 7

5-Bromo-8-methoxy-2-methyl-7-quinolinesulfonyl
Chloride (Formula J-3 wherein $R^1$=Me and $X^1$=Br)
Refer to Chart J

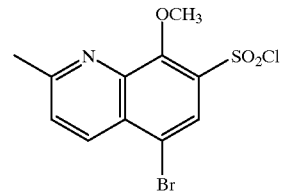

Under N$_2$, a flame-dried, 250-mL, three-necked flask is charged with the title compound of Preparation 6 (2.844 g) and CH$_2$Cl$_2$ (45 mL). The flask is cooled in an ice bath and N-chlorosuccinimide (1.178 g) is added in one portion. After 5 min, the cooling bath is removed and the reaction mixture is stirred for 3 hrs. The reaction mixture is then poured into H$_2$O, a small amount of brine is added, and the layers are separated. The aqueous layer is extracted with two portions CH$_2$Cl$_2$. The combined organic layers are washed with brine, dried over MgSO$_4$, filtered and concentrated to give the title compound as a pale orange solid, which is immediately used in the preparation of compounds of the formula J-4.

PREPARATION 8

5-Bromo-N-[(4-chlorophenyl)methyl]-8-methoxy-2-
methyl-7-quinolinesulfonamide (Formula J-4
wherein $R^1$=Me, $X^1$ =Br, and $R^2$=CH$_2$-4-ClC$_6$H$_4$)
Refer to Chart J

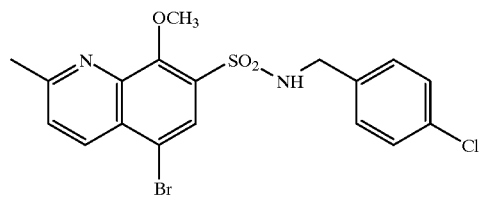

Under N$_2$, a flame-dried, 250-mL, three-necked flask is charged with 4-chlorobenzylamine (980 μL), pyridine (1.3 mL), and CH$_2$Cl$_2$ (10 mL). The title compound of Preparation 7 in 55 mL CH$_2$Cl$_2$ is transferred via cannula to the reaction flask and then is allowed to stir overnight at room temperature. The reaction mixture is concentrated and the residue is taken up in toluene and concentrated twice. Purification by column chromatography (elution with 0.5% MeOH/CH$_2$Cl$_2$) affords 1.47 g of the title compound as a yellow foam.

Physical characteristics are as follows:

MP 108–110° C.; $^1$H NMR (300 MHz, CDCl$_3$) δ 8.43, 8.09, 7.51, 7.14–7.07, 5.50, 4.35, 4.08, 2.84 ppm. MS (ES–) m/z 453 (M–H).

EXAMPLE 17

5-Chloro-N-[(4-chlorophenyl)methyl]-8-hydroxy- 2-methyl-7-quinolinesulfonamide (Formula J-5 wherein R$^1$=Me, X$^1$=Cl, and R$^2$=CH$_2$-4-ClC$_6$H$_4$) Refer to Chart J

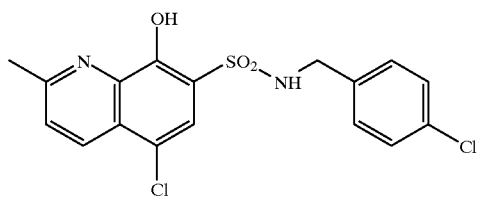

A flame-dried, 100-mL, one-necked flask with attached oven-dried condensor is charged with the title compound of Preparation 8 (0.640 g) and pyridine hydrochloride (8.8 g). The reaction mixture is heated to 215–220° C. for 10 min., and then is poured onto ice. It is neutralized with saturated aqueous NaHCO$_3$ and extracted with CH$_2$Cl$_2$ three times. The combined organic layers are washed with brine, dried over MgSO$_4$, filtered and concentrated. The residue is taken up in toluene and concentrated four times. Crystallization from CH$_2$Cl$_2$/Et$_2$O provides 0.247 g of the title compound as an off-white solid.

Physical characteristics are as follows:

MP 158–161° C. (decompose). $^1$H NMR (300 MHz, CDCl$_3$) δ 8.44, 7.88, 7.56, 7.13–7.05, 5.42, 4.14, 2.80 ppm. MS (ES–) m/z 394.9 (M–H). Anal. found: C, 51.40; H, 3.73; N, 7.09.

PREPARATION 9

5-Chloro-N-[(4-chlorophenyl)methyl]-8-methoxy-7-quinolinesulfonamide (Formula J-4 wherein R$^1$=H, X$^1$=Cl, and R$^2$=CH$_2$-4-ClC$_6$H$_4$) and 5-Chloro-N-[(4-chlorophenyl)methyl]-2-(1,1-dimethylethyl)-8-methoxy-7-quinolinesulfonamide (Formula J-4 wherein R$^1$=t-Bu, X$^1$=Cl, and R$^2$=CH$_2$-4-ClC$_6$H$_4$) Refer to Chart J

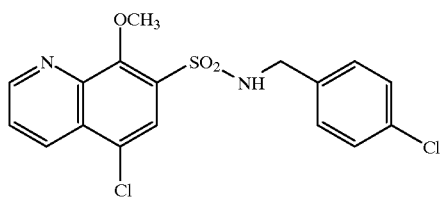

-continued

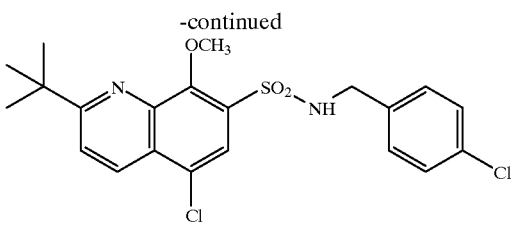

A mixture of the title compounds is prepared according to the procedures described in Preparations 6–8 substituting 5-chloro-7-iodo-8-methoxy-quinoline for 5,7-dibromo-8-methoxy-2-methyl-quinoline and two equivalents of tBuLi for one equivalent of nBuLi in Preparation 6. The title compounds are separated by column chromatography (elution with 5–10% EtOAc/hexanes and 10% MeOH/CH$_2$C$_2$) to give 0.407 g of -Chloro-N-[(4-chlorophenyl)methyl]-8-methoxy-7-quinolinesulfonamide and 0.040 g of -Chloro-N-[(4-chlorophenyl)methyl]-2-(1,1-dimethylethyl)-8-methoxy-7-quinolinesulfonamide.

Physical characteristics for -Chloro-N-[(4-chlorophenyl)methyl]-8-methoxy-7-quinolinesulfonamide are as follows:

$^1$H NMR (300 MHz, CDCl$_3$) δ 9.11, 8.68, 7.70–7.66, 7.14–7.09, 5.50, 4.16–4.11 ppm. MS (ES–) m/z 394.9 (M–H). MS (ES+) m/z 396.9 (M+H).

Physical characteristics for -Chloro-N-[(4-chlorophenyl)methyl]-2-(1,1-dimethylethyl)-8-methoxy-7-quinolinesulfonamide are as follows:

$^1$H NMR (300 MHz, CDCl$_3$) δ 8.50, 7.93, 7.75, 7.16–7.09, 5.49, 4.42, 4.09, 1.50 ppm. MS (ES–) m/z 450.9 (M–H). MS (ES+) m/z 452.9 (M+H).

EXAMPLE 18

5-Chloro-N-[(4-chlorophenyl)methyl]-8-hydroxy-7-quinolinesulfonamide (Formula J-5 wherein R$^1$=H, X$^1$=Cl, and R$^2$=CH$_2$-4-ClC$_6$H$_4$) Refer to Chart J

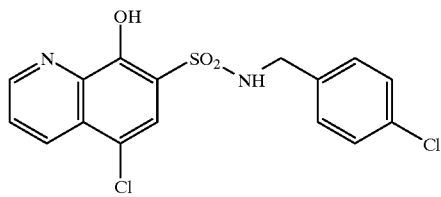

Under N$_2$, a flame-dried, 50-mL, two-necked flask is charged with 5-chloro-N-[(4-chlorophenyl)methyl]-methoxy-7-quinolinesulfonamide (0.322 g), which is the first title compound of Preparation 9, and CH$_2$C$_{12}$ (20 mL) and is cooled in a dry ice/acetone bath. 1.0 M BBr$_3$ (1.05 mL) is added dropwise. The cooling bath is removed and the reaction mixture is allowed to stir for 1.5 hrs. It is then poured into 75 mL 5% NaHCO$_3$ aqueous solution, and the layers are separated. The aqueous layer is extracted twice with CH$_2$Cl$_2$. The combined organic layers are washed with H$_2$O and then brine, dried over MGSO$_4$, filtered and concentrated to a brown residue. Purification by column chromatography (elution with 2–5% MeOH/CH$_2$Cl$_2$ with <1% AcOH) yields 0.037 g of the title compound as a pale yellow solid.

Physical characteristics are as follows:

MP 189–190° C. (decompose). $^1$H NMR (300 MHz, CDCl$_3$) δ 8.96, 8.67, 8.35, 7.81, 7.68, 7.09, 5.44, 4.15 ppm.

IR (mull) 3302, 3088, 1586, 1506, 1492, 1326, 1151, 821, 779 cm$^{-1}$. MS (EI) m/z 382 (M+) 382, 243, 179, 150, 140, 125, 115. HRMS (EI) found 381.9917.

EXAMPLE 19

5-Chloro-N-[(4-chlorophenyl)methyl]-2-(1,1-dimethylethyl)-8-hydroxy-7-quinolinesulfonamide (Formula J-5 wherein $R^1$=t-Bu, $X^1$=Cl, and $R^2$= $CH_2$-4-$ClC_6H_4$) Refer to Chart J

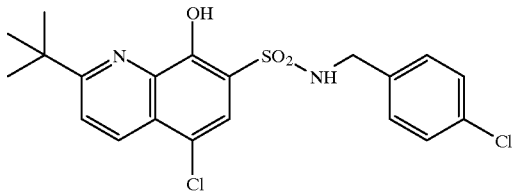

The title compound is prepared from 5-Chloro-N-[(4-chlorophenyl)methyl]-2-(1,1-dimethylethyl)-8-methoxy-7-quinolinesulfonamide, which is the second title compound of Preparation 9, and 6 equivalents of BBr$_3$ according to the procedure described in Example 18. Crystallization from Et$_2$O/hexane affords 0.035 g of tie title compound as a dark tan solid.

Physical characteristics are as follows:

MP 162–163° C. (decompose). $^1$H NMR (300 MHz, CDCl$_3$) δ 8.50, 7.91, 7.82, 7.14–7.06, 5.45, 4.16, 1.51 ppm. IR (mull) 3334, 3302, 2725, 1597, 1562, 1491, 1333, 1320, 1308, 1161, 11.53, 1139, 1129 cmn$^{-1}$. MS (EI) m/z 438 (M+) 235, 220, 218, 193, 179, 150, 140. Anal. found: C, 54.30; H, 4.52; N, 6.23.

PREPARATION 10

5-Chloro-N-(4-chlorophenyl)-8-methoxy-7-quinolinesulfonamide (Formula J-4 wherein $R^1$=H, $X^1$=Cl, and $R^2$=p-ClC$_6$H$_4$) Refer to Chart J

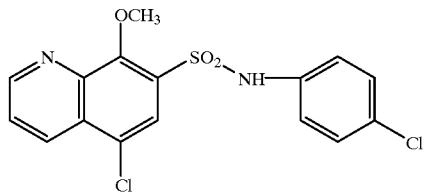

The title compound is prepared according to the procedures described in Preparations 6–8, substituting 5-chloro-7-iodo-8-methoxy-quinoline for 5,7-dibromo-8-methoxy-2-methyl-quinoline and two equivalents of tBuLi for one equivalent of nBuLi in Preparation 6 and 4-chloroaniline for 4-chlorobenzylamine in Preparation 8. Column chromatography (elution with 5–15% EtOAc/hexanes and 2% MeOH/CH$_2$Cl$_2$) affords 0.373 g of the title compound as a solid.

Physical characteristics are as follows:

$^1$H NMR (300 MHz, CDCl$_3$) δ 9.08, 8.73, 7.66, 7.57, 7.18–7.07, 4.08 ppm. MS (ES−) m/z 380.9 (M−H).

EXAMPLE 20

5-Chloro-N-(4-chlorophenyl)-8-hydroxy-7-quinolinesulfonamide (Formula J-5 wherein $R^1$=H, $X^1$=Cl, and $R^2$=4-ClC$_6$H$_4$) Refer to Chart J

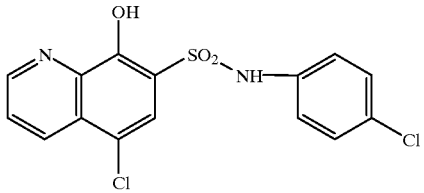

The title compound is prepared from 5-chloro-N-(4-chlorophenyl)-8-methoxy-7-quinolinesulfonamide, which is the fist title compound of Preparation 9, and 6 equivalents of BBr$_3$ according to the procedure described in Example 18. Crystallization from Et$_2$O/hexane/CH$_2$Cl$_2$ affords 0.015 g of the title compound as a red-brown solid.

Physical characteristics are as follows:

MP 97° C. (decompose). $^1$H NMR (300 MHz, CDCl$_3$) δ 8.94, 8.71, 8.30, 7.76, 7.70, 7.17–7.07 ppm. MS (EI) m/z 368 (M+) 370, 368, 178, 150, 128, 127, 126, 115, 99, 63.

PREPARATION 11

5-Chloro-8-methoxy-N-(3-phenylpropyl)-7-quinolinesulfonamide (Formula J-4 wherein $R^1$=H, $X^1$=Cl, and $R^2$=(CH$_2$)$_3$C$_6$H$_5$) Refer to Chart J

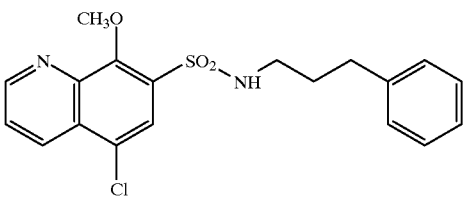

The title compound is prepared according to the procedures described in Preparations 6–8, substituting 5-chloro-7-iodo-8-methoxy-quinoline for 5,7-dibromo-8-methoxy-2-methyl-quinoline and two equivalents of tBuLi for one equivalent of nBuLi in Preparation 6 and 3-phenyl-1-propylamine for 4-chlorobenzylamine in Preparation 8. Column chromatography (elution with 0.5% MeOH/CH$_2$Cl$_2$) affords 0.143 g of the title compound as a solid.

Physical characteristics are as follows:

$^1$H NMR (CDCl$_3$) δ 9.10, 8.74, 7.70, 7.67, 7.23–7.14, 7.05–7.02, 5.16, 4.15, 3.03–2.97, 2.64–2.59, 1.86–1.77 ppm. MS (ES−) m/z 389.0 (M−H).

EXAMPLE 21

5-Chloro-8-hydroxy-N-(3-phenylpropyl)-7-quinolinesulfonamide monohydrobromide (Formula J-5 wherein $R^1$=H, $X^1$=Cl, and $R^2$=$(CH_2)_3C_6H_5$) Refer to Chart J

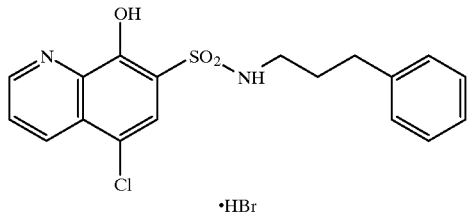

The title compound is prepared from 5-chloro-8-methoxy-N-(3-phenylpropyl)-7-quinolinesulfonamide, which is the title compound of Preparation 11, and 6 equivalents of $BBr_3$ according to the procedure described in Example 18. Crystallization from $CHCl_3$/acetone/EtOH affords 0.063 g of the title compound as a red-brown solid.

Physical characteristics are as follows:

MP 210–212° C. (decompose). $^1$H NMR (300 MHz, $CDCl_3$) δ 9.35, 9.18, 8.06, 7.95, 7.27–7.12, 7.11–7.05, 3.16–3.02, 2.63, 1.83 ppm. IR (mull) 3273, 2757, 1626, 1550, 1444, 1353, 1326, 1297, 1281, 1152 cm$^{-1}$. MS (EI) m/z 376 (M+) 376, 258, 181, 180, 179, 178, 150, 118, 115, 91. HRMS (EI) found 376.0631. Anal found: C, 46.96; H, 4.09; N, 6.08.

EXAMPLE 22

5-Chloro-8-hydroxy-N-(phenylmethyl)-7-quinolinesulfonamide (Formula J-5 wherein $R^1$=Me, $X^1$=Cl, and $R^2$=$CH_2Ph$) Refer to Chart J

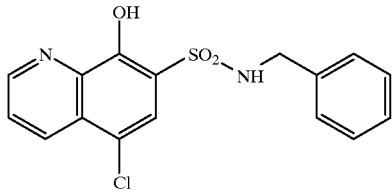

The title compound is prepared from 5,7-dibromo-8-methoxy-quinoline, which is commercially available, according to the procedures described in Preparations 6–8 and Example 17, substituting benzylamine for 4-chlorobenzylamine. Crystallization from $CH_2Cl_2$/$Et_2O$ gives 0.104 g of the title compound as a pale orange solid.

Physical characteristics are as follows:

MP 114–117° C.; $^1$H NMR (300 MHz, DMSO) δ 9.06, 8.54, 8.12, 7.87, 7.77, 7.22, 7.11, 7.03, 4.13 ppm. IR (mull) 3326, 1501, 1415, 1403, 1341, 1152, 1141, 1061, 952, 811, 741, 724, 675, 637, 604 cm$^{-1}$. MS (EI) m/z 348 (M+). Anal found: C, 54.88; H, 3.79; N, 7.90.

EXAMPLE 23

5-Chloro-N-[2-(4-chlorophenyl)ethyl]-8-hydroxy-7-quinolinesulfonamide (Formula J-5 wherein $R^1$=Me, $X^1$=Cl, and $R^2$=$CH_2CH_2$-p-$ClC_6H_4$) Refer to Chart J

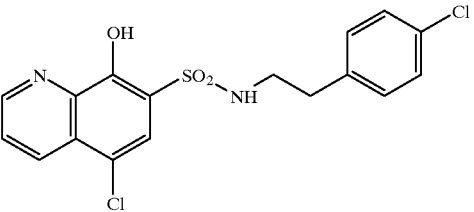

The title compound is prepared from 5,7-dibromo-8-methoxy-quinoline, which is commercially available, according to the procedures described in Preparations 6–8 and Example 17, substituting 2-(4-chlorophenyl)ethylamine for 4-chlorobenzylamine. Crystallization from $CH_2Cl_2$ gives 0.100 g of the title compound as a pale yellow solid.

Physical characteristics are as follows:

MP 192–194° C.; $^1$H NMR (300 MHz, $CDCl_3$) δ 8.94, 8.59, 7.98, 7.72, 7.12, 7.00, 5.07, 3.26, 2.79 ppm. IR (mull) 3332, 1499, 1401, 1329, 1272, 1188, 1155, 1088, 1081, 952, 824, 819, 724, 677, 633 cm$^{-1}$. MS (EI) m/z 396 (M+). Anal found: C, 51.27; H, 3.61; N, 6.98.

EXAMPLE 24

5-Bromo-8-hydroxy-N-(phenylmethyl)-7-quinolinesulfonamide (Formula J-5 wherein $R^1$=Me, $X^1$=Cl, and $R^2$=$CH_2Ph$) Refer to Chart J

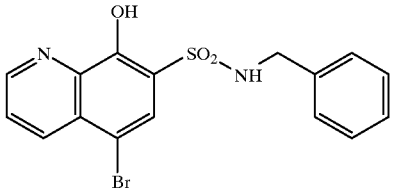

The title compound is prepared from 5,7-dibromo-8-methoxy-quinoline, which is commercially available, according to the procedures described in Preparations 6–8 and Example 18, substituting benzylamine for 4-chlorobenzylamine. Crystallization from $CH_2Cl_2$ gives 0.150 g of the title compound as a light peach solid.

Physical characteristics are as follows:

MP 191–192° C. $^1$H NMR (300 MHz, DMSO) δ 9.04, 8.47, 8.12, 7.94, 7.87, 7.22, 7.11, 7.03, 4.14 ppm. $^{13}$C NMR (75 MHz, DMSO) δ 152.3, 149.8, 139.2, 137.5, 135.2, 128.9, 128.4, 127.7, 127.4, 126.6, 125.2, 123.4, 107.5, 46.1 ppm. IR (mull) 3325, 1498, 1414, 1401, 1340, 1153, 1139, 1060, 932, 810, 791, 725, 695, 674, 630 cm$^{-1}$. MS (EI) m/z 392 (M+). HRMS (EI) found 391.9813. Anal found: C, 49.17; H, 3.59; N, 6.88.

EXAMPLE 25

5-Chloro-N-[2-(2,4-dichlorophenyl)ethyl]-8-hydroxy-2-methyl-7-quinolinesulfonamide (Formula J-5 wherein $R^1$=Me, $X^1$=Cl, and $R^2$=$CH_2CH_2$-2,3-$Cl_2C_6H_3$) Refer to Chart J

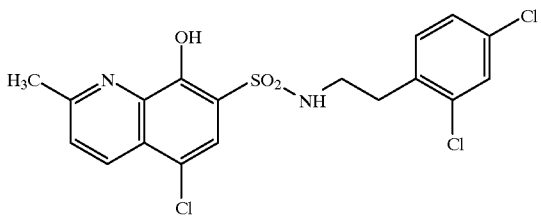

The title compound is prepared in two steps from 5-bromo-8-methoxy-2-methyl-7-quinolinesulfonyl chloride, which is the title compound of Preparation 7, according to the procedures described in Preparation 8 and Example 17, substituting 2,4-dichlorophenethylamine for 4-chlorobenzylamine in the former procedure. Column chromatography (elution with 1–2% MeOH/$CHCl_3$) followed by crystallization from $CH_2Cl_2$/hexane gives 0.35 g of the title compound as a yellow solid.

Physical characteristics are as follows:

MP 132–135° C.; $^1$H NMR (300 MHz, $CDCl_3$) δ 8.53, 7.94, 7.59, 7.19–7.04, 5.30, 3.28, 2.92, 2.88 ppm. IR (mull) 3343, 3321, 3299, 1504, 1419, 1349, 1339, 1330, 1152, 1144, 955, 824, 727, 634, 612 cm$^{-1}$. MS (EI) m/z 444 (M+). HRMS (EI) found 443.9845.

EXAMPLE 26

5-Chloro-8-hydroxy-2-methyl-N-[2-(phenylthio)ethyl]-7-quinolinesulfonamide (Formula J-5 wherein $R^1$=Me, $X^1$=Cl, and $R^2$=$CH_2CH_2SPh$) Refer to Chart J

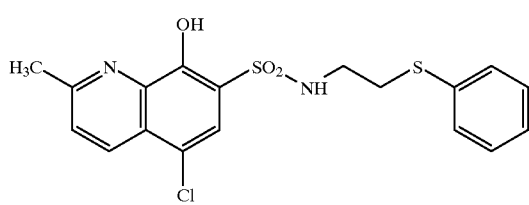

The title compound is prepared in two steps from 5-bromo-8-methoxy-2-methyl-7-quinolinesulfonyl chloride, which is the title compound of Preparation 7, according to the procedures described in Preparation 8 and Example 17, substituting 2-aminoethyl phenyl sulfide for 4-chlorobenzylamine in the former procedure. Column chromatography (elution with 1–2% MeOH/$CHCl_3$) followed by crystallization from $CH_2Cl_2$/hexane gives 0.40 g of the title compound as a yellow solid.

Physical characteristics are as follows:

MP 136–139° C.; $^1$H NMR (300 MHz, $CDCl_3$) δ 8.43, 7.89, 7.56, 7.24–7.07, 5.60, 3.14, 3.02, 2.81 ppm. IR (mull) 3355, 3271, 1438, 1419, 1342, 1329, 1308, 1153, 1141, 1078, 711, 702, 692, 632, 610 cm$^{-1}$. MS (EI) m/z 408 (M+). Anal found: C, 52.50; H, 4.14; N, 6.73; Cl, 8.77; S, 15.31.

EXAMPLE 27

5-Chloro-8-hydroxy-2-methyl-N-(phenylmethyl)-7-quinolinesulfonamide (Formula J-5 wherein $R^1$=Me, $X^1$=Cl, and $R^2$=$CH_2Ph$) Refer to Chart J

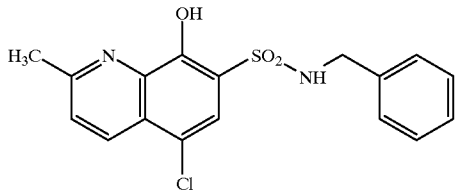

The title compound is prepared in two steps from 5-bromo-8-methoxy-2-methyl-7-quinolinesulfonyl chloride, which is the title compound of Preparation 7, according to the procedures described in Preparation 8 and Example 17, substituting benzylamine for 4-chlorobenzylamine in the former procedure. Column chromatography (elution with 0.5–1% MeOH/$CH_2Cl_2$) followed by crystallization from EtOAc/hexanes gives 0.197 g of the title compound as orange crystals.

Physical characteristics are as follows:

MP 113–114° C.; $^1$H NMR (300 MHz, $CDCl_3$) δ 8.46, 7.94, 7.57, 7.22–7.08, 5.40, 4.15, 2.82 ppm. IR (mull) 3035, 3010, 1548, 1504, 1445, 1440, 1425, 1313, 1148, 1041, 803, 734, 698, 681, 611 cm$^{-1}$. MS (EI) m/z 362 (M+). Anal found: C, 56.49; H, 4.25; N, 7.64.

EXAMPLE 28

5-Chloro-N-(4-chlorophenyl)-8-hydroxy-2-methyl-7-quinolinesulfonamide (Formula J-5 wherein $R^1$=Me, $X^1$=Cl, and $R^2$=4-Cl-$C_6H_4$) Refer to Chart J

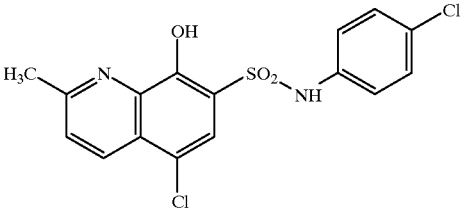

The title compound is prepared in two steps from 5-bromo-8-methoxy-2-methyl-7-quinolinesulfonyl chloride, which is the title compound of Preparation 7, according to the procedures described in Preparation 8 and Example 17, substituting 4-chloroanline for 4-chlorobenzylamine in the former procedure. Column chromatography (elution with 1% MeOH/$CHCl_3$) followed by crystallization from EtOAc/hexane and rinsing with additional EtOAc gives 0.056 g of the title compound as a beige solid.

Physical characteristics are as follows:

MP 284–287° C. (decomposition). $^1$H NMR (300 MHz, $CDCl_3$) δ 8.20, 7.56, 7.41, 6.94–6.90, 2.56 ppm. IR (mull) 1530, 1492, 1335, 1313, 1288, 1276, 1152, 1125, 1109, 1095, 827, 742, 647, 635, 610 cm$^{-1}$. MS (EI) m/z 382 (M+). HRMS (EI) found 381.9940.

EXAMPLE 29

5-Chloro-8-hydroxy-2-methyl-N-octyl-7-quinolinesulfonamide (Formula J-5 wherein $R^1$=Me, $X^1$=Cl, and $R^2$=$(CH_2)_7CH_3$) Refer to Chart J

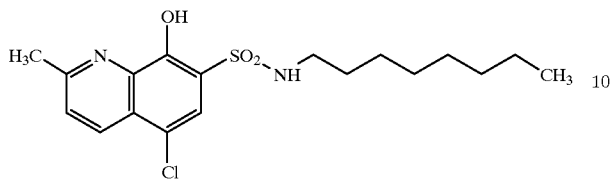

The title compound is prepared in two steps from 5-bromo-8-methoxy-2-methyl-7-quinolinesulfonyl chloride, which is the title compound of Preparation 7, according to the procedures described in Preparation 8 and Example 17, substituting n-octylamine for 4-chlorobenzylamine in the former procedure. Column chromatography (elution with 1–2% MeOH/CHCl$_3$) followed by crystallization from EtOAc/hexane gives 0.045 g of the title compound as an orange solid.

Physical characteristics are as follows:

MP 85–100° C.; $^1$H NMR (300 MHz, CDCl$_3$) δ 8.47, 7.93, 7.56, 5.22, 3.31, 2.82, 1.49–1.44, 1.32–1.09, 0.84 ppm. IR (mull) 3301, 1504, 1415, 1328, 1250, 1158, 1142, 1082, 948, 826, 725, 688, 653, 634, 614 cm$^{-1}$. MS (EI) m/z 384 (M+). HRMS (EI) found 384.1270.

EXAMPLE 30

5-Chloro-N-[4-fluorophenyl)methyl]-8-hydroxy-2-methyl-7-quinolinesulfonamide (Formula J-5 wherein $R^1$=Me, $X^1$=Cl, and $R^2$=CH$_2$-4-F-C$_6$H$_4$) Refer to Chart J

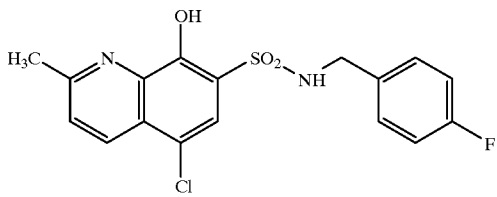

The title compound is prepared in two steps from 5-bromo-8-methoxy-2-methyl-7-quinolinesulfonyl chloride, which is the title compound of Preparation 7, according to the procedures described in Preparation 8 and Example 17, substituting 4-fluorobenzylamine for 4-chlorobenzylamine in the former procedure. Column chromatography (elution with 0.5–1% MeOH/CH$_2$Cl$_2$) gives 0.135 g of the title compound as an orange foam.

Physical characteristics are as follows:

MP 143–146° C.; $^1$H NMR (300 MHz, CDCl$_3$) δ 8.46, 7.92, 7.57, 7.18–7.15, 6.83, 5.40, 4.12, 2.82 ppm. IR (mull) 3318, 3270, 1510, 1425, 1352, 1330, 1319, 1250, 1221, 1152, 1143, 835, 829, 634, 613 cm$^{-1}$. MS (EI) m/z 380 (M+). Anal found: C, 53.96; H, 4.03; N, 7.15.

EXAMPLE 31

5-Chloro-8-hydroxy-2-methyl-N-(1-naphthalenylmethyl)-7-quinolinesulfonamide (Formula J-5 wherein $R^1$=Me, $X^1$=Cl, and $R^2$=CH$_2$-1-naphthyl) Refer to Chart J

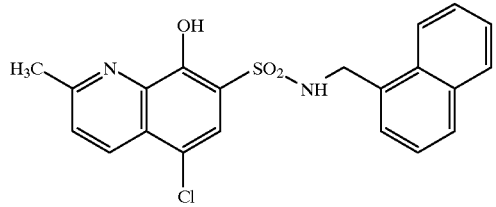

The title compound is prepared in two steps from 5-bromo-8-methoxy-2-methyl-7-quinolinesulfonyl chloride, which is the title compound of Preparation 7, according to the procedures described in Preparation 8 and Example 17, substituting 1-naphthalenemethylamine for 4-chlorobenzylamine in the former procedure. Crystallization from CH$_2$Cl$_2$/hexanes gives 0.127 g of the title compound as light brown crystals.

Physical characteristics are as follows:

MP 203–204° C.; $^1$H NMR (300 MHz, CDCl$_3$) δ 8.39, 7.97, 7.80, 7.60, 7.53, 7.46, 7.36, 7.29–7.17, 5.58, 4.63, 2.77 ppm. IR (mull) 3265, 1440, 1350, 1329, 1155, 1146, 851, 836, 800, 783, 776, 690, 640, 631, 608 cm$^{-1}$. MS (EI) m/z 412 (M+). HRMS (EI) found 412.0643.

EXAMPLE 32

5-Chloro-N-(cyclohexylmethyl)-8-hydroxy-2-methyl-7-quinolinesulfonamide (Formula J-5 wherein $R^1$=Me, $X^1$=Cl, and $R^2$=CH$_2$-cyclohexyl) Refer to Chart J

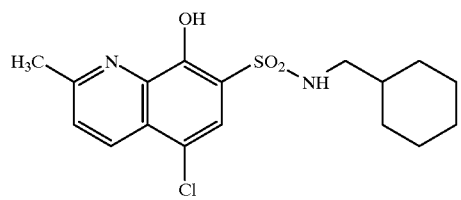

The title compound is prepared in two steps from 5-bromo-8-methoxy-2-methyl-7-quinolinesulfonyl chloride, which is the title compound of Preparation 7, according to the procedures described in Preparation 8 and Example 17, substituting cyclohexanemethylamine for 4-chlorobenzylamine in the former procedure. Column chromatography (elution with MeOH/CH$_2$Cl$_2$) gives 0.257 g of the title compound as an orange foam.

Physical characteristics are as follows:

MP 113–115° C.; $^1$H NMR (300 MHz, CDCl$_3$) δ 8.46, 7.95, 7.57, 5.12, 2.82, 2.74, 1.75–1.62, 1.53–1.42, 1.29–1.08, 0.95–0.82 ppm. IR (mull) 3284, 1503, 1413, 1344, 1338, 1329, 1249, 1159, 1143, 1061, 9413, 825, 725, 688, 610 cm$^{-1}$. MS (EI) m/z 368 (M+). Anal found: C, 55.62; H, 5.89; N, 7.46.

EXAMPLE 33

5-Chloro-N-[(3-chlorophenyl)methyl]-8-hydroxy-2-methyl-7-quinolinesulfonamide (Formula J-5 wherein $R^1$=Me, $X^1$=Cl, and $R^2$=CH$_2$-3-Cl-C$_6$H$_4$) Refer to Chart J

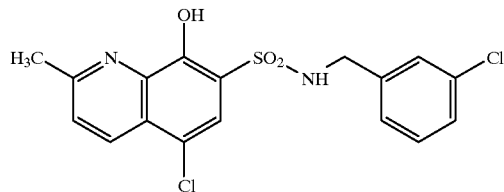

The title compound is prepared in two steps from 5-bromo-8-methoxy-2-methyl-7-quinolinesulfonyl chloride, which is the title compound of Preparation 7, according to the procedures described in Preparation 8 and Example 17, substituting 3-chlorobenzylamine for 4-chlorobenzylamine in the former procedure. Column chromatography (elution with 0.5–2% MeOH/CH$_2$Cl$_2$) gives 0.154 g of the title compound as a solid.

Physical characteristics are as follows:

MP 52–54° C.; $^1$H NMR (300 MHz, CDCl$_3$) δ 8.43, 7.88, 7.56, 7.18–7.00, 5.48, 4.16, 2.80 ppm. IR (mull) 3311, 1600, 1503, 1433, 1329, 1251, 1158, 1143, 952, 829, 727, 704, 687, 634, 617 cm$^{-1}$. MS (EI) m/z 396 (M+). Anal found: C, 51.27; H, 3.64; N, 7.00.

EXAMPLE 34

5-Chlorohydroxy-2-methyl-N-(3-phenylpropyl)-7-quinolinesulfonamide (Formula J-5 wherein $R^1$=Me, $X^1$=Cl, and $R^2$=CH$_2$CH$_2$CH$_2$Ph) Refer to Chart J

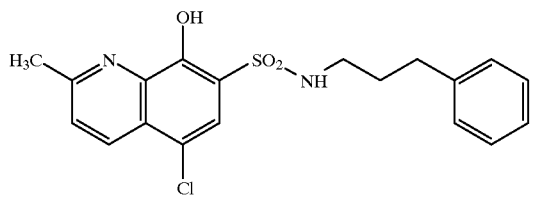

The title compound is prepared in two steps from 5-bromo-8-methoxy-2-methyl-7-quinolinesulfonyl chloride, which is the title compound of Preparation 7, according to the procedures described in Preparation 8 and Example 17, substituting 3-phenylpropylamine for 4-chorobenzylamine in the former procedure. Column chromatography (elution with 0.5% MeOH/0.005% NH$_4$OH/CH$_2$Cl$_2$ to 1% MeOH/0.01% NH$_4$OH/CH$_2$C$_2$) gives 0.343 g of the title compound as an orange foam.

Physical characteristics are as follows:

MP 131–134° C.; $^1$H NMR (300 MHz, CDCl$_3$) δ 8.45, 7.93, 7.56, 7.24–7.10, 7.08, 5.11, 2.97, 2.80, 2.63, 1.83 ppm. IR (mull) 3231, 1416, 1350, 1329, 1253, 1154, 1151, 949, 827, 755, 727, 701, 687, 634, 612 cm$^{-1}$. MS (EI) m/z 390 (M+). HRMS (EI) found 390.0798. Anal found: C, 58.40; H, 5.00; N, 7.04.

EXAMPLE 35

5-Chloro-8-hydroxy-2-methyl-N-(2-phenoxyethyl)-7-quinolinesulfonamide (Formula J-5 wherein $R^1$=Me, $X^1$=Cl, and $R^2$=CH$_2$CH$_2$OPh) Refer to Chart J

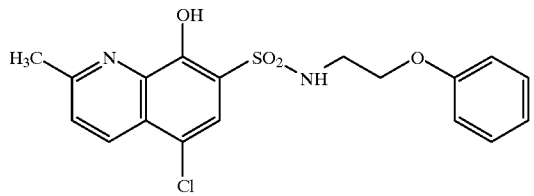

The title compound is prepared in two steps from 5-bromo-8-methoxy-2-methyl-7-quinolinesulfonyl chloride, which is the title compound of Preparation 7, according to the procedures described in Preparation 8 and Example 17, substituting 2-phenoxyethylamine for 4-chlorobenzylamine in the former procedure. Column chromatography (elution with 0.5–1% MeOH/CH$_2$Cl$_2$) followed by crystallization from CH$_2$Cl$_2$/hexanes gives 0.310 g of the title compound as orange crystals.

Physical characteristics are as follows:

MP 106–107° C.; $^1$H NMR (300 MHz, CDCl$_3$) δ 8.38, 7.95, 7.51, 7.12, 6.82, 6.65, 5.72, 3.92, 3.43, 2.77 ppm. IR (mull) 2801, 1550, 1499, 1430, 1421, 1408, 1319, 1246, 1233, 1162, 1150, 782, 758, 699, 689 cm$^{-1}$. MS (EI) m/z 392 (M+). HRMS (EI) found 392.0586.

EXAMPLE 36

5-Chloro-8-hydroxy-2-methyl-N-[3-(4-morpholinyl)propyl]-7-quinoline-sulfonamide (Formula J-5 wherein $R^1$=Me, $X^1$=Cl, and $R^2$=CH$_2$CH$_2$CH$_2$-morpholine) Refer to Chart J

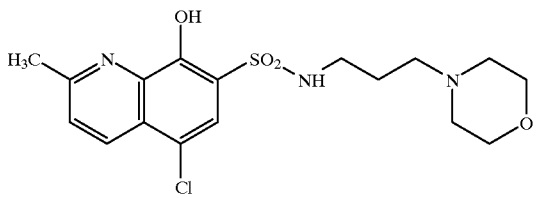

The title compound is prepared in two steps from 5-bromo-8-methoxy-2-methyl-7-quinolinesulfonyl chloride, which is the title compound of Preparation 7, according to the procedures described in Preparation 8 and Example 17, substituting N-(3-aminopropyl)morpholine for 4-chlorobenzylamine in the former procedure. Washing with CH$_2$Cl$_2$ gives 0.029 g of the title compound as a beige solid.

Physical characteristics are as follows:

MP 245–257° C.; $^1$H NMR (300 MHz, CDCl$_3$) δ 8.50, 7,93, 7.58, 6.34, 4.30, 4.00, 3.57, 3.23, 2.98–2.86, 2.85, 2.21 ppm. Ms (EI) m/z 399 (M+). HRMS (EI) found 399.1021.

EXAMPLE 37

5-Chloro-8-hydroxy-N-[3-(1H-imidazol-1-yl)propyl]-2-methyl-7-quinolinesulfonamide (Formula J-5 wherein $R^1$=Me, $X^1$=Cl, and $R^2$=$CH_2CH_2CH_2$-1-imidazole) Refer to Chart J

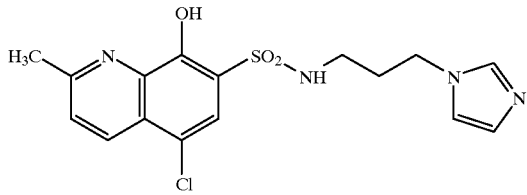

The title compound is prepared in two steps from 5-bromo-8-methoxy-2-methyl-7-quinolinesulfonyl chloride, which is the title compound of Preparation 7, according to the procedures described in Preparation 8 and Example 17, substituting 1-(3-aminopropylimidazole for 4-chlorobenzylamine in the former procedure. Washing with $CH_2Cl_2$ gives 0.042 g of the title compound as a light brown solid.

Physical characteristics are as follows:

MP 194–196° C.; $^1$H NMR (300 MHz, DMSO-$d_6$) δ 8.46, 7.81, 7.67, 7.09, 6.94, 4.11, 2.91, 2.79, 1.95 ppm. MS (EI) m/z 380 (M+). HRMS (EI) found 380.0703.

EXAMPLE 38

5-Chloro-N-(diphenylmethyl)-8-hydroxy-2-methyl-7-quinolinesulfonamide (Formula J-5 wherein $R^1$=Me, $X^1$=Cl, and $R^2$=CH(Ph)$_2$) Refer to Chart J

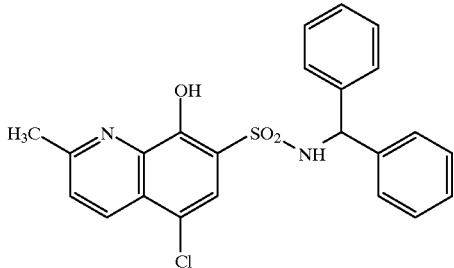

The title compound is prepared in two steps from 5-bromo-8-methoxy-2-methyl-7-quinolinesulfonyl chloride, which is the title compound of Preparation 7, according to the procedures described in Preparation 8 and Example 17, substituting 1,1-diphenylmethylamine for 4-chlorobenzylamine in the former procedure. Column chromatography (elution with 0.5–1% MeOH/$CH_2Cl_2$) gives 0.156 g of the title compound as an orange foam.

Physical characteristics are as follows:

MP 115–119° C.; $^1$H NMR (300 MHz, CDCl$_3$) δ 8.35, 7.73, 7.51, 7.11–6.98, 5.76, 5.58, 2.76 ppm. IR (mull) 3298, 1495, 1422, 1329, 1251, 1161, 1144, 952, 743, 727, 699, 689, 652, 634, 614 cm$^{-1}$. MS (EI) m/z 438 (M+). HRMS (EI) found 438.0971.

EXAMPLE 39

(R)-5-Chloro-8-hydroxy-2-methyl-N-(1-phenylethyl)-7-quinolinesulfonamide (Formula J-5 wherein $R^1$=Me, $X^1$=Cl, and $R^2$=CH(Me)Ph) Refer to Chart J

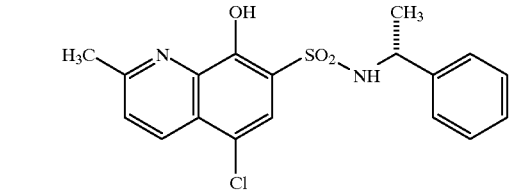

The title compound is prepared in two steps from 5-bromo-8-methoxy-2-methyl-7-quiolinesulfonyl chloride, which is the title compound of Preparation 7, according to the procedures described in Preparation 8 and Example 17, substituting (R)-(+)-α-methylbenzylnine for 4-chlorobenzylamine in the former procedure. Column chromatography (elution with 0.5–1% MeOH/$CH_2Cl_2$) followed by precipitation of contaminant from $CH_2Cl_2$/hexanes gives 0.178 g of the title compound as an orange foam.

Physical characteristics are as follows:

MP 84–88° C.; [α]$_D$ (CHCl$_3$)=49°. $^1$H NMR (300 MHz, CDCl$_3$) δ 8.35, 7.72, 7.51, 7.05, 6.93, 6.84, 5.41, 4.48, 2.77, 1.47 ppm. IR (mull) 3290, 1503, 1496, 1427, 1329, 1251, 1160, 1145, 1120, 952, 727, 701, 689, 635, 623 cm$^{-1}$. MS (EI) m/z 376 (M+).

EXAMPLE 40

(S)-5-Chloro-8-hydroxy-2-methyl-N-(1-phenylethyl)-7-quinolinesulfonamide (Formula J-5 wherein $R^1$=Me, $X^1$=Cl, and $R^2$=CH(Me)Ph) Refer to Chart J

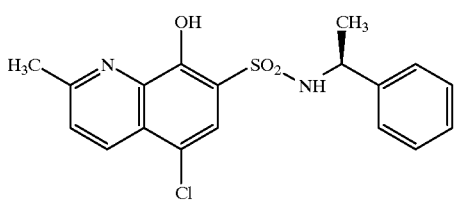

The title compound is prepared in two steps from 5-bromo-8-methoxy-2-methyl-7-quinolinesulfonyl chloride, which is the title compound of Preparation 7, according to the procedures described in Preparation 8 and Example 17, substituting (S)-(−)-α-methylbenylamine for 4-chlorobenzylamine in the former procedure. Column chromatography (elution with 0.5–1% MeOH/$CH_2Cl_2$) gives 0.196 g of the title compound as an orange foam.

Physical characteristics are as follows:

MP 83–87° C.; [α]$_D$ (CHCl$_3$)=+57°. $^1$H NMR (300 MHz, CDCl$_3$) δ 8.36, 7.73, 7.52, 7.05, 6.93, 6.85, 5.40, 4.49, 2.78, 1.48 ppm. IR (mull) 3299, 1503, 1496, 1423, 1329, 1251, 1160, 1146, 1085, 952, 727, 701, 689, 635, 624 cm$^{-1}$. MS (EI) m/z 376 (M+). Anal found: C, 57.73; H, 4.63; N, 7.32.

PREPARATION 11

5-Chloro-8-[(1,1-dimethylethyl)dimethylsilyloxy]-7-iodoquinoline (Formula K-2 wherein $X^1$=Cl, $X^2$=I, $(R)_3$=($Me_2$)t-Bu) Refer to Chart K

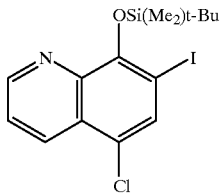

A flame-dried, 50-mL, three-necked flask is charged with 5-chloro-8-hydroxy-7-iodoquinoline (2.814 g), which is commercially available, t-butyldimethylchlorosilane (1.76 g), and 10 mL of DMF. Imidazole (1.66 g) is added, and the resulting mixture is stirred at room temperature for 18 h. The reaction mixture is then quenched with 10 mL of saturated aqueous $NaHCO_3$ and extracted with hexane three times. The combined organic layers are dried over $MgSO_4$, filtered and concentrated to give 3.898 g of the title compound as a pale green solid.

Physical characteristics are as follows:

MP 65–67° C.; $^1$H NMR (300 MHz, DMSO) δ 8.94, 8.48, 8.07, 7.73, 1.08, 0.32 ppm IR (mull) 1570, 1485, 1408, 1356, 1255, 1250, 1244, 1097, 868, 838, 806, 782, 678, 654, 640 cm$^{-1}$. MS (FAB) m/z 420 (MH+). Anal found: C, 43.05; H, 4.63; N, 3.31; Cl, 8.38.

EXAMPLE 41

5-Chloro-7-[(1,1-dimethylethyl)dimethylsilyl]-8-quinolinol (Formula K-3 wherein $X^1$=Cl, and $(R)_3$= ($Me_2$)t-Bu) Refer to Chart K

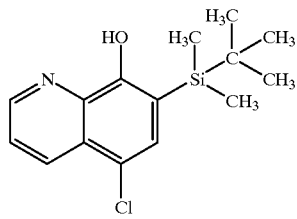

A flame-dried, 25-mL, two-necked flask is charged with the title compound of Preparation 11 (0.431 g) and 7 mL of THF. The resulting solution is cooled to −78° C., and t-butyllithium (1.2 mL of 1.7 M solution in pentane) is added dropwise over 2 min. The reaction mixture is stirred for an additional 15 min at −78° C., the quenched by pouring into 5 mL of half-saturated $NH_4Cl$ (aq). The mixture is extracted with 50 mL of EtOAc. The organic layer is separated, washed with 15 mL of saturated $NaHCO_3$ (aq), dried over $MgSO_4$, filtered and concentrated to give 0.289 g of an off-white solid. Column chromatography (elution with 2% EtOAc/hexane) yields 0.101 g of the title compound as a white solid.

Physical characteristics are as follows:

MP 107–108° C.; $^1$H NMR (300 MHz, DMSO) δ 10.08, 8.94, 8.47, 7.74, 7.49, 0.88, 0.36 ppm. $^{13}$C NMR (75 MHz, DMSO) δ 158.0, 149.0, 138.2, 132.6, 132.2, 126.4, 123.7, 118.4, 118.3, 26.9, 17.6, 4.8 ppm. IR (mull) 3446, 1408, 1398, 1322, 1255, 1194, 949, 875, 836, 823, 810, 786, 775, 718, 675 cm$^{-1}$. MS (FAB) m/z 294 (MH+). HRMS (FAB) found 294.1075.

EXAMPLE 42

5-Chloro-7-[(tris(1-methylethyl)silyl]-8-quinolinol (Formula K-3 wherein $X^1$=Cl, and R=i-Pr) Refer to Chart K

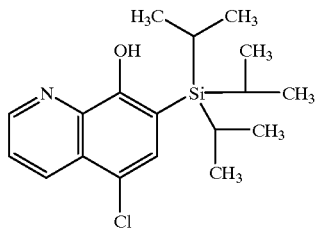

The title compound is prepared in two steps from 5-chloro-8-hydroxy-7-iodoquinoline, which is commercially available, according to the procedures described in Preparation 11 and Example 41, substituting triisopropylchlorosilane for t-butyldimethylchlorosilane in the former procedure. Column chromatography (elution with hexane) gives 0.202 g of the title compound as a white solid.

Physical characteristics are as follows:

MP 107–108° C.; $^1$H NMR (300 MHz, CDCl$_3$) δ 8.80, 8.76, 8.52, 7.57, 7.56, 1.58, 1.13 ppm. IR (mull) 3430, 1485, 1399, 1321, 1256, 1196, 1181, 949, 882, 789, 719, 681, 670, 644, 610 cm$^{-1}$. MS (FAB) m/z 336 (MH+). HRMS (FAB) found 392.2167. Anal found: C, 64.68; H, 7.87; N, 4.04.

EXAMPLE 43

5-Chloro-7-[(1,1-dimethylethyl)diphenylsilyl]-8-quinolinol (Formula K-3 wherein $X^1$=Cl, and $(R)_3$= $Ph_2$t-Bu) Refer to Chart K

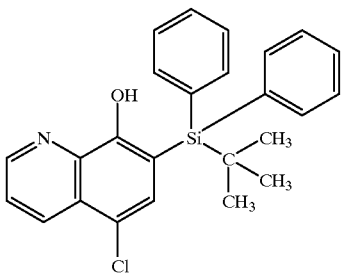

The title compound is prepared in two steps from 5-chloro-8-hydroxy-7-iodoquinoline, which is commercially available, according to the procedures described in Preparation 11 and Example 41, substituting t-butyldiphenylchlorosilane for t-butyldimethylchlorosilane in the former procedure. Column chromatography (elution with 1% EtOAc/hexane) gives 0.078 g of the title compound as a white foam.

Physical characteristics are as follows:

Mp 133–139° C.; $^1$H NMR (300 MHz, CDCl$_3$) δ 8.95, 8.83, 8.54, 7.62–7.56, 7.42–7.31, 1.26 ppm. IR (mull) 3317, 1485, 1428, 1398, 1339, 1198, 1110, 1103, 950, 786, 741, 719, 699, 666, 605 cm$^{-1}$. MS (FAB) m/z 418. HRMS (FAB) found 418.1393. Anal found: C, 71.73; H, 5.72; N, 3.29.

EXAMPLE 44

5-Chloro-7-(trimethylsilyl)-8-quinolinol (Formula K-3 wherein $X^1$=Cl, and R=Me) Refer to Chart K

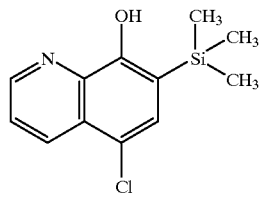

The title compound is prepared in two steps from 5-chloro-8-hydroxy-7-iodoquinoline, which is commercially available, according to the procedures described in Preparation 11 and Example 41, substituting trimethylchlorosilane for t-butyldimethylchlorosilane in the former procedure. Column chromatography (elution with 0–1% EtOAc/hexane) gives 0.147 g of the title compound as a white solid.

Physical characteristics are as follows:

MP 109–111° C.; $^1$H NMR (300 MHz, CDCl$_3$) δ 8.80, 8.55, 8.50, 7.55, 0.41 ppm. IR (mull) 3414, 3377, 1398, 1334, 1243, 1202, 950, 883, 839, 788, 757, 717, 628, 613, 605 cm$^{-1}$. MS (FAB) m/z 252 (MH+). HRMS (FAB) found 252.0597. Anal found: C, 57.50; H, 5.54; N, 5.48.

EXAMPLE 45

5-Chloro-7-dimethylphenylsilyl)-8-quinolinol (Formula K-3 wherein $X^1$=Cl, and (R)$_3$=Me$_2$Ph) Refer to Chart K

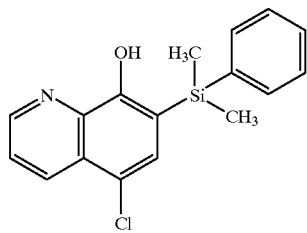

The title compound is prepared in two steps from 5-chloro-8-hydroxy-7-iodoquinoline, which is commercially available, according to the procedures described in Preparation 11 and Example 41, substituting triisopropylchlorosilane for t-butyldimethylchlorosilane in the former procedure. Column chromatography (elution with 1% EtOAc/hexane) gives 0.065 g of the title compound as a white solid.

Physical characteristics are as follows:

MP 101–103° C.; $^1$H NMR (300 MHz, CDCl$_3$) δ 8.80, 8.61, 8.49, 7.65–7.62, 7.55, 7.45, 7.39–7.37. 0.70 ppm. IR (mull) 3323, 1427, 1396, 1324, 1249, 1188, 949, 879, 837, 819, 783, 719, 700, 696, 665 cm$^{-1}$. MS (FAB) m/z 314 (MH+). HRMS (FAB) found 314.0763. Anal found: C, 64.85; H, 5.24; N, 4.46.

EXAMPLE 46

N-[(4-Chlorophenyl)methyl]-4,8-dihydroxy-2-trifluoromethyl-7-quinolinecarboxamide

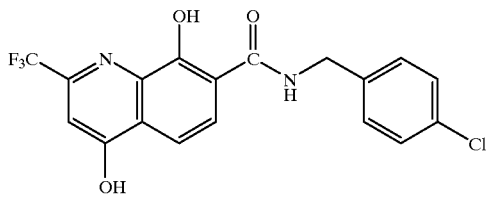

To a solution of the title compound of Preparation 20 (0.273 g) in 10 mL DMF is added 4-chlorobenzylamine (0.134 mL), EDC-HCl (0.210 g) and HOBt-H2O (0.149 g). The mixture is allowed to stir for 3 days, then poured into 50 mL of ice-water. The resulting precipitate is collected and dried. The crude product is recrystallized from EtOAc/hexanes to yield 0.245 g of the title compound as a tan solid.

Physical characteristics are as follows:

MP 135–140° C. (dec). $^1$H NMR (DMSO) δ 13.83, 12.46, 9.60, 8.02, 7.61, 7.39, 7.20, 4.54. IR (mull) 1924, 1905, 1644, 1629, 1600, 1585, 1558, 1527, 1428, 1338, 1270, 1254, 1189, 1174, 1137 cm$^{-1}$. MS (EI) m/z 396 (M+), 398, 396, 256, 255, 229, 140, 127, 126, 125, 89. Anal. found: C, 54.42; H, 3.17; N, 6.85; Cl, 8.66.

PREPARATION 12

2-[2-(4-Methoxyphenyl)ethenyl]-8-quinolinol

A mixture of 8-hydroxyquinaldine (9.93 g) and p-anisaldehyde (20 mL) is heated at 180° C. overnight. The reaction is then cooled to room temperature and vacuum distilled. Once the majority of the p-anisaldehyde is distilled off (below 100° C.), the residue remaining in the flask is taken up in hot 95% EtOH. Any undissolved material is filtered off. H$_2$O is added to the EtOH filtrate and the product is obtained as a yellow solid (3.42 g).

Physical characteristics are as follows:

MP 108–110° C.; $^1$H NMR (300 MHz, CDCl$_3$) δ 8.15, 7.69, 7.59, 7.39, 7.30, 7.27, 7.18, 6.95, 3.86. $^{13}$C NMR (75 MHz, DMSO-d$_6$) δ 160.21, 154.25, 153.30, 138.60, 136.84, 134.58, 129.56, 129.10, 127.97, 127.24, 126.10, 121.25, 118.02, 114.84, 111.59, 55.66. IR (mull) 3420, 2290, 2039, 1943, 1603, 1598, 1558, 1513, 1505, 1273, 1255, 1240. MS (OAMS) 278.2 (M+). Anal. found: C, 77.48; H, 5.37; N, 5.14.

PREPARATION 13

2-(2-Phenylethenyl)-8-quinolinol

A mixture of 8-hydroxyquinaldine (10.02 g) and benzaldehyde (16.8 mL) is heated at reflux overnight. The reaction is cooled to room temperature and vacuum distilled. After the excess benzaldehyde has distilled off, the residue remaining in the flask is dissolved in hot 95% EtOH. Any undissolved material is filtered off. The EtOH filtrate is cooled slowly to give the product as light yellow crystals (5.17 g).

Physical characteristics are as follows:

MP 70–72° C.; $^1$H NMR (300 MHz, CD$_3$OD) δ 8.17, 7.82, 7.77, 7.68, 7.66, 7.44, 7.39, 7.36, 7.31, 7.08. $^{13}$C NMR (75 MHz, CD$_3$OD) δ 154.09, 152.60, 138.23, 136.63, 136.18, 134.19, 128.41, 128.23, 127.97, 127.92, 126.89, 126.74, 119.54, 117.53, 110.55. IR (mull) 1949, 1915, 1903, 1444, 1337, 1260, 1089, 960, 956, 836, 756, 747, 724, 697, 689 cm$^{-1}$. MS (OAMS) 248.2 (M+). Anal. found: C, 82.38; H, 5.28; N, 5.68.

EXAMPLE 47

N-[(4-Chlorophenyl)methyl]-8-hydroxy-2-[2-(4-methoxyphenyl)ethenyl]-7-quinolinecarboxamide The title compound of Preparation 14 (0.25 g) and 4-chlorobenzylamine (0.10 mL) are dissolved in 10 mL DMF. EDC.HCl (0.16 g) and HOBt.H$_2$O (0.11 g) is added in one portion and the reaction is allowed to stir at room temperature overnight. The reaction is then poured into 50 mL ice/water. The resulting orange solid is filtered and chromatographed on silica gel (eluent 2% MeOH:CH$_2$Cl$_2$). The product-containing fractions are evaporated under reduced pressure to give the product as a light brown solid (0.029 g).

Physical characteristics are as follows:

MP 200–201° C.; $^1$H NMR (300 MHz, DMSO-d$_6$) δ 9.28, 8.27, 7.95, 7.88, 7.66, 7.40, 7.37, 7.33, 7.00, 4.56, 3.78. $^{13}$C NMR (75 MHz, DMSO-d$_6$) δ 168.46, 160.33, 156.50, 155.32, 139.29, 138.64, 136.80, 134.97, 131.96, 129.83, 129.71, 129.37, 129.23, 128.82, 126.11, 124.85, 122.46, 117.37, 114.86, 113.31, 60.93, 55.70. IR (mull) 2428, 2287, 2050, 2016, 1951, 1640, 1600, 1535, 1514, 1439, 1266, 1237, 1173, 1107, 846 cm$^{-1}$. MS (OAMS) 322.2 (M$^+$). HRMS (EI) found 444.1247. Anal. found: C, 67.36; H, 4.70; N, 6.11.

PREPARATION 14

8-Hydroxy-2-[2-(4-methoxyphenyl)ethenyl]-7-quinolinecarboxylic Acid

The title compound of Preparation 12 (3.00 g) is mixed with K$_2$CO$_3$ (4.51 g) and loaded into a small stainless steel bomb. The bomb is flushed 3× with 100 psi CO$_2$ and then pressurized to the pressure of the CO$_2$ tank. The bomb is heated at 170° C. for 7 days, maintaining a final pressure of approximately 1200 psi. The bomb is de-pressurized and cooled to room temperature. The residue is dissolved in a minimal amount of warm water. The aqueous mixture is acidified with concentrated HCl. The material which precipitates at pH 7 (starting material) is filtered and the filtrate is further acidified to pH 4. The product is obtained as a yellow/orange solid which is further purified by trituration in iPrOH (0.74 g).

Physical characteristics are as follows:

MP 217–219° C.; $^1$H NMR (300 MHz, DMSO-d$_6$) δ 8.51, 8.17, 7.96, 7.84, 7.67, 7.58, 7.28, 7.03, 3.80. $^{13}$C NMR (75 MHz, DMSO-d$_6$) δ 171.49, 161.15, 159.55, 153.84, 140.30, 138.81, 135.38, 131.05, 129.84, 128.68, 127.56, 122.21, 121.57, 115.41, 115.05, 112.74, 55.79. IR (mull) 2035, 1932, 1628, 1596, 1573, 1515, 1428, 1338, 1328, 1315, 1289, 1269, 1250, 1176, 836 cm$^{-1}$. MS (EI) m/z 321 (M+), 321, 303, 302, 277, 276, 275, 274, 260, 232, 151. HRMS (EI) found 321.1001. Anal. found: C, 66.11; H, 4.77; N, 4.02.

PREPARATION 15

8-Hydroxy-2-(2-phenylethenyl)-7-quinolinecarboxylic Acid

The title compound of Preparation 13 (3.50 g) and K$_2$CO$_3$ (6.00 g) are mixed and placed in a stainless steel bomb. The bomb is flushed 2× with 100 psi CO$_2$ and then pressurized to approximately 800 psi CO$_2$. The reaction us heated at 170° C. for 7 days, maintaining a pressure of 1300 psi. The bomb is then cooled to room temperature and the pressure released. The residue is dissolved in 900 mL H$_2$O warm water. The aqueous mixture is acidified to pH 4 with concentrated HCl to give a bright orange solid. The solid is then triturated in iPrOH to give the product (2.21 g).

Physical characteristics are as follows:

MP 208–210° C.; $^1$H NMR (300 MHz, DMSO-d$_6$) δ 8.43, 8.10, 7.94, 7.82, 7.72, 7.62, 7.43, 7.31. $^{13}$C NMR (75 MHz, DMSO-d$_6$) δ 171.87, 160.31, 154.06, 138.74, 137.54, 136.76, 136.36, 131.34, 129.67, 129.42, 127.90, 127.06, 126.74, 122.10, 116.00, 111.82. IR (mull) 1945, 1904, 1722, 1687, 1617, 1596, 1579, 1563, 1489, 1435, 1419, 15 1410, 1351, 1304, 1208 cm$^{-1}$. MS (EI) m/z 291 (M+) 291, 291, 273, 272, 248, 247, 246, 245, 244, 217, 216. HRMS (EI) found 291.0910. % Water (KF): 1.42. Anal. found: C, 72.28; H, 4.71; N, 4.76.

EXAMPLE 48

N-Heptyl-8-hydroxy-2-[2-(4-methoxyphenyl)ethenyl]-7-quinolinecarboxamide

The title compound of Preparation 14 (0.16 g) and heptylamine (0.08 mL) are dissolved in 6 mL DMF. EDC.HCl (0.10 g) and HOBt.H$_2$O (0.07 g) are added in one portion and the reaction is stirred at room temperature for 3 days. The reaction is poured into 50 mL ice/H$_2$O. The aqueous solution is extracted 3× with EtOAc. The organic layers are combined, dried over MgSO$_4$, evaporated, and adsorbed onto silica. The product is purified by silica gel chromatography (eluent 2% MeOH:CH$_2$Cl$_2$). The product containing fractions are evaporated and the resulting residue is crystallized with Et$_2$O/hexanes to give the product as a tan solid (0.019 g).

Physical characteristics are as follows:

MP 115–116° C.; $^1$H NMR (300 MHz, DMSO-d$_6$) δ 8.77, 8.26, 7.91, 7.87, 7.66, 7.33, 7.31, 7.00, 3.79, 3.33, 1.57, 1.28, 0.84. MS (EI) m/z 418 (M+), 418, 305, 304, 302, 278, 277, 276, 275, 260, 152. HRMS (FAB) found 419.2335. Anal. found: C, 72.67; H, 6.87; N, 6.45.

EXAMPLE 49

N-Heptyl-8-hydroxy-2-(2-phenylethenyl)-7-quinolinecarboxamide

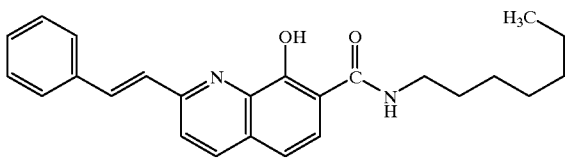

The title compound of Preparation 15 (0.31 g) and heptylamine (0.17 mL) are dissolved in 12 mL DMF. EDC.HCl (0.22 g) and HOBt.H$_2$O (0.16 g) are added and the reaction is stirred at room temperature for 3 days. The reaction is then poured into 50 mL ice/H$_2$O and the aqueous solution is extracted 3x with EtOAc. The EtOAc extracts are combined, dried over MgSO$_4$, evaporated, and the residue is adsorbed onto silica. The product is purified by chromatography (eluent 1% MeOH:CH$_2$Cl$_2$). The product containing fractions are evaporated under reduced pressure and the residue crystallized with Et$_2$O/hexanes to give the product as a light brown solid (0.10 g).

Physical characteristics are as follows:

MP 113–115° C.; $^1$H NMR (300 MH, DMSO-d$_6$), δ 8.78, 8.26, 7.94, 7.89, 7.90, 7.69, 7.47, 7.40, 7.33, 3.33, 1.54, 1.24, 0.81. R (mull) 3387, 2281, 1960, 1944, 1927, 1643, 1600, 1547, 1504, 1441, 1152, 989, 751, 690, 622 cm$^{-1}$. MS (OAMS) 389.2 (M+). HRMS (EI) found: 388.2127. Anal. found: C, 76.75; H, 7.38; N, 7.28.

EXAMPLE 50

8-Hydroxy-N-(2-hydroxy-2-phenylethyl)-2-(2-phenylethenyl)-7-quinolinecarboxamide

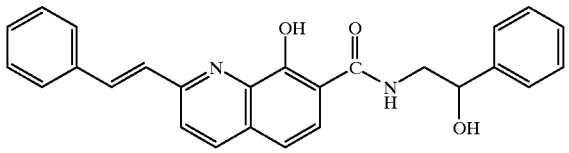

The title compound of Preparation 15 (0.33 g) and 2-amino-1-phenylethanol (0.18 g) are dissolved in 10 mL DMF. EDC.HCl (0.24 g) and HOBt.H$_2$O (0.17 g) are added in one portion and the reaction is allowed to stir at room temperature for 4 days. The reaction is poured into 50 mL ice/H$_2$O and the resulting solid is filtered. The solid is dissolved in EtOAc. To remove unreacted starting material, hexanes are added and the solid is filtered. The product is obtained as a foamy orange solid upon evaporation of the filtrate (0.17 g).

Physical characteristics are as follows:

MP 83–86° C.; $^1$H NMR (300 MHz, DMSO-d$_6$) δ 8.92, 8.31, 8.10, 7.96, 7.89, 7.72, 7.49, 7.34, 5.68, 4.80, 3.65. $^{13}$C NMR (75 MHz, DMSO-d$_6$) δ 167.42, 155.51, 154.83, 144.02, 139.21, 136.93, 136.83, 135.30, 129.81, 129.39, 129.22, 128.58, 128.33, 127.71, 127.62, 126.44, 125.79, 122.84, 117.43, 113.84, 71.45, 60.67, 47.73. IR (mull) 3376, 3059, 3028, 1950, 1640, 1600, 1545, 1506, 1495, 1436, 1418, 1350, 1329, 751, 699 cm$^{-1}$. MS (FAB) m/z 411 (MH+), 487, 413, 412, 411, 410, 304, 303, 275, 274, 248. HRMS (FAB) found 411.1710. Anal. found: C, 75.00; H, 5.40; N, 7.23.

EXAMPLE 51

N-[(4-Chlorophenyl)methyl]-8-hydroxy-2-(2-phenylethenyl)-7-quinolinecarboxamide

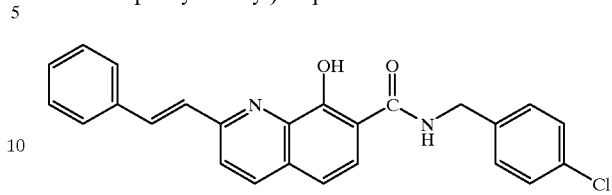

The title compound of Preparation 15 (0.25 g) and 4-chlorobenzylamine (0.12 mL) are dissolved in 10 mL DMF. EDC.HCl (0.19 g) and HOBt.H$_2$O (0.13 g) are added and the reaction is stirred at room temperature for 3 days. The reaction is poured into 50 mL ice/H$_2$O and the resulting solid is filtered and dried. The solid is recrystallized from EtOAc to give the product as a yellow solid (0.12 g).

Physical characteristics are as follows:

MP 192–194° C.; $^1$H NMR (300 MHz, DMSO-d$_6$) δ 9.29, 8.31, 8.01, 7.92, 7.71, 7.49, 7.39, 4.57. $^{13}$C NMR (75 MHz, DMSO-d$_6$) δ 168.44, 156.56, 154.97, 139.35, 138.62, 136.89, 136.77, 135.16, 131.97, 130.01, 129.72, 129.38, 129.22, 128.82, 128.53, 27.71, 125.10, 122.68, 117.43, 113.38, 42.50. IR (mull) 3383, 2285, 1946, 1930, 1641, 1603, 1536, 1506, 1435, 1425, 1341.5, 106, 963, 750, 612 cm$^{-1}$. MS (FAB) m/z 415 (MH+), 418, 417, 416, 415, 414, 275, 274, 247, 125, 123. HRMS (FAB) found 415.1206. Anal. found: C, 70.89; H, 4.72; N, 6.52.

EXAMPLE 52

8-Hydroxy-2-(2-phenylethenyl)-N-[2-(phenylthio)ethyl]-7-quinolinecarboxamide

The title compound of Preparation 15 (0.23 g) and CDI (0.14 g) are dissolved in 15 mL DMF and stirred at room temperature overnight. 2-Aminoethyl phenylsulfide (0.14 g) is added and the reaction is allowed to stir for 5 days. The reaction is then poured into 50 mL ice/H$_2$O and stirred for 2 hours. The resulting light yellow solid is filtered and dried. The solid is recrystallized from EtOAc/hexanes to give the product as a light brown solid (0.18 g).

Physical characteristics are as follows:

MP 131–132° C.; $^1$H NMR (300 MHz, DMSO-d$_6$) δ 9.00, 8.30, 8.00, 7.92, 7.87, 7.72, 7.49, 7.40, 7.33, 7.18, 3.58, 3.21. $^{13}$C NMR (75 MHz, DMSO-d$_6$) δ 168.47, 156.63, 154.97, 139.38, 136.88, 136.77, 135.96, 135.14, 130.02, 129.60, 129.39, 129.22, 128.68, 128.57, 127.72, 126.31, 125.06, 122.65, 117.37, 113.20, 31.81. IR (mull) 3378, 2294, 1943, 1932, 1645, 1603, 1536, 1505, 1435, 1424, 1144, 747, 731, 683, 622 cm$^{-1}$. MS (OAMS) 427.3 (MH+). HRMS (EI) found 426.1390. Anal. found: C, 72.48; H, 5.22; N, 6.55.

EXAMPLE 53

8-Hydroxy-N-(2-hydroxy-2-phenylethyl)-2-[2-(4-methoxyphenyl)ethenyl]-7-quinolinecarboxamide

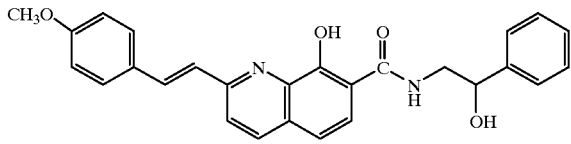

The title compound of Preparation 14 (0.57 g) and 2-amino-1-phenylethanol (0.26 g) are dissolved in 15 mL DMF. EDC.HCl (0.37 g) and HOBt.H$_2$O (0.25 g) Acre added and the reaction is stirred at room temperature for 4 days. The reaction is poured into 100 mL ice/H$_2$O. The resulting solid is filtered, dried, and recrystallized from EtOAc/hexanes to give the product as an orange solid (0.26 g).

Physical characteristics are as follows:

MP 203–205° C.; $^1$H NMR (300 MHz, DMSO-d$_6$) δ 8.92, 8.27, 8.04, 7.93, 7.84, 7.66, 7.42, 7.34, 7.25, 7.01, 4.81, 3.79, 3.64, 3.42. IR (mull) 3365, 2068, 1929, 1638, 1620, 1601, 1555, 1531, 1514, 1438, 1422, 1269, 1236, 1176, 828 cm$^{-1}$. MS (FAB) m/z 441 (MH+), 883, 882, 442, 441, 440, 333, 305, 304, 123, 121. HR;MS (FAB) found 441.1818. Anal. found: C, 73.05; H, 5.39; N, 6.32.

EXAMPLE 54

8-Hydroxy-2-[2-(4-methoxyphenyl)ethenyl]-N-[2-(phenylthio)ethyl]-7-quinolinecarboxamide

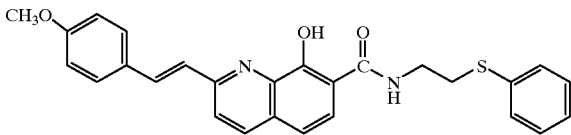

The title compound of Preparation 14 (0.57 g) and 2-aminoethyl phenylsulfide (0.30 g) are dissolved in 15 mL DMF. EDC.HCl (0.36 g) and HOBt.H$_2$O (0.26 g) are added and the reaction is stirred at room temperature for 4 days. The reaction is poured into 100 mL ice/H$_2$O. The resulting solid is filtered, dried, and recrystallized from EtOAc/hexanes. The product is obtained as an orange solid (0.29 g).

Physical characteristics are as follows:

MP 163–165° C.; $^1$H NMR (300 MHz, DMSO-d$_6$) δ 9.00, 8.27, 7.95, 7.87, 7.84, 7.66, 7.42, 7.34, 7.18, 7.00, 3.79, 3.57, 3.20. $^{13}$C NMR (75 MHz, DMSO-d$_6$) δ 168.48, 160.33, 156.56, 155.31, 139.35, 136.72, 135.98, 134.92, 129.83, 129.58, 129.38, 129.21, 128.68, 126.29, 126.19, 124.84, 122.39, 117.29, 114.84, 113.18, 55.67, 31.84. IR (mull) 2425, 2349, 2294, 2042, 1942, 1644, 1599, 1535, 1513, 1442, 1258, 1245, 1176, 826, 739 cm$^{-1}$. MS (EI) m/z 456 (M+), 456, 333, 320, 305, 304, 303, 302, 275, 260, 232. HRMS (EI) found 456.1489. Anal. found: C, 69.99; H, 5.36; N, 5.95.

PREPARATION 16

8-Methoxy-2-(trifluoromethyl)-4-quinolinol

A mixture of o-anisidine (28 mL), ethyl trifluoroacetoacetate (36 mL), and 12 drops 6N HCl is stirred overnight to form the enamine. The water formed during the reaction is removed by evaporation under reduced pressure. The residue is then poured into 60 mL diphenyl ether in a flask equipped with a Dean-Stark trap and condenser. The reaction is heated at 250° C. for 3 hours, cooled, and the resulting solid is filtered. The solid is rinsed thoroughly with hexanes and dried (18.77 g).

Physical characteristics are as follows:

MP 151–153° C.; $^1$H NMR (300 MHz, CDCl$_3$) δ 7.90, 7.37, 7.15, 6.83, 4.05. $^{13}$C (75 MHz, DMSO-d$_6$) δ 163.20, 155.74, 146.63, 146.21, 140.56, 128.02, 122.79, 113.71, 110.36, 100.89, 56.17. IR (mull) 2498, 2471, 1549, 1527, 1481, 1438, 1415, 1288, 1270, 1202, 1182, 1150. MS (OAMS) 244.1 (MH+). Anal. found: C, 54.16; H, 3.36; N, 5.77.

PREPARATION 17

4-Chloro-8-methoxy-2-(trifluoromethyl)quinoline

4-Hydroxy-8-methoxy-2-trifluoromethylquinoline (18.77 g) is dissolved in. 450 mL 8:1 C$_2$Cl$_2$:DMF. POCl$_3$ (50 mL) is added dropwise and the reaction is allowed to stir overnight. The reaction is then poured into 500 mL ice/H$_2$O and the aqueous is extracted 2× with CH$_2$Cl$_2$. The organic portions are combined, washed 1× with brine, dried over MgSO$_4$, and evaporated. The resulting oil crystallizes upon standing. The solid is recrystallized from 95% EtOH. A second crop of crystals could be obtained by concentrating down the EtOH filtrate. The total yield of product is 15.36 g.

Physical characteristics are as follows:

$^1$H NMR (300 MHz, DMSO-d$_6$) δ 8.26, 7.81, 7.44, 4.02.

PREPARATION 18

8-Methoxy-2-(trifluoromethyl)quinoline

To a solution of 4-chloro-8-methoxy-2-trifluoromethylquinoline (0.57 g) in 5 mL absolute EtOH is added 10% Pd/C (125 mg) and NEt$_3$ (0.3 mL). The reaction is hydrogenated under atmospheric pressure for 0.75 h. The reaction is then filtered. over Celite and the filtrate is evaporated. The residue is taken up in Et$_2$O and the triethylamine hydrochloride salt is filtered. The desired product is obtained as a light yellow solid by evaporation of the Et$_2$O filtrate (0.38 g).

Physical characteristics are as follows:

MP 88–89° C.; $^1$H NMR (300 MHz, DMSO-d$_6$) δ 8.63, 7.95, 7.68, 7.63, 7.32, 3.99. $^{13}$C NMR (75 MHz, DMSO-d$_6$) δ 155.71, 145.50, 139.35, 138.83, 130.37, 0.02, 119.81, 117.86, 117.83, 110.20, 56.28. IR (mull) 2354, 2151, 2030, 1996, 1934, 1507, 1442, 1341, 1319, 1287, 1275, 210. MS (OAMS) 228.2 (MH+). Anal. found: C, 57.85; H, 3.34; N, 6.00.

PREPARATION 19

8-Hydroxy-2-(trifluoromethyl)-7-quinolinecarboxylic Acid

8-Hydroxy-2-trifluoromethylquinoline (3.2 g) and K$_2$CO$_3$ (6.22 g) are placed in stainless steel bomb. The bomb is pressurized slightly with CO$_2$ and flushed 3×, hen pressurized to approximately 800 psi CO$_2$. The bomb is heated to 170° C., reaching a final pressure of approximately 1200 psi. This temperature and pressure are maintained for 7 days after which time the bomb is cooled and the pressure released. The solid residue is dissolved in a minimal amount of warm water. Any undissolved material is filtered and the aqueous filtrate is acidified to pH 4 with conc. HCl. The resulting tan solid is filtered and dried. The product is recrystallized with $Et_2O$ to give a light tan solid (1.87 g).

Physical characteristics are as follows:

MP 209–211° C.; $^1H$ NMR (300 MHz, DMSO-$d_6$) δ 8.66, 8.06, 7.98, 7.54. $^{13}C$ NMR (75 MHz, DMSO-$d_6$) δ 172.69, 160.38, 146.32, 139.54, 138.44, 133.29, 128.55, 123.74, 120.09, 120.01, 117.96, 111.33. IR (mull) 3076, 3044, 1988, 1928, 1654, 1623, 1434, 1330, 1264, 1211, 1188, 1150. MS (EI) m/z 257 (M+), 257, 240, 239. Anal. found: C, 51.78; H, 2.67; N, 5.46.

EXAMPLE 55

N-[(4-Chlorophenyl)methyl]-8-hydroxy-2-(trifluoromethyl)-7-quinolinecarboxamide

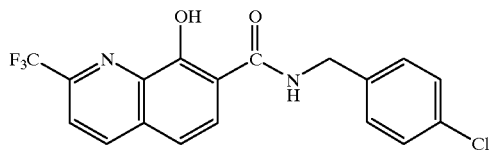

The title compound of Preparation 19 (0.52 g) and 4-chlorobenzylamine (0.26 mL) are dissolved in 10 mL DMF at room temperature. EDC.HCl (0.40 g) and HOBt.$H_2O$ (0.29 g) are added in one portion and the reaction is stirred at room temperature overnight. The reaction is then poured into 50 mL ice/$H_2O$ and the resulting yellow solid is filtered and dried. The product is purified by silica gel chromatography (eluent 2% MeOH:$CH_2Cl_2$ followed by 5% MeOH:$CH_2Cl_2$). The appropriate fractions are rotovapped to give an oily residue which crystallizes upon addition of $CHCl_3$. The product is obtained as a tan solid (0.49 g).

Physical characteristics are as follows:

MP 92–94° C.; $^1H$ NMR (300 MHz, DMSO-$d_6$) δ 13.98, 9.63, 8.63, 8.15, 8.04, 7.57, 7.39, 4.56. IR (mull) 3363, 1996, 1613, 1600, 1552, 1493, 1440, 1352, 1342, 1326, 1136, 1130. MS (EI) m/z 380 (M+), 240, 214, 213. Anal. found: C, 57.37; H, 3.47; N, 7.13.

EXAMPLE 56

N-Heptyl-8-hydroxy-2-(trifluoromethyl)-7-quinolinecarboxamide

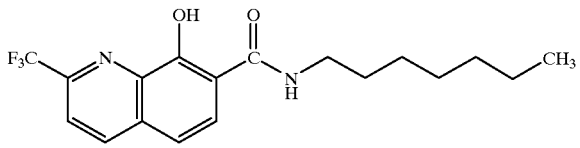

The title compound of Preparation 19 (0.35 g) and heptylamine (0.22 mL) are dissolved in 10 mL DMF. EDC.HCl (0.28 g) and HOBt.$H_2O$ (0.21 g) are added and the reaction is stirred at room temperature overnight. The reaction is poured into 50 mL ice/$H_2O$ and the aqueous is extracted 2x with EtOAc. The combined EtOAc layers are dried over $MgSO_4$, filtered, and evaporated to give an orange oil. The residue is adsorbed onto silica and chromatographed eluting with 2% MeOH:$CH_2Cl_2$ followed by 5% MeOH:$CH_2Cl_2$. The fractions containing desired product are evaporated under reduced pressure to give a pale yellow oil which crystallizes with $CH_2Cl_2$hexanes (0.15 g).

Physical characteristics are as follows:

MP 97–99° C. $^1H$ NMR (300 MHz, DMSO-$d_6$) δ 14.4, 9.06, 8.61, 8.11, 8.02, 7.53, 3.34, 1.56, 1.25, 0.82. $^{13}C$ NMR (75 MHz, DMSO-$d_6$) δ 169.65, 159.52, 146.12, 145.66, 139.32, 138.98, 132.23, 126.60, 119.52, 117.14, 112.67, 31.68, 31.58, 29.19, 28.86, 26.89, 22.51, 14.38. IR (mull) 3371, 1938, 1613, 1602, 1558, 1440, 1358, 1329, 1280, 1211, 1190, 1140. MS (OAMS) 355.1 (MH+). Anal. found: C, 60.68; H, 5.96; N, 7.80.

PREPARATION 20

4,8-Dihydroxy-2-(trifluoromethyl)-7-quinolinecarboxylic Acid

2-Trifluoromethyl-4,8-dihydroxyquinoline (6.0 g) and $K_2CO_3$ (11.0 g) are mixed in a stainless steel bomb. The bomb is flushed and evacuated 3× with 100 psi $CO_2$. The reaction vessel is then pressurized to 800 psi $CO_2$ and heated to 170° C., reaching a final pressure of 1200 psi. The bomb remains at this temperature and pressure for 7 days. The reaction vessel is cooled to room temperature, the pressure is released, and the reaction mixture is dissolved in 300 mL hot water. Any undissolved material is filtered and the filtrate is acidified with conc. HCl. A precipitate at pH 7 is collected (starting material). The filtrate is further acidified to pH 4 where a tan solid is collected (starting material+desired product). Since most of the solid collected is starting material, this material is reacted in the bomb for 7 more days. The same workup as before is done, with the only precipitate collected at pH 4.5. The desired product is filtered, dried, and recrystallized very slowly with EtOAc/hexanes (0.41 g).

Physical characteristics are as follows:

MP 232–234° C. $^1H$ NMR (300 MHz, DMSO-$d_6$) δ 8 7.88, 7.62, 7.22. MS (EI) m/z 273 (M+), 256, 255, 243, 229, 228, 227, 199, 179, 151. HRMS (EI) found 273.0252. Anal. found C, 46.37; H, 3.11; N, 4.69.

PREPARATION 21

2-[2-(2-furyl)ethenyl]-8-quinolinol

A mixture of 8-hydroxyquinaldine (5.09 g) and 2-furaldehyde (8.0 mL) are heated at reflux overnight. The reaction is cooled to room temperature. The residue is taken up in acetone and adsorbed onto silica. A silica gel column eluting with 100% $CH_2Cl_2$ is run and the product-containing fractions evaporated under reduced pressure to give an orange/yellow oil. The product is crystallized with EtOH/$H_2O$, filtered, washed thoroughly with water, and dried (1.18 g).

Physical characteristics are as follows:

MP 80–82° C.; $^1H$ NMR (300 MHz, DMSO-$d_6$) δ 9.55, 8.24, 7.97, 7.78, 7.71, 7.33, 7.19, 7.05, 6.70, 6.61. IR (mull) 3340, 1555, 1508, 1336, 1259, 1229, 1205, 1184, 1158, 1150, 1007, 969, 926, 835, 732 $cm^{-1}$. MS (electrospray) 238.1 (MH+). Anal. found: C, 75.74; H, 4.68; N, 5.85.

PREPARATION 22

2-[2(2-furyl)ethenyl]-8-hydroxy-7-quinolinecarboxylic Acid

The title compound of Preparation 21 (2.85 g) and $K_2CO_3$ (5.11 g) are mixed in a stainless steel bomb. The bomb is pressurized with 100 psi CO$_2$ and flushed 3x. The reaction vessel is then pressurized to 800 psi and heated to 175° C., reaching a final pressure of 1200 psi CO$_2$ where it remained for 7 days. The bomb is cooled to room temperature and de-pressurized. The reaction residue is taken up in 900 mL hot water. Any undissolved material is filtered. The filtrate is acidified to pH 4 with c.HCl and the resulting orange solid filtered and dried. The solid is then recrystallized with iPrOH to give the product as an orange solid (0.37 g).

Physical characteristics are as follows:

MP 190–192° C.; $^1$H NMR (300 MHz, DMSO-d$_6$) δ 8.40, 8.02, 7.84, 7.81, 7.35, 7.28, 6.83, 6.64. IR (mull) 1691, 1651, 1608, 1551, 1482, 1342, 1307, 1287, 1238, 1205, 1019, 960, 883, 747, 729 cm$^{-1}$. HRMS (EI) found 281.0678. Anal. found: C, 67.25; H, 4.04; N, 4.79.

EXAMPLE 57

N-[(4-Chlorophenyl)methyl]-2-[2-(2-furyl)ethenyl]-8-hydroxy-7-quinolinecarboxamide

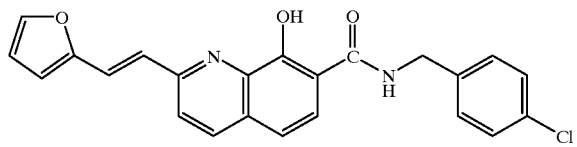

The title compound of Preparation 22 (0.26 g) and 4-chlorobenzylamine (0.13 mL) are dissolved in 10 mL DMF. EDC.HCl (0.19 g), and HOBt.H$_2$O (0.14 g) are added in one portion and the reaction stirred at room temperature over 3 days. The reaction is then poured into 75 mL ice/H$_2$O. The resulting solid is filtered, taken up in EtOAc, and adsorbed onto silica. A column eluting with 2% MeOH/CH$_2$Cl$_2$ is run and the product-containing fractions are evaporated under reduced pressure to give an oil. The product residue is crystallized with CH$_2$Cl$_2$/hexanes. The product is filtered and dried on the vacuum pump (0.19 g).

Physical characteristics are as follows:

MP 165–167° C.; $^1$H NMR (300 MHz, DMSO-d$_6$) δ 9.60, 8.28, 7.90, 7.89, 7.84, 7.79, 7.40, 7.38, 7.21, 6.76, 6.61, 4.56. IR (mull) 3382, 1642, 1602, 1536, 1483, 1439, 1433, 1342, 1135, 1106, 1017, 961, 846, 737, 728 cm$^{-1}$. HRMS (EI) calcd 404.0913. Anal. found (av): C, 60.98; H, 3.90; N, 6.13; Cl, 7.56.

EXAMPLE 58

N-[(4-Chlorophenyl)methyl]-8-hydroxy-7-quinoline-N-oxide Carboxamide

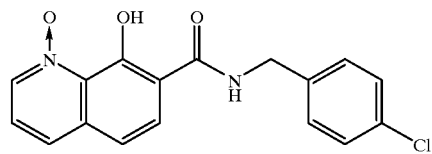

Hydrogen peroxide (0.2 mL of a 30% solution) is added to a solution of the title compound of Example 1 (0.100 g) in acetic acid (2.0 mL) and the solution is refluxed for 2 h. The solution is poured over ice and saturated sodium bicarbonate is slowly added until the pH of the mixture is basic. The mixture is extracted with chloroform and the organic layer is concentrated to give 0.128 g yellow solid. Column chromatography on silica gel (50 g) using 100% chloroform then 1% and 2% methanol/chloroform as eluant yields 35 mg (33%) of the desired product as a yellow solid. An analytical sample is crystallized from ethyl acetate/hexane to give the title compound as an orange solid.

Physical characteristics are as follows:

MP 178–183° C.; IR (mull) 3370, 1649, 1612, 1531, 1492, 1425, 1403, 1394, 1269, 1091, 1049, 830, 807, 693, 608 cm$^{-1}$. MS (FAB) m/z 329 (MH+), 331, 330, 329, 315, 314, 313, 188, 184, 172, 125. HRMS (FAB) 329.0699.

PREPARATION 23

5-Chloro-8-hydroxy-2-methyl-7-quinolinesulfonyl Flouride (Formula P-2) Refer to Chart P

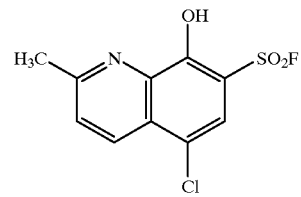

A solution of 5-chloro-8-hydroxy-2-methylquinoline (9.2 g) in 55 mL of fluorosulfonic acid is stirred at 120° C. for 18 h in a tightly stoppered flask. The mixture is then cooled to −78° C. and poured onto an intimate mixture of 250 mL of crushed ice and 250 mL of powdered dry ice. The mixture is allowed to warm to 25° C., and then diluted with distilled water until further addition causes no additional solid to precipitate (ca. 100 mL). The mixture is filtered, and the solid obtained is washed with four 50 mL-portions of 0° C. distilled water and then dried in a stream of air to give 10.7 g of the title compound as an orange powder.

Physical characteristics are as follows:

MP 196–198° C.; $^1$H NMR (400 MHz, DMSO) δ 8.55, 7.89, 7.83, 2.82; MS (ESI+) m/e 276 (M+H), 278.

EXAMPLE 59

5-Chloro-8-hydroxy-2-methyl-N-(2-pyridinylmethyl)-7-quinoline-sulfonamide (Formula P-3 where R=CH$_2$2-pyridyl) Refer to Chart P

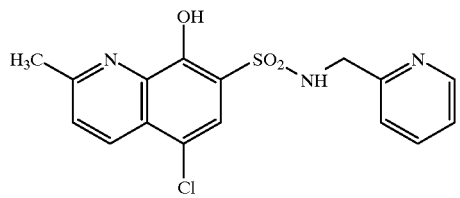

The title compound of Preparation 23 (0.300 g) is added to a solution of 2-(aminomethyl)pyridine (0.23 mL) and N,N-diisopropylethylamine (0.58 mL) in 4 mL of chlorobenzene and warmed to 140° C. for 2 h. The reaction mixture is then allowed to cool to room temperature and diluted with 75 mL of EtOAc. The organic layer is washed with three 25-mL portions of half-sat'd NaH$_2$PO$_4$ (aq), washed with brine, dried over MgSO$_4$, filtered and concentrated to give a white solid. Crystallization from CH$_2$Cl$_2$/hexanes yields 0.205 g of the title compound as white crystals.

Physical characteristics are as follows:

MP 185–186° C.; $^1$H NMR (300 MHz, DMSO) δ 8.39, 8.30, 8.08, 7.72, 7.70, 7.60, 7.37, 7.11–7.07, 4.22, 2.76 ppm; $^{13}$C NMR (75 MHz, DMSO), δ 159.1, 157.0, 150.9, 148.4, 138.4, 136.4, 132.7, 126.0, 125.9, 123.9, 122.3, 122.1, 121.4, 118.1, 47.8, 24.4 ppm; IR (mull) 3331, 1445, 1395, 1327, 1305, 1157, 1143, 1062, 1015, 838, 833, 825, 643, 632, 610 cm$^{-1}$; MS (EI) m/z 363 (M+), 195, 194, 193, 165, 164, 129, 128, 108, 107, 79; HRMS (FAB) found 364.0523; Anal. Found: C, 52.54; H, 4.00; N, 11.41; Cl, 9.59; S, 8.63.

EXAMPLE 60

5-Chloro-N-[2-(4-chlorophenyl)ethyl]-8-hydroxy-2-methyl-7-quinolinesulfonamide (Formula P-3 where R=CH$_2$CH$_2$4-ClC$_6$H$_4$) Refer to Chart P

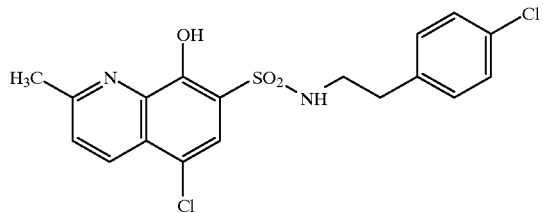

The title compound is prepared according to the procedure described in Example 59, substituting 2-(4-chlorophenyl)ethylamine for 2-(aminomethyl)pyridine. Crystallization from HOAc/H$_2$O/EtOH gives 0.409 g of the title compound as light orange crystals.

Physical characteristics are as follows:

MP 131–133° C.; $^1$H NMR (300 MHz, CDCl$_3$) δ 8.45, 7.91, 7.57, 7.12, 6.99, 5.08, 3.27–3.21, 2.82, 2.78 ppm; $^{13}$C NMR (75 MHz, DMSO) δ 159.1, 150.8, 130.5, 137.7, 132.8, 130.6, 130.4, 127.8, 125.8, 125.9, 123.8, 122.2, 118.1, 43.8, 34.4, 24.4 ppm; IR (mull) 3366, 3346, 1492, 1428, 1346, 1328, 1317, 1246, 1162, 1143, 1083, 1020, 830, 726, 643 cm$^{-1}$; MS (EI) m/z 410 (M+), 287, 285, 258, 256, 208, 195, 194, 193, 192, 164; Anal. Found: C, 52.40; H, 4.07; N, 6.72; Cl, 17.00.

EXAMPLE 61

5-Chloro-8-hydroxy-2-methyl-N-(4-phenylbutyl)-7-quinolinesulfonamide (Formula P-3 where R=(CH$_2$)$_4$Ph) Refer to CHART P

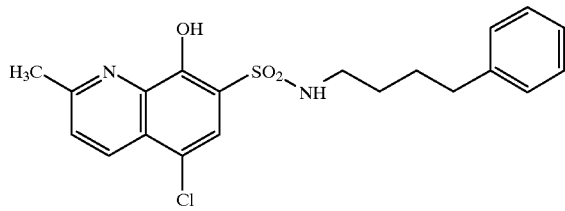

The title compound is prepared according to the procedure described in Example 59, substituting 4-phenylbutylamine for 2-(aminomethyl)pyridine. Column chromatography on silica gel (elution with 25% EtOAc/hexanes and 0–0.5% MeOH/CH$_2$Cl$_2$) gives 0.422 g of the title compound as an orange solid.

Physical characteristics are as follows:

MP 84–86° C.; $^1$H NMR (300 MHz, CDCl$_3$) δ 8.45, 7.94, 7.57, 7.25–7.12, 7.07, 5.06–5.04, 2.96, 2.80, 2.54, 1.65–1.48 ppm; $^{13}$C NMR (75 MHz, DMSO) δ 223.3, 159.15, 150.81, 141.8, 138.5, 132.8, 128.1, 128.0, 126.0, 125.9, 125.4, 123.9, 122.5, 118.1, 42.2, 34.5, 28.7, 27.8, 24.0 ppm; IR (mull) 3368, 3296, 1504, 1418, 1342, 1327, 1251, 1149, 1143, 1087, 952, 771, 701, 669, 612 cm$^{-1}$; MS (EI) m/z 404 (M+), 219, 208, 195, 194, 193, 192, 164, 148, 131, 91; HRMS (EI) found 404.0965; Anal. Found: C, 59.63; H, 5.39; N, 6.79.

EXAMPLE 62

5-Chloro-8-hydroxy-2-methyl-N-[2-(2-pyridinyl)ethyl]-7-quinolinesulfonamide (Formula P-3 where R=CH$_2$CH$_2$2-pyridyl) Refer to Chart P

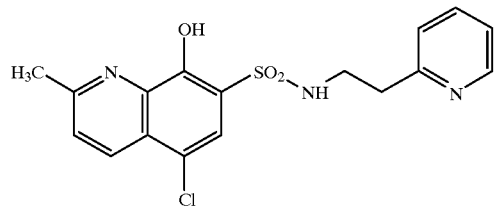

The title compound is prepared according to the procedure described in Example 59, substituting 2-(2-aninoethyl)pyridine for 2-(aminomethyl)pyridine. Crystallization from EtOAc/hexanes gives 0.374 g of the title compound as a light yellow solid.

Physical characteristics are as follows:

MP 153–155° C.; $^1$H NMR (300 MHz, DMSO) δ 8.41, 8.35, 7.73, 7.57, 7.17, 7.08, 3.23, 2.84, 2.76 ppm; $^{13}$C NMR (75 MHz, DMSO) δ 159.2, 158.3, 150.8, 148.7, 138.5, 136.3, 132.8, 126.0, 125.9, 123.9, 123.2, 122.0, 121.4, 118.2, 42.2, 37.1, 24.4 ppm; IR (mull) 1422, 1335, 1314, 1161, 1152, 1138, 1086, 1058, 948, 884, 824, 819, 35 781, 771, 611 cm$^{-1}$; MS (EI) m/z 377 (M+), 377, 256, 208, 195, 193, 192, 164, 121, 94, 93; Anal. Found: C, 53.94; H, 4.33; N, 10.93.

PREPARATION 24

5,7-Dibromo-8-methoxy-2-(2-phenylethenyl)quinoline (Formula Q-2) Refer to Chart Q

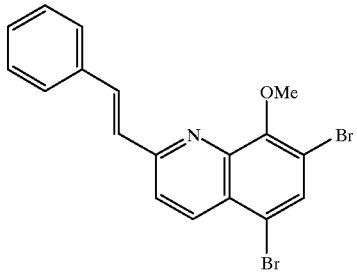

A mixture of 5,7-dibromo-2-methyl-8-methoxyquinoline (10.29 g) and benzaldehyde (15.84 g) is heated at reflux for 18 hrs. Upon cooling to room temperature, a precipitate forms. Methanol is added, and the reaction mixture is sonicated. The solid material is then collected by filtration.

Crystallization from hot absolute ethanol yields 10.872 g of the title compound as a yellow solid.

Physical characteristics are as follows:

MP 150–152° C.; $^1$H NMR (300 MHz, CDCl$_3$) δ 8.42, 7.91, 7.81–7.73, 7.66, 7.47–7.35, 4.25 ppm; $^{13}$C NMR (75 MHz, CDCl$_3$) δ 156.3, 153.3, 143.6, 136.3, 136.2, 135.8, 132.8, 129.0, 128.9, 128.2, 127.4, 127.0, 120.8, 116.5, 116.1, 62.5 ppm; IR (mull) 3061, 3023, 1589, 1495, 1487, 1311, 1143, 993, 971, 966, 913, 865, 819, 745, 685 cm$^{-1}$; MS (EI) m/z 417 (M+), 421, 420, 419, 418, 417, 416, 390, 308, 228, 107; Anal. Found: C, 51.22; H, 3.27; N, 3.32.

EXAMPLE 63

(E)-5-Chloro-8-hydroxy-2-(2-phenylethenyl)-N-[2-(phenylthio)ethyl]-7-quinolinesulfonamide (Formula Q-3, R=CH$_2$CH$_2$SPh) Refer to Chart Q

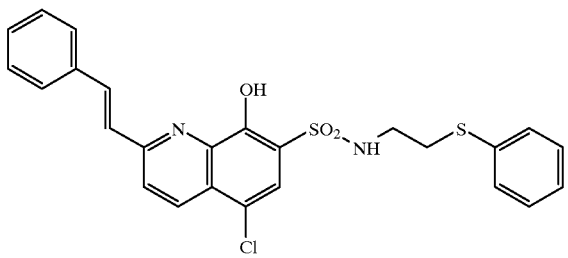

The title compound is prepared according to the procedures described in Preparations 6–8 and Example 17, substituting the title compound of Preparation 24 for 5,7-dibromo-8-methoxy-2-methylquinoline in Preparation 6 and 2-aminoethyl phenyl sulfide for 4-chlorobenzylamine in Preparation 8. Triteration with hot EtOH gives 0.282 g of the title compound as a tan solid.

Physical characteristics are as follows:

MP 187–193° C.; $^1$H NMR (300 MHz, CDCl$_3$) δ 8.51, 7.90–7.88, 7.79, 7.67, 7.50–7.38, 7.26–7.08, 5.61, 3.19–3.15, 3.07–3.04 ppm; $^{13}$C NMR (75 MHz, CDCl$_3$) δ 155.9, 151.7, 139.5, 137.3, 136.6, 135.5, 133.9, 129.6, 129.5, 128.5, 127.9, 127.1, 127.0, 126.3, 125.0, 124.6, 122.9, 118.9, 42.5, 32.3 ppm; IR (mull) 3275, 3246, 1597, 1440, 1420, 1342, 1326, 1162, 1149, 1145, 749, 693, 668, 633, 607 cm$^{-1}$; MS (EI) m/z 496 (M+), 373, 344, 325, 323, 296, 282, 281, 280, 217, 216; HRMS (EI) found 496.0670; Anal. Found: C, 60.08; H, 4.37; N, 5.50.

EXAMPLE 64

5-Chloro-8-hydroxy-N-[2-1H-indol-3-yl)ethyl]-2-methyl-7-quinolinesulfonamide (Formula J-5 where X$^1$=Cl, R$^1$=Me and R$^2$=CH$_2$CH$_2$3-indolyl) Refer to Chart J

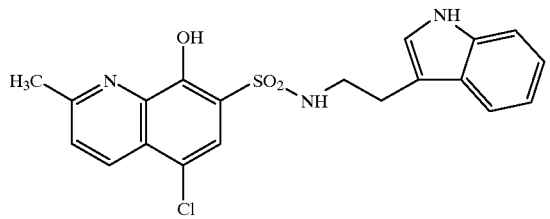

The title compound is prepared in two steps from 5-bromo-8-methoxy-2-methyl-7-quinoline sulfonyl chloride according to the procedures described in Preparation 8 and Example 17, substituting 3-(2-aminoethyl)indole for 4-chlorobenzylamine in the former procedure. Preparative HPLC gives 0.082 g of the title compound as a tan solid.

Physical characteristics are as follows:

MP 163–165° C.; $^1$H NMR (300 MHz, CDCl$_3$) δ 8.44, 8.07, 7.90, 7.53, 7.26–7.20, 7.05, 7.01–6.90, 6.77–6.72, 3.35–3.31, 2.99–2.94, 3.81 ppm; $^{13}$C NMR (75 MHz, CDCl$_3$) δ 159.7, 151.4, 139.1, 136.6, 133.3, 127.3, 126.6, 126.4, 124.5, 123.4, 122.8, 121.3, 118.8, 118.6, 118.3, 111.8, 111.3, 44.0, 26.0, 24.9 ppm; IR (mull) 3397, 3302, 1666, 1552, 1488, 1425, 1331, 1306, 1302, 1200, 1175, 1143, 745, 638, 601 cm$^{-1}$; MS (EI) m/z 415 (M+), 322, 285, 256, 208, 193, 143, 131, 130, 103, 77; HRMS (EI) found 415.0750.

PREPARATION 25

5-Chloro-8-hydroxy-7-iodo-2-methylquinoline (Formula R-2) Refer to Chart R

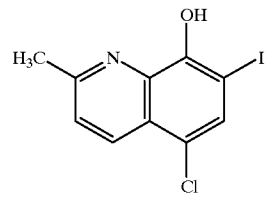

Iodine monchloride (19.0 g) is added to a solution of 5-chloro-8-hydroxy-2-methylquinoline (21.5 g) in 250 mL of MeOH, and the resulting mixture is stirred for 3 h. Additional iodine monochloride (4.5 g) is then added, and the mixture is stirred for another 18 h. The reaction mixture is quenched with sated Na$_2$SO$_3$ (aq), then neutralized with sat'd NaHCO, (aq). The solid precipitate is collected by filtration and dried under vacuum to give 31.22 g of the title compound as a pale green solid.

Physical characteristics are as follows:

MP 85–93° C.; $^1$H NMR (300 MHz, DMSO) δ 8.33, 7.88, 7.61, 2.72 ppm; IR (mull) 3383, 1589, 1434, 1403, 1344, 1322, 1315, 1255, 1249, 1190, 11.37, 947, 719, 617, 607 cm$^{-1}$; MS (ESI+) m/z 320 (M+H)$^+$; MS (ESI−) m/z 318 (M−H)$^−$.

PREPARATION 26

5-Chloro-8-hydroxy-2-methyl-7-quinolinesulfinic acid (Formula R-3) Refer to Chart R

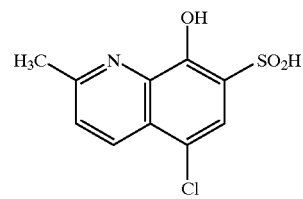

A solution of 5-chloro-8-hydroxy-7-iodo2-methylquinoline (30.8 g) in 500 mL of THF is cooled to −78° C., and methyl magnesium bromide (34.4 mL of 3.0 M solution in ether) is added over 12 min. The resulting mixture is stirred for 20 min, then n-butyllithium (65 mL of 1.6 M solution in pentane) is added over 25 min. The reaction mixture is allowed to stir at −78° C. for 2 h, then SO₂ (g) is introduced via a needle positioned above the reaction surface. After 42 min. the reaction mixture turns a yellow opaque color and gas introduction is terminated (pH=5–6). Sat'd NaHCO₃ (aq) is added until the pH=8, and the precipitate is collected by filtration. The aqueous layer of the filtrate is separated, and the pH is adjusted to 4 with 10% HCl (aq). Gradually, a precipitate forms. This is collected by filtration to afford 8.73 g of the title compound as an orange solid.

Physical characteristics are as follows:

¹H NMR (300 MHz, DMSO) δ 8.43, 7.73, 7.70, 2.76 ppm; MS (ESI–) m/z 256 (M–H)⁻.

PREPARATION 27

5-Chloro-8-hydroxy-2-methyl-7-quinolinesulfonyl Chloride (Formula R-4) Refer to Chart R

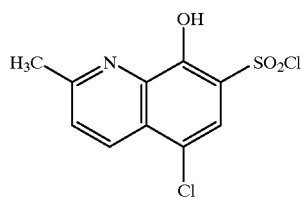

N-Chlorosuccinimide (2.07 g) is added to a solution of the title compound of Preparation 26 (4.0 g) in 70 mL of CH₂Cl₂, and the resulting mixture is stirred at room temperature for 2 h. The yellow-orange solid precipitate is collected by filtration and dried under vacuum at 56° C. for 1.5 h to afford 2.75 g of the title compound, which is used immediately without further purification.

PREPARATION 28

5-Chloro-8-hydroxy-2-methyl-N-[2-(4-aminophenyl) ethyl]-7-quinolinesulfonamide (Formula R-5) Refer to Chart R

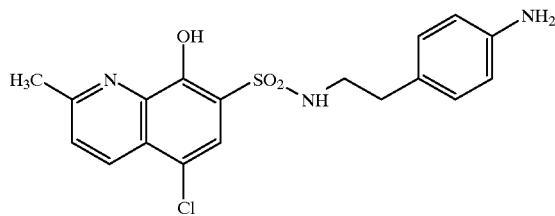

A solution of the title compound of Preparation 27 (1.51 g), 2-(4-aminophenyl)ethylamine (0.68 mL), and pyridine (0.83 mL) in 30 mL of CH₂Cl₂ is stirred at room temperature for 18 h. The resulting precipitate is isolated by filtration and rinsed with CH₂Cl₂ to give 1.82 g of the title compound as an orange solid which is used without further purification.

Physical characteristics are as follows:

MP 249–253° C.; ¹H NMR (300 MHz, CDCl) δ 8.31, 7.70, 7.65, 7.07–6.98, 2.94–2.84, 2.70, 2.69–2.63 ppm.

EXAMPLE 65

5-Chloro-8-hydroxy-2-methyl-N-[2-[4-[[(3,5-dimethyl- 4-isoxazolyl)sulfonyl]amino]phenyl] ethyl]-7-quinolinesulfonamide (Formula R-6, R=3, 5-dimethyl-4-isoxazolyl) Refer to Chart R

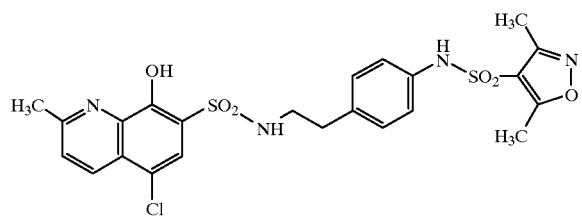

A solution of the title compound of Preparation 28 (0.62 g) and 3,5-dimethylisoxazole-4-sulfonyl chloride (0.31 mL) in 6 mL of pyridine is stirred at room temperature for 54 h. Additional sulfonyl chloride (0.31 mL) is added at 18 h and 36 h. The reaction mixture is then concentrated in vacuo, and the residue is partitioned between EtOAc, pH 4 phosphate buffer and water. The organic layer is separated and concentrated in vacuo to give 1.22 g of an orange solid. Column chromatography on 75 g of silica gel (elution with 0–20% MeOH/CHCl₃) followed by crystallization from CH₂Cl₂hexanes provides 0.041 g of the title compound as a yellow solid.

Physical characteristics are as follows:

MP 147–152° C. (decomposition); ¹H NMR (300 MHz, CDCl₃) δ 8.39, 7.89, 7.47, 7.15, 7.08, 2.95, 2.73, 2.57, 2.50, 2.48 ppm; IR (mull) 1608, 1594, 1506, 1413, 1269, 1234, 1202, 1169, 1147, 1129, 1071, 807, 796, 637, 611 cm⁻¹; MS (EI) m/z 551 (MH+), 553, 552, 551, 153, 139, 123, 106, 105, 103, 91; HRMS (EI) found 551.0850.

EXAMPLE 66

5-Chloro-8-hydroxy-2-methyl-N-[2-[4-[(phenylsulfonyl)amino]phenyl]ethyl]-7-quinolinesulfonamide (Formula R-6, R=Ph) Refer to Chart R

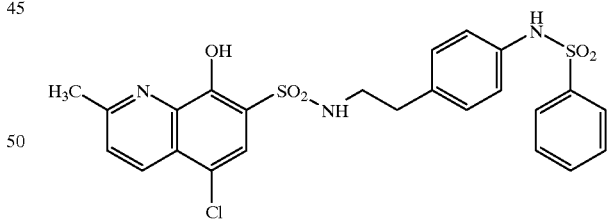

The title compound is prepared according to the procedure described in Example 65, substituting benzenesulfonyl chloride for 3,5-dimethylisoxazole- 4-sulfonyl chloride. Column chromatography (elution with 0–10% MeOH/ CHCl₃) followed by trituration with CHCl₃ gives 0.247 g of the title compound as an off-white solid.

Physical characteristics are as follows:

MP 269–272° C.; ¹H NMR (300 MHz, CDCl₃) δ 8.08, 7.32, 7.68–7.53, 6.92, 6.86, 2.90–2.78, 2.64 ppm; ¹³C NMR (75 MHz, DMSO), 223.2, 184.1, 165.3, 154.8, 145.3, 140.2, 137.4, 133.7, 132.3, 132.2, 129.0, 128.7, 127.5, 126.3, 124.4, 123.9, 121.3, 116.8, 104.9, 43.7, 34.3, 24.2 ppm; IR (mull) 3231, 1532, 1510, 1394, 1329, 1309, 1296, 1266, 1159, 1147, 1126, 1108, 1094, 708, 691 cm$^{-1}$; MS (EI) m/z 531 (M+), 195, 193, 167, 165, 164, 130, 107, 106, 77, 64.

PREPARATION 29

5-fluoro-8-hydroxy-7-quinolinesulfonyl chloride (Formula S-2) Refer to Chart S

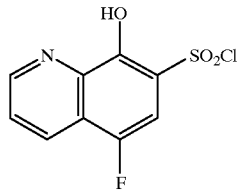

A solution of 5-fluoro-8-hydroxyquinoline (0.50 g) in 4.0 mL of chlorosulfonic acid is stirred for 3 h at 90° C. and then 13 h at 105° C. The mixture is then cooled to 0° C. and poured onto 50 mL of finely divided −15° C. ice. The bright orange-red precipitate is collected by filtration, washed with four 10-mL portions of 0° C. distilled water and three 2 mL portions of diethyl ether, and dried in a stream of air to give 0.208 g of the title compound as a red-orange powder.

Physical characteristics are as follows:

MP 248–250° C. (decomposition); Anal. found: C, 41.01; H, 2.05; N, 5.32; S, 12.25.

EXAMPLE 67

5-Flouro-8-hydroxy-N-(phenylmethyl)-7-quinolinesulfonamide (Formula S-3) Refer to Chart S

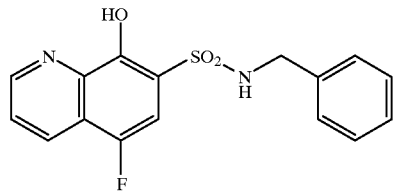

A suspension of 5-fluoro-8-hydroxy-7-quinolinesulfonyl chloride (0.150 g) in 2 mL of THF is cooled to −78° C. and treated with benzylamine (0.186 mL). The mixture is allowed to warm to 25° C. over several hours, then diluted with 50 μL of glacial acetic acid and 2 mL of distilled water. The oil which forms is crystallized by scratching, and the resulting suspension is stirred for one hour. The solid is filtered, washed with two 2 mL portions of distilled water and dried in a stream of air to give 0.121 g of the title compound as a solid.

Physical characteristics are as follows:

MP 185.5–186° C.; $^1$H NMR (400 MHz, DMSO) δ 9.04, 8.48, 8.03, 7.81, 7.47, 7.22, 7.11, 7.03, 4.12; MS (ESI, positive ion mode) m/e 333 (M+H).

EXAMPLE 68

5-Chloro-N-[(4-chlorophenyl)methyl]-8-hydroxy-2-methyl-7-quinolinecarboxamide

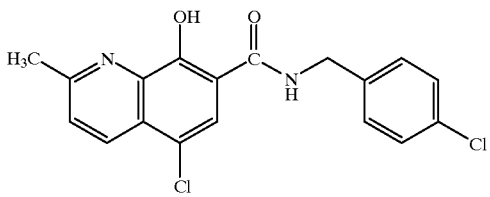

To a solution of 5-chloro8-hydroxy-2-methyl-7-quinolinecarboxylic acid (0.500 g) and 4-chlorobenzylamine (0.28 mL) in 20 mL DMF is added EDC hydrochloride (0.444 g) and hydroxybenzotriazole hydrate (0.312 g). The reaction is stirred at room temperature for 48 h. The mixture is then partitioned between EtOAc and water. The aqueous layer is extracted with EtOAc (3×). The combined organic layers are washed with brine (1×), dried over sodium sulfate and condensed. The residue is stirred in 20 mL 1:1 THF/1N HCl overnight. The solution is neutralized with saturated aqueous NaHCO$_3$. The reaction is partitioned between EtOAc and water. The aqueous layer is extracted with EtOAc (3×). The combined organic layers are washed with brine (1×), dried and condensed. The crude product is chromatographed on silica, eluting with 3% MeOH/CH$_2$Cl$_2$. Fractions homogeneous by TLC are combined and condensed. The residue taken up in a minimal amount of CH$_2$Cl$_2$. Toluene is added to the solution and the mixture is sonicated while adding hexanes until a white solid formed. The solid is collected and dried to yield 0.3310 g of the title product as a white solid.

Physical characteristics are as follows:

MP 128–130° C.; $^1$H NMR (300 MHz, DMSO-d$_6$) δ 9.54, 8.35, 8.09, 7.66, 7.39, 4.54, 2.71; IR (mull) 3399, 3299, 1660, 1603, 1565, 1531, 1500, 1492, 1428, 1350, 1332, 1251, 1226, 798, 630 cm$^{-1}$. MS (EI) m/z 360 (M$^+$), 362, 360, 221, 220, 195, 194, 193, 164, 140, 125. Anal. Found: C, 59.53; H, 4.11; N, 7.71; Cl, 19.38.

EXAMPLE 69

5-chloro-8-hydroxy-2-methyl-N-(3-phenylpropyl)-7-quinolinecarboxamide

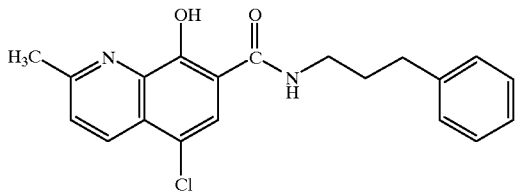

To a solution of 5-chloro-8-hydroxy-2-methyl-7-quinolinecarboxylic acid (0.500 g) and 3-phenylpropylamine (0.33 mL) in 20 mL DMF is added EDC hydrochloride (0.444 g) and hydroxybenzotriazole hydrate (0.312 g). The reaction is stirred at room temperature for 48 h. The mixture is then partitioned between EtOAc and water. The aqueous layer is extracted with EtOAc (3×). The combined organic layers are washed with brine (1×), dried over sodium sulfate and condensed. The residue is stirred in 20 mL 1:1 THF/1N HCl overnight. The solution is neutralized with saturated aqueous NaHCO₃. The reaction is partitioned between EtOAc and water. The aqueous layer is extracted with EtOAc (3×). The combined organic layers are washed with brine (1×), dried and condensed. The crude product is chromatographed on silica, eluting with 3% MeOH/CH₂Cl₂. Fractions homogeneous by TLC are combined and condensed. The residue taken up in a minimal amount of CH₂Cl₂. Toluene is added to the solution and the mixture is sonicated while adding hexanes until a white solid formed. The solid is collected and dried to yield 0.310 g of the title product as a white solid.

Physical characteristics are as follows:

MP 109–111° C.; $^1$H NMR (300 MHz, DMSO-d₆) δ 8.95, 8.36, 8.08, 7.66, 7.30–7.16, 3.35, 2.71, 2.65, 1.87; IR (mull) 3305, 1638, 1602, 1574, 1556, 1503, 1496, 1424, 1350, 1319, 1302, 1265, 943, 745, 698 cm$^{31\ 1}$. MS (EI) m/z 354 (M⁺), 354, 250, 222, 221, 220, 195, 194, 193, 164, 91. Anal. Found: C, 67.75; H, 5.48; N, 7.81; Cl, 9.92.

EXAMPLE 70

5-chloro-8-hydroxy-2-methyl-N-[(2-phenylthio)ethyl]-7-quinolinecarboxamide

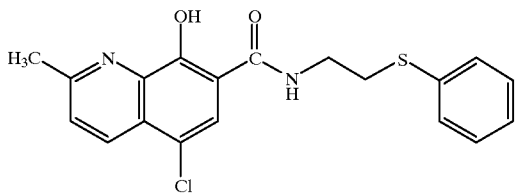

To a solution of 5-chloro-8-hydroxy-2-methyl-7-quinolinecarboxylic acid (0.500 g) and aminoethylphenyl sulfide (0.354 g) in 20 mL DMF is added EDC hydrochloride (0.444 g) and hydroxybenzotriazole hydrate (0.312 g). The reaction is stirred at room temperature for 48 h. The mixture is then partitioned between EtOAc and water. The aqueous layer is extracted with EtOAc (3×). The combined organic layers are washed with brine (1×), dried over sodium sulfate and condensed. The residue is stirred in 20 mL 1:1 THF/1N HCl overnight. The solution is neutralized with saturated aqueous NaHCO₃. The reaction is partitioned between EtOAc and water. The aqueous layer is extracted with EtOAc (3×). The combined organic layers are washed with brine (1×), dried and condensed. The residue taken up in a minimal amount of CH₂Cl₂. Toluene is added to the solution and the mixture is sonicated while adding hexanes until a solid formed. The solid is collected and dried to yield 0.499 g of the title product as an off-white solid.

Physical characteristics are as follows:

MP 131–134° C.; $^1$H NMR (300 MHz, DMSO-d₆) δ 9.28, 8.35, 8.02, 7.66, 7.41, 7.30, 7.17, 3.55, 3.19, 2.71; IR (mull) 3322, 1631, 1612, 1602, 1567, 1553, 1501, 1483, 1439, 1423, 1341, 1317, 1268, 1247, 744 cm$^{-1}$. MS (EI) m/z 372 (M⁺), 372, 238, 236, 222, 221, 220, 219, 164, 136, 135. IRMS (EI) found 372.0701.

EXAMPLE 71

8-hydroxy-N-[5-[[[4-(1-methylethyl)phenylsulfonyl]amino]pentyl]-7-quinolinecarboxamide

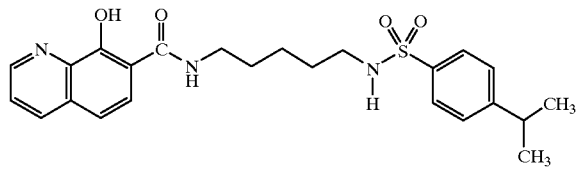

To a solution of 8-hydroxyquinoline-7-carboxylic acid (0.147 g) and N-(5-aminopentyl)-4-(1-methylethyl)benzenesulfonamide monohydrochloride (0.250 g) in 5 mL DMF is added EDC hydrochloride (0.149 g) and hydroxybenzotriazole hydrate (0.105 g), followed by diisopropylethylamine (0.271 mL). The reaction is stirred overnight at room temperature, then poured into 50 mL water. The resulting solution is partitioned between EtOAc and water. The aqueous layers are extracted with EtOAc (3×). The combined organic layers are washed with brine (1×), dried over sodium sulfate and condensed. The crude product is chromatographed on silica, eluting with 3% MeOH/CH₂Cl₂. Fractions homogeneous by TLC are combined, concentrated and recrystallized from acetone/hexanes to yield 0.060 g of the title product as a gold solid.

Physical characteristics are as follows:

MP 106–108° C.; $^1$H NMR (300 MHz, DMSOd₆) δ 8.89, 8.79, 8.31, 7.94, 7.68, 7.62, 7.49–7.38, 3.27, 2.93, 2.71, 1.49, 1.38, 1.27, 1.18; MS (EI) m/z 455 (M), 283, 266, 255, 189, 173, 172, 171, 145, 116, 84. HRMS (EI) found 455.1875. Anal. Found: C, 62.61; H, 6.39; N, 9.00.

EXAMPLE 72

N-(cyanomethyl-8-hydroxy-7-quinolinecarboxamide

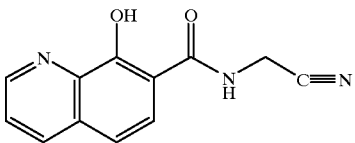

8-hydroxyquinoline-7-carboxylic acid (0.51 g), aminoacetonitrile.HCl (0.27 g), and triethylamine (0.38 mL) are dissolved in 10 mL dimethylformamide. EDC.HCl (0.54 g) and HOBt.H₂O (0.38 g) are added and the reaction is stirred at room temperature for 2 days. The reaction is poured into 50 mL ice/H₂O and stirred.

After approximately 30 minutes, a solid is collected and dried. The desired product is recrystallized from ethyl acetate (0.12 g).

Physical characteristics are as follows:

MP 206–208° C. (dec); $^1$H NMR (300 MHz, DMSO-d₆) δ 9.26, 8.93, 8.39, 7.96, 7.68, 7.44, 4.40. IR (mull) 3309, 3284, 1645, 1625, 1536, 1405, 1397, 1345, 1301, 1279, 1264, 1205, 846, 785, 723 cm$^{-1}$. MS (electrospray) 228.2 (M+H₁), 250.1 (M+Na), 226.1 (M–H₁). Anal. Found: C, 63.43; H, 4.14; N, 18.40.

EXAMPLE 73

8-hydroxy-N-(2-hydroxy-2-phenylethyl)-2-[2-(4-methoxyphenyl)ethyl]-7-quinolinecarboxamide

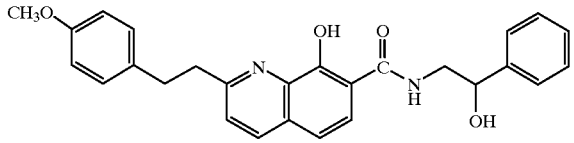

The title compound of Example 53 (0.090 g) is dissolved in 6 mL 1:1 THF:MeOH. Triethylamine (0.04 mL) followed by 20 mg 10% Pd/C is added to the reaction mixture. The reaction is placed under a hydrogen balloon and stirred at room temperature for 2 hours. The reaction is filtered over Celite and the filter cake rinsed thoroughly with ethyl acetate. The filtrate is evaporated under reduced pressure to give a solid which is then recrystallized from EtOAc/hexanes very slowly. The resulting solid is filtered and dried to give the desired product (0.048 g).

Physical characteristics are as follows:

MP 69–72° C.; $^1$H NMR (300 MHz, DMSO-$d_6$) δ 8.95, 8.20, 7.94, 7.51, 7.41, 7.33, 7.25, 7.17, 6.81, 4.82, 3.68, 3.62, 3.39, 3.21, 3.06. IR (mull) 3398, 1636, 1603, 1549, 1512, 1425, 1344, 1241, 1179, 1064, 1032, 839, 744, 729, 698 cm$^{-1}$. MS (electrospray) 443.1 (M+H$_1$), 465.0 (M+Na), 441.0 (M−H$_1$). HRMS (FAB) found 443.1985. Anal. Found: C, 70.43; H, 5.96; N, 6.03.

PREPARATION 30

8-Hydroxyquinoline, 7-carboxylic Acid (formula T-2) Refer to Chart T

A finely ground mixture of 27.8 g of 8-hydroxyquinoline (T-1) and 79.2 g of potassium carbonate is placed in a bomb and heated to 175° C. under 800 psi carbon dioxide gas. After seven days, the reaction is cooled to room temperature. The resulting mixture is treated with 1.2 L of hot water to dissolve most of the material. The suspension is filtered, cooled to room temperature and acidified to pH=7 with concentrated hydrochloric acid. The precipitate is removed by filtration. The filtrate is acidified to pH=3.5 with concentrated hydrochloric acid. The new precipitate is collected by suction filtration, washed with repeatedly isopropanol followed by hexanes. The yellow solid is dried in vacuo to afford 26 g of the title acid.

Physical characteristics are as follows:

1H-NMR (DMSO): 8.9, 8.6, 7.9, 7.8, 7.3.

EXAMPLE 74

N-[2-(3-Chlorophenyl)ethyl]-8-hydroxy-7-quinolinecarboxamide (uninverted CAS name) (formula T-3 wherein R$^0$ is 2-(3-chlorophenyl) ethyl) Refer to Chart T To a suspension of 1.89 g of T-2 of Preparation 30, 1.50 g of 1-hydroxbenzotriazole and 2.30 g of 1-(3-dimethylaminopropyl)-3-ethylcarbodiimide hydrochloride in 50 mL of dichloromethane is added 1.55 mL of 2-(3-chlorophenyl)ethylamine. The reaction is stirred overnight at room temperature. The resulting orange solution is diluted with dichloromethane and partioned against saturated aqueous sodium bicarbonate. The aqueous phase is extracted with additional portions of dichloromethane. The organic layers are combined and washed with pH=4 aqueous phosphate buffer followed by brine. The organic phase is dried over anhydrous magnesium sulfate, filtered and concentrated under reduced pressure. The residue is crystallized from ethyl acetate to afford 2.55 g of the title compound.

Physical characteristics are as follows:

1H-NMR (CDCl$_3$): 10.0, 8.8, 8.2, 8.0, 7.5, 7.3, 7.2, 7.1, 3.8, 3.0; Elem. Anal.: C, 65.82, H, 4.63, N, 8.56; MS-ESI: 327 (+ mode), 325 (− mode).

EXAMPLES 75–151

Following similar procedures to those described above, these additional analogues are prepared:

8-Hydroxy-N-[2-(3-indolyl)ethyl)-7-quinolinecarboxamide;

8-Hydroxy-N-[2-(4-hydroxyphenyl)ethyl]-7-quinolinecarboxamide;

8-Hydroxy-N-[2-(2-[4-phenoxy]phenyl)ethyl]-7-quinolinecarboxamide;

N-[(2,4-Dichlorophenyl)methyl]-8-hydroxy-7-quinolinecarboxamide;

N-[(3,4-Dichlorophenyl)methyl]-8-hydroxy-7-quinolinecarboxamide;

N-Decyl-8-hydroxy-7-quinolinecarboxamide;

8-Hydroxy-N-(4-phenylbutyl)-7-quinolinecarboxamide;

8-Hydroxy-N-octyl-7-quinolinecarboxamide;

8-Hydroxy-N-[[4-(trifluoromethyl)phenyl]methyl]-7-quinolinecarboxamide;

8-Hydroxy-N-[[2-(trifluoromethyl)phenyl]methyl]-7-quinolinecarboxamide;

N-[2-(1-Cyclohexenyl)ethyl]-8-hydroxy-7-quinolinecarboxamide;

N-[2-(2,4-Dichlorophenyl)ethyl]-8-hydroxy-7-quinolinecarboxamide;

8-Hydroxy-N-(cis-myrtanyl)-7-quinolinecarboxamide;

N-[(2-Chlorophenyl)methyl]-8-hydroxy-7-quinolinecarboxamide;

8-Hydroxy-N-[(2-methylphenyl)methyl]-7-quinolinecarboxamide;

8-Hydroxy-N-[(3-methylphenyl)methyl]-7-quinolinecarboxamide;

N-[(4-Chlorophenyl)methyl]-8-hydroxy-7-quinolinecarboxamide;

8-Hydroxy-N-(2-hydroxy-2-phenylethyl)-7-quinolinecarboxamide;

N-(2,2-Diphenylethyl)-8-hydroxy-7-quinolinecarboxamide;

8-Hydroxy-N-(2-phenylpropyl)-7-quinolinecarboxamide;

N-[1-(2-Ethyl)hexyl]-8-hydroxy-7-quinolinecarboxamide;

8-Hydroxy-N-undecyl-7-quinolinecarboxamide;

8Hydroxy-N-otadecyl-7-quinolinecarboxamide;

N-[2-(4-Bromophenyl)ethyl]-8-hydroxy-7-quinolinecarboxamide;

N-[2-(4-Chlorophenyl)ethyl]-8-hydroxy-7-quinolinecarboxamide;

8-Hydroxy-N-[2-(4-methylphenyl)ethyl]-7-quinolinecarboxamide;

N-(3,3-Diphenylpropyl)-8-hydroxy-7-quinolinecarboxamide;

8-Hydroxy-N-(3-phenylpropyl)-7-quinolinecarboxamide;
8Hydroxy-N-nonyl-7-quinolinecarboxamide;
N-[(2,6-Difluorophenyl)methyl]-8-hydroxy-7-quinolinecarboxamide;
N-[(3-Chlorophenyl)methyl]-8-hydroxy-7-quinolinecarboxamide;
8-Hydroxy-N-(2-methylcyclohexyl)-7-quinolinecarboxamide;
N-(2,3-Dimethylcyclohexyl)-8-hydroxy-7-quinolinecarboxamide;
8-Hydroxy-N-(3-methylcyclohexyl)-7-quinolinecarboxamide;
8-Hydroxy-N-(4-methylcyclohexyl)-7-quinolinecarboxamide;
8-Hydroxy-N-[(1,2,3,4-tetrahydro-1-naphthalenyl)methyl]-7-quinolinecarboxamide;
N-Cyclooctyl-8-hydroxy-7-quinolinecarboxamide;
8-Hydroxy-N-(1-indanyl)-7-quinolinecarboxamide;
N-Cycloheptyl-8-hydroxy-7-quinolinecarboxamide;
8-Hydroxy-N-(diphenylmethyl)-7-quinolinecarboxamide;
8-Hydroxy-N-(1-phenylethyl)-7-quinolinecarboxamide;
N-(2-Heptyl)-8-hydroxy-7-quinolinecarboxamide;
8-Hydroxy-N-(2-octyl)-7-quinolinecarboxamide;
N-(4-tert-Butylcyclohexyl)-8-hydroxy-7-quinolinecarboxamide;
S-N-[7-(7-Carboxy-8-hydroxy)quinolyl]-tyrosine, tert-butyl ester;
R-8-Hydroxy-N-[1-(1-naphthyl)ethyl]-7-quinolinecarboxamide;
S-8-Hydroxy-N-[1-(1-naphthyl)ethyl]-7-quinolinecarboxamide;
R-8-Hydroxy-N-(1-phenylethyl)-7-quinolinecarboxamide;
R-N-[1-(4-Bromophenyl)ethyl]-8-hydroxy-7-quinolinecarboxamide;
S-N-[1-(4-Bromophenyl)ethyl]-8-hydroxy-7-quinolinecarboxamide;
N-[2-((1S,2R)-1,2-Diphenyl-1-hydroxy)ethyl]-8-hydroxy-7-quinolinecarboxamide;
N-[2-((1R,2S)-1,2-Diphenyl-1-hydroxy)ethyl]-8-hydroxy-7-quinolinecarboxamide;
8-Hydroxy-N-(2-exo-norboranyl)-7-quinolinecarboxamide;
8-Hydroxy-N-[(4-hydroxy-3-methoxyphenyl)methyl]-7-quinolinecarboxamide;
S-8-Hydroxy-N-[2-(1-hydroxy-3-[4-hydroxyphenyl])propyl]-7-quinolinecarboxamide;
S-N-[7-(7-Carboxy-8-hydroxy)quinolyl]-serine, benzyl ester;
N-[7-(7-Carboxy-8-hydroxy)quinolyl]-tyrosine, methyl ester;
N-[7-(7-Carboxy-8-hydroxy)quinolyl]-tryptophan, ethyl ester;
N-(2-Adamantyl)8-hydroxy-7-quinolinecarboxamide;
S-O-Benzyl-N-[7-(7-Carboxy-8-hydroxy)quinolyl]-tyrosine, methyl ester;
S-N-[7-(7-Carboxy-hydroxy)quinolyl]-4-nitrophenylalanine, methyl ester;
N-[(2,5-Difluorophenyl)methyl]-8-hydroxy-7-quinolinecarboxamide;
8-Hydroxy-N-[1-(1-hydroxymethyl)cyclopentyl]-7-quinolinecarboxamide;
N-[(3-Chloro-4-flurorophenylmethyl]-8-hydroxy-7-quinolinecarboxamide;
N-[(2,3-Dichlorophenyl)methyl]-8-hydroxy-7-quinolinecarboxamide;
N-[(2,5-Dichlorophenyl)methyl]-8-hydroxy-7-quinolinecarboxamide;
N-(2-[([2-chloro-6-fluorophenyl]methyl)thio]ethyl)-8-hydroxy-7-quinolinecarboxamide;
N-[2-([(2,6-Dichlorophenyl)methyl]thio)ethyl]-8-hydroxy-7-quinolinecarboxamide;
N-[(2-Chloro-6-phenoxy-phenyl)methyl]-8-hydroxy-7-quinolinecarboxamide;
8-Hydroxy-N-[(2-[(2-(hydroxymethyl]phenyl)thio]phenyl)methyl]-7-quinolinecarboxamide;
8-Hydroxy-N-(2-[(4-[2-trifluoromethyl]quinolyl)thio]ethyl)-7-quinolinecarboxamide;
N-(Cyclohexylmethyl)-8-hydroxy-7-quinolinecarboxamide;
8-Hydroxy-N-(1-naphthalenylmethyl)-7-quinolinecarboxamide;
N-[2-(3-Chlorophenyl)ethyl]-hydroxy-7-quinolinecarboxamide;
8-Hydroxy-N-[[3-(trifluoromethyl)phenyl]methyl]-7-quinolinecarboxamide;
8-Hydroxy-N-[2-(phenylthio)ethyl]-7-quinolinecarboxamide; and
N-Heptyl-8-hydroxy-7-quinolinecarboxamide.

PREPARATION 31

N-Aryl-8-hydroxy-7-quinolinecarboxamides from Anhydride U-1, Procedure for Single Compounds (GP II) (Refer to Chart U)

Anhydride U-1 (1 eq.) is dissolved in CHCl$_3$ (n mL) at r.t. Pyridinium chloride (1 eq) and then the arylamine (about 1 eq.) are added. The solution is stirred for 6 h at r.t. 1M HCl/H$_2$O (n mL) is added and the biphasic mixture is stirred efficiently overnight. The precipitate is filtered, washed with a little water and CH$_2$Cl$_2$ and dried under high vacuum.

PREPARATION 32

N-Aryl-8-hydroxy-7-quinolinecarboxamides from Anhydride U-1, Procedure for Parallel Synthesis (GP III) (Refer to Chart U)

The aryl amines (0.20 mmol) are laid into syringes corked at their output and set with a frit at the bottom of their large section. A sol. of anhydride U-1 (0.1M) and pyridinium chloride (0.1M) in CHCl$_3$ is prepared. This solution (2 mL/syringe) is added into the syringes; if the arylamine is a liquid, it is added at this stage only; if the arylamine is a hydrochloride salt, DIPEA (33 µL, 1 eq) is added. The syringes are tightly closed at their bottoms and shaken for 6 h at r.t. 1M HCl/H$_2$O (2 mL) is added and the biphasic mixture is shaken efficiently overnight. The precipitate is isolated by sucking the solvent from the bottom of the syringes, washed with a little water and CH$_2$Cl$_2$ and dried under high vacuum.

PREPARATION 33

N-Aryl-8-hydroxy-7-quinolinecarboxamides from the Ester U-3, Procedure for Single Compounds (GP IV) (Refer to Chart U)

Ester U-3 is dissolved in CH$_2$C$_4$ and the arylamine (about 1 eq) and DIPEA (about 1 eq.) are added. The reaction mixture is stirred between 6 h and 6 days. MeOH (same amount as $CH_2Cl_2$) is added and the mixture is stirred between 6 h and 18 h. For the work-up procedures, see specific examples below.

PREPARATION 34

N-Aryl-8-hydroxy-7-quinolinecarboxamides from Ester U-3, Procedure for Parallel Synthesis (GP V) (Refer to Chart U)

The aryl amines (0.2 mmol) are put into syringes corked at their output and set with a frit at the bottom of their large section. A sol. of ester 3 (0.05M) and DIPEA (0.05M) in $CH_2Cl_2$ is prepared and added to the arylamines (4 mL for each amine); if the arylamine is a liquid, it is added at this stage only; if the arylamine is a salt, DIPEA (33 μL, 1 eq) is added. The syringes are tightly closed and shaken for 5 days. MeOH (2–4 mL) is added and the mixture is shaken for 6 h. The precipitate, if any, is isolated by sucking the solvent from the bottom of the syringes, washed with AcOEt and dried under high vacuum (P-fraction). The filtrate is washed with sat. $NaHCO_3/H_2O$ (1×) and an aq. buffer sol. at pH4 (1×); each time, the aq. phase is pipetted out of the seringe. If a precipitate appears during the work-up, it is filtered and dried (WU-fraction). The filtrate is blown down with a nitrogen stream; AcOEt (4 mL) is added and the mixture heated to 65° C. for 30 min. and cooled to 0° C. The solvent is pipetted out and the residue dried under high vacuum (T-fraction). The org. phase is blown down and the residue dried under high vacuum as well (S-fraction). The degree of hydration of the obtained products was not determined.

PREPARATION 35

8-{[(2,2,2-Trichloroethoxy)carbonyl]oxy}-7-quinolinecarboxylic Acid Anhydride with 2,2,2-trichloroethyl Hydrogen carbonate (U-1) (Refer to Chart U)

In a flame-dried flask, 8-hydroxy-7-quinolinecarboxylic acid (2.00 g) is suspended into $CH_2Cl_2$ (100 mL) and DIPEA (3.70 mL) is added. The mixture is stirred until homogeneity is reached and cooled to 0° C. Trichloroethyl chloroformate (3.00 mL) is added and the solution is stirred for 3 h at 0° C., then stirred for another hour while allowed to warm up slowly to r.t. The solution is washed with 1M $HCl/H_2O$ (1×), dried over $Na_2CO_3$ and the solvent removed under reduced pressure. Crystallization of the residue from $CHCl_3$/hexanes yielded the desired product (5.20 g).

Physical characteristics are as follows:

mp: 133–4° C.; $^1$H-NMR ($CDCl_3$, 300 MHz) δ 9.05, 8.26, 8.11, 7.88, 7.61, 4.97, 4.95. $^{13}$C-NMR ($CDCl_3$, 75 MHz) δ: 157.56, 152.13, 151.59, 149.25, 147.71, 141.09, 135.82, 132.64, 126.57, 126.45, 124.44, 119.67, 93.96, 93.42. MS (FAB) m/z 538, 540 and 542 (MH$^+$), 172. HRMS (FAB): found: 537.8609. Anal. Found: C, 35.12; H, 1.85; N, 2.65.

PREPARATION 36

8-Acetoxy-7-quinolinecarboxylic Acid (U-2) (Refer to Chart U)

This compound is prepared according to literature procedure (German patent number 540842, Dec. 10, 1931).

Physical characteristics are as follows:

$^1$H-NMR ($d_6$-DMSO, 300 MHz) δ 13.35, 8.99, 8.46, 8.00, 7.95, 7.67, 2.38. $^{13}$C-NMR ($d_6$-DMSO, 75 MHz) δ 172.46, 169.22, 166.21, 152.08, 147.95, 141.42, 136.61, 131.35, 127.08, 126.13, 124.07, 21.20.

PREPARATION 37

7-(Fluorocarbonyl)quinolin-8-yl acetate (U-3) (Refer to Chart U)

In a flame-dried flask under Ar, 8-acetoxy-7-quinolinecarboxylic acid U-2 (4.30 g) is suspended into $CH_2Cl_2$ (110 mL). Pyridine (1.50 mL) is added and the suspension cooled to –40° C. Cyanuric fluoride (3.00 mL) is added and the mixture stirred for 3 h, while the temperature rose slowly to 0° C. Ice and water and $CH_2Cl_2$ (100 mL) are added. Phases are shaken, separated and the aq. phase extracted with $CH_2Cl_2$ (1×). The combined org. phases are dried over $MgSO_4$, filtered, and the solvent is removed under reduced pressure. Crystallization of the residue from hexanes yielded ester U-3 as white needles (4.10 g).

Physical characteristics are as follows:

mp: 130–132° C.; $^1$H-NMR ($CDCl_3$, 300 MHz) δ 9.05, 8.22, 8.02, 7.80, 7.58, 2.58. $^{13}$C-NMR ($CDCl_3$, 75 MHz) δ 169.06, 156.59, 151.89, 141.42, 136.07, 132.92, 126.77, 126.03, 124.41, 118.10, 117.30, 20.88. MS (FAB) m/z 234 (MH$^+$), 192, 172. HRMS (FAB): 234.0569. Anal. C, 60.98; H, 3.55; N, 6.24.

EXAMPLE 152

8-Hydroxy-N-(4-methoxyphenyl)-7-quinolinecarboxamide Monohydrochloride (V-4) (Refer to Chart V)

According to GP II, starting from anhydride U-1 (50 mg), pyridinium chloride (10.8 mg) and 4-methoxyaniline (11.4 μg) in $CHCl_3$ (2 mL), amide U-4 is obtained as a pale yellow precipitate (10 mg).

Physical characteristics are as follows:

$^1$H-NMR ($CD_3OD$, 300 MHz) δ 9.15, 8.43, 8.18, 7.83, 7.63, 6.96, 3.82. $^{13}$C-NMR ($CD_9OD$, 75 MHz) δ 167.37, 157.63, 153.46, 146.28, 144.61, 131.70, 130.07, 129.69, 126.73, 123.92, 123.51, 117.56, 115.33, 113.67, 54.52. MS (EI) m/z 294 (M$^+$), 172, 123, 116, 108, 89. HRMS (EI): 294.1003.

EXAMPLE 153

N-(4-Cyanophenyl)-8-hydroxy-7-quinolinecarboxamide Monohydrochloride (V-5) (Refer to Chart V)

According to GP II, starting with anhydride U-1 (200 mg), pyridinium chloride (42 mg) and 4-aminobenzonitrile (44 mg) in $CHCl_3$ (8 mL), amide V-5 is obtained as a red powder (50 mg).

Physical characteristics are as follows:

$^1$H-NMR ($d_6$-DMSO, 300 MHz) δ 11.8, 8.96, 8.68, 8.08, 7.94, 7.82, 7.45). $^{13}$C-NMR ($d_6$-DMSO, 75 MHz) δ 166.42, 146.73, 143.49, 140.96, 133.77, 131.59, 128.3, 124.18, 120.66, 119.51, 116.81, 115.57, 105.84. MS (EI) m/z 289 (M$^+$), 172, 116, 89. HRMS (EI): 289.0848.

EXAMPLE 154

N-(3-Chlorophenyl)-8-hydroxy-7-quinolinecarboxamide Monohydrochloride (V-6) (Refer to Chart V)

According to GP II, starting from anhydride U-1 (200 mg), pyridinium chloride (42 mg), 3-chloroaniline (39 μL)

and CHCl$_3$ (8 mL), amide V-6 is obtained as a yellow powder (50 mg).

Physical characteristics are as follows:
$^1$H-NMR (CD$_3$OD, 300 MHz) δ 8.82, 8.28, 7.96, 7.90, 7.62, 7.36, 7.18. $^{13}$C-NMR (d$_6$-DMSO, 75 MHz) δ 166.45, 155.03, 147.30, 140.94, 140.42, 135.93, 133.56, 131.43, 130.95, 127.92, 124.23, 120.43, 119.35, 116.50. MS (EI) m/z 298 and 300 (MH$^+$), 172, 116. Anal. Found: C, 57.09; H, 3.78; N, 8.28.

EXAMPLE 155

N-[3,5-Bis(trifluoromethyl)phenyl]-8-hydroxy-7-quinolinecarboxamide Monohydrochloride (V-7) (Refer to Chart V)

According to GP II, starting from anhydride U-1 (200 mg), pyridinium chloride (42 mg), 3,5-bis(trifluoromethyl) anihine (58 μL and CHCl$_3$ (8 mL), amide V-7 is obtained as an orange powder (30 mg, 20%).

Physical characteristics are as follows:
$^1$H-NMR (d$_6$-DMSO, 300 MHz) δ 11.90, 8.97, 8.64, 8.46, 8.05, 7.84, 7.81, 7.47. $^{13}$C-NMR (d$_6$-DMSO, 75 MHz) δ 166.77, 155.62, 147.30, 141.18, 140.21, 131.55, 131.03, 127.94, 125.53, 124.23, 121.92, 120.37, 116.38. MS (EI) m/z 400 (M$^+$), 172, 116, 89. HRMS (EI) 400.0653.

EXAMPLE 156

N-Fluoren-2-yl-8-hydroxy-7-quinolinecarboxamide Monohydrochloride (V-8) (Refer to Chart V)

According to GP II, starting from anhydride U-1 (200 mg), pyridinium chloride (42 mg), 2-aminofluorene (67 mg) and CHCl$_3$ (8 mL), amide V-8 is obtained as a yellow powder (55 mg).

Physical characteristics are as follows:
$^1$H-NMR (CDCl$_3$, 300 MHz) δ 11.10, 9.02, 8.69, 8.23, 8.07, 7.89, 7.84, 7.72, 7.57, 7.36, 7.27. $^{13}$C-NMR (d$_6$-DMSO, 75 MHz) δ 166.27, 154.91, 147.55, 144.24, 143.42, 141.33, 140.72, 137.77, 137.67, 135.96, 131.34, 127.64, 127.25, 126.81, 125.53, 124.25, 120.66, 120.12, 120.03, 118.04, 116.88, 116.31, 37.01. MS (EI) m/z 352 (M+), 181, 172, 116, 89. HRMS (EI) 352.1190.

EXAMPLE 157

N-{[4-[(3,4-Dimethylisoxazol-5-ylamino)sulfonyl] phenyl}-8-hydroxy-7-quinolinecarboxamide Monohydrochloride (V-9) (Refer to Chart V)

According to GP II, starting from anhydride U-1 (200 mg), pyridinium chloride (42 mg), 4-amino-N-(3,4-dimethylisoxazol-5-yl)benzenesulfonamide (99 mg) and CHCl$_3$, (8 mL), amide V-9 is obtained as an orange powder (47 mg).

Physical characteristics are as follows:
$^1$H-NMR (d$_6$-DMSO, 300 MHz) δ 11.85, 10.95, 8.94, 8.61, 8.04, 7.95, 7.81, 7.75, 7.41, 2.08, 1.63. $^{13}$C-NMR (d$_6$-DMSO, 75 MHz) δ 166.19, 161.90, 156.19, 155.99, 146.92, 143.67, 140.05, 137.29, 134.44, 131.58, 128.47, 128.24, 124.08, 120.27, 116.43, 115.20, 105.64, 10.80, 6.34. MS (EI) m/z 438 (M$^+$), 369, 343, 327, 263, 172, 156, 116. HRMS (FAB) 439.1091.

EXAMPLE 158

N-1,3-Benzodioxol-5-yl-8-hydroxy-7-quinolinecarboxamide Monohydrochloride (V-10) (Refer to Chart V)

According to GP II, starting from anhydride U-1 (200 mg), pyridinium chloride (42 mg), 5-amino-1,3-benzodioxol (51 mg) and CHCl$_3$ (8 mL), amide V-10 is obtained as a yellow powder (60 mg).

Physical characteristics are as follows:
$^1$H-NMR (d$_6$-DMSO, 300 MHz) δ 10.95, 8.98, 8.64, 8.15, 7.82, 7.53, 7.44, 7.11, 6.92, 6.02. $^{13}$C-NMR (d$_6$-DMSO, 75 MHz) δ 166.21, 155.12, 147.72, 147.91, 144.02, 140.15, 132.89, 131.28, 127.35, 124.19, 116.83, 115.92, 114.39, 108.55, 103.40, 101.63, 61.06. MS (EI) m/z 308 (M$^+$), 172, 137, 116, 89. HRMS (EI) 308.0797.

EXAMPLE 159

8-Hydroxy-N-[4-(trifluoromethyl)coumarin-7-yl]-7-quinolinecarboxamide Monohydrochloride (V-11) (Refer to Chart V)

According to GP II, starting from anhydride U-1 (200 mg), pyridinium chloride (42 mg), 7-amino-4-(trifluoromethyl)coumarin (85 mg) and CHCl$_3$ (8 ml.), amide V-11 is obtained as a yellow powder (25 mg).

Physical characteristics are as follows:
$^1$H-NMR (d$_6$-DMSO, 300 MHz) δ 8.94, 8.65, 8.11, 8.05, 7.83, 7.71, 7.66, 7.38, 6.91. $^{13}$C-NMR (d$_6$-DMSO, 75 MHz) δ 166.40, 159.13, 155.28, 146.35, 143.73, 140.72, 131.77, 128.52, 125.91, 124.11, 117.29, 116.40, 114.67, 114.57, 108.91, 107.41. MS (EI) m/z 400 (M$^+$), 172, 116, 89. HRMS (EI) 400.0664.

EXAMPLE 160

N-(3-Fluorophenyl)-8-hydroxy-7-quinolinecarboxamide Monohydrochloride (V-12) (Refer to Chart V)

According to GP II, startng from anhydride U-1 (200 mg), pyridinium chloride (42 mg), 3-fluoroaniline (36 μL) and CHCl$_3$ (8 mL), amide V-12 is obtained as a white powder (45 mg).

Physical characteristics are as follows:
$^1$H-NMR (d$_6$-DMSO, 300 MHz) δ 11.35, 8.96, 8.62, 8.07, 7.83–7.76, 7.47, 7.43, 7.39, 6.95. $^{13}$C-NMR (d$_6$-DMSO, 75 MHz) δ 166.78, 164.09, 160.89, 154.39, 146.87, 142.46, 140.45, 134.36, 131.49, 130.83, 128.13, 124.41, 117.06, 116.90, 126.08. MS (EI) m/z 282 (M$^+$), 172, 116, 89. HRMS (EI) 282.0804.

EXAMPLE 161

N-(3,4-Difluorophenyl)-8-hydroxy-7-quinolinecarboxamide Monohydrochloride (V-13) (Refer to Chart V)

According to GP II, starting from anhydride U-1 (200 mg), pyridinium chloride (42 mg), 3,4-difluoroaniline (37 μL) and CHCl$_3$ (8 mL), amide V-13 is obtained as a light yellow powder (35 mg).

Physical characteristics are as follows:
$^1$H-NMR (d$_6$-DMSO, 300 MHz) δ 11.20, 8.95, 8.60, 8.05, 7.97, 7.79, 7.45. $^{13}$C-NMR (d$_6$-DMSO, 75 MHz) δ 166.25, 155.39, 147.45, 140.03, 136.87, 136.08, 131.38, 127.75, 124.13, 118.46, 117.20, 116.25, 110.42. MS (EI) m/z 300 (M$^+$), 172, 116, 89. HRMS (EI) 300.0724.

EXAMPLE 162

N-(3,5-Difluorophenyl)-8-hydroxy-7-quinolinecarboxamide Monohydrochloride (V-14) (Refer to Chart V)

According to GP II, starting from anhydride U-1 (200 mg), pyridinium chloride (42 mg), 3,5-difluoroaniline (48 mg) and CHCl₃ (8 mL), amide V-14 is obtained as a yellow powder (42 mg).

Physical characteristics are as follows:

$^1$H-NMR (d$_6$-DMSO, 300 MHz) δ 11.60, 8.99, 8.73, 8.07, 7.88, 7.50, 7.50 (m, 2H), 6.97, 6.29. $^{13}$C-NMR (d$_6$-DMSO, 300 MHz) δ 166.53, 164.48, 161.26, 154.99, 146.85, 141.54, 135.64, 131.52, 128.14, 124.27, 116.84, 116.07, 103.62, 99.44. MS (EI) m/z 300 (M$^+$), 172, 129, 116, 102, 89. HRMS 300.0716.

EXAMPLE 163

8-Hydroxy-N-(4-nitrophenyl)-7quinolinecarboxamide (V-15) (Refer to Chart V)

According to GP IV, starting from ester U-3 (100 mg), 4-nitroaniline (60 mg), DIPEA (75 μL) and CH₂Cl₂ (2 mL), stirred for 30 h, then overnight with MeOH. Amide V-15 appears as a red precipitate that is filtered and dried (10 mg).

Physical characteristics are as follows:

$^1$H-NMR (d$_6$-DMSO, 300 MHz) δ 8.90, 8.58, 8.25, 7.97, 7.81, 7.33. MS (EI) m/z 309 (M$^+$), 172, 116, 89. HRMS (EI) 309.0741.

EXAMPLE 164

N-[2-Chloro-5-(trifluoromethyl)phenyl]-8-hydroxy-7-quinolinecarboxamide (V-16) (Refer to Chart V)

According to GP IV, starting from ester U-3 (50 mg), 2-chloro-5-(trifluoromethyl)aniline (30 μL), DIPEA (40 μL) and CH₂Cl₂ (2 mL), stirred for 5 days, then for 6 h with MeOH. The mixture is diluted in some AcOEt, washed with sat. NaHCO₃/H₂O (1×), with an aq. buffer sol. at pH4 (1×), dried over MgSO₄ and the solvent removed under reduced pressure. Crystallization from AcOEt/hexanes leads to amide V-16 as a yellow powder (26 mg).

Physical characteristics are as follows:

mp: 210–211° C.; $^1$H-NMR (CD₃OD, 300 MHz) δ 10.18, 10.05, 8.38, 8.38, 8.09, 7.79, 7.62. MS (EI) m/z 366 and 368 (M$^+$), 172, 116, 89. HRMS (EI) 366.0374.

EXAMPLE 165

N-(5-Fluoro-2-methylphenyl)-8-hydroxy-7-quinolinecarboxamide (V-17) (Refer to Chart V)

According to GP IV, starting from ester U-3 (500 mg), 5-fluoro-2-methylaniline (0.30 mL), DIPEA (0.30 mL) and CH₂Cl₂ (10 mL), stirred for 24 h, then overnight with MeOH. An orange powder precipitated, that is filtered and dried under high vacuum. The filtrate is evaporated under reduced pressure, which leads to another fraction of orange precipitate, that is triturated in hot AcOEt/hexanes. After cooling to r.t., the orange powder is filtered and dried under high vacuum. Both fractions proves to be amide V-17 (366 mg, 58%).

Physical characteristics are as follows:

mp: 209–210° C.; $^1$H-NMR (d$_6$-DMSO, 300 MHz) δ 11.95, 8.87, 8.63, 8.25, 8.17, 7.79, 7.27, 6.84, 2.36. $^{13}$C-NMR (d$_6$-DMSO, 75 MHz) δ 164.38, 161.99, 158.83, 157.66, 144.94, 140.14, 138.77, 136.97, 131.45, 131.07, 128.65, 123.35, 122.63, 115.15, 112.53, 109.25, 106.15. MS (EI) m/z 296 (M$^+$), 268, 172, 116, 89. Anal. Found C, 68.67; H, 4.49; N, 9.43.

Also: According to GP V starting with 5-fluoro-2-methylaniline (26 mg).

Physical characteristics are as follows:

MS (ES) m/z P-fraction: Pos. mode: 297 (MH$^+$); neg. mode: 295 (M–H$^+$).

EXAMPLE 166

N-(2,4-Dimethylphenyl)-8-hydroxy-7-quinolinecarboxamide (V-18) (Refer to Chart V)

According to GP IV, starting from ester U-3 (500 mg), 2,4-dimethylaniline (0.27 mL), DIPEA (0.30 mL) and CH₂Cl₂ (10 mL), stirred for 24 h, then overnight with MeOH. After adding some CH₂Cl₂, the sol. is washed with an aq. buffer sol. at pH4 (2×) and sat. NaHCO₃/H₂O (1×). The org. phase is dried over MgSO₄ and the solvent removed under reduced pressure. The residue is triturated in AcOEt/hexanes at r.t. Amide V-18 precipitates as a white powder that is filtered and dried (378 mg).

Physical characteristics are as follows:

mp: 164–167° C.; $^1$H-NMR (d$_6$-DMSO, 300 MHz) δ 11.0, 8.90, 8.49, 8.14, 7.96, 7.74, 7.38, 7.06, 7.01, 2.29, 2.26. $^{13}$C-NMR (d$_6$-DMSO, 75 MHz) δ 184.14, 164.49, 156.15, 146.22, 138.04, 137.91, 134.28, 133.07, 130.87, 130.74, 128.64, 127.38, 126.64, 123.32, 122.18, 114.80, 20.24, 17.71. MS (EI) m/z 292 (M$^+$), 264, 172, 121, 106, 89. HRMS (EI) 292.1206. Anal. Found: C, 73.28; H, 5.51; N, 9.50.

Also: According to GP V starting with 2,4-dimethylaniline (25 mg).

Physical characteristics are as follows:

MS (ES) m/z T-fraction: Pos mode: 293 (MH$^+$); neg. mode: 291 (M–H$^+$).

EXAMPLE 167

8-Hydroxy-N-(3-methylphenyl)-7-quinolinecarboxamide (V-19) (Refer to Chart V)

According to GP IV, starting from ester U-3 (500 mg), 3-methylaniline (0.23 mL), DIPEA (0.30 mL) and CH₂Cl₂ (10 mL), stirred for 24 h, then overnight with MeOH. After adding some CH₂Cl₂, the sol. is washed with an aq. buffer sol. at pH4 (2×) and sat. NaHCO₃/H₂O (1×). The org. phase is dried over MgSO₄ and the solvent removed under reduced pressure. The residue is triturated with AcOEt/hexanes at 40° C. and amide V-19 precipitated as a red powder that is filtered and dried under high vacuum (276 mg).

Physical characteristics are as follows:

$^1$H-NMR (d$_6$-DMSO, 300 MHz) δ 10.90, 8.92, 8.45, 8.03, 7.70, 7.55, 7.41, 7.24, 6.94. $^{13}$C-NMR (d$_6$-DMSO, 75 MHz) δ 165.10, 155.37, 147.65, 138.45, 138.17, 137.96, 137.37, 130.61, 128.60, 126.83, 124.39, 123.33, 120.60, 117.29, 115.63, 115.29, 21.09. MS (EI) m/z 278 (M$^+$), 172, 116, 107, 89. HRMS (EI) 278.1049. Anal. Found: C, 72.95; H, 5.19; N, 9.95.

Also: According to GP V starting with 3-methylaniline (21 mg).

Physical characteristics are as follows:

MS (ES) m/z WU-fraction: Pos mode: 279 (M$^+$); neg. mode: 277 (M–H$^+$).

EXAMPLE 168

N-(2-Chloro-5-methoxyphenyl)-8-hydroxy-7-quinolinecarboxamide (V-20) (Refer to Chart V)

According to GP IV, starting from ester U-3 (500 mg), 2-chloro-5-methoxyaniline hydrochloride (420 mg), DIPEA (0.06 mL) and CH$_2$Cl$_2$ (10 mL), are stirred for 6 days, then for 24 h with MeOH. After adding some CH$_2$Cl$_2$, the sol. is washed with an aq. buffer sol. at pH4 (2×) and sat. NaHCO$_3$/H$_2$O (1×). The org. phase is dried over MgSO$_4$ and the solvent removed under reduced pressure. The residue, is triturated with AcOEt/hexanes at r.t. and the precipitated grey amide V-20 is filtered and dried under high vacuum (280 mg).

Physical characteristics are as follows:

$^1$H-NMR (d$_6$-DMSO, 300 MHz) δ 12.3, 8.85, 8.58, 8.33, 8.17, 7.77, 7.40, 7.25, 6.70, 3.76. $^{13}$C-NMR (d$_6$-DMSO, 75 MHz) δ 184.16, 164.39, 158.28, 145.09, 145.04, 139.80, 139.74, 136.80, 131.56, 129.40, 128.66, 123.40, 114.72, 113.58, 109.54, 107.31, 55.30. MS (EI) m/z 328 and 330 (M$^+$), 172, 157 and 159, 116, 89. HRMS (EI) 328.0615. Anal. Found: C, 61.38; H, 4.17; N, 8.45.

Also: According to GP V starting with 2-chloro-5-methoxyaniline hydrochloride (39 mL) and DIPEA (33 µL).

Physical characteristics are as follows:

MS (ES) m/z T-fraction: Pos. mode: 329 and 331 (MH$^+$); neg. mode: 327 and 329 (M–H$^+$).

EXAMPLE 169

8-Hydroxy-N-naphth-2-yl-7-quinolinecarboxamide Monohydrochloride (V-21) (Refer to Chart V)

Following GP III starting from 2-aminonaphthalene (29 mg).

Physical characteristics are as follows:

MS (ES) m/z Pos. mode: 315 (MH$^+$); neg. mode: 313 (M–H$^+$).

EXAMPLE 170

8-Hydroxy-N-{4-[(indazo-6-ylamino)sulfonyl]phenyl}-7-quinolinecarboxamide Monohydrochloride (V-22) (Refer to Chart V)

Following GP III starting with N$^1$-indazo-6-ylsulfanilamide (60 mg).

Physical characteristics are as follows:

MS (ES) m/z: Pos. mode 460 (MH$^+$); neg. mode: 458 (M–H$^+$). Contaminated with sulfanilamide.

EXAMPLE 171

N-(3-Bromophenyl)-8-hydroxy-7-quinolinecarboxamide Monohydrochloride (V-23) (Refer to Chart V)

Following GP III starting from 3-bromoaniline (22 µL).

Physical characteristics are as follows:

MS (ES) m/z Pos. mode: 343, 345 (MH$^+$); neg. mode: 341, 343 (M–H$^+$).

EXAMPLE 172

N-(3,4-Dichlorophenyl)-8-hydroxy-7-quinolinecarboxamide Monohydrochloride (V-24) (Refer to Chart V)

Following GP III starting from 3,4-dichloroaniline (33 mg).

Physical characteristics are as follows:

MS (ES) m/z Pos. mode: 333, 335, 337 (MH$^+$); neg. mode: 331, 333, 335 (M–H$^+$). Contaminated with carbamate.

EXAMPLE 173

N-(3,5-Dichlorophenyl)-8-hydroxy-7-quinolinecarboxamide Monohydrochloride (V-25) (Refer to Chart V)

Following GP III starting from 3,5-dichloroaniline (33 mg).

Physical characteristics are as follows:

MS (ES) m/z Pos. mode: 333, 335, 337 (MH$^+$); neg. mode: 331, 333, 335 (M–H$^+$).

EXAMPLE 174

8-Hydroxy-N-(3-iodophenyl)-7-quinolinecarboxamide Monohydrochloride (V-26) (Refer to Chart V)

Following GP III starting from 3-iodoaniline (44 mg).

Physical characteristics are as follows:

MS (ES) m/z Pos. mode: 391 (MH$^+$); neg. mode: 389 (M–H$^+$).

EXAMPLE 175

N-(3-Benzoxyphenyl)-8-hydroxy-7-quinolinecarboxamide Monohydrochloride (V-27) (Refer to Chart V)

Following GP III starting from 3-benzoxyaniline (40 mg).

Physical characteristics are as follows:

MS (ES) m/z Pos. mode: 371 (MH$^+$); neg. mode: 369 (M–H$^+$).

EXAMPLE 176

8-Hydroxy-N-[3-(methylmercapto)phenyl]-7-quinolinecarboxamide Monohydrochloride (V-28) (Refer to Chart V)

Following GP III starting from 3-(methylmercapto)aniline (25 µL).

Physical characteristics are as follows:

MS (ES) m/z Pos. mode: 311 (MH$^+$); neg. mode: 309 (M–H$^+$).

EXAMPLE 177

N-(3,5-Dimethylphenyl)-8-hydroxy-7-quinolinecarboxamide Monohydrochloride (V-29) (Refer to Chart V)

Following GP III starting from 3,5-dimethylaniline (25 µL).

MS (ES) m/z: Pos. mode: 293 (MH$^+$); neg. mode: 291 (M–H$^+$).

EXAMPLE 178

N-(4-Bromophenyl)-8-hydroxy-7-quinolinecarboxamide Monohydrochloride (V-30) (Refer to Chart V)

Following GP III starting from 4-bromoaniline (35 mg).

Physical characteristics are as follows:

MS (ES) m/z Pos. mode: 343, 345 (MH$^+$); neg. mode: 341, 343 (M–H$^+$). Contaminated with carbamate.

EXAMPLE 179

8-Hydroxy-N-(4-phenoxyphenyl)-7-quinolinecarboxamide Monohydrochloride (V-31) (Refer to Chart V)

Following GP III starting from 4-phenoxyaniline (37 mg).

Physical characteristics are as follows:

MS (ES) m/z Pos. mode: 357 (MH$^+$); neg. mode: 355 (M–H$^+$).

EXAMPLE 180

N-(3,5-Dichloro-4-hydroxyphenyl)-8-hydroxy-7-quinolinecarboxamide Monohydrochloride (V-32) (Refer to (Chart V)

Following GP III starting from 3,5-dichloro-4-hydroxyaniline (36 mg).

MS (ES) m/z: Pos. mode: 349, 351, 353 (MH$^+$); neg. mode: 347, 349, 351 (M–H$^+$).

EXAMPLE 181

8-Hydroxy-N-biphen-4-yl-7-quinolinecarboxamide Monohydrochloride (V-33) (Refer to Chart V)

Following GP III starting from 4-aminobiphenyl (34 mg).
Physical characteristics are as follows:
MS (ES) m/z Pos. mode: 341 (MH$^+$); neg. mode: 339 (M–H$^+$).

EXAMPLE 182

8-Hydroxy-N-[4-(4-nitrophenylmercapto)phenyl]-7-quinolinecarboxamide Monohydrochloride (V-34) (Refer to Chart V)

Following GP III starting from 4-(4-nitrophenylmercapto)aniline (49 mg).
Physical characteristics are as follows:
MS (ES) m/z Pos. mode: 418 (MH$^+$); neg. mode: 416 (M–H$^+$).

EXAMPLE 183

N-(4-Benzoxyphenyl)-8-hydroxy-7-quinolinecarboxamide Monohydrochloride (V-35) (Refer to Chart V)

Following GP III starting from 4-benzoxyaniline (47 mg).
Physical characteristics are as follows:
MS (ES) m/z Pos. mode: 371 (MH$^+$); neg. mode: 369 (M–H$^+$).

EXAMPLE 184

8-Hydroxy-N-[4-(4-nitrophenoxy)phenyl]-7-quinolinecarboxamide Monohydrochloride (V-36) (Refer to Chart V)

Following GP III starting from 4-(4-nitrophenoxy)aniline (46 mg).
Physical characteristics are as follows:
MS (ES) m/z Pos. mode: 402 (MH$^+$); neg. mode: 400 (M–H$^+$).

EXAMPLE 185

N-(4-cyclohexylphenyl)-8-hydroxy-7-quinolinecarboxamide Monohydrochloride (V-37) (Refer to Chart V)

Following GP V starting from 4-cyclohexylaniline (35 mg).
Physical characteristics are as follows:
MS (ES) m/z Pos. mode: 347 (MH$^+$); neg. mode: 345 (M–H$^+$).

EXAMPLE 186

8-Hydroxy-N-naphth-1-yl-7-quinolinecarboxamide (V-38) (Refer to Chart V)

Following GP V starting from 1-aminonaphthalene (29 mg).
Physical characteristics are as follows:
MS (ES) m/z T-fraction: Pos. mode: 315 (MH$^+$); neg. mode: 313 (M–H$^+$).

EXAMPLE 187

N-(4-Bromonaphth-1-yl)-8-hydroxy-7-quinolinecarboxamide (V-39) (Refer to Chart V)

Following GP V starting from 1-amino-4-bromonaphthalene (44 mg).
Physical characteristics are as follows:
MS (ES) m/z P-fraction: Neg. mode: 391 and 393 (M–H$^+$).

EXAMPLE 188

8-Hydroxy-N-(2-pyrrol-1-ylphenyl)-7-quinolinecarboxamide (V-40) (Refer to Chart V)

Following GP V starting from 1-(2-aminophenyl)pyrrole (32 mg).
Physical characteristics are as follows:
MS (ES) m/z T-fraction: Pos. mode: 330 (MH$^+$); neg. mode: 328 (M–H$^+$).

EXAMPLE 189

8-Hydroxy-N-indol-5-yl-7-quinolinecarboxamide (V-41) (Refer to Chart V)

Following GP V starting from 5-aminoindole (26 mg).
Physical characteristics are as follows:
MS (ES) m/z P- and WU-fractions: Pos. mode: 304 (MH$^+$); neg. mode: 302 (M–H$^+$).

EXAMPLE 190

N-Benzo-2,1,3-thiadiazol-4-yl-8-hydroxy-7-quinolinecarboxamide (V-42) (Refer to Chart V)

Following GP V starting from 4-aminobenzo-2,1,3-thiadiazole (30 mg).
Physical characteristics are as follows:
MS (ES) m/z P-fraction: neg. mode: 302 (M–H$^+$).

EXAMPLE 191

8-Hydroxy-N-quinolin-5-yl-7-quinolinecarboxamide (V-43) (Refer to Chart V)

Following GP V starting from 5-aminoquinoline (29 mg).
Physical characteristics are as follows:
MS (ES) m/z P- and WU-fractions: Pos. mode: 316 (MH$^+$) and 338 (MNa$^+$); neg. mode: 314 (M–H$^+$).

EXAMPLE 192

8-Hydroxy-N-quinolin-8-yl-7-quinolinecarboxamide (V-44) (Refer to Chart V)

Following GP V starting from 8-aminoquinoline (29 mg).
Physical characteristics are as follows:

MS (ES) m/z P-fraction: Pos. mode: 316 (MP$^+$); neg. mode: 314 (M–H$^+$).

EXAMPLE 193

8-Hydroxy-N-isoquinolin-5-yl-7-quinolinecarboxamide (V-45) (Refer to Chart V)

Following GP V starting from 5-aminoisoquinoline (29 mg).

Physical characteristics are as follows:

MS (ES) m/z P-fraction: Pos. mode: 316 (MH$^+$); neg. mode: 314 (M–H$^+$).

EXAMPLE 194

8-Hydroxy-N-(4-methoxy-2-nitrophenyl)-7-quinolinecarboxamide (V-46) (Refer to Chart V)

Following GP V starting from 4-methoxy-2-nitroaniline (34 mg).

Physical characteristics are as follows:

MS (ES) m/z P-fraction: Neg. mode: 338 (M–H$^+$). Contaminated with quinoline methyl ester.

EXAMPLE 195

8-Hydroxy-N-[2-nitro-4-(trifluoromethyl)phenyl]-7-quinolinecarboxamide (V-47) (Refer to Chart V)

Following GP V starting from 2-nitro-4-(trifluoromethyl)aniline (41 mg).

Physical characteristics are as follows:

MS (ES) m/z P-fraction: Pos mode: 378 (MH$^+$); neg. mode: 338 (M–H$^+$).

EXAMPLE 196

N-(3,5-Dinitrophenyl)-8-hydroxy-7-quinolinecarboxamide (V-413) (Refer to Chart V)

Following GP V starting from 3,5-dinitroaniline (37 mg).
Physical characteristics are as follows:
MS (ES) m/z: P-fraction: Neg. mode 353 (M–H$^+$).

EXAMPLE 197

8-Hydroxy-N-[4-nitro-2-(trifluoromethyl)phenyl]-7-quinolinecarboxamide (V-49) (Refer to Chart V)

Following GP V starting from 4-nitro-2-(trifluoromethyl)aniline (41 mg).

Physical characteristics are as follows:

MS (ES) m/z: P-fraction Pos. mode: 378 (MH$^+$), 400 (MNa$^+$); neg. mode: 376 (M–H$^+$).

EXAMPLE 198

N-(2-Cyanophenyl)-8-hydroxy-7-quinolinecarboxamide (V-50) (Refer to Chart V)

Following GP V starting from 2-aminobenzonitrile (24 mg).

Physical characteristics are as follows:

MS (ES) m/z P-fraction: Pos. mode: 290 (MH$^+$), 312 (MNa$^+$); neg. mode: 388 (M–H$^+$).

EXAMPLE 199

N-(2-Bromophenyl)-8-hydroxy-7-quinolinecarboxamide (V-51) (Refer to Chart V)

Following GP V starting from 2-bromoaniline (35 mg).
Physical characteristics are as follows:

MS (ES) m/z T-fraction: Pos. mode: 343 and 345 (MH$^+$); neg. mode: 341 and 343 (M–H$^+$).

EXAMPLE 200

N-(2,4-Dibromophenyl)-8-hydroxy-7-quinolinecarboxamide (V-52) (Refer to Chart V)

Following GP V starting from 2,4-dibromoaniline (50 mg).

Physical characteristics are as follows:

MS (ES) m/z P-fraction: Neg. mode: 419, 421 and 423 (M–H$^+$). Contaminated with 8-hydroxy-7-quinoline carboxylic acid.

EXAMPLE 201

N-(2,5-Dibromophenyl)-8-hydroxy-7-quinolinecarboxamide (V-53) (Refer to Chart V)

Following GP V starting from 2,5-dibromoaniline (50 mg).

Physical characteristics are as follows:

MS (ES) m/z P-fraction: Pos. mode: 421, 423 and 425 (MH$^+$); neg. mode: 419, 421 and 423 (M–H$^+$).

EXAMPLE 202

N-(2-Fluorophenyl)-8-hydroxy-7-quinolinecarboxamide (V-54) (Refer to Chart V)

Following GP V starting from 2-fluoroaniline (22 mg).

Physical characteristics are as follows:

MS (ES) m/z P-fraction: Pos. mode: 283 (MH$^+$), 305 (MNa$^+$); neg. mode: 281 (M–H$^+$).

EXAMPLE 203

N-(4-Cyano-2,3,5,6-tetrafluorophenyl)-8-hydroxy-7-quinolinecarboxamide (V-55) (Refer to Chart V)

Following GP V starting from 4-amino-2,3,5,6-tetrafluorobenzonitrile (38 mg).

Physical characteristics are as follows:

MS (ES) m/z T-fraction: Pos. mode: 362 (MH$^+$); neg. mode: 260 (M–H$^+$).

EXAMPLE 204

N-(2,4-Difluorophenyl-8-hydroxy-7-quinolinecarboxamide (V-56) (Refer to Chart V)

Following GP V starting from 2,4-difluoroaniline (26 mg).

Physical characteristics are as follows:

MS (ES) m/z P-fraction: Pos. mode: 301 (MH$^+$), 323 (MNa$^+$); neg. mode: 299 (M–H$^+$).

EXAMPLE 205

8-Hydroxy-N-(2,4,5-trifliuorophenyl)-7-quinolinecarboxamide (V-57) (Refer to Chart V)

Following GP V starting from 2,4,5-trifluoroaniline (30 mg).

Physical characteristics are as follows:

MS (ES) m/z T-fraction: Pos. mode: 319 (MH$^+$); neg. mode: 317 (M–H$^+$).

EXAMPLE 206

N-(2-Chlorophenyl)-8-hydroxy-7-quinolinecarboxamide (V-58) (Refer to Chart V)

Following GP V starting from 2-chloroaniline (26 mg).
Physical characteristics are as follows:

EXAMPLE 207

N-(4-Bromo-2-chlorophenyl)-8-hydroxy-7-quinolinecarboxamide (V-59) (Refer to Chart V)

Following GP V starting from 4-bromo-2-chloroaniline (42 mg).
Physical characteristics are as follows:
MS (ES) m/z P-fraction: Pos. mode: 377, 379 and 381 (MH$^+$); neg. mode: 375, 377 and 379 (M–H$^+$).

MS (ES) m/z T-fraction: Pos. mode: 299 and 301 (MH$^+$); neg. mode: 297 and 299 (M–H$^+$). Contaminated with quinoline methyl ester.

EXAMPLE 208

N-(2,4-Dichlorophenyl)-8-hydroxy-7-quinolinecarboxamide (V-60) (Refer to Chart V)

Following GP V starting from 2,4-dichloroaniline (32 mg).
Physical characteristics are as follows:
MS (ES) m/z P-fraction: Pos. mode: 333, 335 and 337 (MH$^+$); neg. mode: 331, 333 and 335 (M–H$^+$).

EXAMPLE 209

N-(2-Chloro-4-nitrophenyl)-8-hydroxy-7-quinolinecarboxamide (V-61) (Refer to Chart V)

Following GP V starting with 2-chloro-4-nitroaniline (35 mg).
Physical characteristics are as follows:
MS (ES) m/z P-fraction: Neg. mode: 342 and 344 (M–H$^+$).

EXAMPLE 210

N-(2,5-Dichlorophenyl)-8-hydroxy-7-quinolinecarboxamide (V-62) (Refer to Chart V)

Following GP V starting from 2,5-dichloroaniline (33 mg).
Physical characteristics are as follows:
MS (ES) m/z P-fraction Pos. mode: 333, 335 and 337 (MH$^+$); neg. mode: 331, 333 and 335 (M–H$^+$).

EXAMPLE 211

N-(2-Chloro-5-methylphenyl)-8-hydroxy-7-quinolinecarboxamide (V-63) (Refer to Chart V)

Following GP V starting from 2-chloro-5-methylaniline (29 mg).
Physical charactezistics are as follows:
MS (ES) m/z T-fraction: Pos. mode: 313 and 315 (MH$^+$); neg. mode: 311 and 313 (M–H$^+$).

EXAMPLE 212

8-Hydroxy-N-(2-iodophenyl)-7-quinolinecarboxamide (V-64) (Refer to Chart V)

Following GP V starting from 2-iodoaniline (44 mg).
Physical characteristics are as follows:
MS (ES) m/z T-fraction: Pos. mode: 391 (MH$^+$); neg. mode: 389 (M–H$^+$). Contaminated with quinoline methyl ester.

EXAMPLE 213

8-Hydroxy-N-(2-nitrophenyl)-7-quinolinecarboxamide (V-65) (Refer to Chart V)

Following GP V starting from 2-nitroaniline (28 mg).
Physical characteristics are as follows:
MS (ES) m/z T-fraction: Neg. mode: 308 (M–H$^+$), 331 (MNa–H$^+$). Contaminated with quinoline methyl ester.

EXAMPLE 214

N-(5-Chloro-2-hydroxyphenyl)-8-hydroxy-7-quinolinecarboxamide (V-66) (Refer to Chart V)

Following GP V starting from 5-chloro-2-hydroxyaniline (29 mg).
Physical characteristics are as follows:
MS (ES) m/z P-fraction: Pos. mode: 357 and 359 (MH$^+$), 379 and 381 (MNa$^+$); neg. mode: 355 and 357 (M–H$^+$).

EXAMPLE 215

8-Hydroxy-N-(2-hydroxy-5-nitrophenyl)-7-quinolinecarboxamide (V-67) (Refer to Chart V)

Following GP V starting from 2-hydroxy-5-nitroaniline (31 mg).
Physical characteristics are as follows:
MS (ES) m/z P-fraction: Neg mode: 324 (M–H$^+$).

EXAMPLE 216

8-Hydroxy-N-(2-hydroxy-5-methylphenyl)-7-quinolinecarboxamide (V-68) (Refer to Chart V)

Following GP V starting from 2-hydroxy-5-methylaniline (25 mg).
Physical characteristics are as follows:
MS (ES) m/z WU-fraction: Pos. mode: 295 (M$^+$); neg. mode: 293 (M–H$^+$).

EXAMPLE 217

N-Biphen-2-yl-8-hydroxy-7-quinolinecarboxamide (V-69) (Refer to Chart V)

Following GP V starting from 2-aminobiphenyl (34 mg).
Physical characteristics are as follows:
MS (ES) m/z T-fraction: Pos. mode: 341 (MH$^+$); neg. mode: 339 (M–H$^+$).

EXAMPLE 218

8-Hydroxy-N-[2-methylmercapto)phenyl]-7-quinolinecarboxamide (V-70) (Refer to Chart V)

Following GP V starting from 2-methylmercaptoaniline (28 mg).
Physical characteristics are as follows:
MS (ES) m/z T-fraction: Pos. mode: 311 (MH$^+$); neg. mode: 309 (M–H$^+$).

EXAMPLE 219

8-Hydroxy-N-[2-(trifluoromethyl)phenyl]-7-quinolinecarboxamide (V-71) (Refer to Chart V)

Following GP V starting from 2-(trifluoromethyl)aniline (33 mg).

Physical characteristics are as follows:
MS (ES) m/z T-fraction: Neg. mode: 331 (M–H$^+$). Contaminated with quinoline methyl ester.

EXAMPLE 220

8-Hydroxy-N-(2-methylphenyl)-7-quinolinecarboxamide (V-72) (Refer to Chart V)

Following GP V starting from 2-methylaniline (22 mg).
Physical characteristics are as follows:
MS (ES) m/z T-fraction: Pos. mode: 279 (MH$^+$); neg. mode: 277 (M–H$^+$).

EXAMPLE 221

8-Hydroxy-N-(2-methyl-3-nitrophenyl)-7-quinolinecarboxamide (V-73) (Refer to Chart V)

Following GP V starting with 2-methyl-3-nitroaniline (31 mg).
Physical characteristics are as follows:
MS (ES) m/z T-fraction: Pos. mode: 324 (MH$^+$); neg. mode: 322 (M–H$^+$).

EXAMPLE 222

N-(2,3-Dimethylphenyl)-8-hydroxy-7-quinolinecarboxamide (V-74) (Refer to Chart V)

Following GP V starting with 2,3-dimethylaniline (25 mg).
Physical characteristics are as follows:
MS (ES) m/z T-fraction: Pos. mode: 293 (MH$^+$); neg. mode: 291 (M–H$^+$).

EXAMPLE 223

8-Hydroxy-N-(2,4,6-trimethylphenyl)-7-quinolinecarboxamide (V-75) (Refer to Chart V)

Following GP V starting from 2,4,6-trimethylaniline (25 mg).
Physical characteristics are as follows:
MS (ES) m/z T- and WU-fractions: Pos. mode: 307 (MH$^+$); neg. mode: 305 (M–H$^+$).

EXAMPLE 224

N-(2-Ethylphenyl)-8-hydroxy-7-quinolinecarboxamide (V-76) (Refer to Chart V)

Following GP V starting with 2-ethylaniline (25 mg).
Physical characteristics are as follows:
MS (ES) m/z T-fraction: Pos. mode: 293 (MH$^+$); neg. mode: 291 (M–H$^+$).

EXAMPLE 225

8-Hydroxy-N-[3-(trifluoromethyl)phenyl]-7-quinolinecarboxamide (V-77) (Refer to Chart V)

Following GP V starting with 3-(trifluoromethyl)aniline (32 mg).
Physical characteristics are as follows:
MS (ES) m/z T-fraction: Pos. mode: 333 (MH$^+$); neg. mode: 231 (M–H$^+$).

EXAMPLE 226

8-Hydroxy-N-(2-methyl-4-fluorophenyl)-7-quinolinecarboxamide (V-78) (Refer to Chart V)

Following GP V starting with 2-methyl-4-fluoroaniline (25 mg).

Physical charactezistics are as follows:
MS (ES) m/z T-fraction: Pos. mode: 297 (MH$^+$); neg. mode: 295 (M–H$^+$).

EXAMPLE 227

N-(4-Chloro-2-methylphenyl)-8-hydroxy-7-quinolinecarboxamide (V-79) (Refer to Chart V)

Following GP V starting with 2-chloro-2-methylaniline (29 mg).
Physical characteristics are as follows:
MS (ES) m/z P-fraction: Pos. mode: 313 and 315 (MH$^+$), 335 and 335 (MNa$^+$); neg. mode: 311 and 313 (M–H$^+$).

EXAMPLE 228

N-(4-Chloro-2-methoxy-5-methylphenyl)-8-hydroxy-7-quinolinecarboxamide (V-80) (Refer to Chart V)

Following GP V startng with 4-chloro-2-methoxy-5-methylaniline (55 mg).
Physical characteristics are as follows:
MS (ES) m/z T-fraction: Pos. mode: 343 and 345 (MH$^+$); neg. mode: 341 and 343 (M–H$^+$).

EXAMPLE 229

N-(4-tert-Butylphenyl)-8-hydroxy-7-quinolinecarboxamide (V-81) (Refer to Chart V)

Following GP V starting with 4-tert-butylaniline (31 mg).
Physical characteristics are as follows:
MS (ES) m/z T-fraction: Pos. mode: 321 (MH$^+$); neg. mode: 319 (M–H$^+$).

EXAMPLE 230

8-Hydroxy-N-(4-propylphenyl)-7-quinolinecarboxamide (V-82) (Refer to Chart V)

Following GP V starting with 4-propylaniline (28 mg).
Physical characteristics are as follows:
MS (ES) m/z T-fraction: Pos. mode: 307 (MH$^+$); neg. mode: 305 (M–H$^+$).

EXAMPLE 231

N-(2,6-Di-i-propylphenyl)-8-hydroxy-7-quinolinecarboxamide V-83) (Refer to Chart V)

Following GP V starting from 2,6-di-i-propylaniline (36 mg).
Physical characterislics are as follows:
MS (ES) m/z T-fraction: Neg. mode: 347 (M–H$^+$).

EXAMPLE 232

N-(4-Bromo-2-fluorophenyl)-8-hydroxy-7-quinolinecaboxamide (V-84) (Refer to Chart V)

Following GP V starting from 4-bromo-2-fluoroaniline (31 mg).
Physical characteristics are as follows:
MS (ES) m/z T- and P-fractions: Pos. mode: 361 and 363 (MH$^+$); neg. mode: 359 and 361 (M–H$^+$).

EXAMPLE 233

8-Hydroxy-N-(2,3,4-trifluorophenyl)-7-quinolinecarboxamide (V-85) (Refer to Chart V)

Following GP V starting from 2,3,4-trifluoroaniline (30 mg).

Physical characteristics are as follows:

MS (ES) m/z P-fraction: Pos. mode: 319 (MH$^+$), 341 (MNa$^+$); neg. mode: 317 (M−H$^+$).

EXAMPLE 234

N-(2-Fluoro-4-iodophenyl)-8-hydroxy-7-quinolinecarboxamide (V-86) (Refer to Chart V)

Following GP V starting from 2-fluoro-4-iodoaniline (48 mg).

Physical characteristics are as follows:

MS (ES) m/z T- and P-fractions: Pos. mode: 409 (MH$^+$); neg. mode: 407 (M−H$^+$).

EXAMPLE 235

8-Hydroxy-N-[4-(hydroxymethyl)phenyl]-7-quinolinecarboxamide (V-87) (Refer to Chart V)

Following GP V starting from 4-(hydroxymethyl)aniline (29 mg).

Physical characteristics are as follows:

MS (ES) m/z P-fraction: Pos. mode: 295 (MH$^+$); neg. mode: 293 (M−H$^+$).

EXAMPLE 236

N-Benzo-1,3-thiazol-6-yl-8-hydroxy-7-quinolinecarboxamide (V-88) (Refer to Chart V)

Following GP V starting from 6-amino-benzo-1,3-thiazole (31 mg).

Physical characteristics are as follows:

MS (ES) m/z P-fraction: Pos. mode: 322 (MH$^+$); neg. mode: 320 (M−H$^+$).

EXAMPLE 237

8-Hydroxy-N-indazol-5-yl-7-quinolinecarboxamide (V-89) (Refer to Chart V)

Following GP V starting from 5-aminoindazole (27 mg).

Physical characteristics are as follows:

MS (ES) m/z P-fraction: Neg. mode: 303 (M−H$^+$).

EXAMPLE 238

8-Hydroxy-N-[2-methoxy-5-(trifluoromethyl)phenyl]-7-quinolinecarboxamide (V-90) (Refer to Chart V)

Following GP V staring from 2-methoxy-5-(trifluoromethyl)aniline (39 mg).

Physical characteristics are as follows:

MS (ES) m/z T-fraction: Pos. mode: 363 (MH$^+$); neg. mode: 361 (M−H$^+$).

EXAMPLE 239

8-Hydroxy-N-(5-iodo-2-methylphenyl)-7-quinolinecarboxamide (V-91) (Refer to Chart V)

Following GP V starting with 5-iodo-2-methylaniline (47 mg).

Physical characteristics are as follows:

MS (ES) m/z T- and P-fractions: Pos. mode: 405 (MH$^+$); neg. mode: 403 (M−H$^+$).

EXAMPLE 240

N-(2-Chloro-4-cyanophenyl)-8-hydroxy-7-quinolinecarboxamide (V-92) (Refer to Chart V)

Following GP V starting with 4-amino-3-chlorobenzonitrile (31 mg).

Physical characteristics are as follows:

MS (ES) m/z T-fraction: Neg. mode: 322 and 324 (M−H$^+$).

EXAMPLE 241

N-(5-Bromopyridin-2-yl)-8-hydroxy-7-quinolinecarboxamide (V-93) (Refer to Chart V)

Following GP V starting with 2-amino-5-bromopyridine (35 mg).

Physical characteristics are as follows:

MS (ES) m/z P-fraction: Pos. mode: 344 and 342 (MH$^+$); neg. mode: 340 and 342 (M−H$^+$).

EXAMPLE 242

8-Hydroxy-N-(8-hydroxyquinolin-2-yl)-7-quinolinecarboxamide (V-94) (Refer to Chart V)

Following GP V starting with 2-amino-8-hydroxyquinoline (33 mg).

Physical characteristics are as follows:

MS (ES) m/z T- and P-fractions: Pos. mode: 332 (MH$^+$); neg. mode: 330 (M−H$^+$).

PREPARATION 38

2-Amino-5-alkylamino-1,3,4-thiadiazoles (GP I) (Refer to Chart W.)

2-Amino-5-bromo-1,3,4-thiadiazole W-95 (1 eq.) is dissolved in DMF at r.t;. The alkyl amine (about 1 eq.) and DIPEA (1–3 eq.) are added respectively and the solution stirred for 20 h. The solvent is removed under reduced pressure, the residue is diluted in AcOEt and washed with an aq. buffer sol. at pH 4 (2×). The org. phase is dried over MgSO$_4$, filtered, and the solvent removed under reduced. pressure. The residue is either crystallized from AcOEt/hexanes or purified by FC.

PREPARATION 39

N-Aryl-8-hydroxy-7-quinolinecarboxamides from Anhydride U-1, Procedure for Single Compounds (GP II)

Anhydride U-1 (1 eq.) is dissolved in CHCl$_3$ (n mL) at r.t. Pyridinium chloride (1 eq) and then the arylamine (about 1 eq.) are added. The solution is stirred for 6 h at r.t. 1M HCl/H$_2$O (n mL) is added and the biphasic mixture is stirred efficierntly overnight. The precipitate is filtered, washed with a little water and CH$_2$Cl$_2$ aad dried under high vacuum.

PREPARATION 40

N-Aryl-8-hydroxy-7-quinolinecarboxamides from Anhydride U-1, Procedure for Parallel Synthesis (GP III)

The aryl amines (0.20 mmol) are laid into syringes corked at their output and set with a frit at the bottom of their large section. A sol. of anhydride U-1 (0.1M) and of pyridinium chloride (0.1) in CHCl$_3$ is prepared. This solution (2 mL/syringe) is added into the syringes; if the arylamine is a liquid, it is added at this stage only; if the arylamine is a hydrochloride salt, DIPEA (33 μL, 1 eq) is added. The syringes are tightly closed at their bottoms and shaken for 6 h at r.t. 1M HCl/H$_2$O (2 mL) is added and the biphasic mixture is shaken efficiently overnight. The precipitate is isolated by sucking the solvent from the bottom of the syringes, is washed with a little water and CH$_2$Cl$_2$ and dried under high vacuum.

PREPARATION 41

N-Aryl-8-hydroxy-7-quinolinecarboxamides from the Ester U-3, Procedure for Single Compounds (GP IV)

Ester U-3 is dissolved in CH$_2$Cl$_2$ and the arylamine (about 1 eq) and DIPEA (about 1 eq.) are added. The reaction mixture is stirred between 6 h and 6 days. MeOH (same amount as CH$_2$Cl$_2$) is added and the mixture is stirred between 6 h and 18 h. For the work-up procedures, see specific examples below.

PREPARATION 42

N-Aryl-8-hydroxy-7-quinolinecarboxamides from Ester U-3, Procedure for Parallel Synthesis (GP V)

The aryl amines (0.2 mmol) are put into syringes corked at their output and set with a frit at the bottom of their large section. A sol. of ester U-3 (0.05M) and of DIPEA (0.05M) in CH$_2$C$_2$ is prepared and added to the arylamines (4 mL for each amine); if the arylamine is a liquid, it is added at this stage only; if the arylamine is a salt, DIPEA (33 μL, 1 eq) is added. The sringes are tightly closed and shaken for 5 days. MeOH (2–4 mL) is added and the mixture is shaken for 6 h. The precipitate, if any, is isolated by sucking the solvent from the bottom of the syringes, washed with AcOEt and dried under high vacuum (P-fraction). The filtrate is washed with sat. NaHCO$_3$/H$_2$O (1×) and an aq. buffer sol. at pH4 (1×); each time, the aq. phase is pipetted out of the seringe. If a precipitate appeared during the work-up, it is filtered and dried (WU-fraction). The filtrate is blown down with a nitrogen stream, AcOEt (4 mL) is added and the mixture heated to 65° C. for 30 min. and cooled to 0° C. The solvent is pipetted out and the residue dried under high vacuum (T-fraction). The org. phase is blown down and the residue dried under high vacuum as well (S-fraction). The degree of hydration of the obtained products was not determined.

PREPARATION 43

Hydrolysis of the Tert-butyl Esters to the Carboxylic Acids (GP VI)

tert-Butyl ester is dissolved in TFA at 0° C. and the solution stirred for 4 h at r.t. The solvent is removed under reduced pressure and the residue triturated in hot EtOH (95%). After cooling down to r.t. or 0° C., the precipitated is filtered, washed with AcOEt and dried under high vacuum.

PREPARATION 44

8-{[(2,2,2-Trichloroethoxy)carbonyl]oxy}-7-quinolinecarboxylic Acid Anhydride with 2,2,2-trichloroethyl Hydrogen Carbonate (U-1)

In a flame-dried flask, 8-hydroxy-7-quinolinecarboxylic acid (2.00 g) is suspended into CH$_2$Cl$_2$ (100 mL) and DIPEA (3.70 mL) is added. The mixture is stirred until homogeneity is reached and cooled to 0° C. Trichloroethyl chloroformate (3.00 mL) is added and the solution is stirred for 3 h at 0° C., then stirred for another hour while allowed to warm up slowly to r.t. The solution is washed with 1M HCl/H$_2$O (1×), dried over Na$_2$CO$_3$ and the solvent removed under reduced pressure. Crystallization of the residue from CHCl$_3$/hexanes yields the desired product (5.20 g).

Physical characteristics are as follows:

mp: 133–4° C.; $^1$H-NMR (CDCl$_3$, 300 MHz) δ 9.05, 8.26, 8.11, 7.88, 7.61, 4.97, 4.95. $^{13}$C-NMR (CDCl$_3$, 75 MHz) δ: 157.56, 152.13, 151.59, 149.25, 147.71, 141.09, 135.82, 132.64, 126.57, 126.45, 124.44, 119.67, 93.96, 93.42. MS (FAB) m/z 538, 540 and 542 (MH$^+$), 172. HRMS (FAB): found: 537.8609. Anal. Found: C, 35.12; H, 1.85; N, 2.65.

PREPARATION 45

8-Acetoxy-7-quinolinecarboxylic Acid (U-2)

This compound is prepared according to literature procedure. (German Patent No. 540842, Dec. 10, 1931.)

Physical characteristics are as follows:

$^1$H-NMR (d$_6$-DMSO, 300 MHz) δ 13.35, 8.99, 8.46, 8.00, 7.95, 7.67, 2.38. $^{13}$C-NMR (d$_6$-DMSO, 75 MHz) δ 172.46, 169.22, 166.21, 152.08, 147.95, 141.42, 136.61, 131.35, 127.08, 126.13, 124.07, 21.20.

PREPARATION 46

7-(Fluorocarbonyl)quinolin-8-yl Acetate (U-3)

In a flame-dried flask under Ar, 8acetoxy-7-quinolinecarboxylic acid U-2(4.30 g) is suspended into CH$_2$Cl$_2$ (110 mL). Pyridine (1.50 mL) is added and the suspension cooled to −40° C. Cyanuric fluoride (3.00 mL) is added and the mixture stirred for 3 h, while the temperature rose slowly to 0° C. Ice and water and CH$_2$Cl$_2$ (100 mL) were added. Phases were shaken, separated and the aq. phase extracted with CH$_2$Cl$_2$ (1×). The combined org. phases were dried over MgSO$_4$, filtered, and the solvent is removed under reduced pressure. Crystallization of the residue from hexanes yields ester U-3 as white needles (4.10 g).

Physical characteristics are as follows:

mp: 130–132° C.; $^1$H-NMR (CDCl$_3$, 300 MHz) δ 9.05, 8.22, 8.02, 7.80, 7.58, 2.58. $^{13}$C-NMR (CDCl$_3$, 75 MHz) δ 169.06, 156.59, 151.89, 141.42, 136.07, 132.92, 126.77, 126.03, 124.41, 118.10, 117.30, 20.88. MS (FAB) m/z 234 (MH$^+$), 192, 172. HRMS (FAB): 234.0569. Anal. C, 60.98; H, 3.55; N, 6.24.

PREPARATION 47

2-Amino-5-bromo-1,3,4-thiadiazole (W-95) (Refer to Chart W.)

To a stirred sol. of 2-amino-1,3,4-thiadiazole (40.5 g) in acetic acid (250 mL) is added bromine (22.7 ml) over about 20 minutes. The flask is surrounded by an ice bath during the addition to maintain the reaction temperature near 25° C. Following the addition, the ice bath is removed and the clear red sol. stirred at r.t. for 18 hours, then added to 1L of cracked ice. Excess bromine is quenched with 10% NaHSO$_3$/H$_2$O and 40 ml of 50% NaOH/H$_2$O is added. The precipitated solid is isolated by filtration and washed well with water, then dissolved in 300 ml of water containing 40 ml conc. HCl. The solution is filtered from a small amount of solid, then 87 g of K$_2$HPO$_4$ in a small quantity of water is added. The resulting slurry is chilled in ice and filtered, and the solid washed well with water. Recrystalization of the product from 400 ml of ethanol provides thiadiazole W-95 (26.3 g) as tan crystals.

Physical characteristics are as follows:
$^1$H-NMR (d$_6$-DMSO) δ 7.51.

PREPARATION 48

2-Amino-5-(2-phenylethyl)amino-1,3,4-thiadiazole (W-96) (Refer to Chart W.)

A mixture of 2-amino-5-bromo-1,3,4-thiadiazole W-95 (360 mg), of phenethylamine (0.38 mL) and of K$_2$HPO$_4$ (522 mg) in DMF (2 mL) is heated under nitrogen at 100° C. for 2 h, then partitioned between water and AcOEt. The organic phase is washed with water and brine, dried over MgSO$_4$, and concentrated under reduced pressure. FC (MeOH/CH$_2$Cl$_2$ 5:95) provides thiadiazole W-96 (261 mg). Recrystallization of 238 mg of this from acetonitrile/toluene affords 205 mg of fine white crystals.

Physical characteristics are as follows:
mp: 156–157° C.; $^1$H-NMR δ 2.92, 3.50, 7.2–7.3. IR 3186, 1565, 1505 cm$^{-1}$ EI MS m/z 221 Anal. Found: C, 54.51; H, 5.47; N, 25.26; S, 14.30.

PREPARATION 49

2-Amino-5-butylamino)-1,3,4-thiadiazole (W-97) (Refer to Chart W.)

To a stirred, cooled (0° C.) mixture of 2-amino-5-bromothiadiazole W-95 (5.40 g) and of K$_2$HPO$_4$ (5.7 g) in DMF (20 mL) is added n-butylamine (5.9 ml). The ice bath is removed and the mixture stirred at room temperature for 18 h, then partitioned between water and AcOEt. Continuous extraction with CH$_2$Cl$_2$ is necessary to remove all product from the aqueous phase. The combined organic phase is dried over MgSO$_4$ and concentrated under reduced pressure. FC (MeOH/CH$_2$Cl$_2$ 7:93) provides thiadiazole W-97 (3.49 g). Recrystallization from acetonitrile/toluene affords 3.34 g of white needles.

Physical characteristics are as follows:
mp: 152–154° C.; $^1$H-NMR δ 0.94, 1.4, 1.6, 3.21, 3.6. IR 3184, 2957, 1562, 1507 cm$^{-1}$ EI MS m/z 173

PREPARATION 50

2-Amino-5-([2-[(tert-butoxy)amido]ethyl}amino)-1,3,4-thiadiazole (W-98) (Refer to Chart W.)

A mixture of 2-amino-5-bromo-1,3,4-thiadiazole W-95 (5.40 g), of K$_2$HPO$_4$ (7.84 g) and Boc-ethylenediamine (9.60 g) in DMF (20 mL) is stirred at r.t. for 18 h. The solid paste obtained is recrystallized from acetonitrile/water to provide thiadiazole W-98 (6.18 g) as pink platelets.

Physical characteristics are as follows:
mp: 219–220° C.; $^1$H-NMR (CD$_3$OD) δ 1.40, 3.2–3.3. IR 2989, 1676, 1577, 1512, 1366 cm$^{-1}$ EI MS m/z 260

PREPARATION 51

Amino-1,3-benzodioxol-5-ylacetonitrile (W-99) (Refer to Chart W.)

Piperonal (6.00 g) is dissolved in THF (25 mL) and aq. NH$_3$ (58%, 4.2 mL), NH$_4$Cl (3.3 g) and KCN (3.9 g) are added. The mixture is stirred efficiently for 24 h. MgSO$_4$ is added and the mixture stirred for 30 min., filtered and washed with THF The filtrate is evaporated under reduced pressure and the residue purified by FC (Et$_2$O/petrol ether 1:2,→2:1,→Et$_2$O). Aminonitrile W-99 is obtained as a brown, unstable oil (2.87 g). The hydrochloride salt is precipitated from sat. HCl/Et$_2$O for analytical purposes.

Physical characteristics are as follows:
Free amino nitrile: R$_f$=0.45 (AcOEt/hexanes 1:1). Hydrochloride salt: mp: 159–164° C. (dec). $^1$H-NMR (D$_2$O, 300 MHz) δ 7.03, 7.02, 6.88, 5.96, 5.58. $^{13}$C-NMR (D$_2$O, 75 MHz) δ 149.43, 148.22, 122.80, 121.74, 115.21, 109.16, 108.00, 102.07. MS (EI) m/z 176 (M$^+$), 160, 150, 122. Anal. Found: C, 50.59; H, 4.25; N, 12.90.

PREPARATION 52

[(2-Amino-1,3,4-thiadiazol-5-yl)amino]-1,3-benzodioxol-5-ylacetonitrile (W-100) (Refer to Chart W.)

According to GP I starting from thiadiazole W-95 (2.70g), aminonitrile W-99 (2.39 g) and DIPEA (2.70 mL) in DMF (60 mL), the product is purified by FC (AcOEt/hexanes 3:1→AcOEt). Nitrile W-100 is isolated as a brown powder (1.70 g).

Physical characteristics are as follows:
R$_f$=0.10 (AcOEt/hexanes 1:1). mp: 144° C. (dec). $^1$H-NMR (CD$_3$OD, 300 MHz) δ 7.06, 7.02, 6.87, 5.99, 5.74. $^{13}$C-NMR (CD$_3$OD, 75 MHz) δ 162.92, 158.60, 148.61, 148.39, 127.48, 120.91, 117.95, 108.07, 107.34, 101.66. HRMS (EI) 275.0461.

PREPARATION 53

N-(2-Amino-1,3,4-thiadiazol-5-yl)phenylalanine Methyl Ester (W-101) (Refer to Chart W.)

According to GP I starting from thiadiazole W-95 (1.50 g), phenylalanine methyl ester hydrochloride (1.80 g) and DIPEA (4.20 mL) in DMF (30 mL), the product is purified by FC (AcOEt/hexanes 3:1→AcOEt). Ester W-101 is obtained as a white powder (0.22 g).

Physical characteristics are as follows:
R$_f$=0.05 (AcOEt/hexanes 1:1). mp: 186–189° C.; $^1$H-NMR (CD$_3$OD, 300 MHz) δ 7.27–7.09, 4.57, 3.67, 3.17, 3.01. $^{13}$C-NMR (CD$_3$OD, 75 MHz) δ 172.74, 161.75, 160.65, 136.77, 128.85, 128.02, 126.45, 58.07, 51.16, 37.48. MS (EI) m/z: 278 (M$^+$), 219, 187, 155, 127, 116. Anal. Found: C, 51.61; H, 4.98; N, 19.91.

PREPARATION 54

N-(2-Amino-1,3,4-thiadiazol-5-yl)-D-phenylalanine Methyl Ester (W-102) (Refer to Chart W.)

According to GP I starting from thiadiazole W-95 (1.50 g), D-phenylalanine methyl ester hydrochloride (1.80g) and DIPEA (4.20 mL) in DMF (30 mL), the product is purified by FC (AcOEt/hexanes 3:1→AcOEt). Ester W-102 is obtained as a white powder (0.19 g).

Physical characteristics are as follows:
R$_f$=0.05 (AcOEt/hexanes 1:1). mp: 186–189° C.; $^1$H-NMR (CD$_3$OD, 300 MHz) δ 7.26–7.19, 4.57, 3.66, 3.17, 3.01. $^{13}$C-NMR (CD$_3$OD, 75 MHz) δ 172.77, 161.75, 160.66, 136.76, 128.86, 128.03, 126.46, 58.07, 51.19, 37.48. MS (EI) m/z: 278 (M$^+$), 219, 187, 155, 127, 116. Anal. Found: C, 51.57; H, 5.14; 19.86.

PREPARATION 55

2-(1,3-Benzodioxol-5-yl)glycine (W-103) (Refer to Chart W.)

Prepared according to literature procedure (E H W Boehm, R E Bambury, R J Baumann, R C Erickson, B L Harrison, P F Hoffman, F J McCarty, R A Schnettler, M J Vaal, D L Wenstrup, J. Med. Chem. 1980, 23, 405).

Physical characterstics are as follows:

$^1$H-NMR (d$_6$-DMSO, 300 MHz) δ 6.22, 6.84, 5.97, 4.10. MS (EI) m/z 195 (M$^+$), 150, 123, 93. HRMS (EI) 195.0530.

PREPARATION 56

2-(1,3-Benzodioxol-5-yl)glycine Tert-butyl Ester (W-104) (Refer to Chart W.)

2-(1,3-Benzodioxol-5-yl)glycine W-95 (5.00 g) is dissolved in a dioxane (50 mL) and conc. H$_2$SO$_4$ (3.90 mL) mixture. Liquid i-butylene (50 mL) is added, the flask rapidly tightly closed and shaken for 24 h. The mixture is poored into a mixtue of 1M NaOH/H$_2$O, ice and AcOEt. After shaking, the phases are separated and the aq. phase is extracted with AcOEt (1x). The combined org. phases are dried over MgSO$_4$. Removing the solvent under reduced pressure yields an oil containing 77% ($^1$H-NMR) of ester W-104 (6.65 g, 5.10 g of product).

Physical characteristics are as follows:

$^1$H-NMR (CDCl$_3$, 300 MHz) δ 6.85–6.80, 6.74, 5.94, 4.42, 1.37.

PREPARATION 57

N-(2-Amino-1,3,4-thiadiazo-5-yl)-2-(1,3-benzodioxol-5-yl)glycine Tert-butyl Ester (W-105) (Refer to Chart W.)

According to GP I starting from thiadiazole W-95 (3.65 g), tert-butyl ester V-104 (5.10 g), DIPEA (6.8 mL) and DMF (150 mL). Crystallization of the crude from AcOEt/hexanes yieldsester W-105 as a white powder (6.15 g).

Physical characteristics are as follows:

R$_f$=0.05 (AcOEt/hexanes 1:1). $^1$H-NMR (d$_6$-DMSO, 300 MHz), δ 7.42, 6.92–6.86, 6.26, 5.99, 5.05, 1.30. $^{13}$C-NMR (d$_6$-DMSO, 75 MHz) δ 170.70, 160.60, 158.81, 147.73, 147.43, 131.33, 121.48, 108.67, 108.10, 101.61, 81.33, 61.03, 28.00. MS (EI) m/z 350 (M$^+$), 249, 179, 148, 57. HRMS (EI) 350.1043.

PREPARATION 58

2-(1,3-Benzodioxol-4-yl)glycine (W-106) (Refer to Chart W.)

Prepared according to literature procedure (E H W Boehm, R E Bambury, R J Baumann, R C Erickson, B L Harrison, P F Hoffman, F J McCarty, R A Schnettler, M J Vaal, D L Wenstrup, J. Med. Chem. 1980, 23, 405).

Physical characteristics are as follows:

$^1$H-NMR (d$_6$-DMSO, 300 MHz) δ 6.62, 6.00, 5.97, 4.23. MS (EI) m/z 195 (M$^+$), 150, 123, 93, 75. HRMS (EI) 195.0527.

PREPARATION 59

2-(1,3-Benzodioxol-4-yl)glycine Tert-butyl Ester (W-107) (Refer to Chart W.)

2-(1,3-Benzodioxol-4-yl)glycine W-106 (1.72 g) is dissolved in a dioxane (20 mL) and conc. H$_2$SO$_4$ (1.35 mL) mixture. liquid i-butylene (20 mL) is added, the flask rapidly tightly closed and shaken for 24 h. The mixture is poored in a mixture of 1M NaOH/H$_2$O, ice and AcOEt. After shaking, the phases are separated and the aq. phase is extracted with AcOEt (1x). The combined org. phases are dried over MgSO$_4$. Removing the solvent under reduced pressure yields an oil containing 78% ($^1$H-NMR) of ester W-107 (1.46 g, 1.14 g of product).

Physical characteristics are as follows:

$^1$H-NMR (CDCl$_3$, 300 MHz) δ 6.79–6.72, 5.97, 5.94, 4.57, 1.39.

PREPARATION 60

N-(2-Amino1,3,4-thiadiazo-5-yl)-2-(1,3-benzodioxol-4-yl)glycine Tert-butyl Ester (W-108) (Refer to Chart W.)

According to GP I starting from thiadiazole W-95 (0.83 g), 2-(1,3-benzodioxol-4-yl)glycine tert-butyl ester W-107 (1.14 g), DIPEA (1.5 mL) and DMF (30 mL). Crystallization of the crude from AcOEt/hexanes yields ester W-108 as a white powder (0.87 g).

Physical characteristics are as follows:

R$_f$=0.05 (AcOEt/hexanes 1:1). $^1$H-NMR (d$_6$-DMSO, 300 MHz) δ 7.52, 6.90–6.78, 6.42, 6.03, 6.02, 5.30, 1.32. $^{13}$C-NMR (d$_6$-DMSO, 75 MHz) δ 169.83, 160.87, 158.70, 147.55, 145.68, 122.18, 120.39, 119.02, 108.77, 101.50, 81.61, 55.41, 27.99. MS (EI) m/z 250 (M$^+$), 249, 233, 148, 57. Anal. Found: C, 51.05; H, 5.35; N, 15.91.

PREPARATION 61

2-Amino-5-[N-(1,3-benzodioxol-5-ylmethyl)amino]-1,3,4-thiadiazole (X-109) (Refer to Chart XI)

According to GP I starting from thiadiazole W-95 (1.00 g), piperonylamine (0.83 mL), DIPEA (1.85 mL) and DMF (10 mL). Purification of the crude by FC (AcOEt→MeOH/AcOEt 1:19→MeOH/CH$_2$Cl$_2$ 1:9) yields thiadiazole X-109 as a white powder (99 mg).

Physical characteristics are as follows:

R$_f$=0.02 (AcOEt/hexanes 1:1). mp: 164–187° C.; $^1$H-NMR (d$_6$-DMSO, 300 MHz) δ 7.18, 6.87, 6.83, 7.78, 6.24, 5.96, 4.20. $^{13}$C-NMR (d$_6$-DMSO, 75 MHz) δ 160.32, 159.77, 147.62, 146.55, 133.78, 121.20, 108.56, 108.42, 101.25, 47.73. MS (EI) m/z 250 (M$^+$), 208, 135, 105, 77,51. HRMS (EI) 250.0528.

PREPARATION 62

N-(2-Amino-1,3,4-thiadiazol-5-yl)tyrosine Tert-butyl Ester (X-110) (Refer to Chart X)

According to GP I starting from thiadiazole W-95 (760 mg), tyrosine tert-butyl ester hydrochloride (1.16 g), DIPEA (1.80 mL) and DMF (20 mL). Crystallization of the crude from AcOEt/hexanes yields ester X-110 as a white powder (0.98 g).

Physical characteristics are as follows:

R$_f$=0.25 (AcOEt). mp: 121–123° C.; $^1$H-NMR (CD$_3$OD, 300 MHz) δ 8.20, 7.27, 6.93, 4.60, 3.08, 1.60. $^{13}$C-NMR (CD$_3$OD, 75 MHz) δ 171.71, 161.65, 160.84, 155.95, 130.07, 127.47, 114.68, 81.37, 59.02, 36.85, 26.81. MS (EI) m/z 336 (M$^+$), 263, 235, 173, 156, 116, 107, 57. HRMS (EI) 336.1259.

PREPARATION 63

N$^1$-(2-Amino-1,3,4-thidiazol-5-yl)-N$^5$-[(benzoy)carbonyl]lysine Tert-butyl Ester (X-111) (Refer to Chart X.)

According to GP I starting from thiadiazole W-95 (730 mg), N$^5$-[(benzoxy)carbonyl]lysine tert-butyl ester hydrochloride (1.50 g), DIPEA (2.05 mL) and DMF (25 mL). Crystallization of the crude from AcOEt/hexanes yields ester X-111 as a white powder (0.96 g).

Physical characteristics are as follows:

$R_f$=0.25 (AcOEt). mp: 131–132° C.; $^1$H-NMR (CD$_3$OD, 300 MHz) δ 7.33, 5.05, 4.13, 3.10, 1.95–1.45, 1.44. $^{13}$C-NMR (CD$_3$OD, 75 MHz) δ 172.40, 161.58, 161.15, 157.53, 137.04, 128.06, 127.54, 127.36, 81.29, 65.92, 57.39, 40.09, 29.11, 26.89, 22.63, 19.24. Anal. Found: C, 55.08; H, 6.69; N, 16.22.

PREPARATION 64

N-(2-Amino-1,3,4-thiadiazol-5-yl)leucine Tert-butyl Ester (X-112) (Refer to Chart X)

According to GP I starting from thiadiazole W-95 (1.00 g), leucine tert-butyl ester hydrochloride (1.50 g), DIPEA (2.80 mL) and DMF (10 mL). Purification of the crude by FC (AcOEt/hexanes 1:1→AcOEt) yields ester X-112 as a white powder (1.06 g).

Physical characteristics are as follows:

$R_f$=0.20 (AcOEt). mp: 138–141° C.; $^1$H-NMR (CD$_3$OD, 300 MHz) δ 4.38, 2.01, 1.82, 1.65, 1.18. $^{13}$C-NMR (CD$_3$OD, 75 MHz); two rotamers visible δ 176.62, 172.89, 172.71, 163.47, 162.05, 160.64, 81.20, 72.76, 56.05, 42.83, 40.87, 35.58, 30.27, 26.86, 24.77, 21.87, 20.65. MS (EI) m/z 286 (M$^+$), 269, 230, 213, 185, 156, 143, 129, 116, 57. HRMS (EI) 286.1461.

PREPARATION 65

N-(2-Amino-1,3,4-thiadiazol-5-yl)proline Tert-butyl Ester (X-113) (Refer to Chart X)

According to GP I starting from thiadiazole W-95 (1.00 g), proline tert-butyl ester hydrochloride (1.46 g), DIPEA (2.80 mL) and DMF (10 mL). Purification of the crude by FC (AcOEt/hexanes 1:1→AcOEt) yields ester X-113 as a white powder (0.55 g).

Physical characteristics are as follows:

$R_f$=0.25 (AcOEt). mp: 141–146° C.; $^1$H-NMR (CD$_3$OD, 300 MHz) δ 4.20, 3.58–3.41, 2.37–2.31, 2.09–2.01, 1.45. $^{13}$C-NMR (CD$_3$OD, 75 MHz) δ 171.91, 161.09, 160.95, 81.64, 63.13, 50.45, 30.29, 26.79, 23.45. MS (EI) m/z 270 (M$^+$), 214, 197, 169, 142, 128, 100, 70, 57. HRMS (EI) 270.1154.

PREPARATION 66

N-(2-Amino-1,3,4-thiadiazol-5-yl)methionine Tert-butyl Ester (X-114) (Refer to Chart X.)

According to GP I sting from thiadiazole W-95 (750 mg), methionine tert-butyl ester hydrochloride (1.00 g), DIPEA (2.10 mL) and DMF (20 mL). Crystallization of the crude from AcOEt/hexanes yields ester X-114 as a white powder (0.60 g).

Physical characteristics are as follows:

$R_f$=0.25 (AcOEt). mp: 172–173° C.; $^1$H-NMR (CD$_3$OD, 300 MHz) δ 4.31, 2.62–2.56, 2.16–1.92, 2.08, 1.45. $^{13}$C-NMR (CD$_3$OD, 75 MHz) δ 172.04, 161.71, 161.09, 81.47, 56.52, 31.38, 29.75, 26.87, 13.85. MS (EI) m/z 304 (M$^+$), 257, 258, 248, 231, 203, 185, 155, 141, 128, 100, 57. Anal. Found: C, 43.59; H, 6.59; N, 18.55.

PREPARATION 67

N-(2-Amino-1,3,4-thiadiazol-5-yl)tryptophane Tert-butyl Ester (X-115) (Refer to Chart X.)

According to GP I starting from thiadiazole W-95 (610 mg), tryptophane tert-butyl ester hydrochloride (1.00 g), DIPEA (1.70 mL) and DMF (20 mL). The crude ester X-115 is dried under high vacuum (0.86 g).

Physical characteristics are as follows:

$R_f$=0.25 (AcOEt). $^1$H-NMR (CD$_3$OD, 300 MHz) δ 7.55, 7.31, 7.09–6.99, 4.54, 3.31–3.21, 1.29. $^{13}$C-NMR (CD$_3$OD, 75 MHz) δ 173.95, 172.07, 163.45, 161.62, 160.98, 136.56, 127.54, 123.11, 120.95, 118.31, 110.78, 81.22, 58.40, 35.54, 30.23, 26.78. MS (EI) m/z 359 (M$^+$), 243, 187, 130, 57. HRMS (EI) 359.1399.

PREPARATION 68

N-(2-Amino-1,3,4-thiadiazol-5-yl)-O$^7$-tert-butyltyrosine Tert-butyl Ester (X-116) (Refer to Chart X)

According to GP I starting from thiadiazole W-95 (580 mg), O$^7$-tert butyltyrosine tert-butyl ester hydrochloride (1.00 g), DIPEA (1.65 mL) and DMF (20 mL). Crystallization of the crude from AcOEt/hexanes yields ester X-116 as a white powder (0.89 g).

Physical characteristics are as follows:

$R_f$=0.35 (AcOEt). mp: 149–151° C.; $^1$H-NMR (CD$_3$OD, 300 MHz) δ 7.15, 6.90, 4.42, 3.03, 2.89, 1.35, 1.30. $^{13}$C-NMR (CDCl$_3$, 75 MHz) δ 171.58, 161.69, 160.74, 153.91, 132.01, 129.66, 123.79, 81.45, 78.13, 58.82, 37.10, 27.80, 26.85. MS (EI) m/z 392 (M$^+$), 276, 235, 220, 173, 164, 116, 107, 57. HRMS EI) 392.1885. Anal. Found: C, 57.96; H, 7.25; N, 13.80.

PREPARATION 69

N-(2-Amino-1,3,4-thiadiazol-5-yl)aspartic Acid Di-tert-butyl Ester (X-117) (Refer to Chart X.)

According to GP I starting from thiadiazole W-95 (640 mg), aspartic acid di-tert-butyl ester hydrochloride (1.00 g), DIPEA (1.80 mL) and DMF (20 mL). Crystallization of the crude from AcOEt/hexanes yields ester X-117 as a white powder (0.84 g).

Physical characteristics are as follows:

$R_f$=0.30 (AcOEt). mp: 142–146° C.; $^1$H-NMR (CD$_3$OD, 300 MHz) δ 4.50, 2.81, 2.71, 1.45, 1.44. $^{13}$C-NMR (CD$_3$OD, 75 MHz) δ 170.46, 169.90, 161.85, 160.75, 81.75, 81.00, 54.20, 37.39, 26.94, 26.83. MS (EI) m/z 344 (M$^+$), 288, 232, 215, 187, 143, 57. HRMS (EI) 344.1512.

EXAMPLE 243

8-Hydroxy-N-[5-(trifluoromethyl)-1,3,4-thiadiazol-2-yl]-7-quinolinecarboxamide (Y-118) (Refer to Chart Y)

According to GP II, starting from anhydride U-1 (50 mg), pyridinium chloride (10.8 mg), 2-amino-5-(trifluoromethyl)-1,3,4-thiadiazole (15.7 mg) and CHCl$_3$ (2 mL), amide Y-118 precipitates as a yellow powder without adding any aq. 1M HCl sol. (16.5 mg).

Physical characteristics are as follows:

mp: 300–302° C. (dec). $^1$H-NMR (d$_6$-DMSO, 300 MHz) δ 8.88, 8.08, 7.96, 7.14. $^{13}$C-NMR (d$_6$-DMSO, 75 MHz) δ 165.70, 163.15, 162.17, 144.83, 142.72, 5.49, 133.44, 130.08, 124.58, 112.61, 109.85. MS (EI) m/z 340 (M$^+$), 172, 116, 89, 63. HRMS (E1) 340.0234. Anal. Found: C, 45.45; H, 2.25; N, 16.33.

EXAMPLE 244

N-(5-Bromo-1,3,4-thiadiazol-2-yl)-8-hydroxy-7-quinolinecarboxamide (Y-119) (Refer to Chart Y)

According to GP II, starting from anhydride U-1 (100 mg), pyridinium chloride (21.4 mg), 2-amino-5-bromo-1,3, 4-thiadiazole W-95 (43 mg) and H$_2$ClCH$_2$HCl (2 mL), amide Y-119 precipitate as an orange powder without adding any aq. 1M HCl sol. (56 mg).

Physical characteristics are as follows:

mp: 250° C. (dec). $^1$H-NMR (d-TFA, 300 MHz) δ 9.35, 9.30, 8.67, 8.37, 8.03. MS (EI) m/z 350 and 352 (M$^+$), 271, 172, 116, 89, 63. HRMS (EI) 349.9469. Anal. Found: C, 41.88; H, 2.31; N, 14.46.

EXAMPLE 245

8-Hydroxy-N-[5-(2-phenylethyl)amino-1,3,4-thiadiazol-2-yl]-7-quinolinecarboxamide Monohydrochloride (Y-120) (Refer to Chart Y)

According to GP II, starting from anhydride U-1 (50 mg), pyridinium chloride (10.8 mg), 2-amino-5-(2-phenylethyl) amino-1,3,4-thiadiazole W-96 (20.5 mg) and. CHCl$_3$ (2 mL), amide Y-120 is obtained as a yellow powder (20 mg).

Physical characteristics are as follows:

$^1$H-NMR (d$_6$-DMSO, 300 MHz) δ 8.93, 8.84, 8.07, 7.90, 7.35–7.10, 3.58, 2.91. $^{13}$C-NMR (d$_6$-DMSO, 75 MHz) δ 166.62, 163.52, 160.78, 144.45, 143.73, 138.88, 134.85, 132.99, 129.60, 129.31, 128.88, 126.92, 124.48, 113.69, 111.70, 46.39, 34.45. MS (EI) m/z 357 (M$^+$), 186, 172, 116, 89. HRMS (EI) 392.1181.

EXAMPLE 246

N-[5(Butylamino)-1,3,4-thiadiazol-2-yl]-8-hydroxy-7-quinolinecarbomide Monohydrochloride (Y-121) (Refer to Chart Y)

According to GP II, starting from anhydride U-1 (50 mg), pyridinium chloride (10.8 mg), 2-amino-5-(butylamino)-1,3,4-thiadiazole W-97 (16.0 mg) and CHC$_3$ (2 mL), amide Y-121 is obtained as a yellow powder (22 mg).

Physical characteristics are as follows:

$^1$H-NMR (d$_6$-DMSO, 300 MHz) δ 8.90, 8.07, 7.97, 7.25, 3.35, 1.58, 1.36, 0.90. $^{13}$C-NMR (d$_6$-DMSO, 75 MHz), δ 166.52, 163.64, 160.67, 145.13, 143.23, 134.55, 133.17, 129.81, 127.79, 124.57, 113.40, 111.07, 45.12, 30.37, 19.87, 14.00. HRMS (EI) 343.1084.

EXAMPLE 247

N-[5-({2-[(tert-Butoxy)amido]ethyl}amino)-1,3,4-thiadiazol-2-yl]-8-hydroxy-7-quinolinecarboxamide Monohydrochloride (Y-122) (Refer to Chart Y)

According to GP II, starting from anhydride U-1 (50 mg), pyridinium chloride (10.8 mg), 2-amino-5-({2-[(tert-butoxy)amido]ethyl}amino)-1,3,4-thiadiazole W-98 (24 mg) and CHCl$_3$ (2 mL), 1M HCl/H$_2$O is not added, but the sol. diluted in some CHCl$_3$, washed with an aq. buffer sol. at pH 4 (1×), dried over MgSO$_4$, filtered and the solvent removed under reduced pressure. Purification of the residue by FC (AcOEt→MeOH/CH$_2$Cl$_2$ 1:9) leads to amide Y-122 as a yellow powder (15 mg).

Physical characteristics are as follows:

$^1$H-NMR (CD$_3$OD, 300 MHz) δ 8.95, 8.83, 8.25, 7.95, 7.43, 3.49, 3.31, 1.43. $^{13}$C-NMR (d$_6$-DMSO, 75 MHz), δ 168.49, 166, 163.84, 156.12, 146.36, 138.73, 135.28, 132.47, 130.75, 128.27, 123.60, 113.14, 111.63, 78.15, 44.09, 36.25, 28.70. MS (FAB) m/z 431 (MH$^+$), 260, 204, 172, 57. HRMS (FAB) 431.1494.

EXAMPLE 248

N-{5-[(1,3-Benzodioxol-5-cyanomethyl)amino]-1,3,4-thiadiazol-2-yl}-8-hydroxy-7-quinolinecarboxamide Monohydrochloride (Y-123) (Refer to Chart Y)

According to GP II, starting from anhydride U-1 (100 mg), pyridinium chloride (21.4 mg), 2-amino-1,3,4-thiadiazol-5-yl)anino]-1,3-benzodioxol-5-ylacetonitrile W-100 (51.0 mg), CHCl$_3$ (4 mL) and THF (0.4 mL), amide Y-123 is obtained as a yellow powder (35 mg).

Physical characteristics are as follows:

$^1$H-NMR (d$_6$-DMSO, 300 MHz) δ 9.00, 8.89, 8.77, 8.14, 7.98, 7.43, 7.14, 7.11, 7.00, 6.07, 6.02. $^{13}$C-NMR (d$_6$-DMSO, 75 MHz) δ 179.5, 160.81, 148.47, 148.22, 145.03, 144.09, 142.28, 134.05, 132.50, 129.37, 127.79, 124.43, 121.88, 118.98, 115.41, 114.28, 109.01, 108.42, 102.07, 60.87, 48.17. MS (FAB) m/z 447 (MH$^+$), 276, 172. HRMS (FAB) 447.0866.

EXAMPLE 249

(S)-N-[5-({Benzyl[(methoxy)carbonyl] methyl}amino)-1,3,4-thiadiazol-2-yl]-8-hydroxy-7-quinolinecarboxamide Monohydrochloride (Y-124) (Refer to Chart Y)

According to GP II, starting from anhydride U-1 (200 mg), pyridinium chloride (42 mg), N(2-amino-1,3,4-thiadiazo-5yl)phenylalanine methyl ester W-101 (103 mg), and CHCl$_3$ (8 mL), amide Y-124 is obtained as a yellow powder (100 mg).

Physical characteristics are as follows:

$^1$H-NMR (d$_6$-DMSO, 300 MHz) δ 8.98, 8.86, 7.50, 8.12, 7.94, 7.40, 7.27, 4.59, 3.14, 3.06. $^{13}$C-NMR (d$_6$-DMSO, 75 MHz) δ 172.18, 167.06, 162.24, 145.07, 143.62, 137.14, 134.41, 132.52, 129.65, 129.27, 128.81, 127.23, 124.36, 115.11, 113.94, 58.44, 52.56, 37.4. MS (EI) m/z 449 (M$^+$), 390, 372, 358, 287, 187, 172, 116. HRMS (FAB) 450.1233.

EXAMPLE 250

(R)-N-[5-({Benzyl[(methoxy)carbonyl] methyl}amino)-1,3,4-thiadiazol-2-yl]-8-hydroxy-7-quinolinecarboxamide Monohydrochloride (Y-125) (Refer to Chart Y)

According to GP II, starting from anhydride U-1 (200 mg), pyridinium chloride (42 mg), N-(2-amino-1,3,4thiadiazo-5-yl)-D-phenylalanine methyl ester W-102 (103 mg), and CHCl$_3$ (8 mL), amide Y-125 is obtained as a yellow powder (105 mg).

Physical characteristics are as follows:

$^1$H-NMR (d$_6$-DMSO, 300 MHz) δ 8.98, 8.86, 7.50, 8.12, 7.94, 7.40, 7.27, 4.59, 3.14, 3.06. $^{13}$C-NMR (d$_6$-DMSO, 75 MHz) δ 172.18, 167.06, 162.24, 145.07, 143.62, 137.14, 134.41, 132.52, 129.65, 129.27, 128.81, 127.23, 124.36, 115.11, 113.94, 58.44, 52.56, 37.41. MS (EI) m/z 449 (M$^+$), 390, 372, 358, 287, 187, 172, 116. HRMS (FAB) 450.1233.

EXAMPLE 251

N-[5-({1,3-Benzodioxol-5-yl-(tert-butoxy)carbonyl] methyl}amino)-1,3,4-thiadiazol-2-yl]-8-hydroxy-7-quinolinecarboxamide Semihydrate (Y-126) (Refer to Chart Y)

According to GP IV, starting from ester U-3 (131 mg), N-(2-amino-1,3,4-thiadiazo-5-yl)-2-(1,3-benzodioxol-5-yl) glycine tert-butyl ester W-105 (197 mg,), DIPEA (0.10 mL) and CH$_2$Cl$_2$ (6 mL). Stirred for 4 h, then overnight with MeOH. After adding MeOH, armide Y-126 precipitated as a yellow powder that is filtered and dried (120 mg).

Physical characteristics are as follows:

mp: 227–229° C.; $^1$H-NMR (d$_6$-DMSO, 300 MHz) δ 8.92, 8.63, 8.05, 7.77, 7.25, 6.97, 6.92, 6.02, 5.21, 1.33.

$^{13}$C-NMR (d$_6$-DMSO, 75 MHz), δ 169.80, 147.26, 147.04, 131.92, 130.28, 123.54, 121.02, 108.24, 107.65, 101.12, 81.04, 60.47, 27.43. MS (EI) m/z 521 (M$^+$), 465, 447, 420, 249, 172, 56. HRMS (FAB) 522.1452. Anal. Found: 56.66; H, 4.49; N, 13.30.

EXAMPLE 252

N-[5-({1,3-Benzodioxol-4-yl-[(tert-butyloxy)carbonyl]methyl}amino)-1,3,4-thiadiazol-2-yl]-8-hydroxy-7-quinolinecarboxamide Semihydrate (Y-127) (Refer to Chart Y)

According to GP IV, starting from ester U-3 (133 mg), N-(2-amino-1,3,4-thiadiazo-5-yl)-2-(1,3-benzodioxol4-yl) glycine tert-butyl ester W-108 (200 mg,), DIPEA (0.10 mL) and CH$_2$Cl$_2$ (6 mL), stirred for 4 h, then overnight with MeOH. The solution is diluted with some CH$_2$Cl$_2$, washed with sat. NaHCO$_3$/H$_2$O (1×) and an aq. buffer sol. at pH 4 (1×), an emulsion formed that separated slowly into two phases. The org. phase is dried over MgSO$_4$, filtered and the solvent removed under reduced pressure. The residue is triturated with AcOEt, filtered and dried. Amide Y-127 is obtained as a yellow powder (140 mg).

Physical characteristics are as follows:

$^1$H-NME (d$_6$-DMSO, 300 MHz) δ 8.88, 8.65, 8.20, 8.05, 7.83, 7.26, 7.00–6.30, 6.05, 5.42, 1.33. $^{13}$C-NMR (d$_6$-DMSO, 75 MHz) δ 168.86, 159.12, 147.08, 145.22, 131.94, 128.37, 123.59, 121.77, 119.90, 117.96, 113.57, 108.53, 101.04, 81.36, 54.93, 27.41. MS (FAB) m/z 522 (MH$^+$), 598, 466, 420, 249, 57. HRMS (FAB) 522.1447.

EXAMPLE 253

N-{5-[(1,3,-Benzodioxol-ylmethyl)amino]-1,3,4-thiadiazol-2-yl}-8-hydroxy-7-quinolinecarboxamide (Y-128) (Refer to Chart Y)

According to GP IV, starting from ester U-3 (85 mg), 2-amino-5-[N-(1,3-benzodioxol-5-ylmethyl)amino]-1,3,4-thiadiazole X-109 (90 mg), DIPEA (70 μL) and CH$_2$Cl$_2$ (4 mL). Stirred for 20 h, then for 5 h with MeOH. After adding MeOH, a yellow precipitate appears, that is filtered and dried (40 mg); this precipitate proved to be the not quite pure amide Y-128 and was not further purified due to its low solubility.

Physical characteristics are as follows:

mp: 280–282° C.; $^1$H-NMR (d$_6$-DMSO, 300 MHz) δ 8.86, 8.53, 8.02, 7.85, 7.76, 7.22, 6.93, 6.85, 5.97, 4.34. $^{13}$C-NMR (d$_6$-DMSO, 75 MHz), due to the low solubility of the product, an incomplete set of signals is obtained δ 147.72, 146.73, 133.15, 132.42, 123.95, 121.36, 121.23, 108.66, 108.54, 101.33. MS (EI) m/z 421 (M$^+$), 270, 250, 208, 172, 150, 135, 116. HRMS (EI) 421.0827.

EXAMPLE 254

(S)-N-[5-({[(tert-Butoxy)carbonyl]-[4-hydroxybenzyl]methyl}amino)-1,3,4-thiadiazol-2-yl]-8-hydroxy-7-quinolinecarboxamide (Y-129) (Refer to Chart Y)

According to GP IV, starting from ester U-3 (500 mg), N-(2-amino-1,3,4-thiadiazol-5-yl)tyrosine tert-butyl ester X-110 (720 mg), DIPEA (0.36 mL) and CH$_2$C$_2$ (10 mL). Stirred for 7 h, then overnight with MeOH. The solvent is almost completely removed until a consistent precipitate appeared that is filtered, washed with AcOEt and MeOH and dried under high vacuum. The product obtained as a yellow powder (0.53 g) was a not unpurified mixture of amide Y-129 (80 mol % by $^1$H-NMR) and acetylated product (20 mol %).

Physical characteristics are as follows:

$^1$H-NMR (d$_6$-DMSO, 300 MHz) δ 8.85, 8.54, 8.01, 7.90–7.70, 7.30–6.95, 4.60–4.30, 3.15–2.85, 1.31. MS (ES) m/z Neg. mode: 506 (MH$^+$), 548 (acetylated product+H$^+$).

EXAMPLE 255

(S)-N-[5-({5-Benzoxylamido-1-[(tert-butoxy)carbonyl]pentyl}amino)-1,3,4-thiadiazol-2-yl]-8-hydroxy-7-quinolinecarboxamide (Y-130) (Refer to Chart Y)

According to GP IV, starting from ester U-3 (500 mg)), N$^1$-(2-amino-1,3,4-thiadiazol-5-yl)-N$^5$-[(benzoxy)carbonyl] lysine tert-butyl ester X-111 (0.93 g), DIPEA (0.36 mL) and CH$_2$Cl$_2$ (10 mL). Stirred for 7 h, then overnight with MeOH. The solvent is almost completely removed until a consistent precipitate appears. It is filtered, washed with AcOEt and MeOH and dried. A yellow foam is obtained (0.50 g) that proved to contain about 90 mol % ($^1$H-NMR) of amide Y-130.

Physical characteristics are as follows:

$^1$H-NMR (d$_6$-DMSO, 300 MHz) δ 8.76, 8.35, 7.95, 7.65–7.50, 7.35–7.20, 7.02, 4.98, 4.15–4.05, 2.97, 1.69, 1.38, 1.23. $^{13}$C-NMR (d$_6$-DMSO, 75 MHz) δ 171.76, 162.63, 155.98, 145.51, 138.21, 137.14, 131.94, 128.22, 127.77, 127.61, 122.97, 122.41, 80.37, 64.99, 56.82, 53.39, 31.16, 28.96, 27.56, 22.57. MS (FAB) m/z 607 (MH$^+$), 551, 288, 172. HRMS (FAB) 607.2345.

EXAMPLE 256

(S)-N-[5-({1-[(tert-Butoxy)carbonyl]-3-methylbutyl}amino)-1,3,4-thiadiazol-2-yl]-8-hydroxy-7-quinolinecarboxamide Monohydrate (Y-131) (Refer to Chart Y)

According to GP IV, starting from ester U-3 (0.97 g)), N-(2-amino-1,3,4-thiadiazol-5-yl)leucine tert-butyl ester X-112 (1.18 g), DIPEA (0.70 mL) and CH$_2$Cl$_2$ (20 mL). Stirred for 7 h, then overnight with MeOH. Amide Y-131 appears as an orange precipitate that is filtered, washed with AcOEt and dried under high vacuum (440 mg).

Physical characteristics are as follows:

mp: 214–5° C.; $^1$H-NMR (d$_6$-DMSO, 300 MHz) δ 8.87, 8.61, 8.05, 7.83–7.65, 7.24, 4.14, 1.85–1.70, 1.65–1.50, 1.38, 0.92, 0.87. $^{13}$C-NMR (d$_6$-DMSO, 75 MHz) δ 172.62, 165.76, 163.20, 159.98, 152.80, 145,62, 140.75, 137.60, 132.45, 128.73, 124.05, 113.91, 113.02, 80.99, 55.96, 40.96, 28.10, 24.95, 23.09, 19.01. MS (EI) m/z 457 (M$^+$), 356, 345, 213, 172, 116, 89, 57. HRMS (EI) 457.1781. Kar-Fischer titration: 3.43% water (0.90 eq). Anal. Found: C, 55.53; H, 6.02; N, 14.59.

EXAMPLE 257

(S)-N-(5-{2-[(tert-Butoxy)carbonyl]pyrrolidin-N-yl}-1,3,4-thiadiazol-2-yl)-8-hydroxy-7-quinolinecarboxamide Semihydrate (Y-132) (Refer to Chart Y)

According to GP IV, starting from ester U-3 (710 mg), N-(2-amino-1,3,4-thiadiazol-5-yl)proline tert-butyl ester X-113 (816 mg), DIPEA (0.51 mL) and CH$_2$Cl$_2$ (14 mL).

Stirred for 7 h, then overnight with MeOH. Amide Y-132 is obtained as an orange precipitate that is filtered, washed with AcOEt and dried under high vacuum (955 mg).

Physical characteristics are as follows:

mp: Turned white between 220° C. and 250° C., then decomposed between 285° C. and 290° C. $^1$H-NMR ($d_6$-DMSO, 300 MHz) δ 8.87, 8.65, 8.05, 7.82, 7.22, 4.28, 3.55–3.45, 2.40–2.20, 2.10–1.95, 1.39. $^{13}$C-NMR ($d_6$-DMBO, 75 MHz) δ 171.57, 163, 160.42, 145.05, 141.5, 137, 132.56, 128.94, 124.10, 113.67, 112.29, 81.40, 62.74, 50.80, 30.66, 28.09, 24.04. MS (EI) m/z 441 (M$^+$), 340, 172, 116, 57. HRMS (EI) 441.1472. Karl-Fischer titration: 2.09% water (0.55 eq). Anal. Found: C, 56.03; H, 5.32; N, 15.56.

EXAMPLE 258

(S)-N-[5-({1-[(tert-Butoxy)carbonyl]-3-[methylmercapto]propyl}amino)-1,3,4-thiadiazol-2-yl]-8-hydroxy-7-quinolinecarboxamide Monohydrate (Y-133) (Refer to Chart Y)

According to GP IV, starting from ester U-3 (450 mg), N-(2-amino-1,3,4-thiadiazol-5yl)methionine tert-butyl ester X-114 (0.60 g), DIPEA (0.33 mL) and $CH_2Cl_2$ (10 mL). Stirred for 7 h, then overnight with MeOH. The orange-red amide Y-133 is filtered, washed with AcOEt and dried under high vacuum (0.60 g).

Physical characteristics are as follows:

mp: 204–205° C.; $^1$H-NMR ($d_6$-DMSO, 300 MHz) δ 8.87, 8.61, 7.79, 7.23, 4.29, 2.57, 2.05, 2.05–1.90, 1.39. $^{13}$C-NMR ($d_6$-DMSO, 75 MHz) δ 171.50, 162.89, 162.86, 159.75, 145.20, 140.35, 137.18, 137.14, 132.17, 128.47, 123.76, 113.55, 112.54, 80.98, 56.08, 31.19, 29.69, 27.70, 14.67. MS (EI) m/z 475 (M$^+$), 401, 327, 270, 213, 172, 116, 61. HRMS (FAB) 476.1427. Karl-Fischer titration: 3.40% water (0.92 eq.). Anal. Found: C, 51.12; H, 5.46; N, 13.99.

EXAMPLE 259

(S)-N-[5-({1-[(tert-Butoxy)carbonyl]-2-indol-3-ylethyl}amino)-1,3,4-thiadiazol-2-yl]-8-hydroxy-7-quinolinecarboxamide Monohydrate (Y-134) (Refer to Chart Y)

According to GP IV, starting from ester U-3 (500 mg), N-(2-amino-1,3,4-thiadiazol-5-yl)tryptophane tert-butyl ester X-115 (770 mg), DIPEA (0.36 mL) and $CH_2Cl_2$ (10 mL). Stirred for 7 h, then overnight with MeOH. Amide Y-134 is obtained as a yellow precipitate that is filtered, washed with AcOEt and dried under high vacuum (0.52 g).

Physical characteristics are as follows:

$^1$H-NMR ($d_6$-DMSO, 300 MHz) δ 10.90, 8.87, 8.58, 8.04, 7.84, 7.77, 7.53, 7.33, 7.23, 7.17, 7.06, 6.98, 4.48, 3.20–3.10, 1.27. $^{13}$C-NMR ($d_6$-DMSO, 75 MHz) δ 171.77, 165.79, 162.99, 160.04, 152.93, 145.67, 140.62, 137.69, 136.57, 132.44, 128.70, 127.68, 124.34, 124.02, 121.44, 118.85, 118.77, 113.93, 113.04, 111.87, 109.91, 80.01, 58.39, 48.86, 27.98. MS (FAB) m/z 531 (MH$^+$), 475, 288, 172. HRMS (FAB) 531.1841. Karl-Fischer titration: 2.61% water (0.79 eq.). Anal. Found: C, 59.24; H, 5.13; N, 15.13.

EXAMPLE 260

(S)-N-(5-{1-[(tert-Butoxy)carbonyl]-2-[4-(tert-butoxy)phenyl]ethyl}amino)-1,3,4-thiadiazol-2-yl]-8-hydroxy-7-quinolinecarboxamide monohydrate (Y-135) (Refer to Chart Y)

According to GP IV, starting from ester U-3 (500 mg), N-(2-amino-1,3,4-thiadiazol-5-yl)-O$^7$-tert-butyltyrosine tert-butyl ester X-116 (840 mg), DIPEA (0.36 mL) and $CH_2Cl_2$ (10 mL). Stirred for 7 h, then overnight with MeOH. The solvent is partially removed under reduced pressure until amide Y-135 appears as a consistent orange precipitate that is filtered and dried under high vacuum (0.80 g).

Physical characteristics are as follows:

mp: 124–125° C. (dec). $^1$H-NMR ($d_6$-DMSO, 300 MHz) δ 8.84, 8.56, 8.02, 7.77, 7.75, 7.17, 6.87, 4.39, 2.97, 1.27, 1.23. $^{13}$C-NMR ($d_6$-DMSO, 75 MHz) δ 170.95, 165.2, 162.29, 160.26, 153.53, 145.16, 139.66, 137.74, 131.91, 131.57, 129.74, 128.08, 123.45, 123.37, 113.19, 112.07, 80.57, 77.59, 58.36, 36.77, 28.39, 27.43. MS (FAB) m/z 564 (MH$^+$), 508, 337, 281, 172, 57. HRMS (FAB) 564.2280. Karl-Fischer titration: 2.25% water (0.72 eq.); Anal. Found: C, 59.75; H, 6.01; N, 12.07.

EXAMPLE 261

(S)-N-[5-({1,2-Di-[(tert-butoxy)carbonyl]ethyl}amino)-1,3,4-thiadiazol-2-yl]-8-hydroxy-7-quinolinecarboxamide Monohydrate, (Y-136) (Refer to Chart Y)

According to GP IV, starting from ester U-3 (500 mg), N-(2-amino-1,3,4-thiadiazol-5-yl)aspartic acid di-tert-butyl ester X-117 (740 mg), DIPEA (0.36 mL) and $CH_2Cl_2$ (10 mL). Stirred for 7 h, then overnight with MeOH. The solvent is removed under reduced pressure until amide Y-136 precipitates as a fine orange powder that is shortly triturated with MeOH, filtered and dried under high vacuum (0.73 g).

Physical characteristics are as follows:

$^1$H-NMR ($d_6$-DMSO, 300 MHz) δ 8.87, 8.62, 8.04, 7.81, 7.22, 4.54, 2.77, 2.67, 1.38. $^{13}$C-NMR ($d_6$-DMSO, 75 MHz) δ 169.80, 169.02, 164.80, 162.45, 159.55, 144.98, 140.43, 131.93, 128.22, 126.74, 123.52, 113.30, 112.28, 81.05, 80.44, 53.60, 37.24, 27.60, 27.48. MS (EI) m/z 515 (M$^+$), 459, 358, 172, 116, 57. HRMS (EI) 535.1826. Karl-Fischer titration: 2.80% (0.82 eq.); Anal. Found: C, 53.75; H, 5.71; N, 13.23.

EXAMPLE 262

N-{2-[(8-Hydroxyquinolin-7-yl)amido]-1,3,4-thiadiazol-5-yl}-2-benzo-1,3-dioxol-5-ylglycine Monohydrotrifluoroacetate (Z137) (Refer to Chart Z.)

According to GP VI starting from N-[5-({1,3-benzodioxol-5-yl-[(tert-butoxy)carbonyl]methyl}amino)-1,3,4-thiadiazol-2-yl]-8-hydroxy-7-quinolinecarboxamide semihydrate Y-126 (72 mg) and TFPA (10 mL). Acid Z-137 is obtained as a yellow powder (68 mg).

Physical characteristics are as follows:

mp: 220–230° C. (dec). $^1$H-NMR ($d_6$-DMSO, 300 MHz) δ 8.90, 8.67, 8.22, 8.07, 7.84, 7.29, 7.00, 6.93, 6.01, 5.24. $^{13}$C-NMR ($d_6$-DMSO, 75 MHz) δ: 172.39, 166.26, 162.22, 159.24, 154.22, 147.86, 147.64, 145.37, 141.93, 136.35, 132.47, 131.10, 128.93, 124.17, 121.66, 114.40, 113.39, 108.78, 108.33, 101.69, 60.44. MS (FAB) m/z 466 (MH$^+$), 288, 123. HRMS (FAB) 466.0826.

EXAMPLE 263

N-{2-[(8-Hydroxyquinolin-7-yl)amido]-1,3,4-thiadiazol-5-yl}-2-benzo-1,3-dioxol-4-ylglycine Monohydrotrifluoroacetate (Z-138) (Refer to Chart Z.)

According to GP VI starting from N-[5-({1,3-benzodioxol-4-yl-[(tert-butoxy)-carbonyl]methyl}amino)-1, 3,4-thiadiazol-2-yl]-8-hydroxy-7-quinolinecarboxamide semihydrate Y-127 (80 mg) and TFA (10 mL). Acid Z-138 is obtained as a yellow powder (50 mg).

Physical characteristics are as follows:

$^1$H-NMR (d$_6$-DMSO, 300 MHz) δ 8.90, 8.68, 8.26, 8.06, 7.83, 7.28, 6.86, 6.06, 6.05, 5.47. $^{13}$C-NMR (d$_6$-DMSO, 75 MHz) δ 171.57, 166.24, 162.30, 159.21, 154.30, 147.67, 145.82, 145.32, 142.04, 136.25, 132.47, 128.97, 124.18, 122.33, 120.69, 118.81, 114.44, 113.37, 108.90, 101.62, 54.87. MS (FAB) m/z 466 (MH$^+$), 542, 420. HRMS (FAB) 466.0830.

EXAMPLE 264

N-{2-[(8-Hydroxyquinlinolin-7-yl)amido]-1,3,4-thiadiazol-5-yl}-tryptophan Monohydrotrifluoroacetate (Z-139) (Refer to Chart Z.)

According to GP VI starting from (S)-N-[5-({1-[(tert-butoxy)carbonyl]-2-indol-3-ylethyl}amino)-1,3,4-thidiazol-2-yl]-8-hydroxy-7-quinolinecarboxamide monohydrate Y-134 (253 mg) and TFA (15 mL). Acid Z-139 is obtained as a yellow powder (270 mg).

Physical characteristics are as follows:

$^1$H-NMR (d$_6$-DMSO, 300 MHz) δ 8.91, 8.72, 8.15, 8.08, 7.77, 8.55, 7.30, 7.16, 7.02, 6.95, 4.54, 3.32, 3.14. $^{13}$C-NMR (d$_6$-DMSO, 75 MHz) δ 173.29, 166.82, 162.67, 158.91, 154.52, 145.04, 143.04, 136.54, 135.27, 132.54, 129.13, 127.67, 124.48, 124.27, 121.44, 118.93, 118.69, 114.69, 113.54, 111.89, 109.63, 57.98. MS (FAB) m/z 475 (H), 551, 529, 305, 172. HRMS (FAB) 475.1198.

Following procedures analogous to those described above, the additional compounds of the present invention of Tables 13 and 14 are prepared.

FORMULA CHART

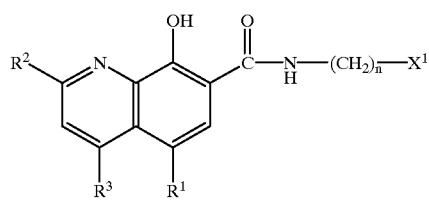

I

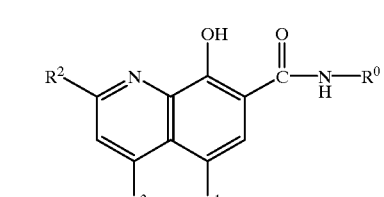

IA

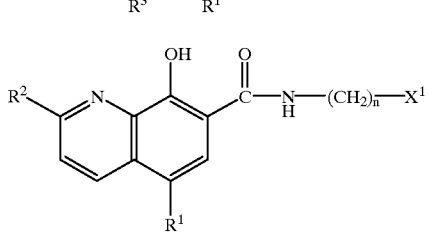

II

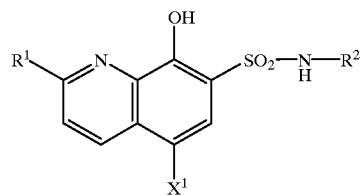

III

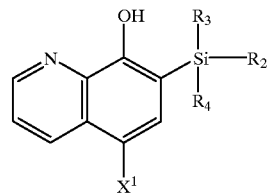

IV

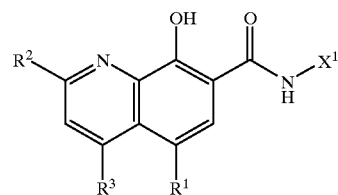

V

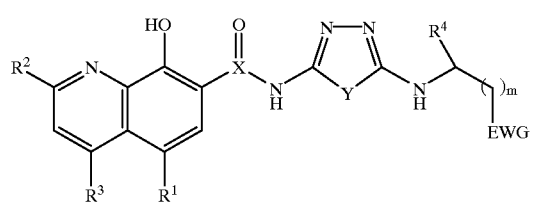

VI

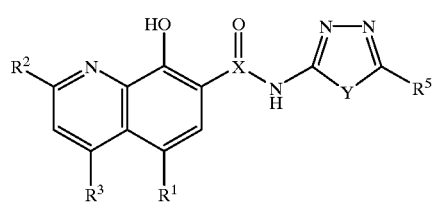

VII

TABLE 1

| Compound of Example No. | CMV pol Assay | | | |
|---|---|---|---|---|
| | Conc (M) | pol type | % Inhib | IC50 μM |
| 1 | | CMV | | 10.2 |
| | 3.13E − 06 | CMV | −1.5 | |
| | 6.25E − 06 | CMV | 22.8 | |
| | 1.30E − 05 | CMV | 66.2 | |
| | 2.50E − 05 | CMV | 94.7 | |
| | 5.00E − 05 | CMV | 98.6 | |
| | 1.00E − 04 | CMV | 100 | |
| 2 | | CMV | | 4.3 |
| | 3.13E − 06 | CMV | 43.6 | |
| | 6.25E − 06 | CMV | 59.2 | |
| | 1.30E − 05 | CMV | 65.7 | |
| | 2.50E − 05 | CMV | 78 | |
| | 5.00E − 05 | CMV | 81.9 | |
| | 1.00E − 04 | CMV | 83 | |
| 3 | | CMV | | 7.1 |
| | 3.13E − 06 | CMV | 20.5 | |
| | 6.25E − 06 | CMV | 36.5 | |
| | 1.30E − 05 | CMV | 75.7 | |
| | 2.50E − 05 | CMV | 97.8 | |

TABLE 1-continued

| Compound of Example No. | Conc (M) | pol type | % Inhib | IC50 μM |
|---|---|---|---|---|
| | 5.00E−05 | CMV | 100.1 | |
| | 1.00E−04 | CMV | 100.2 | |
| 4 | | CMV | | 3.9 |
| | 3.13E−06 | CMV | 48.4 | |
| | 6.25E−06 | CMV | 48 | |
| | 1.30E−05 | CMV | 61.1 | |
| | 2.50E−05 | CMV | 59.3 | |
| | 5.00E−05 | CMV | 47.6 | |
| | 1.00E−04 | CMV | 51.9 | |
| | | CMV | | 3.1 |
| | 3.13E−07 | CMV | 7.2 | |
| | 6.25E−07 | CMV | 15.1 | |
| | 1.25E−06 | CMV | 22.6 | |
| | 2.50E−06 | CMV | 50.4 | |
| | 5.00E−06 | CMV | 65.4 | |
| | 1.00E−05 | CMV | 75.1 | |
| | | CMV | | 5.1 |
| | 7.81E−07 | CMV | 4.1 | |
| | 1.56E−06 | CMV | 20.6 | |
| | 3.13E−06 | CMV | 42.8 | |
| | 6.25E−06 | CMV | 58.1 | |
| | 1.30E−05 | CMV | 69.7 | |
| | 2.50E−05 | CMV | 85.6 | |
| 5 | | CMV | | 6.8 |
| | 3.13E−06 | CMV | 29.1 | |
| | 6.25E−06 | CMV | 44 | |
| | 1.30E−05 | CMV | 69.3 | |
| | 2.50E−05 | CMV | 87.2 | |
| | 5.00E−05 | CMV | 95.9 | |
| | 1.00E−04 | CMV | 98.7 | |
| 6 | | CMV | | 4.1 |
| | 3.13E−06 | CMV | 39.6 | |
| | 6.25E−06 | CMV | 59 | |
| | 1.30E−05 | CMV | 81.1 | |
| | 2.50E−05 | CMV | 95.1 | |
| | 5.00E−05 | CMV | 98.6 | |
| | 1.00E−04 | CMV | 99.6 | |
| 7 | | CMV | | 6.9 |
| | 3.13E−06 | CMV | 29.6 | |
| | 6.25E−06 | CMV | 47.2 | |
| | 1.30E−05 | CMV | 64.2 | |
| | 2.50E−05 | CMV | 83.1 | |
| | 5.00E−05 | CMV | 90.6 | |
| | 1.00E−04 | CMV | 94.7 | |
| 8 | | CMV | | 20.1 |
| | 3.13E−06 | CMV | 19.3 | |
| | 6.25E−06 | CMV | 33.4 | |
| | 1.30E−05 | CMV | 38.1 | |
| | 2.50E−05 | CMV | 52 | |
| | 5.00E−05 | CMV | 59.6 | |
| | 1.00E−04 | CMV | 71 | |
| 9 | | CMV | | 2.5 |
| | 3.13E−06 | CMV | 45.6 | |
| | 6.25E−06 | CMV | 80.3 | |
| | 1.30E−05 | CMV | 93.3 | |
| | 2.50E−05 | CMV | 96.3 | |
| | 5.00E−05 | CMV | 99.2 | |
| | 1.00E−04 | CMV | 98.8 | |
| 10 | | CMV | | 19 |
| | 3.13E−06 | CMV | −8.6 | |
| | 6.25E−06 | CMV | 0.8 | |
| | 1.30E−05 | CMV | 28.4 | |
| | 2.50E−05 | CMV | 77.7 | |
| | 5.00E−05 | CMV | 95.8 | |
| | 1.00E−04 | CMV | 98.6 | |
| 11 | | CMV | | 1.3 |
| | 3.13E−06 | CMV | 66 | |
| | 6.25E−06 | CMV | 90.5 | |
| | 1.30E−05 | CMV | 95.1 | |
| | 2.50E−05 | CMV | 98.2 | |
| | 5.00E−05 | CMV | 97.9 | |
| | 1.00E−04 | CMV | 98.3 | |
| 12 | | CMV | | 15.9 |
| | 3.13E−06 | CMV | −2.5 | |
| | 6.25E−06 | CMV | 3.8 | |
| | 1.30E−05 | CMV | 38.6 | |
| | 2.50E−05 | CMV | 85 | |
| | 5.00E−05 | CMV | 99.4 | |
| | 1.00E−04 | CMV | 99.3 | |
| 13 | | CMV | | >100 |
| | 3.13E−006 | CMV | −12.5 | |
| | 6.25E−006 | CMV | 15.4 | |
| | 1.30E−005 | CMV | 18.8 | |
| | 2.50E−005 | CMV | 26.3 | |
| | 5.00E−005 | CMV | 17.3 | |
| | 1.00E−004 | CMV | 33.8 | |
| 14 | | CMV | | 23.4 |
| | 3.13E−06 | CMV | −4.4 | |
| | 6.25E−06 | CMV | 5.5 | |
| | 1.30E−05 | CMV | 42.4 | |
| | 2.50E−05 | CMV | 59.3 | |
| | 5.00E−05 | CMV | 69.9 | |
| | 1.00E−04 | CMV | 84.5 | |
| 15 | | CMV | | 1.6 |
| | 3.13E−07 | CMV | 12.9 | |
| | 6.25E−07 | CMV | 19.7 | |
| | 1.25E−06 | CMV | 43 | |
| | 2.50E−06 | CMV | 70.2 | |
| | 5.00E−06 | CMV | 87.1 | |
| | 1.00E−05 | CMV | 93.4 | |
| 16 | | CMV | | 5.8 |
| | 3.13E−06 | CMV | 18.2 | |
| | 6.25E−06 | CMV | 46.3 | |
| | 1.30E−05 | CMV | 87.7 | |
| | 2.50E−05 | CMV | 96.6 | |
| | 5.00E−05 | CMV | 95.6 | |
| | 1.00E−04 | CMV | 90.4 | |

TABLE 2

| Example No. | Conc (M) | pol type | % Inhib | IC50 μM |
|---|---|---|---|---|
| 17 | | CMV | | 11.3 |
| | 3.13e−006 | CMV | 0.7 | |
| | 6.25e−006 | CMV | 26.4 | |
| | 1.30e−005 | CMV | 57.1 | |
| | 2.50e−005 | CMV | 89 | |
| | 5.00e−005 | CMV | 95.5 | |
| | 1.00e−004 | CMV | 97.5 | |
| 18 | | CMV | | 27.9 |
| | 3.13e−006 | CMV | 5.3 | |
| | 6.25e−006 | CMV | 14.9 | |
| | 1.30e−005 | CMV | 13.9 | |
| | 2.50e−005 | CMV | 51.7 | |
| | 5.00e−005 | CMV | 79.6 | |
| | 1.00e−004 | CMV | 91.8 | |
| 19 | 3.13e−006 | CMV | 11.8 | |
| | 6.25e−006 | CMV | 20 | |
| | 1.30e−005 | CMV | 28.9 | |
| | 2.50e−005 | CMV | 56.6 | |
| | 5.00e−005 | CMV | 69.1 | |
| | 1.00e−004 | CMV | 83.9 | |
| | | CMV | | 23.6 |
| 20 | | CMV | | 14.5 |
| | 3.13e−006 | CMV | 10.9 | |
| | 6.25e−006 | CMV | 25.5 | |
| | 1.30e−005 | CMV | 41.3 | |
| | 2.50e−005 | CMV | 73.2 | |
| | 5.00e−005 | CMV | 92 | |
| | 1.00e−004 | CMV | 95.4 | |
| 21 | | CMV | | 7.5 |
| | 3.13e−006 | CMV | 33.5 | |
| | 6.25e−006 | CMV | 43.4 | |
| | 1.30e−005 | CMV | 57.2 | |
| | 2.50e−005 | CMV | 85.2 | |
| | 5.00e−005 | CMV | 94.4 | |
| | 1.00e−004 | CMV | 96.6 | |

TABLE 2-continued

| Example No. | Conc (M) | pol type | % Inhib | IC50 μM |
|---|---|---|---|---|
|  |  | CMV |  | 12.6 |
|  | 3.13e − 006 | CMV | 17.6 |  |
|  | 6.25e − 006 | CMV | 35.3 |  |
|  | 1.30e − 005 | CMV | 45.1 |  |
|  | 2.50e − 005 | CMV | 69.9 |  |
|  | 5.00e − 005 | CMV | 90.8 |  |
|  | 1.00e − 004 | CMV | 97.9 |  |
| 22 |  | CMV |  | 8.6 |
|  | 3.13e − 006 | CMV | 13.2 |  |
|  | 6.25e − 006 | CMV | 33.3 |  |
|  | 1.30e − 005 | CMV | 68.9 |  |
|  | 2.50e − 005 | CMV | 90.7 |  |
|  | 5.00e − 005 | CMV | 96.7 |  |
|  | 1.00e − 004 | CMV | 98.2 |  |
|  |  | CMV |  | 4.5 |
|  | 3.13e − 006 | CMV | 43.3 |  |
|  | 6.25e − 006 | CMV | 51.5 |  |
|  | 1.30e − 005 | CMV | 78.3 |  |
| 22 | 2.50e − 005 | CMV | 95.2 |  |
|  | 5.00e − 005 | CMV | 98.6 |  |
|  | 1.00e − 004 | CMV | 99.7 |  |
| 23 |  | CMV |  | 2 |
|  | 3.13e − 006 | CMV | 48 |  |
|  | 6.25e − 006 | CMV | 90.9 |  |
|  | 1.30e − 005 | CMV | 98.8 |  |
|  | 2.50e − 005 | CMV | 99.4 |  |
|  | 5.00e − 005 | CMV | 99.4 |  |
|  | 1.00e − 004 | CMV | 98.3 |  |
|  |  | CMV |  | 3.1 |
|  | 3.13e − 007 | CMV | 16.3 |  |
|  | 6.25e − 007 | CMV | 13 |  |
|  | 1.25e − 006 | CMV | 14.7 |  |
|  | 2.50e − 006 | CMV | 34.6 |  |
|  | 5.00e − 006 | CMV | 83.9 |  |
|  | 1.00e − 005 | CMV | 99.9 |  |
| 24 |  | CMV |  | >100 |
|  | 3.13e − 006 | CMV | 7.9 |  |
|  | 6.25e − 006 | CMV | 8 |  |
|  | 1.30e − 005 | CMV | 9.9 |  |
|  | 2.50e − 005 | CMV | 3.9 |  |
|  | 5.00e − 005 | CMV | −6.4 |  |
|  | 1.00e − 004 | CMV | −0.3 |  |
|  |  | CMV |  | 4.5 |
|  | 3.13e − 006 | CMV | 36.5 |  |
|  | 6.25e − 006 | CMV | 55.4 |  |
|  | 1.30e − 005 | CMV | 82.4 |  |
|  | 2.50e − 005 | CMV | 97.5 |  |
|  | 5.00e − 005 | CMV | 99.3 |  |
|  | 1.00e − 004 | CMV | 98.8 |  |
| 25 | 3.13e − 006 | CMV | 48.7 |  |
|  | 6.25e − 006 | CMV | 63.3 |  |
|  | 1.30e − 005 | CMV | 69.4 |  |
|  | 2.50e − 005 | CMV | 76.6 |  |
|  | 5.00e − 005 | CMV | 83.7 |  |
|  | 1.00e − 004 | CMV | 87.6 |  |
|  |  | CMV |  | 3.6 |
| 26 |  | CMV |  | 4.6 |
|  | 3.13e − 006 | CMV | 32.1 |  |
|  | 6.25e − 006 | CMV | 60.2 |  |
|  | 1.30e − 005 | CMV | 79.5 |  |
|  | 2.50e − 005 | CMV | 86.4 |  |
|  | 5.00e − 005 | CMV | 87.8 |  |
|  | 1.00e − 004 | CMV | 90.1 |  |
| 27 |  | CMV |  | 14.8 |
|  | 3.13e − 006 | CMV | 27.2 |  |
|  | 6.25e − 006 | CMV | 36.6 |  |
|  | 1.30e − 005 | CMV | 33.5 |  |
|  | 2.50e − 005 | CMV | 58.7 |  |
|  | 5.00e − 005 | CMV | 93.5 |  |
|  | 1.00e − 004 | CMV | 96.7 |  |
| 28 |  | CMV |  | 5.5 |
|  | 3.13e − 006 | CMV | 28.1 |  |
|  | 6.25e − 006 | CMV | 52 |  |
|  | 1.30e − 005 | CMV | 78.3 |  |
|  | 2.50e − 005 | CMV | 93 |  |
|  | 5.00e − 005 | CMV | 94.6 |  |
|  | 1.00e − 004 | CMV | 96.4 |  |
| 29 |  | CMV |  | 18.3 |
|  | 3.13e − 006 | CMV | 40.9 |  |
|  | 6.25e − 006 | CMV | 33.9 |  |
|  | 1.30e − 005 | CMV | 36.1 |  |
|  | 2.50e − 005 | CMV | 44.4 |  |
|  | 5.00e − 005 | CMV | 54.1 |  |
|  | 1.00e − 004 | CMV | 71.4 |  |
|  |  | CMV |  | 40.1 |
|  | 3.13e − 006 | CMV | 27.3 |  |
|  | 6.25e − 006 | CMV | 27.3 |  |
|  | 1.30e − 005 | CMV | 32.9 |  |
|  | 2.50e − 005 | CMV | 42 |  |
|  | 5.00e − 005 | CMV | 45.8 |  |
|  | 1.00e − 004 | CMV | 64 |  |
| 30 |  | CMV |  | 4.3 |
|  | 3.13e − 006 | CMV | 42.6 |  |
|  | 6.25e − 006 | CMV | 59.9 |  |
|  | 1.30e − 005 | CMV | 73.4 |  |
|  | 2.50e − 005 | CMV | 87.5 |  |
|  | 5.00e − 005 | CMV | 95.4 |  |
|  | 1.00e − 004 | CMV | 97 |  |
| 31 |  | CMV |  | <3.1 |
|  | 3.13e − 006 | CMV | 82.9 |  |
|  | 6.25e − 006 | CMV | 95 |  |
|  | 1.30e − 005 | CMV | 97.3 |  |
|  | 2.50e − 005 | CMV | 97.8 |  |
|  | 5.00e − 005 | CMV | 97.8 |  |
|  | 1.00e − 004 | CMV | 97.3 |  |
|  |  | CMV |  | 3.7 |
|  | 3.13e − 007 | CMV | −7.9 |  |
|  | 6.25e − 007 | CMV | 20 |  |
|  | 1.25e − 006 | CMV | 22.7 |  |
|  | 2.50e − 006 | CMV | 38.5 |  |
|  | 5.00e − 006 | CMV | 55 |  |
|  | 1.00e − 005 | CMV | 88.2 |  |
| 32 |  | CMV |  | <3.1 |
|  | 3.13e − 006 | CMV | 75.1 |  |
|  | 6.25e − 006 | CMV | 89.1 |  |
|  | 1.30e − 005 | CMV | 94.6 |  |
|  | 2.50e − 005 | CMV | 96.3 |  |
|  | 5.00e − 005 | CMV | 97.5 |  |
|  | 1.00e − 004 | CMV | 98.2 |  |
|  |  | CMV |  | 4.7 |
|  | 3.13e − 007 | CMV | −14.4 |  |
|  | 6.25e − 007 | CMV | 9.8 |  |
|  | 1.25e − 006 | CMV | 20.6 |  |
|  | 2.50e − 006 | CMV | 30.4 |  |
|  | 5.00e − 006 | CMV | 47.9 |  |
|  | 1.00e − 005 | CMV | 85.2 |  |
| 33 |  | CMV |  | 12.8 |
|  | 3.13e − 006 | CMV | −10.5 |  |
|  | 6.25e − 006 | CMV | 38.7 |  |
|  | 1.30e − 005 | CMV | 45.7 |  |
|  | 2.50e − 005 | CMV | 78 |  |
|  | 5.00e − 005 | CMV | 87.9 |  |
|  | 1.00e − 004 | CMV | 95.4 |  |

TABLE 3

| Example No. | Concentration (μM) | % Inhibition | $IC_{50}$ (μM) |
|---|---|---|---|
| 34 | 100 | 97 | 17.2 |
|  | 50 | 54 |  |
|  | 25 | 63 |  |
|  | 12.5 | 57 |  |
|  | 6.25 | 21 |  |
| 35 | 100 | 96 | 10.0 |
|  | 50 | 89 |  |
|  | 12.5 | 44 |  |
|  | 6.25 | 41 |  |
|  | 3.13 | 31 |  |
| 36 | 200 | 19 | >200 |
|  | 100 | 3 |  |
|  | 50 | 15 |  |

TABLE 3-continued

| Example No. | Concentration (μM) | % Inhibition | IC$_{50}$ (μM) |
|---|---|---|---|
|  | 25 | 0 |  |
|  | 12.5 | 6 |  |
|  | 6.25 | −3 |  |
|  | 3.13 | −1 |  |
| 37 | 100 | 55 | 72.3 |
|  | 50 | 50 |  |
|  | 25 | 21 |  |
|  | 12.5 | 12 |  |
|  | 6.25 | 3 |  |
| 38 | 100 | 97 | 10.5 |
|  | 50 | 96 |  |
|  | 25 | 62 |  |
|  | 12.5 | 58 |  |
|  | 6.25 | 36 |  |
| 39 | 200 | 90 | 21.6 |
|  | 100 | 71 |  |
|  | 50 | 79 |  |
|  | 25 | 41 |  |
|  | 12.5 | 43 |  |
|  | 6.25 | 28 |  |
|  | 3.13 | 16 |  |
| 40 | 100 | 94 | 13.7 |
|  | 50 | 80 |  |
|  | 25 | 53 |  |
|  | 12.5 | 47 |  |
|  | 6.25 | 36 |  |
|  | 3.13 | 22 |  |

TABLE 4

| Example No. | Conc (μM) | % Inh-AV | IC50 (AV) |
|---|---|---|---|
| 41 | 2.00e + 000 | 56.0 |  |
|  | 1.00e + 001 | 92.0 | 0.5 |
|  | 5.00e + 001 | 78.0 |  |
|  | 4.00e + 001 | 76.0 |  |
|  | 2.00e + 001 | 76.0 | 1.4 |
|  | 4.00e + 000 | 70.0 |  |
|  | 8.00e − 001 | 39.0 |  |
|  | 4.00e + 001 | 99.0 | 3.8 |
|  | 2.00e + 001 | 86.0 | 3.8 |
|  | 8.00e + 000 | 78.0 | 3.8 |
|  | 4.00e + 000 | 65.0 | 3.8 |
|  | 8.00e − 001 | 0.0 | 3.8 |
| 42 | 8.00e − 001 | 0.0 | 5.2 |
|  | 4.00e + 000 | 51.0 | 5.2 |
|  | 2.00e + 001 | 88.0 | 5.2 |
|  | 4.00e + 001 | 92.0 | 5.2 |
|  | 4.00e + 001 | 99.0 | <0.1 |
|  | 2.00e + 001 | 99.0 | <0.1 |
|  | 4.00e + 000 | 89.0 | <0.1 |
| 43 | 8.00e − 001 | 65.0 | 0.12 |
|  | 4.00e + 000 | 77.0 | 0.12 |
|  | 2.00e + 001 | 90.0 | 0.12 |
|  | 4.00e + 001 | 85.0 | 0.12 |
|  | 4.00e + 001 | 81.0 | 0.44 |
|  | 4.00e + 000 | 88.0 | 0.44 |
|  | 8.00e − 001 | 43.0 | 0.44 |
|  | 4.00e − 001 | 50.0 | 0.44 |
|  | 2.00e + 001 |  | <0.5 |
|  | 1.00e + 001 | 99.0 | <0.5 |
|  | 5.00e + 000 | 99.0 | <0.5 |
|  | 2.50e + 000 | 99.0 | <0.5 |
|  | 1.25e + 000 | 87.0 | <0.5 |
| 44 | 8.00e − 001 | 23.0 | 2.7 |
|  | 4.00e + 000 | 65.0 | 2.7 |
|  | 2.00e + 001 | 88.0 | 2.7 |
|  | 4.00e + 001 | 93.0 | 2.7 |
|  | 4.00e + 001 | 44.0 |  |
|  | 2.00e + 001 | 43.0 |  |
|  | 4.00e + 000 | 59.0 |  |
|  | 8.00e − 001 | 58.0 |  |
| 45 | 8.00e − 001 | 39.0 | 1.2 |

TABLE 4-continued

| Example No. | Conc (μM) | % Inh-AV | IC50 (AV) |
|---|---|---|---|
|  | 4.00e + 000 | 75.0 | 1.2 |
|  | 2.00e + 001 | 83.0 | 1.2 |
|  | 4.00e + 001 | 89.0 | 1.2 |

TABLE 5

| Example No. | Conc (M) | pol type | % Inhib | IC50 μM |
|---|---|---|---|---|
| 46 | 5.00e − 005 | CMV | 67.1 |  |
|  | 1.00e − 004 | CMV | 83.2 |  |
|  | 2.50e − 005 | CMV | 54.2 |  |
|  |  | CMV |  | 23.3 |
|  | 3.13e − 006 | CMV | 13.9 |  |
|  | 6.25e − 006 | CMV | 23 |  |
|  | 1.30e − 005 | CMV | 30.7 |  |
| 47 | 3.13e − 006 | CMV | 76.5 |  |
|  | 6.25e − 006 | CMV | 61.3 |  |
|  | 1.30e − 005 | CMV. | 54.3 |  |
|  | 2.50e − 005 | CMV | 59.4 |  |
|  | 5.00e − 005 | CMV | 65.9 |  |
|  | 1.00e − 004 | CMV | 73.1 |  |
|  |  | CMV |  | 0.35 |
|  | 7.81e − 008 | CMV | 5.6 |  |
|  | 1.56e − 007 | CMV | 20.3 |  |
|  | 3.13e − 007 | CMV | 48.6 |  |
|  | 6.25e − 007 | CMV | 76.7 |  |
|  | 1.25e − 006 | CMV | 88.5 |  |
|  | 2.50e − 006 | CMV | 94.9 |  |
|  | 1.25e − 006 | CMV | 96.4 |  |
|  | 2.50e − 006 | CMV | 96.7 |  |
|  | 5.00e − 006 | CMV | 96.1 |  |
|  | 1.00e − 005 | CMV | 95.5 |  |
|  | 6.25e − 007 | CMV | 93.2 |  |
|  |  | CMV |  | <0.3 |
|  | 3.13e − 007 | CMV | 80.5 |  |
|  |  | CMV |  | 0.5 |
| 48 | 3.13e − 007 | CMV | 32.6 |  |
|  | 6.25e − 007 | CMV | 61.3 |  |
|  | 1.25e − 006 | CMV | 77.2 |  |
|  | 2.50e − 006 | CMV | 87.2 |  |
|  | 5.00e − 006 | CMV | 91.8 |  |
|  | 1.00e − 005 | CMV | 95.6 |  |
|  | 3.13e − 006 | CMV | 97.2 |  |
|  | 6.25e − 006 | CMV | 96.8 |  |
|  | 1.30e − 005 | CMV | 97.5 |  |
|  | 2.50e − 005 | CMV | 97.8 |  |
|  | 5.00e − 005 | CMV | 98.8 |  |
|  | 1.00e − 004 | CMV | 97.8 |  |
|  |  | CMV |  | <3.1 |
| 49 | 3.13e − 006 | CMV | 95.2 |  |
|  | 6.25e − 006 | CMV | 96 |  |
|  | 1.30e − 005 | CMV | 97 |  |
|  | 2.50e − 005 | CMV | 97.3 |  |
|  | 5.00e − 005 | CMV | 97.2 |  |
|  | 1.00e − 004 | CMV | 98.4 |  |
|  |  | CMV |  | <3.1 |
|  |  | CMV |  | 0.6 |
|  | 3.13e − 007 | CMV | 41.2 |  |
|  | 6.25e − 007 | CMV | 49.3 |  |
|  | 1.25e − 006 | CMV | 66.8 |  |
|  | 2.50e − 006 | CMV | 85.5 |  |
|  | 5.00e − 006 | CMV | 92.8 |  |
|  | 1.00e − 005 | CMV | 96.1 |  |
| 50 | 5.00e − 005 | CMV | 92.6 |  |
|  | 1.00e − 004 | CMV | 95.6 |  |
|  | 2.50e − 005 | CMV | 80.9 |  |
|  |  | CMV |  | <3.1 |
|  | 3.13e − 006 | CMV | 83.7 |  |
|  | 6.25e − 006 | CMV | 91.1 |  |
|  | 1.30e − 005 | CMV | 92.6 |  |
|  | 2.50e − 005 | CMV | 96 |  |
|  | 5.00e − 005 | CMV | 97.1 |  |
|  | 1.00e − 004 | CMV | 97.7 |  |

TABLE 5-continued

| Example No. | Conc (M) | pol type | % Inhib | IC50 μM |
|---|---|---|---|---|
| | | CMV | | 1.2 |
| | 3.13e − 006 | CMV | 23.2 | |
| | 6.25e − 006 | CMV | 34.9 | |
| | 1.30e − 005 | CMV | 40.1 | |
| 51 | | CMV | | <3.1 |
| | 3.13e − 006 | CMV | 97.1 | |
| | 6.25e − 006 | CMV | 96.6 | |
| | 1.30e − 005 | CMV | 96.8 | |
| | 2.50e − 005 | CMV | 96.9 | |
| | 5.00e − 005 | CMV | 97.9 | |
| | 1.00e − 004 | CMV | 98.7 | |
| | | CMV | | 0.17 |
| | 3.13e − 006 | CMV | 60.2 | |
| | 6.25e − 006 | CMV | 86.7 | |
| | 1.30e − 005 | CMV | 94.2 | |
| | 2.50e − 005 | CMV | 98.2 | |
| | 5.00e − 005 | CMV | 98.7 | |
| | 1.00e − 004 | CMV | 98.4 | |
| 52 | | CMV | | <3.1 |
| | 3.13e − 006 | CMV | 97.4 | |
| | 6.25e − 006 | CMV | 98.4 | |
| | 1.30e − 005 | CMV | 98.9 | |
| | 2.50e − 005 | CMV | 98.7 | |
| | 5.00e − 005 | CMV | 98.5 | |
| | 1.00e − 004 | CMV | 98.6 | |
| | | CMV | | 0.17 |
| | 3.13e − 006 | CMV | 59.7 | |
| | 6.25e − 006 | CMV | 84.6 | |
| | 1.30e − 005 | CMV | 95.2 | |
| | 2.50e − 005 | CMV | 97.3 | |
| | 5.00e − 005 | CMV | 98.7 | |
| | 1.00e − 004 | CMV | 99 | |
| 53 | | CMV | | <3.1 |
| | 3.13e − 006 | CMV | 94.6 | |
| | 6.25e − 006 | CMV | 94.2 | |
| | 1.30e − 005 | CMV | 94.7 | |
| | 2.50e − 005 | CMV | 95.8 | |
| | 5.00e − 005 | CMV | 92.7 | |
| | 1.00e − 004 | CMV | 95.8 | |
| | | CMV | | 0.3 |
| | 3.13e − 007 | CMV | 46 | |
| | 6.25e − 007 | CMV | 68.2 | |
| | 1.25e − 006 | CMV | 84.8 | |
| | 2.50e − 006 | CMV | 92.8 | |
| | 5.00e − 006 | CMV | 95.4 | |
| 53 | 1.00e − 005 | CMV | 94.9 | |
| 54 | | CMV | | <3.1 |
| | 3.13e − 006 | CMV | 88.7 | |
| | 6.25e − 006 | CMV | 94.4 | |
| | 1.30e − 005 | CMV | 95.1 | |
| | 2.50e − 005 | CMV | 95.6 | |
| | 5.00e − 005 | CMV | 95.6 | |
| | 1.00e − 004 | CMV | 95.3 | |
| | | CMV | | 0.3 |
| | 3.13e − 007 | CMV | 45.9 | |
| | 6.25e − 007 | CMV | 77.8 | |
| | 1.25e − 006 | CMV | 89.6 | |
| | 2.50e − 006 | CMV | 94.2 | |
| | 5.00e − 006 | CMV | 97.3 | |
| | 1.00e − 005 | CMV | 98.7 | |
| 55 | | CMV | | 31.5 |
| | 3.13e − 006 | CMV | 17.2 | |
| | 6.25e − 006 | CMV | 27.4 | |
| | 1.30e − 005 | CMV | 27.7 | |
| | 2.50e − 005 | CMV | 42.9 | |
| | 5.00e − 005 | CMV | 51.4 | |
| | 1.00e − 004 | CMV | 73.5 | |
| 56 | | CMV | | 19.7 |
| | 3.13e − 006 | CMV | 27.9 | |
| | 6.25e − 006 | CMV | 30 | |
| | 1.30e − 005 | CMV | 36.8 | |
| | 2.50e − 005 | CMV | 48.4 | |
| | 5.00e − 005 | CMV | 59.8 | |
| | 1.00e − 004 | CMV | 81.8 | |
| 58 | 3.13e − 006 | CMV | −2.9 | |
| | 6.25e − 006 | CMV | 2.4 | |
| | 1.30e − 005 | CMV | 27.9 | |
| | 2.50e − 005 | CMV | 40.2 | |
| | 5.00e − 005 | CMV | 46.2 | |
| | 1.00e − 004 | CMV | 65 | |
| | 3.13e − 006 | CMV | −2.9 | |
| | 6.25e − 006 | CMV | 2.4 | |
| | 1.30e − 005 | CMV | 27.9 | |
| | 2.50e − 005 | CMV | 40.2 | |
| | 5.00e − 005 | CMV | 46.2 | |
| | 1.00e − 004 | CMV | 65 | |
| | 3.13e − 006 | CMV | −2.9 | |
| | 6.25e − 006 | CMV | 2.4 | |
| | 1.30e − 005 | CMV | 27.9 | |
| | 2.50e − 005 | CMV | 40.2 | |
| | 5.00e − 005 | CMV | 46.2 | |
| | 1.00e − 004 | CMV | 65 | |
| | | CMV | | 49.7 |
| | 3.13e − 006 | CMV | −2.9 | |
| | 6.25e − 006 | CMV | 2.4 | |
| | 1.30e − 005 | CMV | 27.9 | |
| | 2.50e − 005 | CMV | 40.2 | |
| | 5.00e − 005 | CMV | 46.2 | |
| | 1.00e − 004 | CMV | 65 | |
| 57 | | CMV | | 8.0 |

TABLE 6

| Example No. | Concentration (μM) | % Inhibition | $IC_{50}$ (μM) |
|---|---|---|---|
| Example 59 | 200 | 43 | >200 |
| | 100 | 31 | |
| | 50 | 14 | |
| | 25 | 0 | |
| | 12.5 | −3 | |
| | 6.25 | −6 | |
| | 3.13 | −7 | |
| Example 60 | 200 | 70 | 57.4 |
| | 100 | 55 | |
| | 50 | 51 | |
| | 25 | 32 | |
| | 12.5 | 31 | |
| | 6.25 | 19 | |
| | 3.13 | 30 | |
| Example 61 | 200 | 51 | >200 |
| | 100 | 38 | |
| | 50 | 30 | |
| | 25 | 30 | |
| | 12.5 | 23 | |
| | 6.25 | 15 | |
| | 3.13 | 13 | |
| Example 62 | 200 | 42 | >200 |
| | 100 | 33 | |
| | 50 | 14 | |
| | 25 | 10 | |
| | 12.5 | 6 | |
| | 6.25 | 3 | |
| | 3.13 | 1 | |
| Example 63 | 100 | 92 | 11.4 |
| | 50 | 74 | |
| | 25 | 71 | |
| | 12.5 | 49 | |
| | 6.25 | 34 | |
| | 3.13 | 29 | |
| Example 64 | 200 | 84 | 29.8 |
| | 100 | 58 | |
| | 50 | 75 | |
| | 25 | 46 | |
| | 12.5 | 25 | |
| | 6.25 | 25 | |
| | 3.13 | 16 | |
| Example 65 | 200 | −8 | >200 |
| | 100 | −23 | |
| | 50 | −23 | |
| | 25 | −21 | |

TABLE 6-continued
| Example No. | Concentration (μM) | % Inhibition | IC$_{50}$ (μM) |
|---|---|---|---|
|  | 12.5 | −13 |  |
|  | 6.25 | −8 |  |
|  | 3.13 | −8 |  |
| Example 66 | 200 | 89 | 11.0 |
|  | 100 | 86 |  |
|  | 50 | 64 |  |
|  | 25 | 57 |  |
|  | 12.5 | 60 |  |
|  | 6.25 | 41 |  |
|  | 3.13 | 32 |  |
|  | 200 | 88 | 17.9 |
|  | 100 | 91 |  |
|  | 50 | 71 |  |
|  | 25 | 77 |  |
|  | 12.5 | 37 |  |
|  | 6.25 | 30 |  |
|  | 3.13 | 13 |  |
| Example 67 | 200 | 94 | 23.6 |
|  | 100 | 86 |  |
|  | 50 | 76 |  |
|  | 25 | 41 |  |
|  | 12.5 | 25 |  |
TABLE 6-continued
| Example No. | Concentration (μM) | % Inhibition | IC$_{50}$ (μM) |
|---|---|---|---|
|  | 6.25 | 23 |  |
|  | 3.13 | 13 |  |
TABLE 7
| Example Number, Structure | Antiviral Selective Polymerase IC50 Values | |
|---|---|---|
|  | Polymerase | IC50 (uM) |
| Example 69 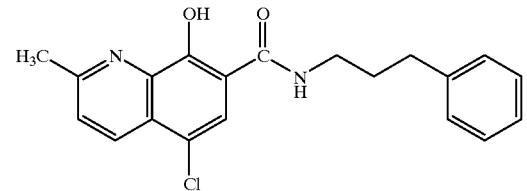 | CMV | 9.7<br>9.4 |
| Example 70 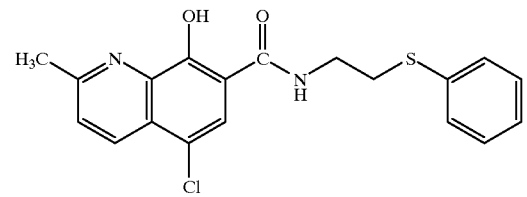 | CMV | 42.8 |
| Example 71 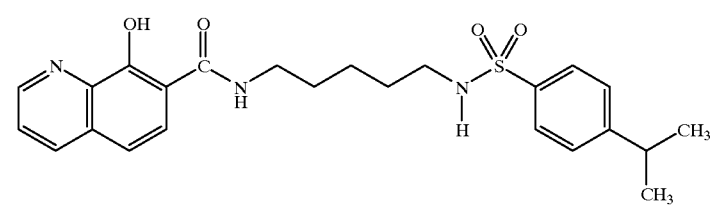 | CMV | <3.1 |

TABLE 7-continued
| Example 73 | | CMV | 13.3 |
|---|---|---|---|
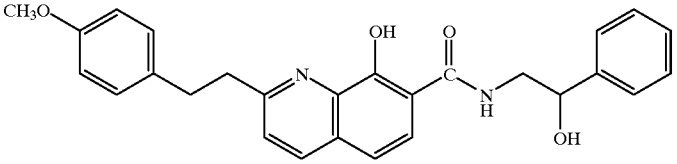
| | | CMV Antiviral Assay | |
|---|---|---|---|
| Example Number, Structure | Conc (uM) | % Inh — AV | IC50 (AV) |
| Example 72 | 2.00e+001 | 90.0 | 3 |
| | 4.00e+000 | 41.0 | 3 |
| | 8.00e−001 | 34.0 | 3 |
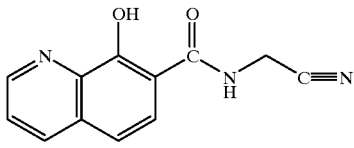
| Example 68 | 4.00e+001 | 99.0 | 3 |
|---|---|---|---|
| | 2.00e+001 | 96.0 | 3 |
| | 4.00e+000 | 12.0 | 3 |
| | 8.00e+001 | 21.0 | 3 |
| | 4.00e+001 | 66.0 | 14.1 |
| | 3.00e+001 | 52.0 | 14.1 |
| | 2.00e+001 | 54.0 | 14.1 |
| | 1.00e+001 | 50.0 | 14.1 |
| | 8.00e+000 | 35.0 | 14.1 |
| | 4.00e+000 | 8.0 | 14.1 |
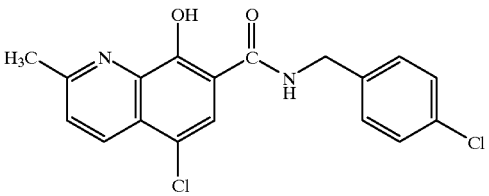
TABLE 8
| Compound | MS-ESI (+) | MS-ESI (−) | NMR (d) (CDCl3) | Elem. Anal. |
|---|---|---|---|---|
| 75 | 332 | 330 | 8.8, 8.2, 8.1, 7.9, 7.5, 7.4, 7.3, 7.2, 7.1, 3.9, 3.2 | |
| 76 | 309 | 307 | | |
| 77 | 385 | 383 | | |
| 78 | 347 | 345 | | |
| 79 | 347 | 345 | | |
| 80 | 329 | 327 | | |
| 81 | 321 | 319 | | |
| 82 | 301 | 299 | 8.8, 8.2, 7.8, 7.5, 7.4, 3.5, 1.7, 1.5–1.2, 0.9 | |
| 83 | 347 | 345 | | |
| 84 | 347 | 345 | | |
| 85 | 297 | 295 | | |
| 86 | 361 | 359 | 8.8, 8.2, 7.9, 7.5, 7.4, 7.2, 3.8, 3.1 | |
| 87 | 325 | 323 | | |
| 88 | 313 | 311 | | |
| 89 | 293 | 291 | | |
| 90 | 293 | 291 | | |
| 91 | 313 | 311 | | |
| 92 | 309 | 307 | 8.8, 8.3, 8.2, 7.6, 7.5, 7.4, 5.0, 4.0, 3.7 | |
| 93 | 369 | 367 | | |
| 94 | 308 | 306 | | |
| 95 | 301 | 299 | 8.8, 8.2, 7.8, 7.5, 7.4, 3.5, 1.6, 1.5–1.2, 1.0, 0.9 | |
| 96 | 343 | 341 | | |
| 97 | 441 | 439 | | |
| 98 | 371 | 369 | | |
| 99 | 327 | 325 | | |
| 100 | 307 | 305 | | |
| 101 | 383 | 381 | | |

TABLE 8-continued

| Compound | MS-ESI (+) | MS-ESI (−) | NMR (d) (CDCl3) | Elem. Anal. |
|---|---|---|---|---|
| 102 | 307 | 305 | | |
| 103 | 315 | 313 | 8.8, 8.2, 7.8, 7.5, 7.4, 3.5, 1.7, 1.5–1.2, 0.9 | |
| 104 | 315 | 313 | | |
| 105 | 313 | 311 | | |
| 106 | 285 | 283 | | |
| 107 | 299 | 297 | | |
| 108 | 285 | 283 | | |
| 109 | 285 | 283 | | |
| 110 | 319 | 317 | | |
| 111 | 299 | 297 | | |
| 112 | 305 | 303 | | |
| 113 | 285 | 283 | | |
| 114 | 355 | 353 | | |
| 115 | 293 | 291 | | |
| 116 | 287 | 282 | | |
| 117 | 301 | 299 | | |
| 118 | 327 | 325 | | |
| 119 | 409 | 407 | | |
| 120 | 343 | 341 | | |
| 121 | 343 | 341 | | |
| 122 | 293 | 291 | | |
| 123 | 373 | 371 | | |
| 124 | 373 | 371 | | |
| 125 | 385 | 383 | | |
| 126 | 385 | 383 | | |
| 127 | 283 | 281 | | |
| 128 | 325 | 323 | | |
| 129 | 339 | 337 | | |
| 130 | 367 | 365 | 8.8, 8.2, 8.1, 7.5, 7.4–7.2, 5.3, 5.0, 4.2 | |
| 131 | 367 | 355 | 8.8, 8.2, 8.1, 7.5, 7.4, 7.1, 6.8, 5.1, 3.8, 3.2 | |
| 132 | 404 | 402 | | |
| 133 | 323 | 321 | | |
| 134 | 457 | 455 | | |
| 135 | 396 | 394 | | |
| 136 | 315 | 313 | | |
| 137 | 287 | 285 | | |
| 138 | 331 | 329 | | |
| 139 | 347 | 345 | | |
| 140 | 347 | 345 | | |
| 141 | 391 | 389 | | |
| 142 | 407 | 405 | | |
| 143 | 405 | 403 | | |
| 144 | 417 | 415 | | |
| 145 | 444 | 442 | | |
| 146 | 285 | 283 | 8.8, 8.2, 7.9, 7.5, 7.4, 3.4, 1.9–1.6, 1.4–1.0 | C 71.57, H 7.08, N 9.87 |
| 147 | 329 | 327 | 8.8, 8.2, 7.8, 7.6–7.4, 7.3, 5.2 | C 76.52, H 5.19, N 8.59 |
| 148 | 327 | 325 | 10.0, 8.8, 8.2, 8.0, 7.5, 7.3, 7.2, 7.1, 3.8, 3.0 | C 65.82, H 4.63, N 8.56 |
| 149 | 347 | 345 | 9.6, 8.8, 8.4, 8.2, 7.7–7.3, 4.8 | C 66.22, H 4.09, N 8.04 |
| 150 | 325 | 323 | 10.0, 8.8, 8.2, 8.1, 7.5, 7.4, 7.3, 7.2, 7.1, 3.8, 3.2 | C 66.48, H 5.06, N 8.55 |
| 151 | 287 | 285 | 10, 8.8, 8.1, 7.8, 7.5, 7.3, 3.5, 1.7, 1.5–1.2, 0.9 | |

TABLE 9
| Example Number, Structure | CMV pol Assay - IC50 uM |
|---|---|
| Example 93 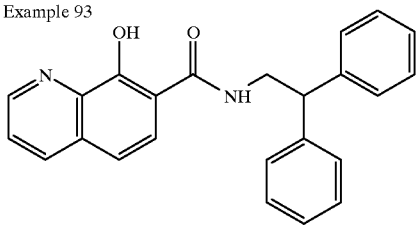 | 0.9 |
| Example 101 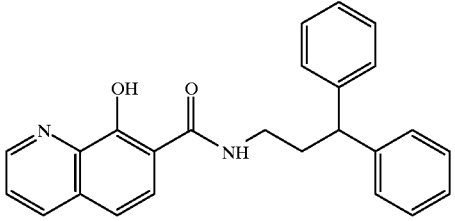 | <1.5 |
| Example 87 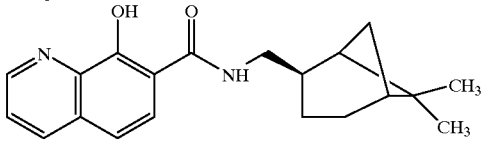 | 1.5 |
| Example 114 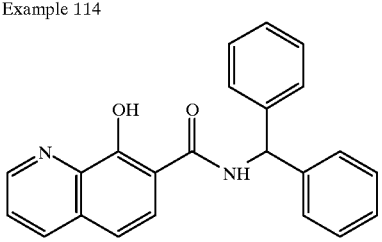 | <3.1<br>1.6<br>20 |
| Example 117 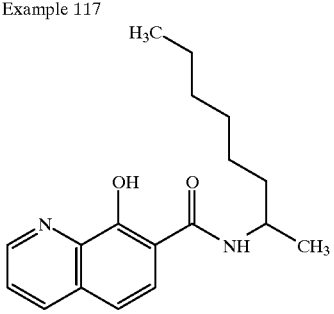 | 1.7 |

TABLE 9-continued

| Example Number, Structure | CMV pol Assay - IC50 uM |
|---|---|
| Example 126 | 2.2<br>4.7 |
| Example 103 | 2.2 |
| Example 118 | 2.3 |
| Example 120 | <3.1<br>2.4<br>10.8 |
| Example 124 | 2.6 |
| Example 125 | 2.9<br>6.4 |

TABLE 9-continued

| Example Number, Structure | CMV pol Assay - IC50 uM |
|---|---|
| Example 143 | 3 |
| Example 143 | 3.1 |
| Example 96 | <3.1 |
| Example 106 | <3.1 >10 |
| Example 129 | 3.1 |
| Example 95 | 3.2 |
| Example 147 | 3.7 |

TABLE 9-continued

| Example Number, Structure | CMV pol Assay - IC50 uM |
| --- | --- |
| Example 77 | 4.5 |
| Example 123 | 4.6 |
| Example 134 | 4.9 |
| Example 98 | 5 |
| Example 78 | 5.2 |
| Example 151 | 5.2 |

TABLE 9-continued

| Example Number, Structure | CMV pol Assay - IC50 uM |
| --- | --- |
| Example 82 — 8-hydroxyquinoline-7-carboxamide N-octyl | 5.6 |
| Example 79 — 8-hydroxyquinoline-7-carboxamide N-(3,4-dichlorobenzyl) | 5.6 |
| Example 137 — 8-hydroxyquinoline-7-carboxamide N-(1-(hydroxymethyl)cyclopentyl) | 6.6 |
| Example 99 — 8-hydroxyquinoline-7-carboxamide N-(2-(4-chlorophenyl)ethyl) | 6.7 |
| Example 148 — 8-hydroxyquinoline-7-carboxamide N-(2-(3-chlorophenyl)ethyl) | 6.9 |
| Example 104 — 8-hydroxyquinoline-7-carboxamide N-(2,6-difluorobenzyl) | 7.1 |
| Example 80 — 8-hydroxyquinoline-7-carboxamide N-nonyl | 7.1 |

TABLE 9-continued

| Example Number, Structure | CMV pol Assay - IC50 uM |
|---|---|
| Example 81 | 7.4 |
| Example 111 | 7.6 |
| Example 110 | 7.6 |
| Example 92 | 7.8 |
| Example 116 | 7.9 |
| Example 119 | 8.1 |

TABLE 9-continued
| Example Number, Structure | CMV pol Assay - IC50 uM |
|---|---|
| Example 91 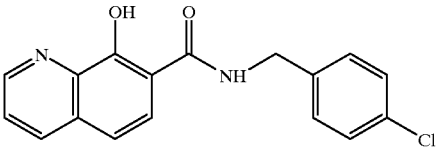 | 8.1 |
| Example 142 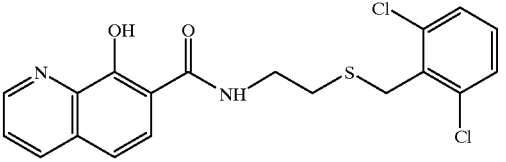 | 8.4 |
| Example 97 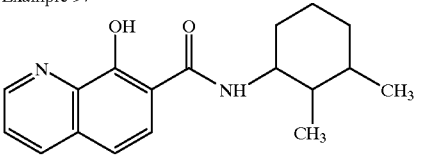 | 8.4 |
| Example 149 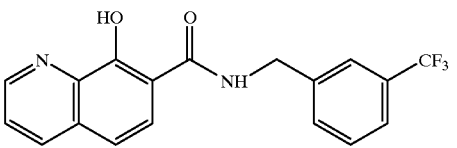 | 8.5 |
| Example 105 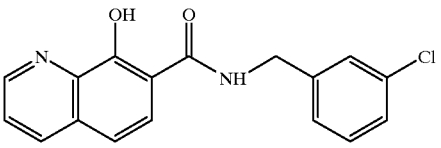 | 8.7 |
| Example 86 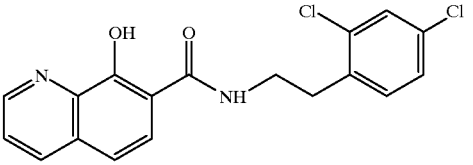 | 9 |

TABLE 9-continued

| Example Number, Structure | CMV pol Assay - IC50 uM |
|---|---|
| Example 130 ![structure] | 11.3 9.2 |
| Example 150 ![structure] | 9.2 |
| Example 102 ![structure] | 9.3 |
| Example 144 ![structure] | 9.4 |
| Example 141 ![structure] | 9.6 |
| Example 135 ![structure] | 10.8 |

TABLE 9-continued

| Example Number, Structure | CMV pol Assay - IC50 uM |
|---|---|
| Example 75 | 11.1 |
| Example 131 | 12.1 |
| Example 145 | 12.6 |
| Example 112 | 13.2 |
| Example 83 | 13.7 |
| Example 139 | 14.6 |

TABLE 9-continued

| Example Number, Structure | CMV pol Assay - IC50 uM |
|---|---|
| Example 94 | 14.8 |
| Example 84 | 15.7 |
| Example 100 | 16.8 |
| Example 140 | 17 |
| Example 138 | 17.5 |
| Example 127 | 19.2 |

TABLE 9-continued

| Example Number, Structure | CMV pol Assay - IC50 uM |
|---|---|
| Example 128 | 19.3 |
| Example 88 | 19.7 |
| Example 76 | 20.1 |
| Example 108 | 20.6 |
| Example 97 | 20.7 |
| Example 85 | 21.1 |
| Example 115 | 22.2 |

TABLE 9-continued
| Example Number, Structure | CMV pol Assay - IC50 uM |
|---|---|
| Example 136 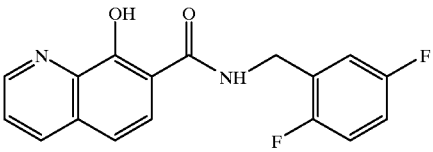 | 22.3 |
| Example 90 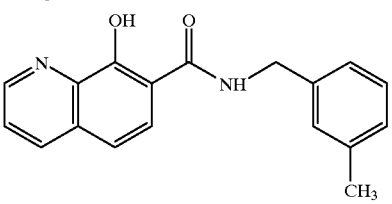 | 22.6 |
| Example 89 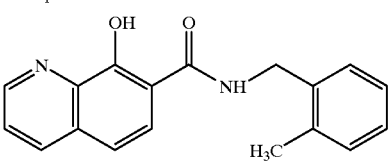 | 23.2 |
| Example 109 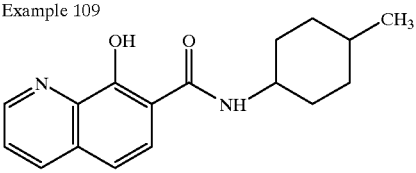 | 23.3 |
| Example 113 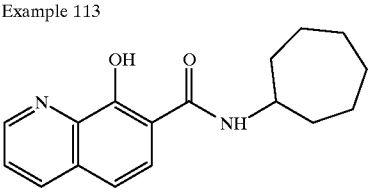 | 23.8 |
| Example 146 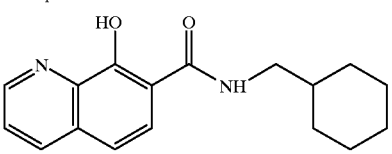 | 24.2 |
| Example 133 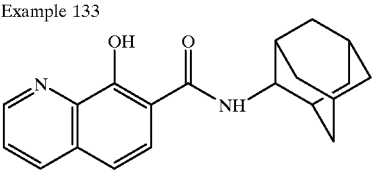 | 24.3 |

TABLE 9-continued

| Example Number, Structure | CMV pol Assay - IC50 uM |
|---|---|
| Example 122 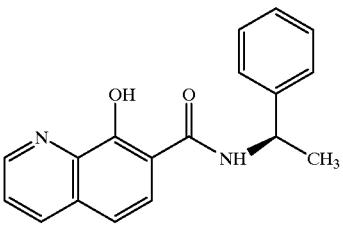 | 24.5 |
| Example 132 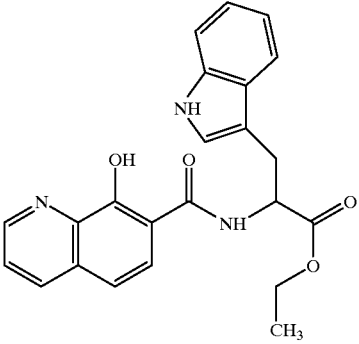 | 24.6<br>29.4 |

TABLE 10

| Example Number, Structure | CMV pol Assay | | | |
|---|---|---|---|---|
| | Conc (M) | pol type | % Inhib | IC50 uM |
| Example 152 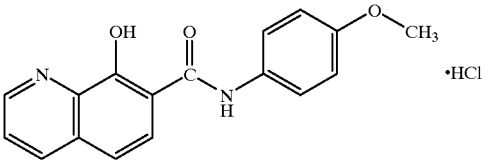 | 1.00e-004<br>5.00e-005<br><br>3.13e-006<br>6.25e-006<br>1.30e-005<br>2.50e-005<br>1.00e-004 | CMV<br>CMV<br>CMV<br>CMV<br>CMV<br>CMV<br>CMV<br>CMV | 98.7<br>87.6<br><br>2.5<br>3.4<br>11.8<br>43.1<br>98.2 | <br><br>30.1 |
| Example 153 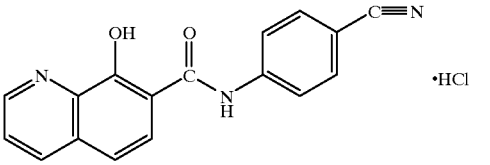 | <br>3.13e-006<br>6.25e-006<br>1.30e-005<br>2.50e-005<br>5.00e-005<br>1.00e-004<br>1.00e-004 | CMV<br>CMV<br>CMV<br>CMV<br>CMV<br>CMV<br>CMV<br>CMV | 7<br>6.2<br>12.8<br>23.1<br>28.5<br>44<br>99.9<br> | >100 |
| Example 154 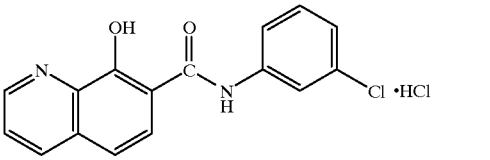 | <br>3.13e-006<br>6.25e-006<br>1.30e-005<br>2.50e-005<br>5.00e-005<br>1.00e-004<br>1.00e-004 | CMV<br>CMV<br>CMV<br>CMV<br>CMV<br>CMV<br>CMV<br>CMV | <br>56.8<br>90.6<br>99.7<br>99.8<br>100.8<br>100.3<br>99.9 | 1.7 |

TABLE 10-continued

| Example Number, Structure | CMV pol Assay | | | |
|---|---|---|---|---|
| | Conc (M) | pol type | % Inhib | IC50 uM |
| Example 155 | | CMV | | 68.2 |
| | 3.13e-006 | CMV | 2.6 | |
| | 6.25e-006 | CMV | 9.8 | |
| | 1.30e-005 | CMV | 13.6 | |
| | 2.50e-005 | CMV | 28.9 | |
| | 5.00e-005 | CMV | 40.7 | |
| | 1.00e-004 | CMV | 60 | |
| | 1.00e-004 | CMV | 63.8 | |
| Example 156 | | CMW | | 1.8 |
| | 3.13e-007 | CMV | 13.8 | |
| | 6.25e-007 | CMV | 32.1 | |
| | 1.25e-006 | CMV | 40.9 | |
| | 2.50e-006 | CMV | 57.8 | |
| | 5.00e-006 | CMV | 65.3 | |
| | 1.00e-005 | CMV | 74.6 | |
| | | CMV | | 3.1 |
| | 3.13e-006 | CMV | 78.1 | |
| | 6.25e-006 | CMV | 79.8 | |
| | 1.30e-005 | CMV | 82.9 | |
| | 2.50e-005 | CMV | 83.6 | |
| | 5.00e-005 | CMV | 82.8 | |
| | 1.00e-004 | CMV | 90.8 | |
| Example 157 | | CMV | | 90 |
| | 3.13e-006 | CMV | −3.9 | |
| | 6.25e-006 | CMV | 3.3 | |
| | 1.30e-005 | CMV | 6.6 | |
| | 2.50e-005 | CMV | 15.8 | |
| | 5.00e-005 | CMV | 20.5 | |
| | 1.00e-004 | CMV | 57.2 | |
| Example 158 | | CMV | | 16.4 |
| | 3.13e-006 | CMV | −4.2 | |
| | 6.25e-006 | CMV | 11.9 | |
| | 1.30e-005 | CMV | 39.1 | |
| | 2.50e-005 | CMV | 75.6 | |
| | 5.00e-005 | CMV | 98.2 | |
| | 1.00e-004 | CMV | 100 | |
| Example 159 | | CMV | | 9.5 |
| | 3.13e-006 | CMV | 26.8 | |
| | 6.25e-006 | CMV | 44.1 | |
| | 1.30e-005 | CMV | 55.4 | |
| | 2.50e-005 | CMV | 63.4 | |
| | 5.00e-005 | CMV | 76.3 | |
| | 1.00e-004 | CMV | 86.2 | |

TABLE 10-continued

| | | CMV pol Assay | | |
|---|---|---|---|---|
| Example Number, Structure | Conc (M) | pol type | % Inhib | IC50 uM |
| Example 160 (8-hydroxyquinoline-7-carboxamide, N-(3-fluorophenyl), ·HCl) | | CMV | | 16.9 |
| | 3.13e-006 | CMV | 3.1 | |
| | 6.25e-006 | CMV | 4.8 | |
| | 1.30e-005 | CMV | 30 | |
| | 2.50e-005 | CMV | 82.9 | |
| | 5.00e-005 | CMV | 100 | |
| | 1.00e-004 | CMV | 100.3 | |
| | 1.00e-004 | CMV | 98.7 | |
| Example 161 (8-hydroxyquinoline-7-carboxamide, N-(3,4-difluorophenyl), ·HCl) | | CMV | | 82.9 |
| | 3.13e-006 | CMV | 0.4 | |
| | 6.25e-006 | CMV | 7.1 | |
| | 1.30e-005 | CMV | 8.4 | |
| | 2.50e-005 | CMV | 26.2 | |
| | 5.00e-005 | CMV | 26.5 | |
| | 1.00e-004 | CMV | 59 | |
| Example 162 (8-hydroxyquinoline-7-carboxamide, N-(3,5-difluorophenyl), ·HCl) | | CMV | | 26.3 |
| | 3.13e-006 | CMV | 1.1 | |
| | 6.25e-006 | CMV | 6.6 | |
| | 1.30e-005 | CMV | 32.7 | |
| | 2.50e-005 | CMV | 58.1 | |
| | 5.00e-005 | CMV | 68.8 | |
| | 1.00e-004 | CMV | 80.6 | |
| Example 163 (8-hydroxyquinoline-7-carboxamide, N-(4-nitrophenyl)) | 1.25e-007 | CMV | −0.2 | |
| | 6.25e-006 | CMV | 10.4 | |
| | 1.30e-005 | CMV | 18.3 | |
| | 2.50e-005 | CMV | 34.6 | |
| | 5.00e-005 | CMV | 50.3 | |
| | 1.00e-004 | CMV | 71.3 | |
| | | CMV | | 48.4 |
| Example 164 (8-hydroxyquinoline-7-carboxamide, N-(2-chloro-5-trifluoromethylphenyl)) | 1.00e-004 | CMV | 93.2 | |
| | | CMV | | 14 |
| | 3.13e-006 | CMV | 12 | |
| | 6.25e-006 | CMV | 24.4 | |
| | 1.30e-005 | CMV | 45.5 | |
| | 2.50e-005 | CMV | 74.3 | |
| | 5.00e-005 | CMV | 88.1 | |
| Example 165 (8-hydroxyquinoline-7-carboxamide, N-(5-fluoro-2-methylphenyl)) | | CMV | | 14.7 |
| | 3.13e-006 | CMV | 7.8 | |
| | 3.13e-006 | CMV | 29.7 | |
| | 6.25e-006 | CMV | 11.2 | |
| | 6.25e-006 | CMV | 47.1 | |
| | 1.30e-005 | CMV | 9.4 | |
| | 1.30e-005 | CMV | 88.8 | |
| | 2.50e-005 | CMV | 19.5 | |
| | 2.50e-005 | CMV | 102.4 | |
| | 5.00e-005 | CMV | 48.8 | |
| | 5.00e-005 | CMV | 103 | |
| | 1.00e-004 | CMV | 91.1 | |
| | 1.00e-004 | CMV | 102.7 | |

TABLE 10-continued

| Example Number, Structure | CMV pol Assay | | | |
|---|---|---|---|---|
| | Conc (M) | pol type | % Inhib | IC50 uM |
| Example 166 | | CMV | | 22.4 |
| | 3.13e-006 | CMV | 6 | |
| | 3.13e-006 | CMV | 26.3 | |
| | 6.25e-006 | CMV | 2.3 | |
| | 6.25e-006 | CMV | 35.6 | |
| | 1.30e-005 | CMV | 5.8 | |
| | 1.30e-005 | CMV | 69.7 | |
| | 2.50e-005 | CMV | 9.5 | |
| | 2.50e-005 | CMV | 101.8 | |
| | 5.00e-005 | CMV | 18.1 | |
| | 5.00e-005 | CMV | 103.6 | |
| | 1.00e-004 | CMV | 65.8 | |
| | 1.00e-004 | CMV | 102.8 | |
| Example 167 | | CMV | | 12.2 |
| | 3.13e-006 | CMV | 17 | |
| | 6.25e-006 | CMV | 18.6 | |
| | 1.30e-005 | CMV | 41.9 | |
| | 2.50e-005 | CMV | 91.9 | |
| | 5.00e-005 | CMV | 102.8 | |
| | 1.00e-004 | CMV | 102.9 | |
| Example 169 | 2.50e-005 | CMV | 73.7 | |
| | | CMV | | 15.5 |
| | 3.13e-006 | CMV | 13.2 | |
| | 6.25e-006 | CMV | 21.2 | |
| | 1.30e-005 | CMV | 29.7 | |
| | 2.50e-005 | CMV | 77.9 | |
| | 5.00e-005 | CMV | 98.6 | |
| | 1.00e-004 | CMV | 100 | |
| Example 170 | 2.50e-005 | CMV | 90.8 | |
| | | CMV | | 2.4 |
| | 1.56e-006 | CMV | 26 | |
| | 3.13e-006 | CMV | 58.1 | |
| | 6.25e-006 | CMV | 87.3 | |
| | 1.30e-005 | CMV | 97.6 | |
| | 2.50e-005 | CMV | 99 | |
| | 5.00e-005 | CMV | 99.4 | |
| Example 171 | 2.50e-005 | CMV | 90.6 | |
| | | CMV | | 9.2 |
| | 1.56e-006 | CMV | 10 | |
| | 3.13e-006 | CMV | 15.6 | |
| | 6.25e-006 | CMV | 26.7 | |
| | 1.30e-005 | CMV | 68.5 | |
| | 2.50e-005 | CMV | 96.3 | |
| | 5.00e-005 | CMV | 99.8 | |
| Example 172 | 2.50e-005 | CMV | 71.5 | |
| | | CMV | | 32.7 |
| | 3.13e-006 | CMV | 9.8 | |
| | 6.25e-006 | CMV | 15.5 | |
| | 1.30e-005 | CMV | 19.9 | |
| | 2.50e-005 | CMV | 59.5 | |
| | 5.00e-005 | CMV | 69.9 | |
| | 1.00e-004 | CMV | 51.4 | |

TABLE 10-continued

| Example Number, Structure | CMV pol Assay | | | |
|---|---|---|---|---|
| | Conc (M) | pol type | % Inhib | IC50 uM |
| Example 173 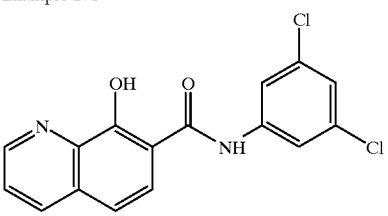 | 250e-005 | CMV | 30.6 | |
| Example 174 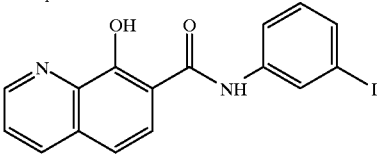 | 5.00e-005<br>2.50e-005<br>2.50e-005<br><br>1.56e-006<br>3.13e-006<br>6.25e-006<br>1.30e-005 | CMV<br>CMV<br>CMV<br>CMV<br>CMV<br>CMV<br>CMV<br>CMV | 99.6<br>98<br>95.4<br><br>13.9<br>23<br>47.4<br>87.7 | <br><br><br>5.9 |
| Example 175 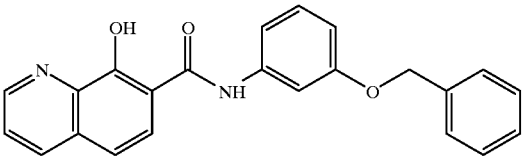 | 2.50e-005<br><br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 85.3<br><br>17.4<br>49.8<br>85.1<br>97.2<br>98.3<br>99.1 | <br>2.9 |
| Example 176 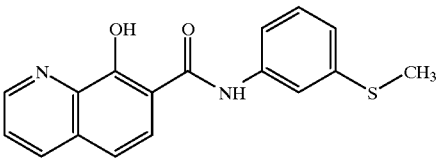 | 2.50e-005<br><br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 91.9<br><br>7.7<br>15.2<br>11.9<br>19.5<br>57.3<br>91.1 | <br>25.5 |
| Example 177 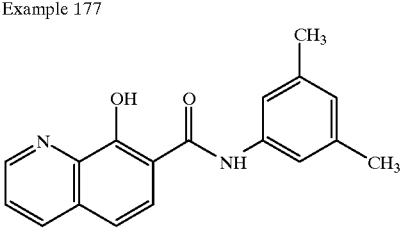 | 6.25e-006<br>1.30e-005<br>2.50e-005<br>5.00e-005<br>3.13e-006<br>2.50e-005<br><br>1.56e-006 | CMV<br>CMV<br>CMV<br>CMV<br>CMV<br>CMV<br>CMV<br>CMV | 13.1<br>23.1<br>75.4<br>99.1<br>11.1<br>84<br><br>5.9 | <br><br><br><br><br><br>19.2 |
| Example 178 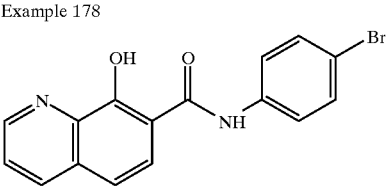 | 2.50e-005<br><br>3.13e-006<br>6.25e-006<br>1.30e-005<br>2.50e-005<br>5.00e-005<br>1.00e-004 | CMV<br>CMV<br>CMV<br>CMV<br>CMV<br>CMV<br>CMV<br>CMV | 79.6<br><br>10.7<br>16<br>14.4<br>37.1<br>85.3<br>99.7 | <br>29.7 |

TABLE 10-continued

| | CMV pol Assay | | | |
|---|---|---|---|---|
| Example Number, Structure | Conc (M) | pol type | % Inhib | IC50 uM |
| Example 179 | 1.00e-004 | CMV | 99.2 | |
| | 5.00e-005 | CMV | 98.3 | |
| | 2.50e-005 | CMV | 68 | |
| | | CMV | | 6.9 |
| | 3.13e-006 | CMV | 17.2 | |
| | 6.25e-006 | CMV | 39.8 | |
| | 1.30e-005 | CMV | 78.5 | |
| | 2.50e-005 | CMV | 95.3 | |
| Example 180 | 2.50e-005 | CMV | 67.1 | |
| | | CMV | | 30.5 |
| | 3.13e-006 | CMV | 8.9 | |
| | 6.25e-006 | CMV | 15.2 | |
| | 1.30e-005 | CMV | 19.5 | |
| | 2.50e-005 | CMV | 38.9 | |
| | 5.00e-005 | CMV | 77.2 | |
| | 1.00e-004 | CMV | 98.8 | |
| Example 181 | 2.50e-005 | CMV | 37.8 | |
| Example 182 | | CMV | | >100 |
| | 3.13e-006 | CMV | 24.7 | |
| | 6.25e-006 | CMV | 26.3 | |
| | 1.30e-005 | CMV | 30.5 | |
| | 2.50e-005 | CMV | 43 | |
| | 5.00e-005 | CMV | 41.3 | |
| | 1.00e-004 | CMV | 52.7 | |
| | 2.50e-005 | CMV | 41.8 | |
| Example 183 | | CMV | | 4.1 |
| | 3.13e-006 | CMV | 30.8 | |
| | 6.25e-006 | CMV | 63 | |
| | 1.30e-005 | CMV | 88.9 | |
| | 2.50e-005 | CMV | 97 | |
| | 5.00e-005 | CMV | 97.8 | |
| | 1.00e-004 | CMV | 98 | |
| | 2.50e-005 | CMV | 42.7 | |
| Example 184 | 2.50e-005 | CMV | 87.3 | |
| | 5.00e-005 | CMV | 77.3 | |
| | 1.00e-004 | CMV | 71.8 | |
| | | CMV | | 3.9 |
| | 3.13e-006 | CMV | 31.3 | |
| | 6.25e-006 | CMV | 65.7 | |
| | 1.30e-005 | CMV | 82.9 | |
| | 2.50e-005 | CMV | 37.5 | |

TABLE 10-continued
| Example Number, Structure | CMV pol Assay | | | |
|---|---|---|---|---|
| | Conc (M) | pol type | % Inhib | IC50 uM |
| Example 185 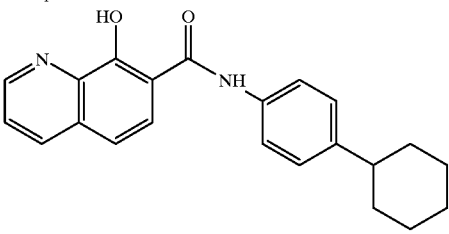 | 2.50e-005 | CMV | 37.6 | |
| Example 186 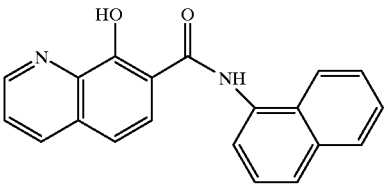 | 2.50e-005　1.56e-006　3.13e-006　6.25e-006　1.30e-005　2.50e-005　5.00e-005 | CMV　CMV　CMV　CMV　CMV　CMV　CMV　CMV | 91.3　　23.8　32.2　53　86.3　98.5　99.5 | 4.9 |
| Example 187 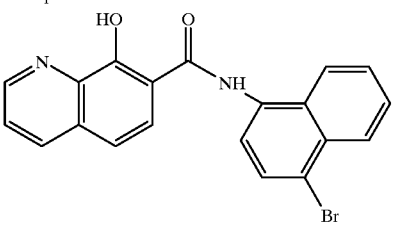 | 2.50e-005 | CMV | 30.5 | |
| Example 188 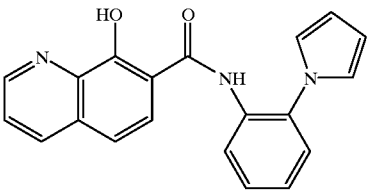 | 2.50e-005　1.56e-006　3.13e-006　6.25e-006　1.30e-005　2.50e-005　5.00e-005 | CMV　CMV　CMV　CMV　CMV　CMV　CMV　CMV | 81.8　　−6　−5.4　−0.7　2.7　27.6　83.2 | 27.9 |
| Example 189 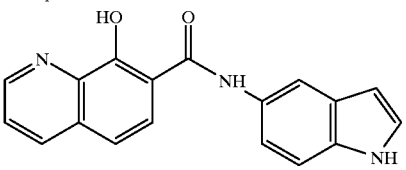 | 2.50e-005　1.56e-006　3.13e-006　6.25e-006　1.30e-005　2.50e-005　5.00e-005 | CMV　CMV　CMV　CMV　CMV　CMV　CMV　CMV | 52　　12.3　17　13.3　40.9　91.4　100.9 | 13.6 |
| Example 190 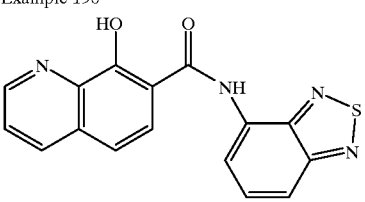 | 2.50e-005 | CMV | 30.8 | |

TABLE 10-continued

| Example Number, Structure | CMV pol Assay | | | |
|---|---|---|---|---|
| | Conc (M) | pol type | % Inhib | IC50 uM |
| Example 191 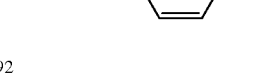 | 2.50e-005 | CMV | 22.3 | |
| Example 192  | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 76.6<br><br>6.2<br>27.6<br>32.7<br>55.9<br>78.5<br>85.2 | 10.3 |
| Example 193 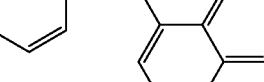 | 2.50e-005 | CMV | 39.3 | |
| Example 194 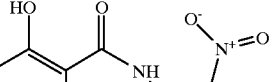 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 52.2<br><br>10.8<br>17.6<br>16.8<br>33.2<br>51.1<br>75.5 | 22.4 |
| Example 195  | 2.50e-005 | CMV | 33.1 | |
| Example 196 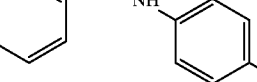 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 79.2<br><br>2.8<br>31.7<br>49.6<br>70.5<br>81.1<br>89.7 | 7.1 |

TABLE 10-continued

| Example Number, Structure | CMV pol Assay | | | |
|---|---|---|---|---|
| | Conc (M) | pol type | % Inhib | IC50 uM |
| Example 197 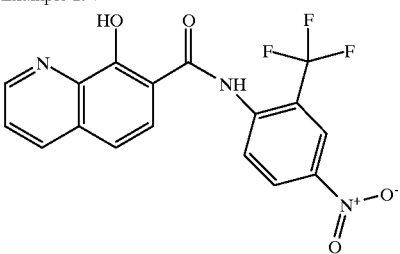 | 2.50e-005 | CMV | 35.9 | |
| Example 198 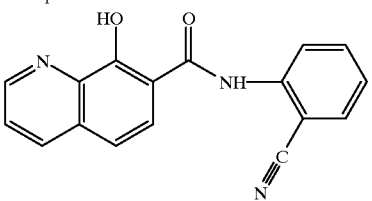 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 46.7<br><br>5.4<br>4<br>4.1<br>10<br>7<br>45.7 | >50 |
| Example 199 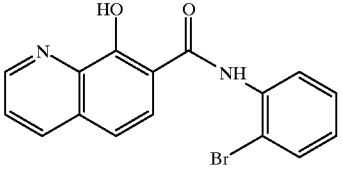 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 63.3<br><br>7.7<br>14<br>5.1<br>37<br>85.5<br>100 | 16 |
| Example 200 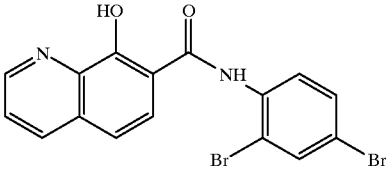 | 2.50e-005 | CMV | 35 | |
| Example 201 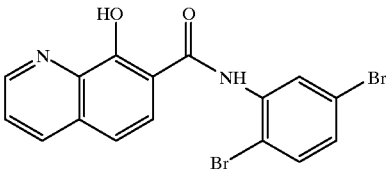 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 47.7<br><br>7.9<br>15<br>19.8<br>65.4<br>96.9<br>100.8 | 10.1 |
| Example 202 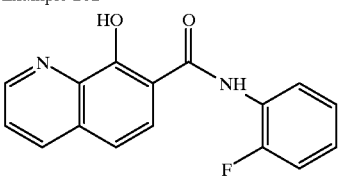 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 57.5<br><br>7.6<br>8<br>10.4<br>17.8<br>36.2<br>95.5 | 27.3 |

TABLE 10-continued

| | CMV pol Assay | | | |
|---|---|---|---|---|
| Example Number, Structure | Conc (M) | pol type | % Inhib | IC50 uM |
| Example 203 (8-hydroxyquinoline-7-carboxamide with 2,3,5,6-tetrafluoro-4-cyanophenyl) | 2.50e-005 | CMV | 63.9 | |
| | | CMV | | 18.5 |
| | 1.56e-006 | CMV | 12.3 | |
| | 3.13e-006 | CMV | 15.9 | |
| | 6.25e-006 | CMV | 9 | |
| | 1.30e-005 | CMV | 30 | |
| | 2.50e-005 | CMV | 72 | |
| | 5.00e-005 | CMV | 99.6 | |
| Example 204 (8-hydroxyquinoline-7-carboxamide with 2,4-difluorophenyl) | 2.50e-005 | CMV | 73.9 | |
| | | CMV | | 26.8 |
| | 1.56e-006 | CMV | 2.1 | |
| | 3.13e-006 | CMV | 13.6 | |
| | 6.25e-006 | CMV | 14.3 | |
| | 1.30e-005 | CMV | 20.6 | |
| | 2.50e-005 | CMV | 35.7 | |
| | 5.00e-005 | CMV | 93.9 | |
| Example 205 (8-hydroxyquinoline-7-carboxamide with 2,4,5-trifluorophenyl) | 2.50e-005 | CMV | 61.4 | |
| | | CMV | | 27.4 |
| | 1.56e-006 | CMV | 5.3 | |
| | 3.13e-006 | CMV | 8.3 | |
| | 6.25e-006 | CMV | 7.9 | |
| | 1.30e-005 | CMV | 13.4 | |
| | 2.50e-005 | CMV | 31.2 | |
| | 5.00e-005 | CMV | 98.4 | |
| Example 206 (8-hydroxyquinoline-7-carboxamide with 2-chlorophenyl) | 2.50e-005 | CMV | 94.6 | |
| | | CMV | | 9.4 |
| | 1.56e-006 | CMV | 26.5 | |
| | 3.13e-006 | CMV | 27.1 | |
| | 6.25e-006 | CMV | 32 | |
| | 1.30e-005 | CMV | 48.7 | |
| | 2.50e-005 | CMV | 92.7 | |
| | 5.00e-005 | CMV | 99.4 | |
| Example 207 (8-hydroxyquinoline-7-carboxamide with 2-chloro-4-bromophenyl) | 2.50e-005 | CMV | 22.4 | |
| Example 208 (8-hydroxyquinoline-7-carboxamide with 2,4-dichlorophenyl) | 2.50e-005 | CMV | 29.3 | |

TABLE 10-continued

| Example Number, Structure | CMV pol Assay | | | |
|---|---|---|---|---|
| | Conc (M) | pol type | % Inhib | IC50 uM |
| Example 209 | 2.50e-005 | CMV | 91.7 | |
| | | CMV | | 3.3 |
| | 1.56e-006 | CMV | 30.1 | |
| | 3.13e-006 | CMV | 50.5 | |
| | 6.25e-006 | CMV | 64.1 | |
| | 1.30e-005 | CMV | 80.2 | |
| | 2.50e-005 | CMV | 89.5 | |
| | 5.00e-005 | CMV | 95.7 | |
| Example 210 | 2.50e-005 | CMW | 46.9 | |
| | | CMV | | 6.9 |
| | 1.56e-006 | CMV | 18.1 | |
| | 3.13e-006 | CMV | 44.5 | |
| | 6.25e-006 | CMV | 69.7 | |
| | 1.30e-005 | CMV | 55 | |
| | 2.50e-005 | CMV | 49.7 | |
| | 5.00e-005 | CMV | 52.9 | |
| | | CMV | | 18.9 |
| | 1.56e-006 | CMV | 17.8 | |
| | 3.13e-006 | CMV | 29.4 | |
| | 6.25e-006 | CMV | 38.9 | |
| | 1.30e-005 | CMV | 50 | |
| | 2.50e-005 | CMV | 47.2 | |
| | 5.00e-005 | CMV | 56.5 | |
| Example 211 | 2.50e-005 | CMV | 96.6 | |
| | | CMV | | 7.5 |
| | 1.56e-006 | CMV | 22.4 | |
| | 3.13e-006 | CMV | 26.3 | |
| | 6.25e-006 | CMV | 33.1 | |
| | 1.30e-005 | CMV | 68.3 | |
| | 2.50e-005 | CMV | 99 | |
| | 5.00e-005 | CMV | 99.4 | |
| Example 212 | 2.50e-005 | CMV | 88.9 | |
| | | CMV | | 12.5 |
| | 1.56e-006 | CMV | 23.4 | |
| | 3.13e-006 | CMV | 24.4 | |
| | 6.25e-006 | CMV | 21.4 | |
| | 1.30e-005 | CMV | 46 | |
| | 2.50e-005 | CMV | 77.9 | |
| | 5.00e-005 | CMV | 98.3 | |
| Example 213 | 2.50e-005 | CMV | 78.7 | |
| | | CMV | | >100 |
| | 1.56e-006 | CMV | −1.3 | |
| | 3.13e-006 | CMV | 9.7 | |
| | 6.25e-006 | CMV | 3.3 | |
| | 1.30e-005 | CMV | 3.7 | |
| | 2.50e-005 | CMV | 1.2 | |
| | 5.00e-005 | CMV | −6.5 | |
| Example 214 | 2.50e-005 | CMV | 29.4 | |
| | | CMV | | 13.8 |
| | 1.56e-006 | CMV | 24.8 | |
| | 3.13e-006 | CMV | 33.6 | |
| | 6.25e-006 | CMV | 30.4 | |
| | 1.30e-005 | CMV | 35.6 | |
| | 2.50e-005 | CMV | 53.8 | |
| | 5.00e-005 | CMV | 78.4 | |

TABLE 10-continued

| | CMV pol Assay | | | |
|---|---|---|---|---|
| Example Number, Structure | Conc (M) | pol type | % Inhib | IC50 uM |
| Example 215 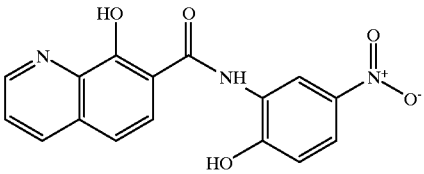 | 2.50e-005 | CMV | 91.5 | |
| Example 216 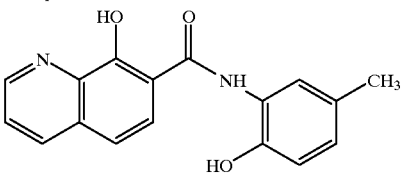 | 2.50e-005 | CMV | 37 | |
| Example 217 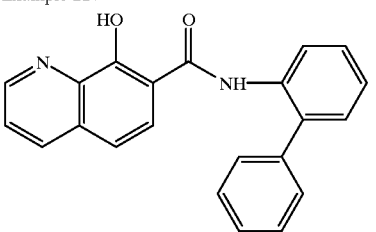 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 97.5<br><br>23.3<br>30.1<br>61.5<br>92.8<br>98.4<br>99.5 | 4.3 |
| Example 218 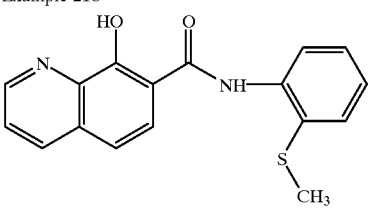 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 97.5<br><br>20.6<br>23.4<br>34.2<br>62.8<br>95.4<br>99.7 | 8.2 |
| Example 219 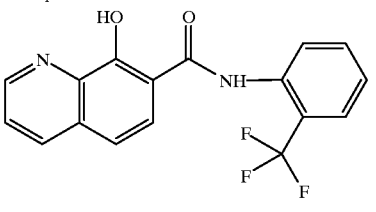 | 2.50e-005 | CMV | 24 | |
| Example 220 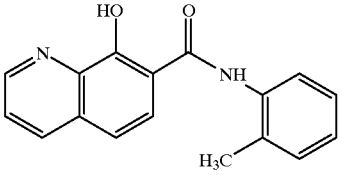 | 2.50e-005<br>1.56e-006<br>3.13e-006<br>6.25e-006<br>1.30e-005<br>2.50e-005<br>5.00e-005 | CMV<br>CMV<br>CMV<br>CMV<br>CMV<br>CMV<br>CMV<br>CMV | 83.8<br><br>17.7<br>20.3<br>21.9<br>37.8<br>84.5<br>98.7 | 13.4 |

TABLE 10-continued

| Example Number, Structure | CMV pol Assay | | | |
|---|---|---|---|---|
| | Conc (M) | pol type | % Inhib | IC50 uM |
| Example 221 | 2.50e-005 | CMV | 88 | |
| | | CMV | | 5.5 |
| | 1.56e-006 | CMV | 21.9 | |
| | 3.13e-006 | CMV | 30.4 | |
| | 6.25e-006 | CMV | 44.9 | |
| | 1.30e-005 | CMV | 85.5 | |
| | 2.50e-005 | CMV | 99.3 | |
| | 5.00e-005 | CMV | 99.3 | |
| Example 222 | 2.50e-005 | CMV | 96.9 | |
| | | CMV | | 8.6 |
| | 1.56e-006 | CMV | 28.8 | |
| | 3.13e-006 | CMV | 27.3 | |
| | 6.25e-006 | CMV | 31.9 | |
| | 1.30e-005 | CMV | 54.6 | |
| | 2.50e-005 | CMV | 94.7 | |
| | 5.00e-005 | CMV | 99.4 | |
| Example 166 | 2.50e-005 | CMV | 97.6 | |
| | | CMV | | 8.1 |
| | 1.56e-006 | CMV | 19 | |
| | 3.13e-006 | CMV | 20.7 | |
| | 6.25e-006 | CMV | 32.4 | |
| | 1.30e-005 | CMV | 67.9 | |
| | 2.50e-005 | CMV | 98.9 | |
| | 5.00e-005 | CMV | 99.8 | |
| Example 223 | 2.50e-005 | CMV | 82.2 | |
| Example 224 | 2.50e-005 | CMV | 97.5 | |
| | | CMV | | 7.3 |
| | 1.56e-006 | CMV | 11.6 | |
| | 3.13e-006 | CMV | 22.1 | |
| | 6.25e-006 | CMV | 37.7 | |
| | 1.30e-005 | CMV | 76.3 | |
| | 2.50e-005 | CMV | 98.4 | |
| | 5.00e-005 | CMV | 99.7 | |
| Example 165 | 2.50e-005 | CMV | 73.5 | |
| | | CMV | | 6.6 |
| | 1.56e-006 | CMV | 7.4 | |
| | 3.13e-006 | CMV | 23.7 | |
| | 6.25e-006 | CMV | 36.9 | |
| | 1.30e-005 | CMV | 89.6 | |
| | 2.50e-005 | CMV | 100.3 | |
| | 5.00e-005 | CMV | 100.7 | |

TABLE 10-continued

| Example Number, Structure | CMV pol Assay | | | |
|---|---|---|---|---|
| | Conc (M) | pol type | % Inhib | IC50 uM |
| Example 225 | 2.50e-005 | CMV | 69.2 | |
| | | CMV | | 18.4 |
| | 1.56e-006 | CMV | 12.2 | |
| | 3.13e-006 | CMV | 18.9 | |
| | 6.25e-006 | CMV | 28.5 | |
| | 1.30e-005 | CMV | 73.9 | |
| | 2.50e-005 | CMV | 96.5 | |
| | 5.00e-005 | CMV | 100 | |
| Example 167 | 2.50e-005 | CMV | 97 | |
| | | CMV | | 7 |
| | 1.56e-006 | CMV | 29.6 | |
| | 3.13e-006 | CMV | 31.2 | |
| | 6.25e-006 | CMV | 35.6 | |
| | 1.30e-005 | CMV | 64.3 | |
| | 2.50e-005 | CMV | 98.1 | |
| | 5.00e-005 | CMV | 99.6 | |
| Example 226 | 2.50e-005 | CMV | 94.2 | |
| | | CMV | | 10.2 |
| | 1.56e-006 | CMV | 22.7 | |
| | 3.13e-006 | CMV | 26.5 | |
| | 6.25e-006 | CMV | 31 | |
| | 1.30e-005 | CMV | 46.4 | |
| | 2.50e-005 | CMV | 88.6 | |
| | 5.00e-005 | CMV | 99.4 | |
| Example 227 | 2.50e-005 | CMV | 87 | |
| | | CMV | | 3.6 |
| | 3.13e-006 | CMV | 36.5 | |
| | 6.25e-006 | CMV | 64 | |
| | 1.30e-005 | CMV | 93.6 | |
| | 2.50e-005 | CMV | 99.3 | |
| | 5.00e-005 | CMV | 99.7 | |
| | 1.00e-004 | CMV | 99.6 | |
| Example 228 | 2.50e-005 | CMV | 49 | |
| | | CMV | | 7.9 |
| | 3.13e-006 | CMV | 24.4 | |
| | 6.25e-006 | CMV | 45 | |
| | 1.30e-005 | CMV | 60.8 | |
| | 2.50e-005 | CMV | 81.5 | |
| | 5.00e-005 | CMV | 92.1 | |
| | 1.00e-004 | CMV | 94 | |
| Example 229 | 2.50e-005 | CMV | 39 | |

TABLE 10-continued

| Example Number, Structure | CMV pol Assay | | | |
|---|---|---|---|---|
| | Conc (M) | pol type | % Inhib | IC50 uM |
| Example 230 | 2.50e-005 | CMV | 95 | |
| | | CMV | | 3.1 |
| | 3.13e-006 | CMV | 33.5 | |
| | 6.25e-006 | CMV | 77.7 | |
| | 1.30e-005 | CMV | 97.6 | |
| | 2.50e-005 | CMV | 99.8 | |
| | 5.00e-005 | CMV | 99.7 | |
| | 1.00e-004 | CMV | 100 | |
| Example 231 | 2.50e-005 | CMV | 24 | |
| Example 232 | 2.50e-005 | CMV | 67 | |
| | | CMV | | 6.9 |
| | 3.13e-006 | CMV | 27.4 | |
| | 6.25e-006 | CMV | 47.9 | |
| | 1.30e-005 | CMV | 66.5 | |
| | 2.50e-005 | CMV | 79.4 | |
| | 5.00e-005 | CMV | 85.9 | |
| | 1.00e-004 | CMV | 87.9 | |
| Example 233 | 2.50e-005 | CMV | 25 | |
| Example 234 | 2.50e-005 | CMV | 83 | |
| Example 168 | 2.50e-005 | CMV | 97 | |
| | | CMV | | 7 |
| | 3.13e-006 | CMV | 23.8 | |
| | 6.25e-006 | CMV | 40.8 | |
| | 1.30e-005 | CMV | 69.9 | |
| | 2.50e-005 | CMV | 95.6 | |
| | 5.00e-005 | CMV | 99.5 | |
| | 1.00e-004 | CMV | 99.7 | |

TABLE 10-continued
| Example Number, Structure | CMV pol Assay | | | |
|---|---|---|---|---|
| | Conc (M) | pol type | % Inhib | IC50 uM |
| Example 235 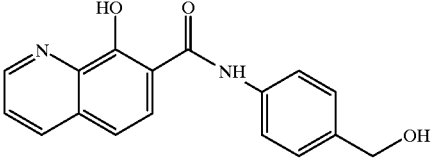 | 2.50e-005 | CMV | 96 | |
| | | CMV | | 3.7 |
| | 3.13e-006 | CMV | 38.2 | |
| | 6.25e-006 | CMV | 66 | |
| | 1.30e-005 | CMV | 86.1 | |
| | 2.50e-005 | CMV | 97.3 | |
| | 5.00e-005 | CMV | 99.3 | |
| | 1.00e-004 | CMV | 99.6 | |
| Example 236 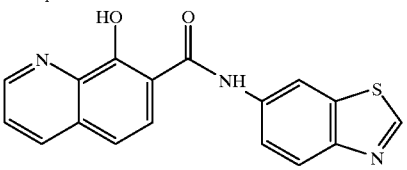 | 2.50e-005 | CMV | 35 | |
| Example 237 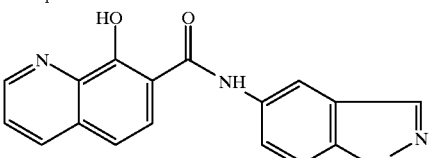 | 2.50e-005 | CMW | 84 | |
| | | CMV | | <3.1 |
| | 3.13e-006 | CMV | 70.9 | |
| | 6.25e-006 | CMV | 94.5 | |
| | 1.30e-005 | CMV | 99 | |
| | 2.50e-005 | CMV | 99.2 | |
| | 5.00e-005 | CMV | 99.1 | |
| | 1.00e-004 | CMV | 99.7 | |
| | | CMV | | 2.8 |
| | 3.13e-007 | CMV | 15.5 | |
| | 6.25e-007 | CMV | 19.5 | |
| | 1.25e-006 | CMV | 19.8 | |
| | 2.50e-006 | CMV | 37.9 | |
| | 5.00e-006 | CMV | 82.7 | |
| | 1.00e-005 | CMV | 99.5 | |
| Example 238 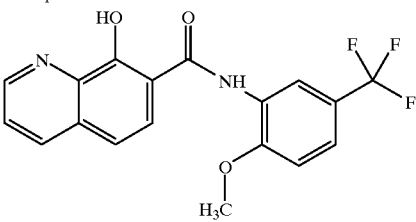 | 2.50e-005 | CMV | 29 | |
| Example 239 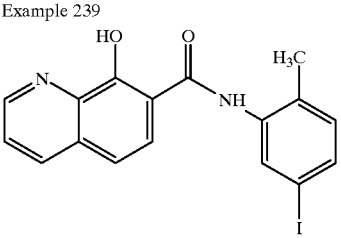 | 2.50e-005 | CMW | 94 | |
| | | CMV | | <3.1 |
| | 3.13e-006 | CMV | 89.6 | |
| | 6.25e-006 | CMV | 98.5 | |
| | 1.30e-005 | CMV | 99.6 | |
| | 2.50e-005 | CMV | 99.9 | |
| | 5.00e-005 | CMV | 99.4 | |
| | 1.00e-004 | CMV | 99.8 | |
| | | CMV | | 2 |
| | 3.13e-007 | CMV | 14.5 | |
| | 6.25e-007 | CMV | 19.7 | |
| | 1.25e-006 | CMV | 20.4 | |
| | 2.50e-006 | CMV | 62.8 | |
| | 5.00e-006 | CMV | 95.2 | |
| | 1.00e-005 | CMV | 98.4 | |

TABLE 10-continued

| Example Number, Structure | CMV pol Assay | | | |
|---|---|---|---|---|
| | Conc (M) | pol type | % Inhib | IC50 uM |
| Example 240 | 2.50e-005 | CMV | 23 | |
| Example 241 | 2.50e-005 | CMV | 43.2 | |
| | | CMV | | 21.6 |
| | 1.56e-006 | CMV | 18 | |
| | 3.13e-006 | CMV | 24.7 | |
| | 6.25e-006 | CMV | 28.6 | |
| | 1.30e-005 | CMV | 37.5 | |
| | 2.50e-005 | CMV | 54.9 | |
| | 5.00e-005 | CMV | 58.1 | |
| Example 242 | 2.50e-005 | CMV | 82.3 | |
| | | CMV | | 14.5 |
| | 1.56e-006 | CMV | 16.8 | |
| | 3.13e-006 | CMV | 14.1 | |
| | 6.25e-006 | CMV | 16.6 | |
| | 1.30e-005 | CMV | 43.6 | |
| | 2.50e-005 | CMV | 78.5 | |
| | 5.00e-005 | CMV | 96.3 | |

TABLE 11

| Example Number, Structure | CMV pol Assay IC50 uM |
|---|---|
| Example 243 | 71 |
| Example 244 | 93.2 |
| Example 245 | 2.4 |

TABLE 11-continued

| Example Number, Structure | CMV pol Assay IC50 uM |
|---|---|
| Example 246 | 2.5 |
| Example 247 | 14.3 |
| Example 248 | 3.1 |
| Example 249 | 15.4 |
| Example 250 | 9.4 |

TABLE 11-continued
| Example Number, Structure | CMV pol Assay IC50 uM |
|---|---|
| Example 251 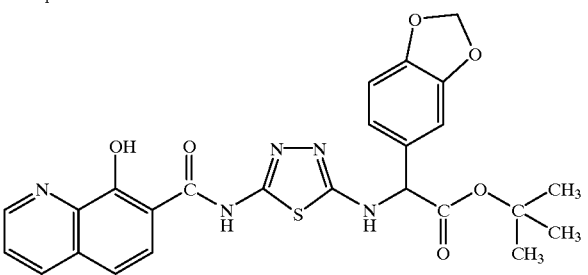 | 4.3 |
| Example 252 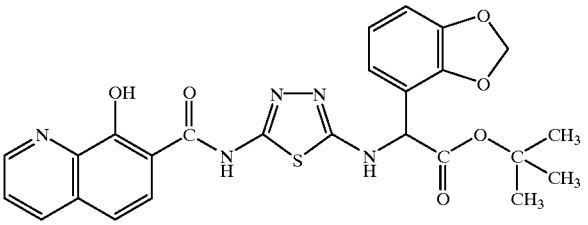 | 4.7 |
| Example 253 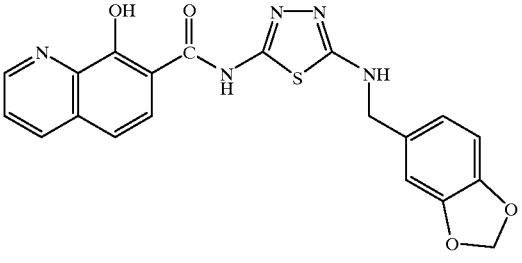 | 7.1 |
| Example 254 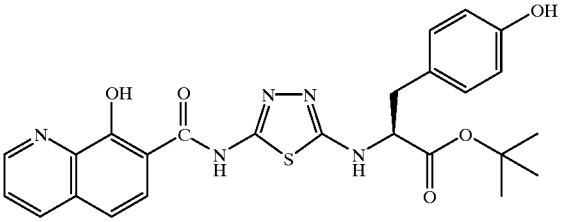 | <3.1 |

TABLE 11-continued
| Example Number, Structure | CMV pol Assay IC50 uM |
|---|---|
| Example 255 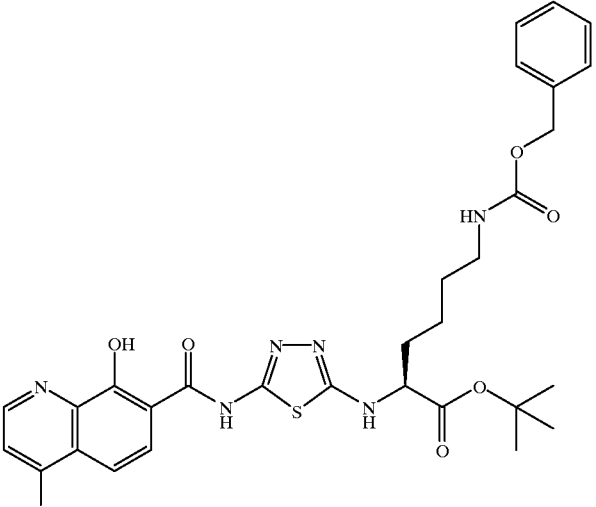 | <3.1 |
| Example 256 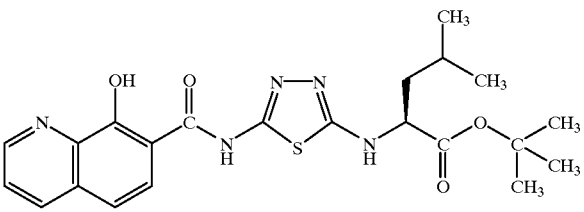 | 11.4 |
| Example 257 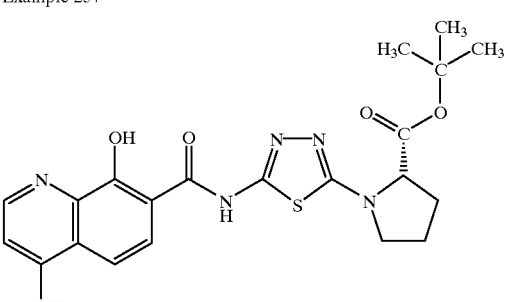 | 13.9 |
| Example 258 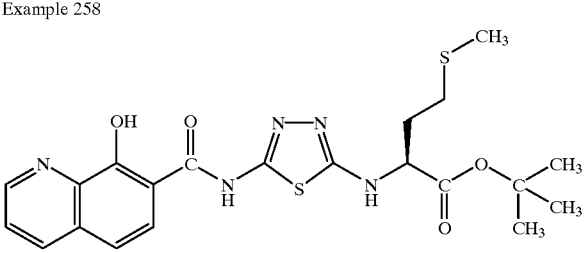 | 26.6 |

TABLE 11-continued

| Example Number, Structure | CMV pol Assay IC50 uM |
|---|---|
| Example 259 | <3.1 |
| Example 260 | 4.5 |
| Example 261 | 24.2 |
| Example 262 | 22.6 |

TABLE 11-continued

| Example Number, Structure | CMV pol Assay IC50 uM |
|---|---|
| Example 263 | 18.9 |
| Example 264 | 8.5 |

TABLE 12

| Example Number, Structure | CMV Antiviral Assay | | |
|---|---|---|---|
| | Conc (uM) | % Inh — AV | IC50 (AV) |
| Example 13 | 4.00e+001 | 33.0 | 25.5 |
| | 2.00e+001 | 50.0 | 25.5 |
| | 4.00e+000 | 34.0 | 25.5 |
| | 8.00e−001 | 28.0 | 25.5 |
| Example 36 | 4.00e+001 | 90.0 | 2.5 |
| | 2.00e+001 | 74.0 | 2.5 |
| | 4.00e+000 | 66.0 | 2.5 |
| | 8.00e−001 | 29.0 | 2.5 |
| | 2.00e+001 | 78.0 | 3.6 |
| | 8.00e+000 | 12.0 | 3.6 |
| | 4.00e+000 | 62.0 | 3.6 |
| | 1.00e+000 | 20.0 | 3.6 |
| Example 59 | 4.00e+001 | 94.0 | 14.4 |
| | 2.00e+001 | 69.0 | 14.4 |
| | 1.00e+001 | 8.0 | 14.4 |
| | 4.00e+000 | 1.0 | 14.4 |
| | 8.00e−001 | 4.0 | 14.4 |
| | 2.00e+001 | 78.0 | 9.4 |
| | 1.50e+001 | 60.0 | 9.4 |
| | 1.00e+001 | 45.0 | 9.4 |
| | 5.00e+000 | 36.0 | 9.4 |

TABLE 12-continued

| | CMV Antiviral Assay | | |
|---|---|---|---|
| Example Number, Structure | Conc (uM) | % Inh — AV | IC50 (AV) |
| Example 61 | 2.00e+001 | 93.0 | 3.5 |
| | 1.00e+001 | 97.0 | 3.5 |
| | 4.00e+000 | 54.0 | 3.5 |
| | 8.00e−001 | 0.0 | 3.5 |
| Example 62 | 2.00e+001 | 79.0 | 14.6 |
| | 1.00e+001 | 26.0 | 14.6 |
| | 4.00e+000 | 17.0 | 14.6 |
| | 8.00e−001 | 35.0 | 14.6 |
| Example 65 | | | |
| Example 153 | 8.00e+000 | 63.0 | 3.9 |
| | 4.00e+000 | 53.0 | 3.9 |
| | 2.00e+000 | 48.0 | 3.9 |
| | 1.00e+000 | 0.0 | 3.9 |

TABLE 13

| Structure and Name | MP (° C.) | Mass Spec | IC$_{50}$ ($\mu$M) |
|---|---|---|---|
| N-[(4-Chlorophenyl)methyl]-8-hydroxy-4-methyl-2-(trifluoromethyl)-7-quinolinecarboxamide | 55–58 | (EI) 394, M$^+$ | 35% inhibition @ 100 uM |

TABLE 13-continued

| Structure and Name | MP (° C.) | Mass Spec | IC$_{50}$ ($\mu$M) |
|---|---|---|---|
| 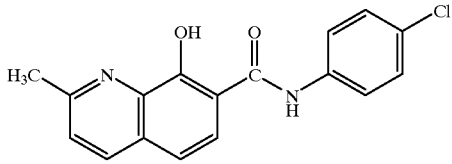 N-(4-Chlorophenyl)-8-hydroxy-2-methyl-7-quinolinecarboxamide | 163–165 | (EI) 312, M$^+$ | 7.6 |
| 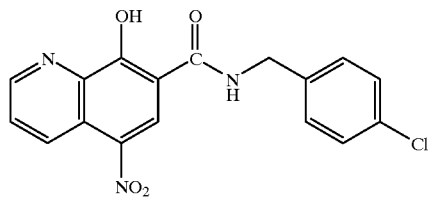 N-[(4-Chlorophenyl)methyl]-8-hydroxy-5-nitro-7-quinolinecarboxamide | 218–220 (dec) | (EI) 357, M$^+$ | 2.6 |
| 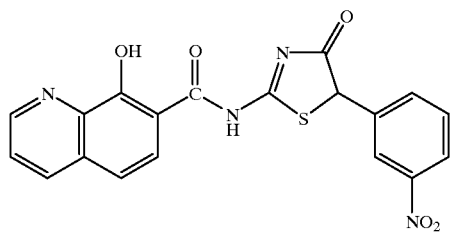 N-[4,5-dihydro-[5-(3-nitrophenyl)]-4-oxo-2-thiazolyl]-8-hydroxy-7-quinolinecarboxamide | 289–290 (dec) | (EI) 408, M$^+$ | 5.2 |
| 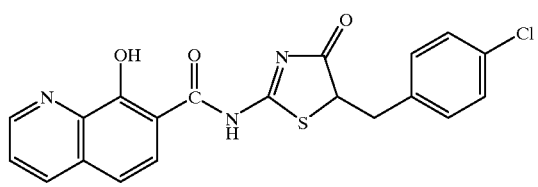 N-[5-[3-(4-Chlorophenyl)methyl]-4,5-dihydro-4-oxo-2-thiazolyl]-8-hydroxy-7-quinolinecarboxamide | 249–250 (dec) | (EI) 411, M$^+$ | 1.7 |
| 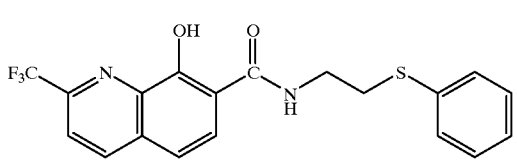 8-Hydroxy-N-[2-(phenylthio)ethyl]-2-(trifluoromethyl)-7-quinolinecarboxamide | 127–129 | (ESI) 393, M + H | 41.6 |

TABLE 13-continued

| Structure and Name | MP (° C.) | Mass Spec | IC$_{50}$ ($\mu$M) |
|---|---|---|---|
| 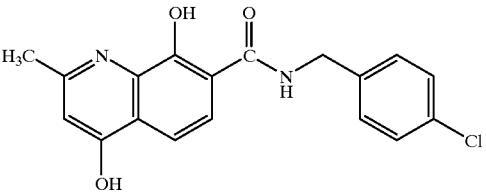<br>N-[(4-Chlorophenyl)methyl]-4,8-dihydroxy-2-methyl-7-quinolinecarboxamide | 274–276 | (EI) 342, M$^+$ | 102 |
| 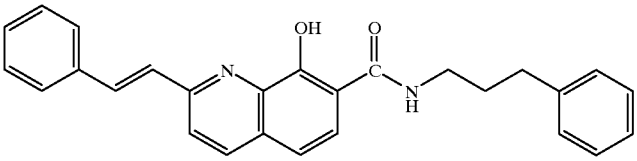<br>(E)-8-Hydroxy-2-(2-phenylethenyl)-N-(3-phenylpropyl)-7-quinolinecarboxamide | 110–111 | (ESI) 393, M + H | 5.1 |

TABLE 14

| Structure and Name | Mass Spec | IC50 ($\mu$M) |
|---|---|---|
| 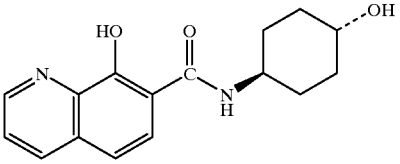<br>8-Hydroxy-quinoline-7-carboxylic acid trans-4-hydroxy-cyclohexylamide | ESI -MS:<br>M + H = 287<br>ESI-MS:<br>M − H = 285 | 21 % inhibition at 25 uM |
| 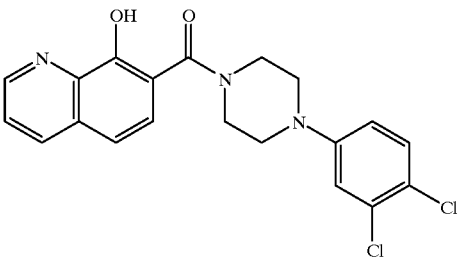<br>[4-(3,4-Dichlorophenyl)-piperazin-yl]-(8-hydroxy-quinolin-7-yl)-methanone | ESI -MS:<br>M + H = 402<br>ESI-MS:<br>M − H = 400 | 14 |
| 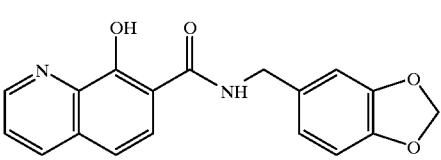<br>8-Hydroxy-quinoline-7-carboxylic acid bezo[1,3]dioxol-5-ylmethylamide | ESI -MS:<br>M + H = 323<br>ESI-MS:<br>M − H = 321 | 26 |

TABLE 14-continued

| Structure and Name | Mass Spec | IC50 (μM) |
|---|---|---|
| 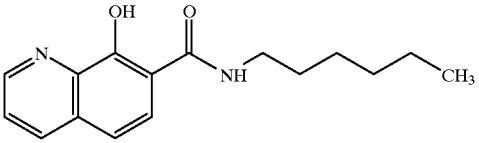<br>N-Hexyl-8-hydroxy-7-quinolinecarboxamide | ESI -MS:<br>M + H = 273<br>ESI-MS:<br>M − H = 271 | 27 |
| 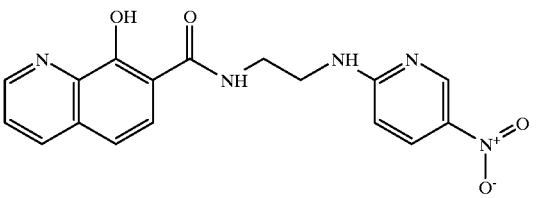<br>8-Hydroxy-quinoline-7-carboxylic acid 2-(5-nitro-pyridin-2-ylamino)-ethylamide | ESI -MS:<br>M + H = 354<br>ESI-MS:<br>M − H = 352 | 42 |
| 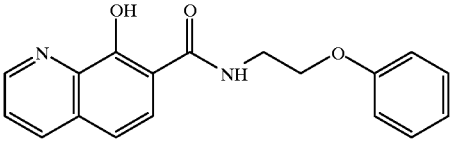<br>8-Hydroxy-N-[2-(phenyloxy)ethyl]-7-quinolinecarboxamide | ESI -MS:<br>M + H = 309<br>ESI-MS:<br>M − H = 307 | 29 |
| 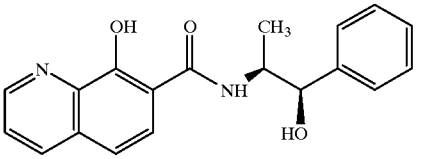<br>8-Hydroxy-quinoline-7-carboxylic acid 2-(R)-hydroxy-1-(S)-methyl-2-phenyl-ethylamide | ESI -MS:<br>M + H = 323<br>ESI-MS:<br>M − H = 321 | 41 |
| 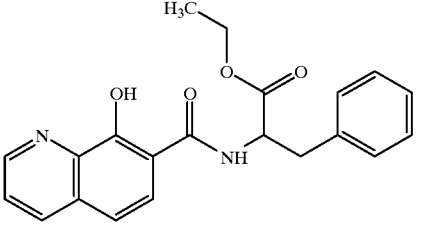<br>(S)-2-[(8-Hydroxy-quinoline-7-carbonyl)-amino]-3-phenyl-propionic acid ethyl ester | ESI -MS:<br>M + H = 365<br>ESI-MS:<br>M − H = 363 | 41 |
| 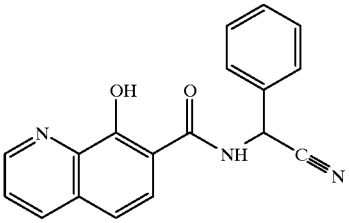<br>8-Hydroxy-quinoline-7- | ESI -MS:<br>M + H = 304<br>ESI-MS:<br>M − H = 302 | 54 |

TABLE 14-continued

| Structure and Name | Mass Spec | IC50 (μM) |
|---|---|---|
| carboxylic acid cyano-phenylylamide | | |
| (S)-2-[(8-Hydroxy-quinoline-7-carbonyl)-amino]-4-methyl-penatnoic acid tert-butyl | ESI -MS:<br>M + H = 359<br>ESI-MS:<br>M − H = 357 | 51 |
| (S,S)-8-Hydroxy-quinoline-7-carboxylic acid 2-hydroxy-1-(hydroxy-phenyl-methyl)-ethylamide | ESI -MS:<br>M + H = 339<br>ESI-MS:<br>M − H = 337 | 14 |
| (S,S)-8-Hydroxy-quinoline-7-carboxylic acid 1-hydroxymethyl-2-methyl-butylamide | ESI -MS:<br>M + H = 289<br>ESI-MS:<br>M − H = 287 | 26 |
| (S)-8-Hydroxy-quinoline-7-carboxylic acid 1-benzyl-2-hydroxy-ethylamide | ESI -MS:<br>M + H = 323<br>ESI-MS:<br>M − H = 321 | 93% inhibition at 25 uM |
| | ESI -MS:<br>M + H = 285<br>ESI-MS:<br>M − H = 283 | 34 |

TABLE 14-continued

| Structure and Name | Mass Spec | IC50 (μM) |
|---|---|---|
| 8-Hydroxy-quinoline-7-carboxylic acid thiophen-2-ylmethylamide | | |
| 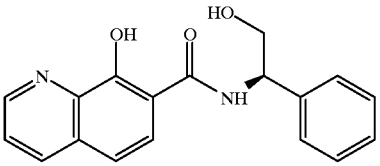<br>(R)-8-Hydroxy-quinoline-7-carboxylic acid 2-hydroxy-1-phenyl-ethylamide | ESI -MS:<br>M + H = 309<br>ESI-MS:<br>M − H = 307 | 19 |
| 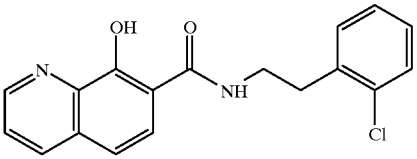<br>N-[2-(2-chlorophenyl)ethyl]-8-hydroxy-7-quinolinecarboxamide | ESI -MS:<br>M + H = 327<br>ESI-MS:<br>M − H = 325 | 26 |
| 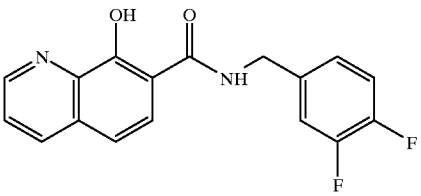<br>N-[3,4-Difluorophenyl)methyl]-8-hydroxy-7-quinolinecarboxamide | ESI -MS:<br>M + H = 315<br>ESI-MS:<br>M − H = 313 | 42 |
| 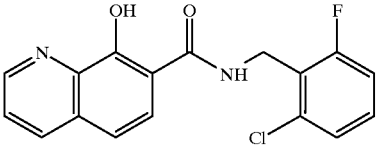<br>N-[(2-Chloro-6-fluoro-phenyl)methyl]-8-hydroxy-7-quinolinecarboxamide | ESI -MS:<br>M + H = 331<br>ESI-MS:<br>M − H = 329 | 30 |
| 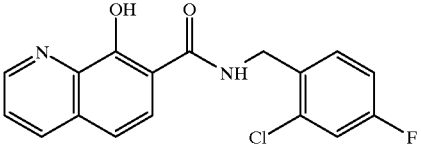<br>N-[(2-Chloro-4-fluoro-phenyl)methyl]-8-hydroxy-7-quinolinecarboxamide | ESI -MS:<br>M + H = 331<br>ESI-MS:<br>M − H = 329 | 28 |

TABLE 14-continued

| Structure and Name | Mass Spec | IC50 (μM) |
|---|---|---|
| 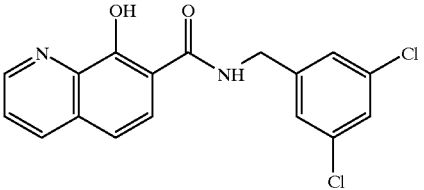<br>N-[(3,5-Dichloro-phenyl)methyl]-8-hydroxy-7-quinolinecarboxamide | ESI -MS:<br>M + H = 347<br>ESI-MS:<br>M − H = 345 | 27 |
| 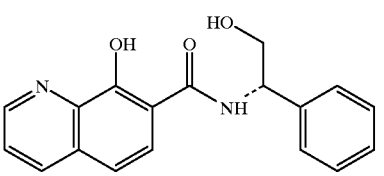<br>(S)-8-Hydroxy-quinoline-7-carboxylic acid 2-hydroxy-1-phenyl-ethylamide | ESI -MS:<br>M + H = 309<br>ESI-MS:<br>M − H = 307 | 39% inhibition at 25 uM |
| 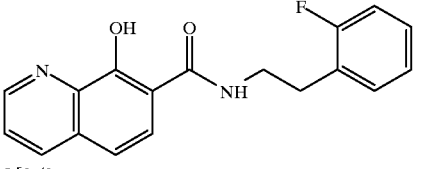<br>N-[2-(2-fluorophenyl)ethyl]-8-hydroxy-7-quinolinecarboxamide | ESI -MS:<br>M + H = 311<br>ESI-MS:<br>M − H = 309 | 39% inhibition at 25 uM |
| 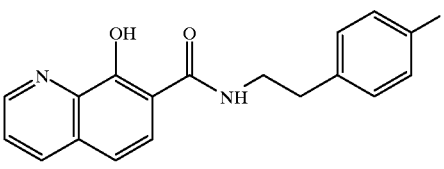<br>N-[2-(4-fluorophenyl)ethyl]-8-hydroxy-7-quinolinecarboxamide | ESI -MS:<br>M + H = 311<br>ESI-MS:<br>M − H = 309 | 42% inhibition at 25 uM |
| 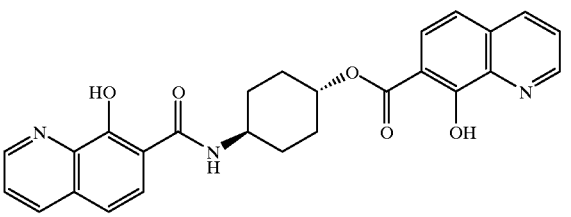<br>trans-8-Hydroxy-quinoline-7-carboxylic acid 4-[(8-hydroxy-quinoline-7-carbonyl)-amino]-cyclohexyl ester | ESI -MS:<br>M + H = 458<br>ESI-MS:<br>M − H = 456 | 4 |

What is claimed is:
1. A compound of formula IA

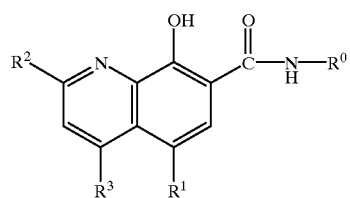

wherein $R^0$ is
a) —$(CH_2)_n$-phenyl substituted with Cl, Br, —O-phenyl, $CF_3$, or —S-phenyl substituted with ethoxy; provided that when $R^0$ is a), $R_1$ is H, F, Cl, or Br; $R_2$ is H, —CH=CH-furanyl, or —CH=CH-phenyl, optionally substituted with methoxy, and $R_3$ is H;
b) —$(CH_2)_n$-phenyl substituted with two Cl atoms or two F atoms provided that the F atom is at 2-, or 6-position of the phenyl ring;
c) —$(CH_2)_n$-indolyl,
d) —$(CH_2)_n$-benzothiazolyl,
e) —$(CH_2)_n$-naphthyl,
f) —$(CH_2)_n$-biphenyl,
g) —$(CH_2)_n$-tetrahydro-naphthyl,
h) —$(CH_2)_n$-fluorenyl;
i) —$(CH_2)_n$-Y,
j) —$(CH_2)_p W^1 X^2$,
k) —$(CH_2)_p W^1 CH_2 X^1$, or
l) —$(CH_2)_n$—$CHR^9$—$(CH_2)_n$—$X^1$,
wherein $R^1$ is
a) —H,
b) —F,
c) —Cl,
d) —Br,
e) —$CF_3$, or
f) —$NO_2$;
wherein $R^2$ is
a) —H,
b) —$C_1$-$C_3$alkyl,
c) —OH,
d) —$CF_3$,
e) —CH=CH-furanyl,
f) —CH=CH-phenyl substituted by zero (0) or one (1) $R^4$,
g) —CH=CH-pyridinyl,
h) —$(CH_2)_p$-phenyl substituted by zero (0) or one (1) $R^4$,
i) —$NHV^1$,
j) —$CH_2NHV^1$, or
k) —$CH_2Z^1$;
wherein $R^3$ is
a) —H,
b) —OH,
c) —$CF_3$, or
d) —$C_1$-$C_3$alkyl;
wherein $R^4$ is
a) —H
b) —F,
c) —Cl,
d) —Br,
e) —$NO_2$,
f) —$CF_3$,
g) —$W^1$—$R^{10}$,
h) —$C_1$-$C_6$ alkyl,
i) —$C_3$-$C_8$ cycloalkyl,
j) —$(CH_2)_n$-aryl,
k) —$CH_2$—$C_3$-$C_8$ cycloalkyl,
l) —$SO_2NH$-indazoyl
m) —CN,
n) —I, or
o) —$CH_2$—OH;
wherein $R^8$ is
a) —$C_1$-$C_4$ alkyl,
b) —$W^1$—H, or
c) —$CH_2W^1H$;
wherein $R^9$ is
a) —$C_1$-$C_7$ alkyl,
b) —$C_3$-$C_8$ cycloalkyl,
c) —$C(O)R^{11}$,
d) —$C(O)NHR^{11}$,
e) —$CH(OH)R^{11}$,
f) —$CH_2OH$,
g) —$CO_2R^{11}$, or
h) -aryl;
wherein $R^{10}$ is
a) —H,
b) —$C_1$-$C_6$ alkyl,
c) —$C_3$-$C_8$ cycloalkyl,
d) —$(CH_2)_n$-aryl optionally substituted with F, Cl, $CH_2OH$ or —$NO_2$,
e) —$CH_2$—$C_3$-$C_8$ cycloalkyl,
wherein $R^{11}$ is
a) —$C_1$-$C_7$ alkyl,
b) —$C_3$-$C_8$ cycloalkyl,
c) —$(CH_2)_nX^1$, or
d) —$CH_2$—$C_3$-$C_8$ cycloalkyl;
wherein Y is
a) —CH(OH)-phenyl,
b) —S-phenyl,
c) —$NHSO_2$-phenyl substituted by one (1), two (2) or three (3) $R^4$,
d) —CN,
e) —$C_3$-$C_8$ cycloalkyl substituted by ethoxy, t-butyl or two (2) $R^8$, or
f) -4-cyano-2,3,5,6-tetrafluoro-phenyl;
wherein $X^1$ is
a) -aryl substituted by zero (0), one (1), two (2), or three (3) $R^4$,
b) -het substituted by zero (0), one (1) or two (2) $R^5$,
c) —$C_7$-$C_8$ alkyl, provided that when $X^1$ is alkyl, $R^9$ is not alkyl;
d) —CH(OH)-phenyl,
e) —S-phenyl,
f) —$NHSO_2$-phenyl substituted by one (1), two (2) or three (3) $R^4$,
g) —CN,
h) —$C_3$-$C_8$ cycloalkyl substituted by ethoxy, t-butyl or two (2) $R^8$, or
i) -4-cyano-2,3,5,6-tetrafluorophenyl;

wherein $X^2$ is
  a) -aryl substituted by zero (0), one (1), two (2) or three (3) $R^4$,
  b) —$C_1$–$C_8$ alkyl,
  c) —CH(OH)-phenyl, or
  d) —$C_3$–$C_8$ cycloalkyl substituted by zero (0), one (1) or two (2) $R^8$;
wherein $W^1$ is
  a) oxygen, provided that when $X^1$ or $X^2$ is phenyl, $W^1$ is not oxygen,
  b) —NH, or
  b) -sulfur,
wherein $V^1$ is
  a) —$R_{11}$,
  b) —C(O)$R^{11}$,
  c) —SO$_2$$R^{11}$, or
  d) —C(O)NH$R^{11}$;
wherein $Z^1$ is
  a) —$C_1$–$C_7$ alkyl,
  b) —$C_3$–$C_8$ cycloalkyl,
  c) —C(O)$R^{11}$,
  d) —C(O)NH$R^{11}$, or
  e) —CO$_2$$R^{11}$;
wherein -aryl is
  a) -phenyl,
  b) -naphthyl,
  c) -biphenyl,
  d) -tetrahydro-naphthyl, or
  e) fluorenyl;
wherein -het is a 5-membered saturated or unsaturated ring having from one (1) to three (3) heteroatoms selected from the group consisting of nitrogen, oxygen and sulfur,
wherein -cycloalkyl is a saturated or unsaturated hydrocarbon ring, optionally fused to a benzene ring;
n is zero (0) to six (6), inclusive, provided that where $R^0$ is a)–h), n is at least one; and p is one (1), two (2) or three (3); or a pharmaceutically acceptable salt or N-oxide thereof.

2. A compound of formula IA as shown in claim 1 which is

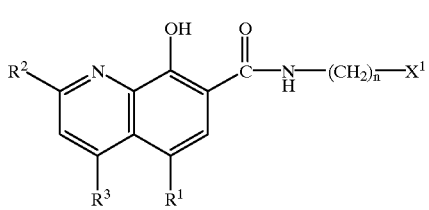

wherein $R^1$ is
  a) —H,
  b) —F,
  c) —Cl,
  d) —Br,
  e) —CF$_3$, or
  f) —NO$_2$;
wherein $R^2$ is
  a) —H,
  b) —$C_1$–$C_3$alkyl,
  c) —OH,
  d) —CF$_3$,
  e) —CH=CH-furanyl,
  f) —CH=CH-phenyl substituted by zero (0) or one (1) $R^4$,
  g) —CH=CH-pyridinyl, or
  h) —(CH$_2$)$_p$-phenyl substituted by zero (0) or one (1) $R^4$;
wherein $R^3$ is
  a) —H,
  b) —OH,
  c) —CF$_3$, or
  d) —$C_1$–$C_3$alkyl;
wherein $X^1$ is
  a) phenyl substituted with Cl, Br, —O-phenyl, CF$_3$, or —S-phenyl substituted with ethoxy; provided that when $X^1$ is a), $R_1$ is H, F, Cl, or Br; $R_2$ is H, —CH=CH-furanyl, or —CH=C-phenyl, optionally substituted with methoxy, and $R_3$ is H;
  b) phenyl substituted with two Cl atoms or two F atoms provided that the F atom is at 2-, or 6-position of the phenyl ring;
  c) indoyl,
  d) benzothiazolyl,
  e) —$C_7$–$C_{12}$ alkyl,
  f) —CH(OH)-phenyl,
  g) —S-phenyl,
  h) -naphthyl,
  i) —NHSO$_2$-phenyl substituted by one (1) $R^4$, or
  j) —CN;
wherein $R^4$ is
  a) —H
  b) —F,
  c) —Cl,
  d) —Br,
  e) —NO$_2$,
  f) —OCH$_3$,
  g) —CF$_3$, or
  h) —$C_1$–$C_4$ alkyl;
n is zero (0) to three (3) inclusive, provided that where $X^1$ is a)–d), n is at least one; and p is one (1), two (2) or three (3);
or a pharmaceutically acceptable salt or a N-oxide thereof.

3. A compound of formula IA as shown in claim 1 which is

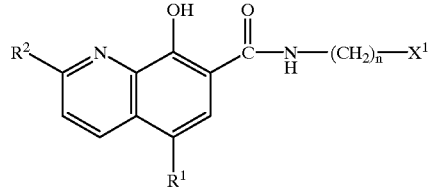

wherein $R^1$ is
  a) —H,
  b) —Cl,
  c) —Br, or
  d) —NO$_2$;
wherein $R^2$ is
  a) —H,
  b) —CH$_3$,
  c) —CF$_3$, d) —(CH$_2$)$_p$-phenyl substituted by zero (0) or one (1) R$^4$, e) —CH═CH-furanyl, or f) —CH═CH-phenyl substituted by zero (0) or one (1) R$^4$;

wherein X$^1$ is a) phenyl substituted with Cl, Br, —O-phenyl, or CF$_3$, provided that when X$^1$ is a), R$_1$ is H, Cl, or Br; R$_2$ is H, —CH═CH-furanyl, or —CH═CH-phenyl, optionally substituted with methoxy, and R$_3$ is H;

b) phenyl substituted with two Cl atoms or two F atoms provided that the F atom is at 2-, or 6-position of the phenyl ring;

c) indoyl, d) benzothiazolyl, e) —CH(OH)-phenyl, f) —S-phenyl, g) -naphthyl, h) —NHSO$_2$-phenyl substituted by one (1), two (2) or three (3) R$^4$, or i) —CN;

wherein R$^4$ is a) —H, b) —Cl, c) —Br, or d) —NO$_2$;

n is zero (0) to six (3) inclusive, provided that where X$^1$ is a)–d), n is at least one; and p is one (1), two (2) or three (3).

4. A compound of claim 1 which is:

1) 5-Bromo-N-[(4-chloropbenyl)methyl]-8-hydroxy-7-quinolinecarboxamide;
2) 5-Chloro-N-[(4-chlorophenyl)methyl]-8-hydroxy-7-quinolinecarboxamide;
3) 5-Fluoro-N-[[4-chlorophenyl]methyl]-8-hydroxy-7-quinolinecarboxamide;
4) N-[(4-Chlorophenyl)methyl]-8-hydroxy-2-(2-phenylethenyl)-7-quinolinecarboxamide;
5) 8-Hydroxy-2-(2-phenylethenyl)-N-[2-(phenylthio)ethyl]-7-quinolinecarboxamide;
6) 8-Hydroxy-2-[2-(4-methoxyphenyl)ethenyl]-N-[2-(phenylthio)ethyl]-7-quinolinecarboxamide;
7) N-[(4-Chlorophenyl)methyl]-2-[2-(2-furyl)ethenyl]-8-hydroxy-7-quinolinecarboxamide;
8) 5-chloro-8-hydroxy-2-methyl-N-[(2-phenylthio)ethyl]-7-quinolinecarboxamide;
9) 8-hydroxy-N-[5-[4-[(1-methylethyl)phenylsulfonyl]amino]pentyl]-7-quinolinecarboxamide;
10) 8-Hydroxy-N-[2-(3-indolyl)ethyl]-7-quinolinecarboxamide;
11) N-[2-(2,4-Dichlorophenyl)ethyl]-8-hydroxy-7-quinolinecarboxamide;
12) N-[(2-Chlorophenyl)methyl]-8-hydroxy-7-quinolinecarboxamide;
13) 8-Hydroxy-N-[(3-methylphenyl)methyl]-7-quinolinecarboxamide;
14) N-[(4-Chlorophenyl)methyl]-8-hydroxy-7-quinolinecarboxamide;
15) N-(2,2-Diphenylethyl)-8-hydroxy-7-quinolinecarboxamide;
16) N-[2-(4-Bromophenyl)ethyl]-8-hydroxy-7-quinolinecarboxamide;
17) N-[2-(4-Chlorophenyl)ethyl]-8-hydroxy-7-quinolinecarboxamide;
18) N-(3,3-Diphenylpropyl)-8-hydroxy-7-quinolinecarboxamide;
19) N-[(2,6-Difluorophenyl)methyl]-8-hydroxy-7-quinolinecarboxamide;
20) N-[(3-Chlorophenyl)methyl]-8-hydroxy-7-quinolinecarboxamide;
21) N-(2,3-Dimethylcyclohexyl)-8-hydroxy-7-quinolinecarboxamide;
22) 8-Hydroxy-N-[(1,2,3,4-tetrahydro-1-naphthalenyl)methyl]-7-quinolinecarboxamide;
23) N-(4-tert-Butylcyclohexyl)-8-hydroxy-7-quinolinecarboxamide;
24) R-8-Hydroxy-N-[1-(1-naphthyl)ethyl]-7-quinolinecarboxamide;
25) N-[2-((1S,2R)-1,2-Diphenyl-1-hydroxy)ethyl]-8-hydroxy-7-quinolinecarboxamide;
26) N-[2-((1R,2S)-1,2-Diphenyl-1-hydroxy)ethyl]-8-hydroxy-7-quinolinecarboxamide;
27) 8-Hydroxy-N-[1-(1-hydroxyethyl)cyclopentyl]-7-quinolinecarboxamide;
28) N-[(2,3-Dichlorophenyl)methyl]-8-hydroxy-7-quinolinecarboxamide;
29) N-[(2,5-Dichlorophenyl)methyl]-8-hydroxy-7-quinolinecarboxamide;
30) N-[2-([(2,6-Dichlorophenyl)methyl]thio)ethyl]-8-hydroxy-7-quinolinecarboxamide;
31) 8-Hydroxy-N-(2-[(4-[2-trifluoromethyl]quinolyl)thio]ethyl)-7-quinolinecarboxamide;
32) 8-Hydroxy-N-(1-naphthalenylmethyl)-7-quinolinecarboxamide;
33) N-[2-(3-Chlorophenyl)ethyl]-8-hydroxy-7-quinolinecarboxamide; or
34) 8-Hydroxy-N-[2-(phenylthio)ethyl]-7-quinolinecarboxamide.

5. A compound of claim 1 which is:

1) N-[(4-Chlorophenyl)methyl]-8-hydroxy-7-quinolinecarboxamide;
2) 5-Bromo-N-[(4-chlorophenyl)methyl]-8-hydroxy-7-quinolinecarboxamide;
3) N-[(4-Chlorophenyl)methyl]-8-hydroxy-2-methyl-7-quinolinecarboxamide;
4) 5-Chloro-N-[(4-chlorophenyl)methyl]-8-hydroxy-7-quinolinecarboxamide;
5) 8-Hydroxy-N-[(4-nitrophenyl)methyl]-7-quinolinecarboxamide;
6) N-[(4-Chlorophenyl)methyl]-8-hydroxy-2-[2-(4-methoxyphenyl)ethenyl]-7-quinolinecarboxamide;
7) 8-Hydroxy-N-(2-hydroxy-2-phenylethyl)-2-(2-phenylethenyl)-7-quinolinecarboxamide;
8) N-[(4-Chlorophenyl)methyl]-8-hydroxy-2-(2-phenylethenyl)-7-quinolinecarboxamide;
9) 8-Hydroxy-2-(2-phenylethenyl)-N-[2-(phenylthio)ethyl]-7-quinolinecarboxamide;
10) 8-Hydroxy-N-(2-hydroxy-2-phenylethyl)-2-[2-(4-methoxyphenyl)ethenyl]-7-quinolinecarboxamide;
11) 8-Hydroxy-2-[2-(4-methoxyphenyl)ethenyl]-N-[2-(phenylthio)ethyl]-7-quinolinecarboxamide;
12) N-[(4-Chlorophenyl)methyl]-8-hydroxy-2-(trifluoromethyl)-7-quinolinecarboxamide;

13) N[(4-Chlorophenyl)methyl]-2-[2-(2-furyl)ethenyl]-8-hydroxy-7-quinolinecarboxamide;
14) N-[(4-Chlorophenyl)methyl]-8-hydroxy-7-quinoline-N-oxide carboxamide;
15) 5-chloro-8-hydroxy-2-methyl-N-(3-phenylpropyl)-7-quinolinecarboxamide;
16) 5-chloro-8-hydroxy-2-methyl-N-[(2-phenylthio)ethyl]-7-quinolinecarboxamide;
17) 8-hydroxy-N-[5-[4-[(1-methylethyl)phenylsulfonyl]amino]pentyl]-7-quinolinecarboxamide;
18) 8-hydroxy-N-(2-hydroxy-2-phenylethyl)-2-[2-(4-methoxyphenyl)ethyl]-7-quinolinecarboxamide;
19) N-[2-(3-Chlorophenyl)ethyl]-8-hydroxy-7-quinolinecarboxamide;
20) 8-Hydroxy-N-[2-(3-indolyl)ethyl]-7-quinolinecarboxamide;
21) N-[(2,4-Dichlorophenyl)methyl]-8-hydroxy-7-quinolinecarboxamide;
22) N-[(3,4-Dichlorophenyl)methyl]-8-hydroxy-7-quinolinecarboxamide;
24) 8-Hydroxy-N-(4-phenylbutyl)-7-quinolinecarboxamide;
25) N-[2-(2,4-Dichlorophenyl)ethyl]-8-hydroxy-7-quinolinecarboxamide;
26) N-[(2-Chlorophenyl)methyl]-8-hydroxy-7-quinolinecarboxamide;
27) 8-Hydroxy-N-(2-hydroxy-2-phenylethyl)-7-quinolinecarboxamide;
28) N-[2-(4-Bromophenyl)ethyl]-8-hydroxy-7-quinolinecarboxamide;
29) N-[2-(4-Chlorophenyl)ethyl]-8-hydroxy-7-quinolinecarboxamide;
30) 8-Hydroxy-N-[2-(4-methylphenyl)ethyl]-7-quinolinecarboxamide;
31) N-[(3-Chlorophenyl)methyl]-8-hydroxy-7-quinolinecarboxamide;
32) N-(2,3-Dimethylcyclohexyl)-8-hydroxy-7-quinolinecarboxamide;
33) 8-Hydroxy-N-[(1,2,3,4-tetrahydro-1-naphthalenyl)methyl]-7-quinolinecarboxamide;
34) N-(4-tert-Butylcyclohexyl)-8-hydroxy-7-quinolinecarboxamide;
35) N-[(2,3-Dichlorophenyl)methyl]-8-hydroxy-7-quinolinecarboxamide;
36) N-[(2,5-Dichlorophenyl)methyl]-8-hydroxy-7-quinolinecarboxamide;
37) N-[2-([(2,6-Dichlorophenyl)methyl]thio)ethyl]-8-hydroxy-7-quinolinecarboxamide;
38) 8-Hydroxy-N-(1-naphthalenylmethyl)-7-quinolinecarboxamide;
39) N-[2-(3-Chlorophenyl)ethyl]-8-hydroxy-7-quinolinecarboxamide; or
40) 8-Hydroxy-N-[2-(phenylthio)ethyl]-7-quinolinecarboxamide.

6. A compound of formula V

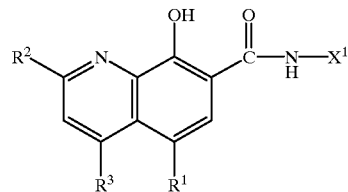

wherein $R_1$, $R_2$, and $R_3$ are independently hydrogen;

$X^1$ is
a) phenyl substituted by one Cl, I, —CH$_2$OH, ethyl, propyl, ethoxy, —O-benzyl, —O-phenyl, —SO$_2$NH-indazoyl, or NO$_2$;
b) 2-methylphenyl,
c) 2-bromophenyl,
d) phenyl substituted by two substituents wherein one substituent is (Cl, Br, I, methyl or NO$_2$, the other substituent is F, Cl, methyl, NO$_2$, or methoxy;
e) phenyl substituted by Cl, methyl, and methoxy,
f) naphthyl substituted by F, Br, Cl, or OH;
g) fluorenyl
h) het, or
i) 4-cyano-2,3,5,6-tetrafluorophenyl;

and het is
a) coumarinyl,
b) indazoyl,
c) indolyl,
d) benzothiazolyl,
e) benzothiadiazolyl, or
f) quinolinyl.

7. A compound of claim 6 which is
1) N-(3-Chlorophenyl)-8-hydroxy-7-quinolinecarboxamide;
2) 8-hydroxy-N-(4-nitrophenyl)-7-quinolinecarboxamide;
3) N-(5-Fluoro-2-methylphenyl)-8-hydroxy-7-quinolinecarboxamide;
4) N-(2,4-Dimethylphenyl)-8-hydroxy-7-quinolinecarboxamide;
5) 8-Hydroxy-N-(3-methylphenyl)-7-quinolinecarboxamide;
6) N-(2-Chloro-5-methoxyphenyl)-8-hydroxy-7-quinolinecarboxamide;
7) N-(3,4-Dichlorophenyl)-8-hydroxy-7-quinolinecarboxamide;
8) N-(3,5-Dichlorophenyl)-8-hydroxy-7-quinolinecarboxamide;
9) 8-Hydroxy-N-(3-benzyloxyphenyl)-7-quinolinecarboxamide;
10) N-(3,5-Dimethylphenyl)-8-hydroxy-7-quinolinecarboxamide;
11) 8-hydroxy-N-(4-phenoxyphenyl)-7-quinolinecarboxamide;
12) 8-Hydroxy-N-(4-benzoxyphenyl)-7-quinolinecarboxamide;

13) 8-Hydroxy-N-indol-5-yl-7-quinolinecarboxamide;
14) N-Benzo-2,1,3-thiadiazol-4-yl-8-hydroxy-7-quinolinecarboxamide;
15) 8-Hydroxy-N-quinolin-5-yl-7-quinolinecarboxamide;
16) 8-Hydroxy-N-quinolin-8-yl-7-quinolinecarboxamide;
17) 8-Hydroxy-N-isoquinolin-5-yl-7-quinolinecarboxamide;
18) 8-Hydroxy-N-(4-methoxy-2-nitrophenyl)-7-quinolinecarboxamide;
19) N-(3,5-Dinitrophenyl)-8-hydroxy-7-quinolinecarboxamide;
20) N-(2-Bromophenyl)-8-hydroxy-7-quinolinecarboxamide;
21) N-(2-Chlorophenyl)-8-hydroxy-7-quinolinecarboxamide;
22) N-(4-Bromo-2-chlorophenyl)-8-hydroxy-7-quinolinecarboxamide;
23) N-(2,4-Dichlorophenyl)-8-hydroxy-7-quinolinecarboxamide;
24) N-(2-Chloro-4-nitrophenyl)-8-hydroxy-7-quinolinecarboxamide;
25) N-(2,5-Dichlorophenyl)-8-hydroxy-7-quinolinecarboxamide;
26) N-(2-Chloro-5-methylphenyl)-8-hydroxy-7-quinolinecarboxamide;
27) 8-hydroxy-N-(2-nitrophenyl)-7-quinolinecarboxamide;
28) 8-Hydroxy-N-(2-methylphenyl)-7-quinolinecarboxamide;
29) 8-Hydroxy-N-(2-methyl-3-nitrophenyl)-7-quinolinecarboxamide;
30) N-(2,3-Dimethylphenyl)-8-hydroxy-7-quinolinecarboxamide;
31) N-(2-Ethylphenyl)-8-hydroxy-7-quinolinecarboxamide;
32) 8-Hydroxy-N-(2-methyl-4-fluorophenyl)-7-quinolinecarboxamide;
33) N-(4-Chloro-2-methoxy-5-methylphenyl)-8-hydroxy-7-quinolinecarboxamide;
34) 8-Hydroxy-N-(4-propylphenyl)-7-quinolinecarboxamide;
35) N-(4-Bromo-2-fluorophenyl)-8-hydroxy-7-quinolinecarboxamide;
36) N-Benzo-1,3-thiazol-6-yl-8-hydroxy-7-quinolinecarboxamide;
37) 8-Hydroxy-N-indazol-5-yl-7-quinolinecarboxamide;
38) 8-hydroxy-N-(5-iodo-2-methylphenyl)-7-quinolinecarboxamide;
39) 8-hydroxy-N-(2-fluoro-4-iodophenyl)-7-quinolinecarboxamide;
40) 8-hydroxy-N-(2-iodophenyl)-7-quinolinecarboxamide; or
41) 8-hydroxy-N-(3-iodophenyl)-7-quinolinecarboxamide.

8. A compound of formula IA

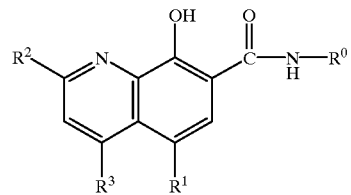

wherein $R^0$ is
a) —$(CH_2)_p W^1 X^2$,
b) —$(CH_2)_p W^1 CH_2 X^1$, or
c) —$(CH_2)_n$—$CH^9$—$(CH_2)_n X^1$;
wherein $R^1$ is
a) —H,
b) —F,
c) —Cl,
d) —Br,
e) —$CF_3$, or
f) —$NO_2$;
wherein $R^2$ is
a) —H,
b) —$C_1$–$C_3$alkyl,
c) —OH,
d) —$CF_3$,
e) —CH=CH-furanyl,
f) —CH=CH-phenyl substituted by zero (0) or one (1) $R^4$,
g) —CH=CH-pyridinyl,
h) —$(CH_2)_p$-phenyl substituted by zero (0) or one (1) $R^4$,
i) —$NHV^1$,
j) —$CH_2 NHV^1$, or
k) —$CH_2 Z^1$;
wherein $R^3$ is
a) —H,
b) —OH,
c) —$CF_3$, or
d) —$C_1$–$C_3$alkyl;
wherein $R^4$ is
a) —H
b) —F,
c) —$C_1$,
d) —Br,
e) —$NO_2$,
f) —$CF_3$,
g) —$W^1$—$R^{10}$,
h) —$C_1$–$C_6$ alkyl,
i) —$C_3$—$C_8$ cycloalkyl,
j) —$(CH_2)_n$-aryl,
k) —$CH_2$—$C_3$-$C_8$ cycloalkyl,
l) —$SO_2 NH$-indazoyl,
m) —CN,
n) —I, or
o) —$CH_2$—OH;
wherein $R^5$ is
a) —H,
b) —F, c) —Cl,
d) —Br,
e) —W$^1$—R$^{10}$,
f) —CF$_3$,
g) —C$_1$-C$_6$ alkyl,
h) —C$_3$-C$_8$ cycloalkyl,
i) —(CH$_2$)$_n$-aryl substituted by R$^6$, or
j) —CH$_2$—C$_3$-C$_8$ cycloalkyl;
wherein R$^6$ is
 a) —H,
 b) —F,
 c) —Cl, or
 d) —Br;
wherein R$^8$ is
 a) —C$_1$-C$_4$ alkyl,
 b) —W$^1$—H, or
 c) —CH$_2$W$^1$H;
wherein R$^9$ is
 a) —C$_1$-C$_7$ alkyl,
 b) —C$_3$-C$_8$ cycloalkyl,
 C) —C(O)R$^{11}$,
 d) —C(O)NHR$^{11}$,
 e) —CH(OH)R$^{11}$,
 f) —CH$_2$OH,
 g) —CO$_2$R$^{11}$, or
 h) -aryl;
wherein R$^{10}$ is
 a) —H,
 b) —C$_1$-C$_6$ alkyl,
 c) —C$_3$-C$_8$ cycloalkyl,
 d) —(CH$_2$)$_n$-aryl optionally substituted with F, Cl, CH$_2$OH or —NO$_2$,
 e) —CH$_2$—C$_3$-C$_8$ cycloalkyl;
wherein R$^{11}$ is
 a) —C$_1$-C$_7$ alkyl,
 b) —C$_3$-C$_8$ cycloalkyl,
 c) —(CH$_2$)$_n$X$^1$, or
 d) —CH$_2$—C$_3$-C$_8$ cycloalkyl;
wherein X$^1$ is
 a) -aryl substituted by zero (0), one (1), two (2), or three (3) R$^4$,
 b) -het substituted by zero (0), one (1) or two (2) R$^5$,
 c) —C$_7$-C$_8$ alkyl, provided that when X$^1$ is alkyl, R$^9$ is not alkyl;
 d) —CH(OH)-phenyl,
 e) —S-phenyl,
 f) —NHSO$_2$-phenyl substituted by one (1), two (2) or three (3) R$^4$,
 g) —CN,
 h) —C$_3$-C$_8$ cycloalkyl substituted by ethoxy, t-butyl or two (2) R$^8$, or
 i) -4-cyano-2,3,5,6-tetrafluoro-phenyl;
wherein X$^2$ is
 a) -aryl substituted by zero (0), one (1), two (2) or three (3) R$^4$,
 b) —C$_1$-C$_8$ alkyl,
 c) —CH(OH)-phenyl, or
 d) —C$_3$-C$_8$ cycloalkyl substituted by zero (0), one (1) or two (2) R$^8$;
wherein W$^1$ is
 a) oxygen, provided that when X$^1$ or X$^2$ is phenyl, W$^1$ is not oxygen,
 b) —NH, or
 c) -sulfur,
wherein V$^1$ is
 a) —R$^{11}$,
 b) —C(O)R$^{11}$,
 c) —SO$_2$R$^{11}$, or
 d) —C(O)NHR$^{11}$;
wherein Z$^1$ is
 a) —C$_1$-C$_7$ alkyl,
 b) —C$_3$-C$_8$ cycloalkyl,
 c) —C(O)R$^{11}$,
 d) —C(O)NHR$^{11}$, or
 e) —CO$_2$R$^{11}$;
wherein -aryl is
 a) -phenyl,
 b) -naphthyl,
 c) -biphenyl,
 d) -tetrahydro-naphthyl, or
 e) fluorenyl;
wherein -het is a 5-membered saturated or unsaturated ring having from one (1) to three (3) heteroatoms selected from the group consisting of nitrogen, oxygen and sulfur,
wherein -cycloalkyl is a saturated or unsaturated hydrocarbon ring, optionally fused to a benzene ring; wherein n is zero (0) to six (6), inclusive, provided that where X$^1$ is a) or b), n is at least one; p is one (1), two (2) or three (3);
or a pharmaceutically acceptable salt or N-oxide thereof.

9. A compound which is
8-Hydroxy-N-(cis-myrtanyl)-7-quinolinecarboxamide; or
N-(2-Adamantyl)-8-hydroxy-7-quinolinecarboxamide.

* * * * *